US012715866B2

(12) United States Patent
Shin et al.

(10) Patent No.: US 12,715,866 B2
(45) **Date of Patent: *Aug. 25, 2026**

(54) BICYCLIC COMPOUND AND USE THEREOF

(71) Applicant: SK BIOPHARMACEUTICALS CO., LTD., Gyeonggi-do (KR)

(72) Inventors: Yong Je Shin, Gyeonggi-do (KR); Jin Hee Kim, Gyeonggi-do (KR); Jun Lee, Gyeonggi-do (KR); Sook Kyung Park, Gyeonggi-do (KR); Ho Yeon Lee, Gyeonggi-do (KR); Hyun Suk Choi, Gyeonggi-do (KR); Se Hyuk Kim, Gyeonggi-do (KR); Eun Ji Kang, Gyeonggi-do (KR); Ho Youl Lee, Gyeonggi-do (KR); Soo Yeon Jung, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/207,401

(22) Filed: Jun. 8, 2023

(65) Prior Publication Data

US 2024/0051951 A1 Feb. 15, 2024

Related U.S. Application Data

(63) Continuation of application No. 17/378,957, filed on Jul. 19, 2021, now Pat. No. 11,725,001, which is a continuation of application No. 17/102,871, filed on Nov. 24, 2020, now Pat. No. 11,111,237, which is a continuation of application No. PCT/KR2020/013424, filed on Sep. 29, 2020.

(30) Foreign Application Priority Data

Oct. 2, 2019 (KR) ........................ 10-2019-0122177

(51) Int. Cl.

| | |
|---|---|
| ***C07D 413/06*** | (2006.01) |
| ***C07D 401/06*** | (2006.01) |
| ***C07D 413/14*** | (2006.01) |
| ***C07D 491/08*** | (2006.01) |
| ***C07D 491/107*** | (2006.01) |

(52) U.S. Cl.

CPC ......... *C07D 413/06* (2013.01); *C07D 401/06* (2013.01); *C07D 413/14* (2013.01); *C07D 491/08* (2013.01); *C07D 491/107* (2013.01)

(58) Field of Classification Search

CPC .................................................... C07D 413/06
USPC .................................................... 514/210.16
See application file for complete search history.

(56) References Cited

U.S. PATENT DOCUMENTS

| | | | | |
|---|---|---|---|---|
| 11,111,237 | B2 * | 9/2021 | Shin | A61K 31/5513 |
| 11,725,001 | B2 * | 8/2023 | Shin | A61P 35/00<br>514/210.16 |
| 2014/0024637 | A1 | 1/2014 | Rice | |
| 2014/0066431 | A1 | 3/2014 | Rice et al. | |

FOREIGN PATENT DOCUMENTS

| | | | |
|---|---|---|---|
| WO | WO-2014-100695 | A1 | 6/2014 |
| WO | WO-2014/100716 | A1 | 6/2014 |
| WO | WO-2014-100734 | A1 | 6/2014 |
| WO | WO-2014-100764 | A2 | 6/2014 |
| WO | WO-2015-200677 | A2 | 12/2015 |
| WO | WO-2016-034675 | A1 | 3/2016 |
| WO | WO-2018-167276 | A1 | 9/2018 |
| WO | WO-2018/181345 | A1 | 10/2018 |
| WO | WO-2019-102494 | A1 | 5/2019 |
| WO | WO-2019/173804 | A1 | 9/2019 |

OTHER PUBLICATIONS

International Search Report from corresponding PCT Application No. PCT/KR2020/013424,, dated Jan. 15, 2021.

Office Action from corresponding U.S. Appl. No. 17/102,871, dated Feb. 24, 2021.

Office Action (Non-Final) from Corresponding U.S. Appl. No. 17/378,957 dated Dec. 16, 2022.

Notice of Allowance from corresponding U.S. Appl. No. 17/378,957, dated Mar. 22, 2023.

* cited by examiner

*Primary Examiner* — Kahsay Habte

(74) *Attorney, Agent, or Firm* — Harness, Dickey & Pierce, P.L.C.

(57) ABSTRACT

The present disclosure relates to a compound derivative containing a 6-7 bicyclic ring and use thereof. The compound according to the present invention can be effectively used in the prevention or treatment of diseases caused by PRMT5 by acting as a PRMT5 inhibitor.

19 Claims, No Drawings

BICYCLIC COMPOUND AND USE THEREOF

CROSS-REFERENCE TO RELATED APPLICATIONS

This application is a continuation application of U.S. patent application Ser. No. 17/378,957, filed on Jul. 19, 2021, which is a continuation application of U.S. patent application Ser. No. 17/102,871, filed on Nov. 24, 2020 which is a continuation application of PCT Application No. PCT/KR2020/013424, filed on Sep. 29, 2020, which claims the benefit and priority to Korean Patent Application No. 10-2019-0122177, filed on Oct. 2, 2019. The entire disclosures of the applications identified in this paragraph are incorporated herein by references.

FIELD

The present disclosure relates to a compound derivative containing a 6-7 bicyclic ring and use thereof. The compound according to the present invention can be effectively used in the prevention or treatment of diseases caused by protein arginine methyltransferases 5 (PRMT5) by acting as a PRMT5 inhibitor.

BACKGROUND

PRMT (protein arginine methyltransferases) are enzymes that transfer methyl groups to arginine in target proteins using the cofactor SAM (S-adenosyl methionine). Up to now, there are a total of 9 PRMT isoforms (PRMT1-9) have been known, and these are largely divided into 3 types. It has been known that PRMT1, 2, 3, 4, 6 and 8—which belong to type I PRMT—cause monomethylation and asymmetric dimethylation of arginine, and PRMT5 and PRMT9 belonging to type II PRMT induce monomethylation and symmetric dimethylation of arginine. Meanwhile, PRMT7—which is a type III PRMT—mainly causes monomethylation of arginine. PRMT induces methylation of various substrates present in the nucleus and cytoplasm, thereby regulating important biological processes in cells such as cell proliferation, differentiation and splicing.

PRMT5 is a major arginine methyl group transfer enzyme among type II PRMTs. It forms a functional complex with methylosome protein 50 (MEP50) to cause methylation of the target protein. PRMT5 is involved in the formation of leukemia, lymphoma, glioblastoma, lung cancer and breast cancer by methylating target proteins including histone protein in the nucleus and non-histone protein such as p53, NFκB, PI3K/AKT and CRAF. Specifically, it is well known that cancer formation by PRMT5 occurs as the proliferation, differentiation, invasion and migration of tumor cells are promoted. In addition, according to several reports, it is known that the higher the expression of PRMT5 is, the poorer the prognosis of cancer patients is. To the contrary, it has been observed that when the expression of PRMT5 is inhibited, the proliferation of tumor cells can be suppressed.

Meanwhile, it has been recently reported that diseases other than cancer can also be mediated by PRMT5.

SUMMARY

An object of the present invention is to provide a novel compound based on a 6-7 bicyclic ring showing excellent PRMT5 inhibitory effect, or an optical isomer, a stereoisomer or an isotopic variant thereof, or a pharmaceutically acceptable salt thereof.

Another object of the present invention is to provide a pharmaceutical composition comprising the above novel compound based on a 6-7 bicyclic ring, or an optical isomer, a stereoisomer or an isotopic variant thereof, or a pharmaceutically acceptable salt thereof as an active ingredient.

To achieve the above object, the present invention provides a compound represented by the following Formula 1, or an optical isomer, a stereoisomer or an isotopic variant thereof, or a pharmaceutically acceptable salt thereof:

[Formula 1]

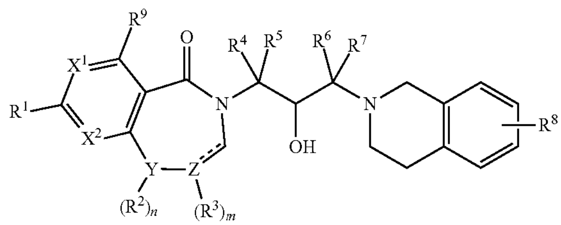

wherein $X^1$ and $X^2$ are each independently carbon or nitrogen;

Y is carbon, oxygen or nitrogen;

Z is carbon;

n is an integer of 0 or 1;

m is an integer of 0 to 2;

$\overset{---}{---}$ is a single bond or a double bond;

$R^1$ is -D-$R^{10}$; wherein D is a direct bond, —O—, —C(═O)—, —C≡C— or —$CR^{11}R^{12}$—; $R^{10}$ is hydrogen, halo, hydroxy, cyano, alkyl, hydroxyalkyl, haloalkyl, haloalkylsulfonate, dialkylamino, alkylaminoalkyl, dialkylaminoalkyl, dialkylaminocarbonylalkyl, saturated or unsaturated carbocyclyl, saturated or unsaturated heterocyclyl, saturated or unsaturated carbocyclyl-alkyl, or saturated or unsaturated heterocyclyl-alkyl; $R^{11}$ and $R^{12}$ are each independently hydrogen, hydroxy or alkyl; the carbocycle or heterocycle may be substituted with one or more substituents selected from hydroxy, halo, oxo, formyl (—CHO), nitrile, alkyl, alkoxy, hydroxyalkyl, hydroxyhaloalkyl, alkoxyalkyl, haloalkyl, nitrilealkyl, alkylcarbonyl, alkylthiocarbonyl, alkoxycarbonyl, haloalkylcarbonyl, carbocyclyl, carbocyclylcarbonyl, (alkyl)(haloalkyl)amino, (alkyl)(heterocyclyl)amino, heterocyclyl and heterocyclyl-alkyl;

$R^2$ is hydrogen or alkyl;

$R^3$ is hydrogen or alkyl;

$R^4$, $R^5$, $R^6$ and $R^7$ are each independently hydrogen or alkyl;

$R^8$ is hydrogen, halo, alkyl, alkoxy or amino; and $R^9$ is hydrogen, halo or alkyl.

Unless indicated otherwise, the term "alkyl" used herein, either alone or in combination with additional terms (for example, haloalkyl), refers to a radical of a saturated aliphatic hydrocarbon group having, for example 1 to 7 carbon atoms of a linear or branched chain. For example, the alkyl may include such as methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl and 1, 2-dimethylpropyl, but is not limited thereto.

Unless indicated otherwise, the term "alkoxy" used herein refers to alkyloxy having, for example 1 to 7 carbon atoms.

Unless indicated otherwise, the term "halo" used herein, either alone or in combination with additional terms (for example, haloalkyl), refers to a radical of fluorine (F), chlorine (Cl), bromine (Br) or iodine (I).

Unless indicated otherwise, the term "haloalkyl" used herein refers to an alkyl defined as above in which one or more of the hydrogen atoms are replaced with one or more same or different halogen atoms. Exemplary haloalkyl may include —$CH_2Cl$, —$CH_2CF_3$, —$CH_2CCl_3$ or perfluoroalkyl (e.g., —$CF_3$).

Unless indicated otherwise, the term "oxo" used herein refers to the group of ═O (that is, oxygen having a double bond). For example, 1-oxo-ethyl group is an acetyl group.

Unless indicated otherwise, the term "hydroxyalkyl" used herein refers to an alkyl in which one or more of the hydrogen atoms are replaced with one or more hydroxy (—OH) groups. For example, it may include that the hydrogen atoms are replaced with 2 or 3 hydroxy groups.

Unless indicated otherwise, the term "saturated or unsaturated carbocyclyl" used herein refers to a radical of a hydrocarbon that is unsaturated or partially or fully saturated, forming a single or fused cyclic ring having, for example 3 to 24 carbon atoms. Specifically, the carbocyclyl may have 3 to 10 carbon atoms. The carbocycle may include a bridged structure or a spiro structure. In addition, the unsaturated carbocycle may include an aromatic hydrocarbon such as aryl.

According to one embodiment of the present invention, the carbocycle may be cyclohexane, cyclohexene, cyclopropane, cyclobutane or cyclopentane, but is not limited thereto.

Unless indicated otherwise stated, the term "saturated or unsaturated heterocyclyl" used herein refers to 3- to 24-membered hydrocarbon that is unsaturated or partially or fully saturated, forming a single or fused cyclic ring, and having one or more heteroatoms, for example 1 to 8 heteroatoms selected from the group consisting of nitrogen (N), oxygen (O) and sulfur (S) Specifically, the heterocyclyl may be a 4- to 10-membered hydrocarbon having 1 to 3 hetero atoms. The heterocycle may include a bridged structure or a spiro structure. In addition, the unsaturated heterocyclyl may include an aromatic hydrocarbon such as heteroaryl.

According to one embodiment of the present invention, the heterocycle may be tetrahydropyridine, dihydropyridine, piperidine, dihydropyran, tetrahydropyran, pyrrolidine, 2-oxa-6-azaspiroheptane, azetidine, morpholine, 3,3a,4,5,6,6a-hexahydro-1H-cyclopenta[c]pyrrole, pyrrolidine, oxazepane, 2-oxa-5-azabicyclo[2.2.1]heptane, pyridyl, tetrahydrofuran, 8-azabicyclo[3.2.1]octane, piperazine, 2-azaspiro[3.3]heptane, 2-oxa-7-azaspiro[3.4]octane, 2-azabicyclo[2.2.1]heptane, 3-oxa-8-azabicyclo[3.2.1]octane, 3,4-dihydro-1H-pyrrolo[1,2-a]pyrazine, 3,4,6,7,8,8a-hexahydro-1H-pyrrolo[1,2]-a]pyrazine, pyrimidine, pyrazole, 2-oxa-7-azaspiro[3.5]nonane or oxetane, but is not limited thereto.

According to one embodiment of the present invention, in the above Formula 1, $X^1$ and $X^2$ are each independently CH or N.

According to one embodiment of the present invention, in the above Formula 1, Y is $CH_2$, O or NH, when n is 0; and Y is CH or N, when n is 1.

According to one embodiment of the present invention, in the above Formula 1, Z is $CH_2$ or CH, when m is 0; Z is CH or C, when m is 1; and Z is C, when m is 2.

According to one embodiment of the present invention, in the above Formula 1, ⎓ is a single bond or a double bond.

According to one embodiment of the present invention, in the above Formula 1, $R^1$ is -D-$R^{10}$; wherein D is a direct bond, —O—, —C(═O)—, —C≡C— or —$CR^{11}R^{12}$—.

According to one embodiment of the present invention, in the above Formula 1, $R^{10}$ is hydrogen, halo, hydroxy, cyano, $C_1$-$C_7$ alkyl, hydroxy-$C_1$-$C_7$ alkyl, halo-$C_1$-$C_7$ alkyl, halo-$C_1$-$C_7$ alkylsulfonate, di($C_1$-$C_7$ alkyl)amino, $C_1$-$C_7$ alkylamino-$C_1$-$C_7$ alkyl, di($C_1$-$C_7$ alkyl)amino-$C_1$-$C_7$ alkyl, di($C_1$-$C_7$ alkyl)aminocarbonyl-$C_1$-$C_7$ alkyl, saturated or unsaturated $C_3$-$C_{10}$ carbocyclyl, saturated or unsaturated, 4- to 10-membered heterocyclyl, saturated or unsaturated $C_3$-$C_{10}$ carbocyclyl-$C_1$-$C_7$ alkyl, or saturated or unsaturated, 4- to 10-membered heterocyclyl-alkyl.

According to one embodiment of the present invention, in the above Formula 1, $R^1$ and $R^{12}$ are each independently hydrogen, hydroxy or $C_1$-$C_7$ alkyl.

According to one embodiment of the present invention, in the above Formula 1, the carbocycle or heterocycle may be substituted with 1 to 5 substituents selected from hydroxy, halo, oxo, formyl, nitrile, $C_1$-$C_7$ alkyl, $C_1$-$C_7$ alkoxy, hydroxy-$C_1$-$C_7$ alkyl, hydroxyhalo-$C_1$-$C_7$ alkyl, $C_1$-$C_7$ alkoxy-$C_1$-$C_7$ alkyl, halo-$C_1$-$C_7$ alkyl, nitrile-$C_1$-$C_7$ alkyl, $C_1$-$C_7$ alkylcarbonyl, $C_1$-$C_7$ alkylthiocarbonyl, $C_1$-$C_7$ alkoxycarbonyl, halo-$C_1$-$C_7$ alkylcarbonyl, saturated or unsaturated $C_3$-$C_{10}$ carbocyclyl, saturated or unsaturated $C_3$-$C_{10}$ carbocyclylcarbonyl, ($C_1$-$C_7$ alkyl)(halo-$C_1$-$C_7$ alkyl)amino, ($C_1$-$C_7$ alkyl)(saturated or unsaturated, 4- to 10-membered heterocyclyl)amino, saturated or unsaturated, 4- to 10-membered heterocyclyl and saturated or unsaturated, 4- to 10-membered heterocyclyl-$C_1$-$C_7$ alkyl.

According to one embodiment of the present invention, in the above Formula 1, $R^2$ is hydrogen or $C_1$-$C_7$ alkyl.

According to one embodiment of the present invention, in the above Formula 1, $R^3$ is hydrogen or $C_1$-$C_7$ alkyl.

According to one embodiment of the present invention, in the above Formula 1, $R^4$, $R^5$, $R^6$ and $R^7$ are each independently hydrogen or $C_1$-$C_7$ alkyl.

According to one embodiment of the present invention, in the above Formula 1, $R^8$ is hydrogen, halo, $C_1$-$C_7$ alkyl, $C_1$-$C_7$ alkoxy or amino.

According to one embodiment of the present invention, in the above Formula 1, $R^9$ is hydrogen, halo or $C_1$-$C_7$ alkyl.

According to one embodiment of the present invention, in the above Formula 1, $X^1$ and $X^2$ are each independently CH or N; Y is $CH_2$, O or NH, when n is 0; Y is CH or N, when n is 1; Z is $CH_2$ or CH, when m is 0; Z is CH or C, when m is 1; Z is C, when m is 2; and ⎓ is a single bond or a double bond.

According to one embodiment of the present invention, in the above Formula 1, $R^1$ is -D-$R^{10}$; wherein D is a direct bond, —O—, —C(═O)—, —C≡C— or —$CR^{11}R^{12}$—; $R^{10}$ is hydrogen, halo, hydroxy, cyano, $C_1$-$C_7$ alkyl, hydroxy-$C_1$-$C_7$ alkyl, halo-$C_1$-$C_7$ alkyl, halo-$C_1$-$C_7$ alkylsulfonate, di($C_1$-$C_7$ alkyl)amino, $C_1$-$C_7$ alkylamino-$C_1$-$C_7$ alkyl, di($C_1$-$C_7$ alkyl)amino-$C_1$-$C_7$ alkyl, di($C_1$-$C_7$ alkyl)aminocarbonyl-$C_1$-$C_7$ alkyl, saturated or unsaturated $C_3$-$C_{10}$ carbocyclyl, saturated or unsaturated, 4- to 10-membered heterocyclyl, saturated or unsaturated $C_3$-$C_{10}$ carbocyclyl-$C_1$-$C_7$ alkyl, or saturated or unsaturated, 4- to 10-membered heterocyclyl-alkyl; and $R^{11}$ and $R^{12}$ are each independently hydrogen, hydroxy or $C_1$-$C_7$ alkyl.

According to one embodiment of the present invention, in the above Formula 1, $R^{10}$ is halo, $C_1$-$C_7$ alkyl, hydroxy-$C_1$-$C_7$ alkyl, halo-$C_1$-$C_7$ alkyl, saturated or unsaturated $C_3$-$C_{10}$ carbocyclyl, saturated or unsaturated, 4- to 10-membered heterocyclyl, or saturated or unsaturated, 4- to 10-membered heterocyclyl-alkyl.

According to one embodiment of the present invention, in the above Formula 1, the carbocycle or heterocycle may be substituted with 1 to 5 substituents selected from hydroxy, halo, oxo, formyl, nitrile, $C_1$-$C_7$ alkyl, $C_1$-$C_7$ alkoxy, hydroxy-$C_1$-$C_7$ alkyl, hydroxyhalo-$C_1$-$C_7$ alkyl, $C_1$-$C_7$ alkoxy-$C_1$-$C_7$ alkyl, halo-$C_1$-$C_7$ alkyl, nitrile-$C_1$-$C_7$ alkyl, $C_1$-$C_7$ alkylcarbonyl, $C_1$-$C_7$ alkylthiocarbonyl, $C_1$-$C_7$ alkoxycarbonyl, halo-$C_1$-$C_7$ alkylcarbonyl, saturated or unsaturated $C_3$-$C_{10}$ carbocyclyl, saturated or unsaturated $C_3$-$C_{10}$ carbocyclylcarbonyl, ($C_1$-$C_7$ alkyl)(halo-$C_1$-$C_7$ alkyl)amino, ($C_1$-$C_7$ alkyl)(saturated or unsaturated, 4- to 10-membered heterocyclyl)amino, saturated or unsaturated, 4- to 10-membered heterocyclyl and saturated or unsaturated, 4- to 10-membered heterocyclyl-$C_1$-$C_7$ alkyl.

According to one embodiment of the present invention, in the above Formula 1, the carbocycle or heterocycle may be substituted with 1 to 5 substituents selected from hydroxy, halo, formyl, $C_1$-$C_7$ alkyl, hydroxy-$C_1$-$C_7$ alkyl, $C_1$-$C_7$ alkoxy-$C_1$-$C_7$ alkyl, halo-$C_1$-$C_7$ alkyl, $C_1$-$C_7$ alkylcarbonyl, $C_1$-$C_7$ alkoxycarbonyl, halo-$C_1$-$C_7$ alkylcarbonyl, saturated or unsaturated $C_3$-$C_{10}$ carbocyclyl, saturated or unsaturated $C_3$-$C_{10}$ carbocyclylcarbonyl, ($C_1$-$C_7$ alkyl)(halo-$C_1$-$C_7$ alkyl)amino, ($C_1$-$C_7$ alkyl)(saturated or unsaturated, 4- to 10-membered heterocyclyl)amino and saturated or unsaturated, 4- to 10-membered heterocyclyl-$C_1$-$C_7$ alkyl.

According to one embodiment of the present invention, in the above Formula 1, the heterocycle may be substituted with 1 or 2 substituents selected from hydroxy, halo, formyl, $C_1$-$C_7$ alkyl, hydroxy-$C_1$-$C_7$ alkyl, $C_1$-$C_7$ alkoxy-$C_1$-$C_7$ alkyl, halo-$C_1$-$C_7$ alkyl, $C_1$-$C_7$ alkylcarbonyl, $C_1$-$C_7$ alkoxycarbonyl, halo-$C_1$-$C_7$ alkylcarbonyl, saturated or unsaturated $C_3$-$C_{10}$ carbocyclyl, saturated or unsaturated $C_3$-$C_{10}$ carbocyclylcarbonyl and saturated or unsaturated, 4- to 10-membered heterocyclyl-$C_1$-$C_7$ alkyl.

According to one embodiment of the present invention, in the above Formula 1, the carbocycle may be substituted with 1 or 2 substituents selected from halo-$C_1$-$C_7$ alkyl, ($C_1$-$C_7$ alkyl)(halo-$C_1$-$C_7$ alkyl)amino and ($C_1$-$C_7$ alkyl)(saturated or unsaturated, 4- to 10-membered heterocyclyl)amino.

According to one embodiment of the present invention, in the above Formula 1, $R^1$ is -D-$R^{10}$; wherein D is a direct bond; $R^{10}$ is hydrogen, halo, cyano, $C_1$-$C_7$ alkyl, halo-$C_1$-$C_7$ alkyl, di($C_1$-$C_7$ alkyl)amino-$C_1$-$C_7$ alkyl, saturated or unsaturated, 4- to 10-membered heterocyclyl, saturated or unsaturated $C_3$-$C_{10}$ carbocyclyl, or saturated or unsaturated, 4- to 10-membered heterocyclyl-alkyl; and the heterocycle may be substituted with 1 or 2 substituents selected from hydroxy, halo, formyl, $C_1$-$C_7$ alkyl, $C_1$-$C_7$ alkoxy, hydroxy-$C_1$-$C_7$ alkyl, halo-$C_1$-$C_7$ alkyl, nitrile-$C_1$-$C_7$alkyl, $C_1$-$C_7$ alkylcarbonyl, $C_1$-$C_7$alkoxy-$C_1$-$C_7$ alkyl, $C_1$-$C_7$ alkoxycarbonyl, halo-$C_1$-$C_7$ alkylcarbonyl, and saturated or unsaturated, 4- to 10-membered heterocyclyl.

According to one embodiment of the present invention, in the above Formula 1, $R^2$ is hydrogen or $C_1$-$C_7$ alkyl; $R^3$ is hydrogen or $C_1$-$C_7$ alkyl; $R^4$, $R^5$, $R^6$ and $R^7$ are each independently hydrogen or $C_1$-$C_7$ alkyl; $R^8$ is hydrogen, halo, $C_1$-$C_7$ alkyl, $C_1$-$C_7$ alkoxy or amino; and $R^9$ is hydrogen, halo or $C_1$-$C_7$ alkyl.

According to one embodiment of the present invention, in the above Formula 1, $\equiv$ is a single bond.

According to one embodiment of the present invention, in the above Formula 1, the heterocycle is a saturated or unsaturated, 4- to 8-membered hydrocarbon having 1 or 2 heteroatoms selected from N and O.

According to one embodiment of the present invention, in the above Formula 1, the heterocycle is selected from the group consisting of tetrahydropyridine, dihydropyridine, piperidine, dihydropyran, tetrahydropyran, pyrrolidine, 2-oxa-6-azaspiroheptane, azetidine, morpholine, 3,3a,4,5,6,6a-hexahydro-1H-cyclopenta[c]pyrrole, oxazepane, 2-oxa-5-azabicyclo[2.2.1]heptane, pyridyl, tetrahydrofuran, 8-azabicyclo[3.2.1]octane, piperazine, 2-azaspiro[3.3]heptane, 2-oxa-7-azaspiro[3.4]octane, 2-azabicyclo[2.2.1]heptane, 3-oxa-8-azabicyclo[3.2.1]octane, 3,4-dihydro-1H-pyrrolo[1,2-a]pyrazine, 3,4,6,7,8,8a-hexahydro-1H-pyrrolo[1,2]-a]pyrazine, pyrimidine, pyrazole, 2-oxa-7-azaspiro[3.5]nonane, and oxetane.

According to one embodiment of the present invention, in the above Formula 1, the heterocycle is selected from the group consisting of tetrahydropyridine, dihydropyridine, piperidine, tetrahydropyran, pyrrolidine, 2-oxa-6-azaspiroheptane, azetidine, morpholine, 3,3a,4,5,6,6a-hexahydro-1H-cyclopenta[c]pyrrole, pyridyl, 8-azabicyclo[3.2.1]octane, piperazine, 2-azaspiro[3.3]heptane, pyrazole, and oxetane.

According to one embodiment of the present invention, in the above Formula 1, the carbocycle is selected from the group consisting of cyclohexane, cyclohexene, cyclopropane, cyclobutane, and cyclopentane.

According to one embodiment of the present invention, in the above Formula 1, D is a direct bond, —O—, —C(═O)— or —C≡C—; $R^{10}$ is halo, $C_1$-$C_7$ alkyl, hydroxy-$C_1$-$C_7$ alkyl, halo-$C_1$-$C_7$ alkyl, saturated or unsaturated $C_3$-$C_{10}$ carbocyclyl, saturated or unsaturated, 4- to 10-membered heterocyclyl, or saturated or unsaturated, 4- to 10-membered heterocyclyl-alkyl; the carbocycle or heterocycle may be substituted with 1 to 5 substituents selected from hydroxy, halo, formyl, $C_1$-$C_7$ alkyl, hydroxy-$C_1$-$C_7$ alkyl, $C_1$-$C_7$ alkoxy-$C_1$-$C_7$ alkyl, halo-$C_1$-$C_7$ alkyl, $C_1$-$C_7$ alkylcarbonyl, $C_1$-$C_7$ alkoxycarbonyl, halo-$C_1$-$C_7$ alkylcarbonyl, saturated or unsaturated $C_3$-$C_{10}$ carbocyclyl, saturated or unsaturated $C_3$-$C_{10}$ carbocyclylcarbonyl, ($C_1$-$C_7$ alkyl)(halo-$C_1$-$C_7$ alkyl)amino, ($C_1$-$C_7$ alkyl)(saturated or unsaturated, 4- to 10-membered heterocyclyl)amino, and saturated or unsaturated, 4- to 10-membered heterocyclyl-$C_1$-$C_7$ alkyl; the heterocycle is selected from the group consisting of tetrahydropyridine, dihydropyridine, piperidine, tetrahydropyran, pyrrolidine, 2-oxa-6-azaspiroheptane, azetidine, morpholine, 3,3a,4,5,6,6a-hexahydro-1H-cyclopenta[c]pyrrole, pyridyl, 8-azabicyclo[3.2.1]octane, piperazine, 2-azaspiro[3.3]heptane, pyrazole, and oxetane; and the carbocycle is selected from the group consisting of cyclohexane, cyclohexene, and cyclopropane.

Representative examples of the compound of Formula 1 according to the present invention may include compounds shown in Table 1, but are not limited thereto.

TABLE 1

| No. | Compound Name |
| --- | --- |
| 1 | 4-[3-(3,4-dihydro-1H-isoquinolin-2-yl)-2-hydroxy-propyl]-8-methoxy-2,3-dihydro-1,4-benzoxazepin-5-one |
| 2 | 2-[3-(3,4-dihydro-1H-isoquinolin-2-yl)-2-hydroxy-propyl]-7-methoxy-4,5-dihydro-3H-2-benzazepin-1-one |
| 3 | 2-[3-(3,4-dihydro-1H-isoquinolin-2-yl)-2-hydroxy-propyl]-7-hydroxy-4,5-dihydro-3H-2-benzazepin-1-one |

TABLE 1-continued

| No. | Compound Name |
|---|---|
| 4 | 2-[3-(3,4-dihydro-1H-isoquinolin-2-yl)-2-hydroxy-propyl]-7-(trifluoromethoxy)-4,5-dihydro-3H-2-benzazepin-1-one |
| 5 | 4-[(2R)-3-(3,4-dihydro-1H-isoquinolin-2-yl)-2-hydroxy-propyl]-8-(trifluoromethyl)-2,3-dihydro-1,4-benzoxazepin-5-one |
| 6 | 2-[(2R)-3-(3,4-dihydro-1H-isoquinolin-2-yl)-2-hydroxy-propyl]-7-(trifluoromethoxy)-4,5-dihydro-3H-2-benzazepin-1-one |
| 7 | 2-[(2R)-3-(3,4-dihydro-1H-isoquinolin-2-yl)-2-hydroxy-propyl]-7-ethoxy-4,5-dihydro-3H-2-benzazepin-1-one |
| 8 | [2-[(2R)-3-(3,4-dihydro-1H-isoquinolin-2-yl)-2-hydroxy-propyl]-1-oxo-4,5-dihydro-3H-2-benzazepin-7yl] trifluoromethanesulfonate |
| 9 | 2-[(2R)-3-(3,4-dihydro-1H-isoquinolin-2-yl)-2-hydroxy-propyl]-1-oxo-4,5-dihydro-3H-2-benzazepin-7-carbonitrile |
| 10 | 4-[(2R)-3-(3,4-dihydro-1H-isoquinolin-2-yl)-2-hydroxy-propyl]-8-methyl-2,3-dihydro-1,4-benzoxazepin-5-one |
| 11 | 4-[(2R)-3-(3,4-dihydro-1H-isoquinolin-2-yl)-2-hydroxy-propyl]-8-propyl-2,3-dihydro-1,4-benzoxazepin-5-one |
| 12 | 4-[(2R)-3-(3,4-dihydro-1H-isoquinolin-2-yl)-2-hydroxy-propyl]-8-isobutyl-2,3-dihydro-1,4-benzoxazepin-5-one |
| 13 | 4-[(2R)-3-(3,4-dihydro-1H-isoquinolin-2-yl)-2-hydroxy-propyl]-8-(3,3,3-trifluoropropyl)-2,3-dihydro-1,4-benzoxazepin-5-one |
| 14 | tert-butyl 4-[4-[(2R)-3-(3,4-dihydro-1H-isoquinolin-2-yl)-2-hydroxy-propyl]-5-oxo-2,3-dihydro-1,4-benzoxazepin-8-yl]-3,6-dihydro-2H-pyridine-1-carboxylate |
| 15 | 4-[(2R)-3-(3,4-dihydro-1H-isoquinolin-2-yl)-2-hydroxy-propyl]-8-(1,2,3,6-tetrahydropyridin-4-yl)-2,3-dihydro-1,4-benzoxazepin-5-one |
| 16 | 8-(1-acetyl-3,6-dihydro-2H-pyridin-4-yl)-4-[(2R)-3-(3,4-dihydro-1H-isoquinolin-2-yl)-2-hydroxy-propyl]-2,3-dihydro-1,4-benzoxazepin-5-one |
| 17 | 8-(1-acetyl-4-piperidyl)-4-[(2R)-3-(3,4-dihydro-1H-isoquinolin-2-yl)-2-hydroxy-propyl]-2,3-dihydro-1,4-benzoxazepin-5-one |
| 18 | 4-[(2R)-3-(3,4-dihydro-1H-isoquinolin-2-yl)-2-hydroxy-propyl]-8-(1-ethyl-3,6-dihydro-2H-pyridin-4-yl)-2,3-dihydro-1,4-benzoxazepin-5-one |
| 19 | 4-[(2R)-3-(3,4-dihydro-1H-isoquinolin-2-yl)-2-hydroxy-propyl]-8-(1-isopropyl-3,6-dihydro-2H-pyridin-4-yl)-2,3-dihydro-1,4-benzoxazepin-5-one |
| 20 | 4-[(2R)-3-(3,4-dihydro-1H-isoquinolin-2-yl)-2-hydroxy-propyl]-8-(3,6-dihydro-2H-pyran-4-yl)-2,3-dihydro-1,4-benzoxazepin-5-one |
| 21 | 4-[(2R)-3-(3,4-dihydro-1H-isoquinolin-2-yl)-2-hydroxy-propyl]-8-tetrahydropyran-4-yl-2,3-dihydro-1,4-benzoxazepin-5-one |
| 22 | 4-[(2R)-3-(3,4-dihydro-1H-isoquinolin-2-yl)-2-hydroxy-propyl]-8-(morpholinomethyl)-2,3-dihydro-1,4-benzoxazepin-5-one |
| 23 | 4-[(2R)-3-(3,4-dihydro-1H-isoquinolin-2-yl)-2-hydroxy-propyl]-8-(1-piperidylmethyl)-2,3-dihydro-1,4-benzoxazepin-5-one |
| 24 | 4-[(2R)-3-(3,4-dihydro-1 H-isoquinolin-2-yl)-2-hydroxy-propyl]-8-(pyrrolidin-1-ylmethyl)-2,3-dihydro-1,4-benzoxazepin-5-one |
| 25 | 4-[(2R)-3-(3,4-dihydro-1H-isoquinolin-2-yl)-2-hydroxy-propyl]-8-[(dimethylamino)methyl]-2,3-dihydro-1,4-benzoxazepin-5-one |
| 26 | 8-(diethylaminomethyl)-4-[(2R)-3-(3,4-dihydro-1H-isoquinolin-2-yl)-2-hydroxy-propyl]-2,3-dihydro-1,4-benzoxazepin-5-one |
| 27 | 4-[(2R)-3-(3,4-dihydro-1H-isoquinolin-2-yl)-2-hydroxy-propyl]-8-[(4-methyl-1-piperidyl)methyl]-2,3-dihydro-1,4-benzoxazepin-5-one |
| 28 | 4-[(2R)-3-(3,4-dihydro-1H-isoquinolin-2-yl)-2-hydroxy-propyl]-8-(2-oxa-6-azaspiro[3.3]heptan-6-ylmethyl)-2,3-dihydro-1,4-benzoxazepin-5-one |
| 29 | 4-[(2R)-3-(3,4-dihydro-1H-isoquinolin-2-yl)-2-hydroxy-propyl]-8-[(3-methoxyazetidin-1-yl)methyl]-2,3-dihydro-1,4-benzoxazepin-5-one |
| 30 | 4-[(2R)-3-(3,4-dihydro-1H-isoquinolin-2-yl)-2-hydroxy-propyl]-8-[(2-methylmorpholin-4-yl)methyl]-2,3-dihydro-1,4-benzoxazepin-5-one |
| 31 | 8-[(4,4-difluoro-1-piperidyl)methyl]-4-[(2R)-3-(3,4-dihydro-1H-isoquinolin-2-yl)-2-hydroxy-propyl]-2,3-dihydro-1,4-benzoxazepin-5-one |
| 32 | 4-[(2R)-3-(3,4-dihydro-1H-isoquinolin-2-yl)-2-hydroxy-propyl]-8-[(4-fluoro-1-piperidyl)methyl]-2,3-dihydro-1,4-benzoxazepin-5-one |
| 33 | 4-[(2R)-3-(3,4-dihydro-1H-isoquinolin-2-yl)-2-hydroxy-propyl]-8-[(3,5-dimethyl-1-piperidyl)methyl]-2,3-dihydro-1,4-benzoxazepin-5-one |
| 34 | 8-(3,3a,4,5,6,6a-hexahydro-1H-cyclopenta[c]pyrrol-2-ylmethyl)-4-[(2R)-3-(3,4-dihydro-1H-isoquinolin-2-yl)-2-hydroxy-propyl]-2,3-dihydro-1,4-benzoxazepin-5-one |
| 35 | 4-[(2R)-3-(3,4-dihydro-1H-isoquinolin-2-yl)-2-hydroxy-propyl]-8-[(3-hydroxypyrrolidin-1-yl)methyl]-2,3-dihydro-1,4-benzoxazepin-5-one |
| 36 | 4-[(2R)-3-(3,4-dihydro-1H-isoquinolin-2-yl)-2-hydroxy-propyl]-8-[[(2R)-2-methylpyrrolidin-1-yl]methyl]-2,3-dihydro-1,4-benzoxazepin-5-one |
| 37 | 4-[(2R)-3-(3,4-dihydro-1H-isoquinolin-2-yl)-2-hydroxy-propyl]-8-[[3-(hydroxymethyl)-1-piperidyl]methyl]-2,3-dihydro-1,4-benzoxazepin-5-one |
| 38 | 4-[(2R)-3-(3,4-dihydro-1H-isoquinolin-2-yl)-2-hydroxy-propyl]-8-[(4-methoxy-1-piperidyl)methyl]-2,3-dihydro-1,4-benzoxazepin-5-one |
| 39 | 4-[(2R)-3-(3,4-dihydro-1H-isoquinolin-2-yl)-2-hydroxy-propyl]-8-(1,4-oxazepan-4-ylmethyl)-2,3-dihydro-1,4-benzoxazepin-5-one |
| 40 | 4-[(2R)-3-(3,4-dihydro-1H-isoquinolin-2-yl)-2-hydroxy-propyl]-8-[(3-hydroxy-3-methyl-pyrrolidin-1-yl)methyl]-2,3-dihydro-1,4-benzoxazepin-5-one |
| 41 | 4-[(2R)-3-(3,4-dihydro-1H-isoquinolin-2-yl)-2-hydroxy-propyl]-8-[[3-(hydroxymethyl)morpholin-4-yl]methyl]-2,3-dihydro-1,4-benzoxazepin-5-one |

TABLE 1-continued

| No. | Compound Name |
|---|---|
| 42 | 8-[(3,3-difluoro-1-piperidyl)methyl]-4-[(2R)-3-(3,4-dihydro-1H-isoquinolin-2-yl)-2-hydroxy-propyl]-2,3-dihydro-1,4-benzoxazepin-5-one |
| 43 | 4-[(2R)-3-(3,4-dihydro-1H-isoquinolin-2-yl)-2-hydroxy-propyl]-8-[(3-fluoro-1-piperidyl)methyl]-2,3-dihydro-1,4-benzoxazepin-5-one |
| 44 | 4-[(2R)-3-(3,4-dihydro-1H-isoquinolin-2-yl)-2-hydroxy-propyl]-8-[(3-hydroxy-1-piperidyl)methyl]-2,3-dihydro-1,4-benzoxazepin-5-one |
| 45 | 4-[(2R)-3-(3,4-dihydro-1H-isoquinolin-2-yl)-2-hydroxy-propyl]-8-[(4-hydroxy-1-piperidyl)methyl]-2,3-dihydro-1,4-benzoxazepin-5-one |
| 46 | 4-[(2R)-3-(3,4-dihydro-1H-isoquinolin-2-yl)-2-hydroxy-propyl]-8-[[(2S)-2-(hydroxymethyl)pyrrolidin-1-yl]methyl]-2,3-dihydro-1,4-benzoxazepin-5-one |
| 47 | 4-[(2R)-3-(3,4-dihydro-1H-isoquinolin-2-yl)-2-hydroxy-propyl]-8-[[(2R)-2-(hydroxy-methyl)pyrrolidin-1-yl]methyl]-2,3-dihydro-1,4-benzoxazepin-5-one |
| 48 | 4-[(2R)-3-(3,4-dihydro-1H-isoquinolin-2-yl)-2-hydroxy-propyl]-8-[(2-ethylpyrrolidin-1-yl)methyl]-2,3-dihydro-1,4-benzoxazepin-5-one |
| 49 | 4-[(2R)-3-(3,4-dihydro-1H-isoquinolin-2-yl)-2-hydroxy-propyl]-8-[[(2S)-2-(methoxymethyl)pyrrolidin-1-yl]methyl]-2,3-dihydro-1,4-benzoxazepin-5-one |
| 50 | 4-[(2R)-3-(3,4-dihydro-1H-isoquinolin-2-yl)-2-hydroxy-propyl]-8-[[(2R)-2-(methoxymethyl)pyrrolidin-1-yl]methyl]-2,3-dihydro-1,4-benzoxazepin-5-one |
| 51 | 4-[(2R)-3-(3,4-dihydro-1H-isoquinolin-2-yl)-2-hydroxy-propyl]-8-[(3-fluoropyrrolidin-1-yl)methyl]-2,3-dihydro-1,4-benzoxazepin-5-one |
| 52 | 8-[(3,3-difluoropyrrolidin-1-yl)methyl]-4-[(2R)-3-(3,4-dihydro-1H-isoquinolin-2-yl)-2-hydroxy-propyl]-2,3-dihydro-1,4-benzoxazepin-5-one |
| 53 | 8-[(4-acetylpiperazin-1-yl)methyl]-4-[(2R)-3-(3,4-dihydro-1H-isoquinolin-2-yl)-2-hydroxy-propyl]-2,3-dihydro-1,4-benzoxazepin-5-one |
| 54 | 4-[(2R)-3-(3,4-dihydro-1H-isoquinolin-2-yl)-2-hydroxy-propyl]-8-[(4-methylpiperazin-1-yl)methyl]-2,3-dihydro-1,4-benzoxazepin-5-one |
| 55 | 4-[(2R)-3-(3,4-dihydro-1H-isoquinolin-2-yl)-2-hydroxy-propyl]-8-(2-oxa-5-azabicyclo[2.2.1]heptan-5-ylmethyl)-2,3-dihydro-1,4-benzoxazepin-5-one |
| 56 | 4-[(2R)-3-(3,4-dihydro-1H-isoquinolin-2-yl)-2-hydroxy-propyl]-8-(3-pyridylmethoxy)-2,3-dihydro-1,4-benzoxazepin-5-one |
| 57 | 4-[(2R)-3-(3,4-dihydro-1H-isoquinolin-2-yl)-2-hydroxy-propyl]-8-(4-pyridylmethoxy)-2,3-dihydro-1,4-benzoxazepin-5-one |
| 58 | 4-[(2R)-3-(3,4-dihydro-1H-isoquinolin-2-yl)-2-hydroxy-propyl]-8-[(2-fluoro-4-pyridyl)methoxy]-2,3-dihydro-1,4-benzoxazepin-5-one |
| 59 | 8-[(2,6-dichloro-4-pyridyl)methoxy]-4-[(2R)-3-(3,4-dihydro-1H-isoquinolin-2-yl)-2-hydroxy-propyl]-2,3-dihydro-1,4-benzoxazepin-5-one |
| 60 | 8-[(2,3-difluoro-4-pyridyl)methoxy]-4-[(2R)-3-(3,4-dihydro-1H-isoquinolin-2-yl)-2-hydroxy-propyl]-2,3-dihydro-1,4-benzoxazepin-5-one |
| 61 | 4-[(2R)-3-(3,4-dihydro-1H-isoquinolin-2-yl)-2-hydroxy-propyl]-8-[(6-fluoro-3-pyridyl)methoxy]-2,3-dihydro-1,4-benzoxazepin-5-one |
| 62 | 4-[(2R)-3-(3,4-dihydro-1H-isoquinolin-2-yl)-2-hydroxy-propyl]-8-[(3-fluoro-4-pyridyl)methoxy]-2,3-dihydro-1,4-benzoxazepin-5-one |
| 63 | 4-[(2R)-3-(3,4-dihydro-1H-isoquinolin-2-yl)-2-hydroxy-propyl]-8-[(5-fluoro-2-pyridyl)methoxy]-2,3-dihydro-1,4-benzoxazepin-5-one |
| 64 | 4-[(2R)-3-(3,4-dihydro-1H-isoquinolin-2-yl)-2-hydroxy-propyl]-8-tetrahydropyran-4-yloxy-2,3-dihydro-1,4-benzoxazepin-5-one |
| 65 | 4-[(2R)-3-(3,4-dihydro-1H-isoquinolin-2-yl)-2-hydroxy-propyl]-8-(tetrahydropyran-2-ylmethoxy)-2,3-dihydro-1,4-benzoxazepin-5-one |
| 66 | 8-(cyclohexylmethoxy)-4-[(2R)-3-(3,4-dihydro-1H-isoquinolin-2-yl)-2-hydroxy-propyl]-2,3-dihydro-1,4-benzoxazepin-5-one |
| 67 | 4-[(2R)-3-(3,4-dihydro-1H-isoquinolin-2-yl)-2-hydroxy-propyl]-8-(tetrahydrofuran-2-ylmethoxy)-2,3-dihydro-1,4-benzoxazepin-5-one |
| 68 | 4-[(2R)-3-(3,4-dihydro-1H-isoquinolin-2-yl)-2-hydroxy-propyl]-8-[(1-methyl-3-piperidyl)oxy]-2,3-dihydro-1,4-benzoxazepin-5-one |
| 69 | 4-[(2R)-3-(3,4-dihydro-1H-isoquinolin-2-yl)-2-hydroxy-propyl]-8-[(1-ethyl-3-piperidyl)oxy]-2,3-dihydro-1,4-benzoxazepin-5-one |
| 70 | 8-[(1-acetyl-4-piperidyl)methoxy]-4-[(2R)-3-(3,4-dihydro-1H-isoquinolin-2-yl)-2-hydroxy-propyl]-2,3-dihydro-1,4-benzoxazepin-5-one |
| 71 | 4-[(2R)-3-(3,4-dihydro-1H-isoquinolin-2-yl)-2-hydroxy-propyl]-8-(2,2,2-trifluoroethoxy)-2,3-dihydro-1,4-benzoxazepin-5-one |
| 72 | 4-[(2R)-3-(3,4-dihydro-1H-isoquinolin-2-yl)-2-hydroxy-propyl]-8-[2-(dimethylamino)ethoxy]-2,3-dihydro-1,4-benzoxazepin-5-one |
| 73 | 4-[(2R)-3-(3,4-dihydro-1H-isoquinolin-2-yl)-2-hydroxy-propyl]-8-(2-morpholinoethoxy)-2,3-dihydro-1,4-benzoxazepin-5-one |
| 74 | 4-[(2R)-3-(3,4-dihydro-1H-isoquinolin-2-yl)-2-hydroxy-propyl]-8-[2-(2-oxopyrrolidin-1-yl)ethoxy]-2,3-dihydro-1,4-benzoxazepin-5-one |
| 75 | 4-[(2R)-3-(3,4-dihydro-1H-isoquinolin-2-yl)-2-hydroxy-propyl]-8-(2-pyridyloxy)-2,3-dihydro-1,4-benzoxazepin-5-one |
| 76 | 4-[(2R)-3-(3,4-dihydro-1H-isoquinolin-2-yl)-2-hydroxy-propyl]-8-[(6-oxo-3-piperidyl)oxy]-2,3-dihydro-1,4-benzoxazepin-5-one |
| 77 | tert-butyl 4-[[4-[(2R)-3-(3,4-dihydro-1H-isoquinolin-2-yl)-2-hydroxy-propyl]-5-oxo-2,3-dihydro-1,4-benzoxazepin-8-yl]oxy]piperidine-1-carboxylate |
| 78 | 8-[(1-acetyl-4-piperidyl)oxy]-4-[(2R)-3-(3,4-dihydro-1H-isoquinolin-2-yl)-2-hydroxy-propyl]-2,3-dihydro-1,4-benzoxazepin-5-one |
| 79 | 8-[(1-acetyl-3-piperidyl)oxy]-4-[(2R)-3-(3,4-dihydro-1H-isoquinolin-2-yl)-2-hydroxy-propyl]-2,3-dihydro-1,4-benzoxazepin-5-one |

TABLE 1-continued

| No. | Compound Name |
|---|---|
| 80 | 8-(1-acetylpyrrolidin-3-yl)oxy-4-[(2R)-3-(3,4-dihydro-1H-isoquinolin-2-yl)-2-hydroxy-propyl]-2,3-dihydro-1,4-benzoxazepin-5-one |
| 81 | 8-[(3R)-1-acetylpyrrolidin-3-yl]oxy-4-[(2R)-3-(3,4-dihydro-1H-isoquinolin-2-yl)-2-hydroxy-propyl]-2,3-dihydro-1,4-benzoxazepin-5-one |
| 82 | 8-[(3S)-1-acetylpyrrolidin-3-yl]oxy-4-[(2R)-3-(3,4-dihydro-1H-isoquinolin-2-yl)-2-hydroxy-propyl]-2,3-dihydro-1,4-benzoxazepin-5-one |
| 83 | 8-(1-acetylazetidin-3-yl)oxy-4-[(2R)-3-(3,4-dihydro-1H-isoquinolin-2-yl)-2-hydroxy-propyl]-2,3-dihydro-1,4-benzoxazepin-5-one |
| 84 | 4-[(2R)-3-(3,4-dihydro-1H-isoquinolin-2-yl)-2-hydroxy-propyl]-8-(1-propanoylazetidin-3-yl)oxy-2,3-dihydro-1,4-benzoxazepin-5-one |
| 85 | 8-[1-(cyclopropanecarbonyl)azetidin-3-yl]oxy-4-[(2R)-3-(3,4-dihydro-1H-isoquinolin-2-yl)-2-hydroxy-propyl]-2,3-dihydro-1,4-benzoxazepin-5-one |
| 86 | methyl 3-[[4-[(2R)-3-(3,4-dihydro-1H-isoquinolin-2-yl)-2-hydroxy-propyl]-5-oxo-2,3-dihydro-1,4-benzoxazepin-8-yl]oxy]azetidin-1-carboxylate |
| 87 | 4-[(2R)-3-(3,4-dihydro-1H-isoquinolin-2-yl)-2-hydroxy-propyl]-8-[(1-methyl-4-piperidyl)oxy]-2,3-dihydro-1,4-benzoxazepin-5-one |
| 88 | 4-[(2R)-3-(3,4-dihydro-1H-isoquinolin-2-yl)-2-hydroxy-propyl]-8-[(1-ethyl-4-piperidyl)oxy]-2,3-dihydro-1,4-benzoxazepin-5-one |
| 89 | 4-[(2R)-3-(3,4-dihydro-1H-isoquinolin-2-yl)-2-hydroxy-propyl]-8-[(1-isopropyl-4-piperidyl)oxy]-2,3-dihydro-1,4-benzoxazepin-5-one |
| 90 | 8-[(1-cyclopropyl-4-piperidyl)oxy]-4-[(2R)-3-(3,4-dihydro-1H-isoquinolin-2-yl)-2-hydroxy-propyl]-2,3-dihydro-1,4-benzoxazepin-5-one |
| 91 | 8-[(1-cyclobutyl-4-piperidyl)oxy]-4-[(2R)-3-(3,4-dihydro-1H-isoquinolin-2-yl)-2-hydroxy-propyl]-2,3-dihydro-1,4-benzoxazepin-5-one |
| 92 | 4-[(2R)-3-(3,4-dihydro-1H-isoquinolin-2-yl)-2-hydroxy-propyl]-8-[[1-(oxetan-3-yl)-4-piperidyl]oxy]-2,3-dihydro-1,4-benzoxazepin-5-one |
| 93 | 4-[(2R)-3-(3,4-dihydro-1H-isoquinolin-2-yl)-2-hydroxy-propyl]-8-(1-methylazetidin-3-yl)oxy-2,3-dihydro-1,4-benzoxazepin-5-one |
| 94 | 4-[(2R)-3-(3,4-dihydro-1H-isoquinolin-2-yl)-2-hydroxy-propyl]-8-(1-ethylazetidin-3-yl)oxy-2,3-dihydro-1,4-benzoxazepin-5-one |
| 95 | 4-[(2R)-3-(3,4-dihydro-1H-isoquinolin-2-yl)-2-hydroxy-propyl]-8-(1-isopropylazetidin-3-yl)oxy-2,3-dihydro-1,4-benzoxazepin-5-one |
| 96 | 4-[(2R)-3-(3,4-dihydro-1H-isoquinolin-2-yl)-2-hydroxy-propyl]-8-[1-(oxetan-3-yl)azetidin-3-yl]oxy-2,3-dihydro-1,4-benzoxazepin-5-one |
| 97 | 4-[(2R)-3-(3,4-dihydro-1H-isoquinolin-2-yl)-2-hydroxy-propyl]-8-[(1-ethylazetidin-3-yl)methoxy]-2,3-dihydro-1,4-benzoxazepin-5-one |
| 98 | 4-[(2R)-3-(3,4-dihydro-1H-isoquinolin-2-yl)-2-hydroxy-propyl]-8-(1-methylpyrrolidin-3-yl)oxy-2,3-dihydro-1,4-benzoxazepin-5-one |
| 99 | 4-[(2R)-3-(3,4-dihydro-1H-isoquinolin-2-yl)-2-hydroxy-propyl]-8-[(3R)-1-ethylpyrrolidin-3-yl]oxy-2,3-dihydro-1,4-benzoxazepin-5-one |
| 100 | 4-[(2R)-3-(3,4-dihydro-1H-isoquinolin-2-yl)-2-hydroxy-propyl]-8-(2-pyridyloxy)-2,3-dihydro-1,4-benzoxazepin-5-one |
| 101 | 4-[(2R)-3-(3,4-dihydro-1H-isoquinolin-2-yl)-2-hydroxy-propyl]-8-[[(2S)-1-isopropylpyrrolidin-2-yl]methoxy]-2,3-dihydro-1,4-benzoxazepin-5-one |
| 102 | 4-[(2R)-3-(3,4-dihydro-1H-isoquinolin-2-yl)-2-hydroxy-propyl]-8-[(1-methyl-4-piperidyl)methoxy]-2,3-dihydro-1,4-benzoxazepin-5-one |
| 103 | 4-[(2R)-3-(3,4-dihydro-1H-isoquinolin-2-yl)-2-hydroxy-propyl]-8-[(1-ethyl-4-piperidyl)methoxy]-2,3-dihydro-1,4-benzoxazepin-5-one |
| 104 | 4-[(2R)-3-(3,4-dihydro-1H-isoquinolin-2-yl)-2-hydroxy-propyl]-8-[(4-methylmorpholin-2-yl)methoxy]-2,3-dihydro-1,4-benzoxazepin-5-one |
| 105 | 4-[(2R)-3-(3,4-dihydro-1H-isoquinolin-2-yl)-2-hydroxy-propyl]-8-[(4-ethylmorpholin-2-yl)methoxy]-2,3-dihydro-1,4-benzoxazepin-5-one |
| 106 | 4-[(2R)-3-(3,4-dihydro-1H-isoquinolin-2-yl)-2-hydroxy-propyl]-8-[(1-methylpyrrolidin-3-yl)methoxy]-2,3-dihydro-1,4-benzoxazepin-5-one |
| 107 | 4-[(2R)-3-(3,4-dihydro-1H-isoquinolin-2-yl)-2-hydroxy-propyl]-8-[(1-methyl-3-piperidyl)methoxy]-2,3-dihydro-1,4-benzoxazepin-5-one |
| 108 | 4-[(2R)-3-(3,4-dihydro-1H-isoquinolin-2-yl)-2-hydroxy-propyl]-6-fluoro-8-(morpholinomethyl)-2,3-dihydro-1,4-benzoxazepin-5-one |
| 109 | 4-[(2R)-3-(3,4-dihydro-1H-isoquinolin-2-yl)-2-hydroxy-propyl]-6-fluoro-8-[(1-methyl-4-piperidyl)oxy]-2,3-dihydro-1,4-benzoxazepin-5-one |
| 110 | 4-[(2R)-3-(3,4-dihydro-1H-isoquinolin-2-yl)-2-hydroxy-propyl]-8-[(1-ethyl-4-piperidyl)oxy]-2,2-dimethyl-3H-1,4-benzoxazepin-5-one |
| 111 | 4-[(2R)-3-(3,4-dihydro-1H-isoquinolin-2-yl)-2-hydroxy-propyl]-2,2-dimethyl-8-(morpholinomethyl)-3H-1,4-benzoxazepin-5-one |
| 112 | 4-[(2R)-3-(3,4-dihydro-1H-isoquinolin-2-yl)-2-hydroxy-propyl]-2,2-dimethyl-8-[(1-methyl-4-piperidyl)oxy]-3H-1,4-benzoxazepin-5-one |
| 113 | 4-[(2R)-3-(3,4-dihydro-1H-isoquinolin-2-yl)-2-hydroxy-propyl]-2,2-dimethyl-8-(4-pyridylmethoxy)-3H-1,4-benzoxazepin-5-one |
| 114 | 8-(1-acetylazetidin-3-yl)oxy-4-[(2R)-3-(3,4-dihydro-1H-isoquinolin-2-yl)-2-hydroxy-propyl]-2,2-dimethyl-3H-1,4-benzoxazepin-5-one |
| 115 | 4-[(2R)-3-(3,4-dihydro-1H-isoquinolin-2-yl)-2-hydroxy-propyl]-1-methyl-8-(morpholinomethyl)-2,3-dihydro-1,4-benzodiazepin-5-one |
| 116 | 4-[(2R)-3-(3,4-dihydro-1H-isoquinolin-2-yl)-2-hydroxy-propyl]-1-methyl-8-(3,3,3-trifluoropropyl)-2,3-dihydro-1,4-benzodiazepin-5-one |
| 117 | 8-(cyclohexylmethyl)-4-[(2R)-3-(3,4-dihydro-1H-isoquinolin-2-yl)-2-hydroxy-propyl]-1-methyl-2,3-dihydro-1,4-benzodiazepin-5-one |

TABLE 1-continued

| No. | Compound Name |
|---|---|
| 118 | 8-(cyclohexen-1-yl)-4-[(2R)-3-(3,4-dihydro-1H-isoquinolin-2-yl)-2-hydroxy-propyl]-1-methyl-2,3-dihydro-1,4-benzodiazepin-5-one |
| 119 | 4-[(2R)-3-(3,4-dihydro-1H-isoquinolin-2-yl)-2-hydroxy-propyl]-1-methyl-8-[4-(trifluoromethyl)cyclohexen-1-yl]-2,3-dihydro-1,4-benzodiazepin-5-one |
| 120 | tert-butyl 4-[4-[(2R)-3-(3,4-dihydro-1H-isoquinolin-2-yl)-2-hydroxy-propyl]-1-methyl-5-oxo-2,3-dihydro-1,4-benzodiazepin-8-yl]-3,6-dihydro-2H-pyridine-1-carboxylate |
| 121 | 8-[(1-acetyl-4-piperidyl)oxy]-4-[(2R)-3-(3,4-dihydro-1H-isoquinolin-2-yl)-2-hydroxy-propyl]-1-methyl-2,3-dihydro-1,4-benzodiazepin-5-one |
| 122 | 8-(1-acetylazetidin-3-yl)oxy-4-[(2R)-3-(3,4-dihydro-1H-isoquinolin-2-yl)-2-hydroxy-propyl]-1-methyl-2,3-dihydro-1,4-benzodiazepin-5-one |
| 123 | 8-[(3R)-1-acetylpyrrolidin-3-yl]oxy-4-[(2R)-3-(3,4-dihydro-1H-isoquinolin-2-yl)-2-hydroxy-propyl]-1-methyl-2,3-dihydro-1,4-benzodiazepin-5-one |
| 124 | 8-[(3S)-1-acetylpyrrolidin-3-yl]oxy-4-[(2R)-3-(3,4-dihydro-1H-isoquinolin-2-yl)-2-hydroxy-propyl]-1-methyl-2,3-dihydro-1,4-benzodiazepin-5-one |
| 125 | 4-[(2R)-3-(3,4-dihydro-1H-isoquinolin-2-yl)-2-hydroxy-propyl]-1-methyl-8-[(1-methyl-4-piperidyl)oxy]-2,3-dihydro-1,4-benzodiazepin-5-one |
| 126 | 4-[(2R)-3-(3,4-dihydro-1H-isoquinolin-2-yl)-2-hydroxy-propyl]-8-[(1-ethyl-4-piperidyl)oxy]-1-methyl-2,3-dihydro-1,4-benzodiazepin-5-one |
| 127 | 8-[(1-cyclobutyl-4-piperidyl)oxy]-4-[(2R)-3-(3,4-dihydro-1H-isoquinolin-2-yl)-2-hydroxy-propyl]-1-methyl-2,3-dihydro-1,4-benzodiazepin-5-one |
| 128 | 4-[(2R)-3-(3,4-dihydro-1H-isoquinolin-2-yl)-2-hydroxy-propyl]-1-methyl-8-[(1-tetrahydrofuran-3-yl-4-piperidyl)oxy]-2,3-dihydro-1,4-benzodiazepin-5-one |
| 129 | 4-[(2R)-3-(3,4-dihydro-1H-isoquinolin-2-yl)-2-hydroxy-propyl]-1-methyl-8-[[1-(oxetan-3-yl)-4-piperidyl]oxy]-2,3-dihydro-1,4-benzodiazepin-5-one |
| 130 | 4-[(2R)-3-(3,4-dihydro-1H-isoquinolin-2-yl)-2-hydroxy-propyl]-1-methyl-8-[(1-methyl-3-piperidyl)oxy]-2,3-dihydro-1,4-benzodiazepin-5-one |
| 131 | 4-[(2R)-3-(3,4-dihydro-1H-isoquinolin-2-yl)-2-hydroxy-propyl]-1-methyl-8-[(1-methylpyrrolidin-3-yl)methoxy]-2,3-dihydro-1,4-benzodiazepin-5-one |
| 132 | 4-[(2R)-3-(3,4-dihydro-1H-isoquinolin-2-yl)-2-hydroxy-propyl]-1-methyl-8-(1-methylpyrrolidin-3-yl)oxy-2,3-dihydro-1,4-benzodiazepin-5-one |
| 133 | 4-[(2R)-3-(3,4-dihydro-1H-isoquinolin-2-yl)-2-hydroxy-propyl]-1-methyl-8-[(1-methyl-3-piperidyl)methoxy]-2,3-dihydro-1,4-benzodiazepin-5-one |
| 134 | 4-[(2R)-3-(3,4-dihydro-1H-isoquinolin-2-yl)-2-hydroxy-propyl]-8-[(3-fluoro-4-pyridyl)methoxy]-1-methyl-2,3-dihydro-1,4-benzodiazepin-5-one |
| 135 | 4-[(2R)-3-(3,4-dihydro-1H-isoquinolin-2-yl)-2-hydroxy-propyl]-8-[(3-fluoro-4-piperidyl)oxy]-1-methyl-2,3-dihydro-1,4-benzodiazepin-5-one dihydrochloride |
| 136 | 4-[(2R)-3-(3,4-dihydro-1H-isoquinolin-2-yl)-2-hydroxy-propyl]-8-[(1-ethyl-3-fluoro-4-piperidyl)oxy]-1-methyl-2,3-dihydro-1,4-benzodiazepin-5-one |
| 137 | 4-[(2R)-3-(3,4-dihydro-1H-isoquinolin-2-yl)-2-hydroxy-propyl]-8-[(8-ethyl-8-azabicyclo[3.2.1]octan-3-yl)oxy]-1-methyl-2,3-dihydro-1,4-benzodiazepin-5-one |
| 138 | 4-[(2R)-3-(3,4-dihydro-1H-isoquinolin-2-yl)-2-hydroxy-propyl]-1-methyl-8-[(2-methyl-4-piperidyl)oxy]-2,3-dihydro-1,4-benzodiazepin-5-one dihydrochloride |
| 139 | 4-[(2R)-3-(3,4-dihydro-1H-isoquinolin-2-yl)-2-hydroxy-propyl]-8-[(5-fluoro-2-pyridyl)methoxy]-1-methyl-2,3-dihydro-1,4-benzodiazepin-5-one |
| 140 | 4-[(2R)-3-(3,4-dihydro-1H-isoquinolin-2-yl)-2-hydroxypropyl]-2-methyl-8-(4-piperidyloxy)-2,3-dihydro-1,4-benzoxazepin-5-one dihydrochloride |
| 141 | 4-[(2R)-3-(3,4-dihydro-1H-isoquinolin-2-yl)-2-hydroxypropyl]-2-methyl-8-[(1-methyl-4-piperidyl)oxy]-2,3-dihydro-1,4-benzoxazepin-5-one |
| 142 | (2R)-8-(1-acetylazetidin-3-yl)oxy-4-[(2R)-3-(3,4-dihydro-1H-isoquinolin-2-yl)-2-hydroxypropyl]-2-methyl-2,3-dihydro-1,4-benzoxazepin-5-one |
| 143 | (2R)-4-[(2R)-3-(3,4-dihydro-1H-isoquinolin-2-yl)-2-hydroxypropyl]-2-methyl-8-[(1-methyl-4-piperidyl)oxy]-2,3-dihydro-1,4-benzoxazepin-5-one |
| 144 | 4-[(2R)-3-(3,4-dihydro-1H-isoquinolin-2-yl)-2-hydroxypropyl]-2-methyl-8-[(1-methyl-4-piperidyl)oxy]-2,3-dihydropyrido[3,2-f][1,4]oxazepin-5-one |
| 145 | 4-[(2R)-3-(3,4-dihydro-1H-isoquinolin-2-yl)-2-hydroxypropyl]-2,2-dimethyl-8-[(1-methyl-4-piperidyl)oxy]-3H-pyrido[3,2-f][1,4]oxazepin-5-one |
| 146 | (2S)-4-[(2R)-3-(3,4-dihydro-1H-isoquinolin-2-yl)-2-hydroxypropyl]-2-methyl-8-[(1-methyl-4-piperidyl)oxy]-2,3-dihydro-1,4-benzoxazepin-5-one |
| 147 | 4-[3-(3,4-dihydro-1H-isoquinolin-2-yl)-2-hydroxy-propyl]-2,3-dihydro-1,4-benzoxazepin-5-one |
| 148 | 2-[3-(3,4-dihydro-1H-isoquinolin-2-yl)-2-hydroxy-propyl]-4,5-dihydro-3H-2-benzazepin-1-one |
| 149 | 4-[(2R)-3-(3,4-dihydro-1H-isoquinolin-2-yl)-2-hydroxy-propyl]-2,3-dihydro-1,4-benzoxazepin-5-one |
| 150 | 4-[(2R)-3-(3,4-dihydro-1H-isoquinolin-2-yl)-2-hydroxy-propyl]-8-fluoro-2,3-dihydro-1,4-benzoxazepin-5-one |
| 151 | 8-bromo-4-[(2R)-3-(3,4-dihydro-1H-isoquinolin-2-yl)-2-hydroxy-propyl]-2,3-dihydro-1,4-benzoxazepin-5-one |
| 152 | 4-[(2R)-3-(3,4-dihydro-1H-isoquinolin-2-yl)-2-hydroxy-propyl]-2,3-dihydropyrido[4,3-f][1,4]oxazepin-5-one |
| 153 | 8-chloro-4-[(2R)-3-(3,4-dihydro-1H-isoquinolin-2-yl)-2-hydroxy-propyl]-2,3-dihydropyrido[3,2-f][1,4]oxazepin-5-one |
| 154 | 7-chloro-2-[(2R)-3-(3,4-dihydro-1H-isoquinolin-2-yl)-2-hydroxy-propyl]-4,5-dihydro-3H-2-benzazepin-1-one |
| 155 | 7-bromo-2-[(2R)-3-(3,4-dihydro-1H-isoquinolin-2-yl)-2-hydroxy-propyl]-4,5-dihydro-3H-2-benzazepin-1-one |

TABLE 1-continued

| No. | Compound Name |
|---|---|
| 156 | 8-bromo-4-[(2R)-3-(3,4-dihydro-1H-isoquinolin-2-yl)-2-hydroxy-propyl]-1-methyl-2,3-dihydro-1,4-benzodiazepin-5-one |
| 157 | 8-bromo-4-[(2R)-3-(3,4-dihydro-1H-isoquinolin-2-yl)-2-hydroxy-propyl]-1-ethyl-2,3-dihydro-1,4-benzodiazepin-5-one |
| 158 | 8-bromo-4-[(2R)-3-(3,4-dihydro-1H-isoquinolin-2-yl)-2-hydroxy-propyl]-1-ethyl-3H-1,4-benzodiazepin-2,5-dione |
| 159 | 2-[4-[[4-(2R)-3-(3,4,-dihydro-1H-isoquinolin-2-yl)-2-hydroxy-propyl]-5-oxo-2,3,-dihydro-1,4,-benzoxazepin-8-yl]-1-piperidyl]acetonitrile |
| 160 | 8-[[1-(2,2-difluoroacetyl)-4-piperidyl]oxy]-4-[(2R)-3-(3,4-dihydro-1H-isoquinolin-2-yl)-2-hydroxy-propyl]-2,3-dihydro-1,4-benzoxazepin-5-one |
| 161 | 8-[[1-(2,2-difluoroacetyl)azetidin-3-yl]oxy-4-[(2R)-3-(3,4-dihydro-1H-isoquinolin-2-yl)-2-hydroxy-propyl]-2,3-dihydro-1,4-benzoxazepin-5-one |
| 162 | 4-[(2R)-3-(3,4-dihydro-1H-isoquinolin-2-yl)-2-hydroxy-propyl]-8-[[1-(2-hydroxyethyl)-4-piperidyl]oxy]-2,3-dihydro-1,4-benzoxazepin-5-one |
| 163 | 4-[(2R)-3-(3,4-dihydro-1H-isoquinolin-2-yl)-2-hydroxy-propyl]-8-[[1-(2-fluoroethyl)-4-piperidyl]oxy]-2,3-dihydro-1,4-benzoxazepin-5-one |
| 164 | 4-[(2R)-3-(3,4-dihydro-1H-isoquinolin-2-yl)-2-hydroxy-propyl]-8-[[1-(2-fluoroethyl)-4-piperidyl]oxy]-2,3-dihydropyrido[3,2-f][1,4]oxazepin-5-one |
| 165 | 4-[(2R)-3-(3,4-dihydro-1H-isoquinolin-2-yl)-2-hydroxypropyl]-8-[[1-[(3-methyloxetan-3-yl)methyl]-4-piperidyl]oxy]-2,3-dihydro-1,4-benzoxazepin-5-one |
| 166 | 4-[[4-[(2R)-3-(3,4-dihydro-1H-isoquinolin-2-yl)-2-hydroxypropyl]-5-oxo-2,3-dihydro-1,4-benzoazepin-8-yl]oxy]piperidine-1-carbonitrile |
| 167 | 8-[(4-acetylpiperazin-1-yl)methyl]-4-[(2R)-3-(3,4-dihydro-1H-isoquinolin-2-yl)-2-hydroxy-propyl]-2,2-dimethyl-3H-1,4-benzoxazepin-5-one |
| 168 | 3-[[4-[(2R)-3-(3,4-dihydro-1H-isoquinolin-2-yl)-2-hydroxy-propyl]-2,2-dimethyl-5-oxo-3H-1,4-benzoxazepin-8-yl]oxy]azetidin-1-carbaldehyde |
| 169 | 4-[[4-[(2R)-3-(3,4-dihydro-1H-isoquinolin-2-yl)-2-hydroxy-propyl]-2,2-dimethyl-5-oxo-3H-1,4-benzoxazepin-8-yl]methyl]piperazin-1-carbaldehyde |
| 170 | 4-[(2R)-3-(3,4-dihydro-1H-isoquinolin-2-yl)-2-hydroxy-propyl]-2,2-dimethyl-8-(2-oxa-6-azaspiro[3.3]heptan-6-ylmethyl)-3H-1,4-benzoxazepin-5-one |
| 171 | 4-[(2R)-3-(3,4-dihydro-1H-isoquinolin-2-yl)-2-hydroxy-propyl]-8-[(8-ethyl-8-azabicyclo[3.2.1]octan-3-yl)oxy]-2,3-dihydro-1,4-benzoxazepin-5-one |
| 172 | 4-[(2R)-3-(3,4-dihydro-1H-isoquinolin-2-yl)-2-hydroxy-propyl]-8-[(2-ethyl-2-azaspiro[3.3]heptan-6-yl)oxy]-2,3-dihydro-1,4-benzoxazepin-5-one |
| 173 | 8-[(8-acetyl-8-azabicyclo[3.2.1]octan-3-yl)oxy]-4-[(2R)-3-(3,4-dihydro-1H-isoquinolin-2-yl)-2-hydroxy-propyl]-2,3-dihydro-1,4-benzoxazepin-5-one |
| 174 | 8-[(2-acetyl-2-azaspiro[3.3]heptan-6-yl)oxy]-4-[(2R)-3-(3,4-dihydro-1H-isoquinolin-2-yl)-2-hydroxy-propyl]-2,3-dihydro-1,4-benzoxazepin-5-one |
| 175 | 4-[(2R)-3-(3,4-dihydro-1H-isoquinolin-2-yl)-2-hydroxy-propyl]-8-(pyrrolidin-1-carbonyl)-2,3-dihydro-1,4-benzoxazepin-5-one |
| 176 | 4-[(2R)-3-(3,4-dihydro-1H-isoquinolin-2-yl)-2-hydroxy-propyl]-8-(piperidine-1-carbonyl)-2,3-dihydro-1,4-benzoxazepin-5-one |
| 177 | 8-(3,3-difluoropyrrolidin-1-carbonyl)-4-[(2R)-3-(3,4-dihydro-1H-isoquinolin-2-yl)-2-hydroxy-propyl]-2,3-dihydro-1,4-benzoxazepin-5-one |
| 178 | 4-[(2R)-3-(3,4-dihydro-1H-isoquinolin-2-yl)-2-hydroxy-propyl]-8-(4-methylpiperazin-1-carbonyl)-2,3-dihydro-1,4-benzoxazepin-5-one |
| 179 | 4-[(2R)-3-(3,4-dihydro-1H-isoquinolin-2-yl)-2-hydroxy-propyl]-2,2-dimethyl-8-(pyrrolidin-1-ylmethyl)-3H-1,4-benzoxazepin-5-one |
| 180 | 8-[(1-acetyl-4-piperidyl)oxy]-4-[(2R)-3-(3,4-dihydro-1H-isoquinolin-2-yl)-2-hydroxy-propyl]-2,2-dimethyl-3H-1,4-benzoxazepin-5-one |
| 181 | 4-[[4-[(2R)-3-(3,4-dihydro-1H-isoquinolin-2-yl)-2-hydroxy-propyl]-2,2-dimethyl-5-oxo-3H-1,4-benzoxazepin-8-yl]oxy]piperidine-1-carbaldehyde |
| 182 | 4-[(2R)-3-(3,4-dihydro-1H-isoquinolin-2-yl)-2-hydroxy-propyl]-2,2-dimethyl-8-[[4-(oxetan-3-yl)piperazin-1-yl]methyl]-3H-1,4-benzoxazepin-5-one |
| 183 | 4-[(2R)-3-(3,4-dihydro-1H-isoquinolin-2-yl)-2-hydroxy-propyl]-2,2-dimethyl-8-(2-oxa-7-azaspiro[3.4]octan-7-ylmethyl)-3H-1,4-benzoxazepin-5-one |
| 184 | 4-[(2R)-3-(3,4-dihydro-1H-isoquinolin-2-yl)-2-hydroxy-propyl]-8-(4-fluoropiperidine-1-carbonyl)-2,3-dihydro-1,4-benzoxazepin-5-one |
| 185 | 4-[(2R)-3-(3,4-dihydro-1H-isoquinolin-2-yl)-2-hydroxy-propyl]-8-[3-(trifluoromethyl)piperidine-1-carbonyl]-2,3-dihydro-1,4-benzoxazepin-5-one |
| 186 | 4-[(2R)-3-(3,4-dihydro-1H-isoquinolin-2-yl)-2-hydroxy-propyl]-8-[4-(trifluoromethyl)piperidine-1-carbonyl]-2,3-dihydro-1,4-benzoxazepin-5-one |
| 187 | 4-[(2R)-3-(3,4-dihydro-1H-isoquinolin-2-yl)-2-hydroxy-propyl]-8-(2,6-dimethylmorpholin-4-carbonyl)-2,3-dihydro-1,4-benzoxazepin-5-one |
| 188 | 8-(2-azabicyclo[2.2.1]heptane-2-carbonyl)-4-[(2R)-3-(3,4-dihydro-1H-isoquinolin-2-yl)-2-hydroxy-propyl]-2,3-dihydro-1,4-benzoxazepin-5-one |
| 189 | 4-[(2R)-3-(3,4-dihydro-1H-isoquinolin-2-yl)-2-hydroxy-propyl]-8-(3-oxa-8-azabicyclo[3.2.1]octan-8-carbonyl)-2,3-dihydro-1,4-benzoxazepin-5-one |
| 190 | 4-[(2R)-3-(3,4-dihydro-1H-isoquinolin-2-yl)-2-hydroxy-propyl]-8-(2-methylmorpholin-4-carbonyl)-2,3-dihydro-1,4-benzoxazepin-5-one |
| 191 | 4-[(2R)-3-(3,4-dihydro-1H-isoquinolin-2-yl)-2-hydroxy-propyl]-8-(3-methylmorpholin-4-carbonyl)-2,3-dihydro-1,4-benzoxazepin-5-one |
| 192 | 4-[(2R)-3-(3,4-dihydro-1H-isoquinolin-2-yl)-2-hydroxy-propyl]-2,2-dimethyl-8-(morpholinomethyl)-3H-pyrido[3,2-f][1,4]oxazepin-5-one |
| 193 | 8-(3,3a,4,5,6,6a-hexahydro-1H-cyclopenta[c]pyrrol-2-carbonyl)-4-[(2R)-3-(3,4-dihydro-1H-isoquinolin-2-yl)-2-hydroxy-propyl]-2,3-dihydro-1,4-benzoxazepin-5-one |
| 194 | 4-[(2R)-3-(3,4-dihydro-1H-isoquinolin-2-yl)-2-hydroxy-propyl]-8-(3-fluoropiperidine-1-carbonyl)-2,3-dihydro-1,4-benzoxazepin-5-one |

TABLE 1-continued

| No. | Compound Name |
|---|---|
| 195 | 8-(2,2-difluoromorpholin-4-carbonyl)-4-[(2R)-3-(3,4-dihydro-1H-isoquinolin-2-yl)-2-hydroxy-propyl]-2,3-dihydro-1,4-benzoxazepin-5-one |
| 196 | 8-(4,4-difluoropiperidine-1-carbonyl)-4-[(2R)-3-(3,4-dihydro-1H-isoquinolin-2-yl)-2-hydroxy-propyl]-2,3-dihydro-1,4-benzoxazepin-5-one |
| 197 | 4-[(2R)-3-(3,4-dihydro-1H-isoquinolin-2-yl)-2-hydroxy-propyl]-2,2-dimethyl-8-(1-piperidylmethyl)-3H-pyrido[3,2-f][1,4]oxazepin-5-one |
| 198 | 4-[(2R)-3-(3,4-dihydro-1H-isoquinolin-2-yl)-2-hydroxypropyl]-8-[4-[methyl(oxetan-3-yl)amino]cyclohexoxy]-2,3-dihydro-1,4-benzoxazepin-5-one |
| 199 | 4-[(2R)-3-(3,4-dihydro-1H-isoquinolin-2-yl)-2-hydroxypropyl]-8-[4-[2-fluoroethyl(methyl)amino]cyclohexoxy]-2,3-dihydro-1,4-benzoxazepin-5-one |
| 200 | (2S)-4-[(2R)-3-(3,4-dihydro-1H-isoquinolin-2-yl)-2-hydroxy-propyl]-8-[(1-ethanethiol-4-piperidyl)oxy]-2-methyl-2,3-dihydro-1,4-benzoxazepin-5-one |
| 201 | (2S)-4-[(2R)-3-(3,4-dihydro-1H-isoquinolin-2-yl)-2-hydroxy-propyl]-8-[1-(2-fluoroethyl)azetidin-3-yl]oxy-2-methyl-2,3-dihydro-1,4-benzoxazepin-5-one |
| 202 | (2S)-4-[(2R)-3-(3,4-dihydro-1H-isoquinolin-2-yl)-2-hydroxy-propyl]-8-[1-(2-fluoroethyl)-4-piperidyl]oxy-2-methyl-2,3-dihydro-1,4-benzoxazepin-5-one |
| 203 | 4-[(2R)-3-(3,4-dihydro-1H-isoquinolin-2-yl)-2-hydroxy-propyl]-2,2-dimethyl-8-(3-oxa-8-azabicyclo[3.2.1]octan-8-carbonyl)-3H-1,4-benzoxazepin-5-one |
| 204 | 4-[(2R)-3-(3,4-dihydro-1H-isoquinolin-2-yl)-2-hydroxy-propyl]-2,2-dimethyl-8-(2-oxa-5-azabicyclo[2.2.1]heptan-5-carbonyl)-3H-1,4-benzoxazepin-5-one |
| 205 | 4-[(2R)-3-(3,4-dihydro-1H-isoquinolin-2-yl)-2-hydroxy-propyl]-8-(3,5-dimethylmorpholin-4-carbonyl)-2,2-dimethyl-3H-1,4-benzoxazepin-5-one |
| 206 | 4-[(2R)-3-(3,4-dihydro-1H-isoquinolin-2-yl)-2-hydroxy-propyl]-8-[(3-fluoro-1-methyl-4-piperidyl)oxy]-2,3-dihydro-1,4-benzoxazepin-5-one |
| 207 | 4-[(2R)-3-(3,4-dihydro-1H-isoquinolin-2-yl)-2-hydroxy-propyl]-8-[[3-fluoro-1-(2-fluoroethyl)-4-piperidyl]oxy]-2,3-dihydro-1,4-benzoxazepin-5-one |
| 208 | 4-[(2R)-3-(3,4-dihydro-1H-isoquinolin-2-yl)-2-hydroxy-propyl]-8-[[3-fluoro-1-(2-hydroxyethyl)-4-piperidyl]oxy]-2,3-dihydro-1,4-benzoxazepin-5-one |
| 209 | 4-[(2R)-3-(3,4-dihydro-1H-isoquinolin-2-yl)-2-hydroxy-propyl]-8-(3,4-dihydro-1H-pyrrolo[1,2-a]pyrazine-2-carbonyl)-2,2-dimethyl-3H-1,4-benzoxazepin-5-one |
| 210 | 8-(3,4,6,7,8,8a-hexahydro-1H-pyrrolo[1,2-a]pyrazine-2-carbonyl)-4-[(2R)-3-(3,4-dihydro-1H-isoquinolin-2-yl)-2-hydroxy-propyl]-2,2-dimethyl-3H-1,4-benzoxazepin-5-one |
| 211 | 4-[(2R)-3-(3,4-dihydro-1H-isoquinolin-2-yl)-2-hydroxy-propyl]-8-(5-fluoropyrimidin-2-yl)oxy-2,3-dihydro-1,4-benzoxazepin-5-one |
| 212 | 4-[(2R)-3-(3,4-dihydro-1H-isoquinolin-2-yl)-2-hydroxy-propyl]-8-[[1-(2-hydroxypropyl)-4-piperidyl]oxy]-2,3-dihydro-1,4-benzoxazepin-5-one |
| 213 | 4-[(2R)-3-(3,4-dihydro-1H-isoquinolin-2-yl)-2-hydroxy-propyl]-8-[(1-methyl-3-piperidyl)oxy]-2,3-dihydro-1,4-benzoxazepin-5-one |
| 214 | 4-[(2R)-3-(3,4-dihydro-1H-isoquinolin-2-yl)-2-hydroxy-propyl]-8-propanoyl-2,3-dihydro-1,4-benzoxazepin-5-one |
| 215 | 4-[(2R)-3-(3,4-dihydro-1H-isoquinolin-2-yl)-2-hydroxy-propyl]-8-[[8-2-fluoroethyl]-8-azabicyclo[3.2.1]octan-3-yl)oxy]-2,3-dihydro-1,4-benzoxazepin-5-one |
| 216 | 8-(cyclopropanecarbonyl)-4-[(2R)-3-(3,4-dihydro-1H-isoquinolin-2-yl)-2-hydroxy-propyl]-2,3-dihydro-1,4-benzoxazepin-5-one |
| 217 | 8-(cyclopentanecarbonyl)-4-[(2R)-3-(3,4-dihydro-1H-isoquinolin-2-yl)-2-hydroxy-propyl]-2,3-dihydro-1,4-benzoxazepin-5-one |
| 218 | 4-[(2R)-3-(3,4-dihydro-1H-isoquinolin-2-yl)-2-hydroxypropyl]-8-[(1-methyl-3-piperidyl)oxy]-2,3-dihydro-1,4-benzoxazepin-5-one |
| 219 | (2R)-4-[(2R)-3-(3,4-dihydro-1H-isoquinolin-2-yl)-2-hydroxy-propyl]-8-[[1-(2-hydroxyethyl)-4-piperidyl]oxy]-2-methyl-2,3-dihydro-1,4-benzoxazepin-5-one |
| 220 | (2R)-4-[(2R)-3-(3,4-dihydro-1H-isoquinolin-2-yl)-2-hydroxy-propyl]-8-[[1-(2-hydroxy-2-methyl-propyl)-4-piperidyl]oxy]-2-methyl-2,3-dihydro-1,4-benzoxazepin-5-one |
| 221 | 4-[(2R)-3-(3,4-dihydro-1H-isoquinolin-2-yl)-2-hydroxy-propyl]-8-(1-morpholinoethyl)-2,3-dihydro-1,4-benzoxazepin-5-one |
| 222 | 4-[(2R)-3-(3,4-dihydro-1H-isoquinolin-2-yl)-2-hydroxy-propyl]-8-[1-(2-oxa-6-azaspiro[3.3]heptan-6-yl)ethyl]-2,3-dihydro-1,4-benzoxazepin-5-one |
| 223 | 4-[(2R)-3-(3,4-dihydro-1H-isoquinolin-2-yl)-2-hydroxy-propyl]-8-(3-hydroxypro-1-pynyl)-2,3-dihydro-1,4-benzoxazepin-5-one |
| 224 | (2R)-4-[(2R)-3-(3,4-dihydro-1H-isoquinolin-2-yl)-2-hydroxy-propyl]-8-[[1-(2-methoxyethyl)-4-piperidyl]oxy]-2-methyl-2,3-dihydro-1,4-benzoxazepin-5-one |
| 225 | 4-[(2R)-3-(3,4-dihydro-1H-isoquinolin-2-yl)-2-hydroxy-propyl]-8-(4-pyridyl)-2,3-dihydro-1,4-benzoxazepin-5-one |
| 226 | 4-[(2R)-3-(3,4-dihydro-1H-isoquinolin-2-yl)-2-hydroxy-propyl]-8-[2-(4-pyridyl)ethynyl]-2,3-dihydro-1,4-benzoxazepin-5-one |
| 227 | 4-[(2R)-3-(3,4-dihydro-1H-isoquinolin-2-yl)-2-hydroxy-propyl]-8-[2-(3-pyridyl)ethynyl]-2,3-dihydro-1,4-benzoxazepin-5-one |
| 228 | 4-[(2R)-3-(3,4-dihydro-1H-isoquinolin-2-yl)-2-hydroxy-propyl]-8-(3-hydroxybu-1-tynyl)-2,3-dihydro-1,4-benzoxazepin-5-one |
| 229 | 4-[(2R)-3-(3,4-dihydro-1H-isoquinolin-2-yl)-2-hydroxy-propyl]-8-[3-(methylamino)pro-1-pynyl]-2,3-dihydro-1,4-benzoxazepin-5-one |
| 230 | 4-[(2R)-3-(3,4-dihydro-1H-isoquinolin-2-yl)-2-hydroxy-propyl]-8-(3-pyridyl)-2,3-dihydro-1,4-benzoxazepin-5-one |
| 231 | 4-[(2R)-3-(3,4-dihydro-1H-isoquinolin-2-yl)-2-hydroxy-propyl]-8-(1,3-dimethylpyrazol-4-yl)-2,3-dihydro-1,4-benzoxazepin-5-one |
| 232 | 4-[(2R)-3-(3,4-dihydro-1H-isoquinolin-2-yl)-2-hydroxy-propyl]-8-(1-methylpyrazol-4-yl)-2,3-dihydro-1,4-benzoxazepin-5-one |
| 233 | 4-[(2R)-3-(3,4-dihydro-1H-isoquinolin-2-yl)-2-hydroxy-propyl]-8-(1,5-dimethylpyrazol-4-yl)-2,3-dihydro-1,4-benzoxazepin-5-one |

TABLE 1-continued

| No. | Compound Name |
|---|---|
| 234 | 4-[(2R)-3-(3,4-dihydro-1H-isoquinolin-2-yl)-2-hydroxy-propyl]-8-[[1-(2-hydroxyethyl)-4-piperidyl]oxy]-2,2-dimethyl-3H-pyrido[3,2-f][1,4]oxazepin-5-one |
| 235 | 4-[(2R)-3-(3,4-dihydro-1H-isoquinolin-2-yl)-2-hydroxy-propyl]-2,2-dimethyl-8-[[(3R)-1-methyl-3-piperidyl]oxy]-3H-pyrido[3,2-f][1,4]oxazepin-5-one |
| 236 | 4-[(2R)-3-(3,4-dihydro-1H-isoquinolin-2-yl)-2-hydroxy-propyl]-8-[[(1-(2-fluoroethyl)-3-piperidyl)oxy]-2,3-dihydro-1,4-benzoxazepin-5-one |
| 237 | 4-[(2R)-3-(3,4-dihydro-1H-isoquinolin-2-yl)-2-hydroxy-propyl]-8-[[(1-(2-hydroxy)-3-piperidyl)oxy]-2,3-dihydro-1,4-benzoxazepin-5-one |
| 238 | 4-[(2R)-3-(3,4-dihydro-1H-isoquinolin-2-yl)-2-hydroxy-propyl]-8-[[1-(2-hydroxy-2-methyl-propyl)-4-piperidyl]oxy]-2,3-dihydro-1,4-benzoxazepin-5-one |
| 239 | 4-[(2R)-3-(3,4-dihydro-1H-isoquinolin-2-yl)-2-hydroxy-propyl]-8-(6-fluoro-2-pyridyl)-2,3-dihydro-1,4-benzoxazepin-5-one |
| 240 | (2R)-4-[(2R)-3-(3,4-dihydro-1H-isoquinolin-2-yl)-2-hydroxy-propyl]-8-[[1-(2-ethoxyethyl)-4-piperidyl]oxy]-2-methyl-2,3-dihydro-1,4-benzoxazepin-5-one |
| 241 | (2R)-4-[(2R)-3-(3,4-dihydro-1H-isoquinolin-2-yl)-2-hydroxy-propyl]-8-[[8-2-hydroxy]-8-azabicyclo[3.2.1]octan-3-yl]oxy]-2-methyl-2,3-dihydro-1,4-benzoxazepin-5-one |
| 242 | (2R)-4-[(2R)-3-(3,4-dihydro-1H-isoquinolin-2-yl)-2-hydroxy-propyl]-8-[[8-2-fluoroethyl]-8-azabicyclo[3.2.1]octan-3-yl]oxy]-2-methyl-2,3-dihydro-1,4-benzoxazepin-5-one |
| 243 | 4-[(2R)-3-(3,4-dihydro-1H-isoquinolin-2-yl)-2-hydroxy-propyl]-8-[[1-(2-methoxyethyl)-4-pyridyl]oxy]-2-methyl-2,3-dihydro-1,4-benzoxazepin-5-one |
| 244 | 4-[(2R)-3-(3,4-dihydro-1H-isoquinolin-2-yl)-2-hydroxy-propyl]-8-(6-methoxy-2-pyridyl)-2,3-dihydro-1,4-benzoxazepin-5-one |
| 245 | (2R)-4-[(2R)-3-(3,4-dihydro-1H-isoquinolin-2-yl)-2-hydroxy-propyl]-8-[[1-(2-hydroxypropyl)-4-piperidyl]oxy]-2-methyl-2,3-dihydro-1,4-benzoxazepin-5-one |
| 246 | 4-[(2R)-3-(3,4-dihydro-1H-isoquinolin-2-yl)-2-hydroxy-propyl]-2,2-dimethyl-8-(1-morpholinoethyl)-3H-pyrido[3,2-f][1,4]oxazepin-5-one |
| 247 | 4-[(2R)-3-(3,4-dihydro-1H-isoquinolin-2-yl)-2-hydroxy-propyl]-2,2-dimethyl-8-[1-(2-oxa-6-azaspiro[3.3]heptan-6-yl)ethyl]-3H-pyrido[3,2-f][1,4]oxazepin-5-one |
| 248 | 4-[(2R)-3-(3,4-dihydro-1H-isoquinolin-2-yl)-2-hydroxy-propyl]-8-[[1-(2-hydroxypropyl)-4-piperidyl]oxy]-2,2-dimethyl-3H-pyrido[3,2-f][1,4]oxazepin-5-one |
| 249 | 4-[(2R)-3-(3,4-dihydro-1H-isoquinolin-2-yl)-2-hydroxypropyl]-8-(3,4-dihydro-1H-pyrrolo[1,2-a]pyrazin-2-ylmethyl)-2,3-dihydro-1,4-benzoxazepin-5-one |
| 250 | (2R)-4-[(2R)-3-(3,4-dihydro-1H-isoquinolin-2-yl)-2-hydroxypropyl]-2-methyl-8-(2-oxa-6-azaspiro[3.3]heptan-6-ylmethyl)-2,3-dihydro-1,4-benzoxazepin-5-one |
| 251 | 4-[(2R)-3-(3,4-dihydro-1H-isoquinolin-2-yl)-2-hydroxypropyl]-8-(2-oxa-7-azaspiro[3.5]nonan-7-ylmethyl)-2,3-dihydro-1,4-benzoxazepin-5-one |
| 252 | (2R)-4-[(2R)-3-(3,4-dihydro-1H-isoquinolin-2-yl)-2-hydroxypropyl]-2-methyl-8-(2-oxa-7-azaspiro[3.5]nonan-7-ylmethyl)-2,3-dihydro-1,4-benzoxazepin-5-one |
| 253 | 4-[(2R)-4-[(2R)-3-(3,4-dihydro-1H-isoquinolin-2-yl)-2-hydroxy-propyl]-8-[[(3R,4R)-3-fluoro-1-(2-hydroxyethyl)-4-piperidyl]oxy]-2-methyl-2,3-dihydro-1,4-benzoxazepin-5-one dihydrochloride |
| 254 | 4-[(2R)-3-(3,4-dihydro-1H-isoquinolin-2-yl)-2-hydroxy-propyl]-8-[[(3R,4R)-3-fluoro-1-(2-hydroxypropyl)-4-piperidyl]oxy]-2-methyl-2,3-dihydro-1,4-benzoxazepin-5-one dihydrochloride |
| 255 | (2R)-4-[(2R)-3-[(2R)-3-(3,4-dihydro-1H-isoquinolin-2-yl)-2-hydroxy-propyl]-8-[[(3R,4R)-3-fluoro-1-(2-hydroxyethyl)-4-piperidyl]oxy]-2-methyl-2,3-dihydro-1,4-benzoxazepin-5-one dihydrochloride |
| 256 | 8-[[3,3-difluoro-1-(2-hydroxyethyl)-4-piperidyl]oxy]-4-[(2R)-3-(3,4-dihydro-1H-isoquinolin-2-yl)-2-hydroxy-propyl]-2,2-dimethyl-3H-pyrido[3,2-f][1,4]oxazepin-5-one |
| 257 | 4-[(2R)-3-(3,4-dihydro-1H-isoquinolin-2-yl)-2-hydroxypropyl]-8-[1-(1-piperidyl)ethyl]-2,3-dihydro-1,4-benzoxazepin-5-one |
| 258 | 4-[(2R)-3-(3,4-dihydro-1H-isoquinolin-2-yl)-2-hydroxypropyl]-8-[1-(4-hydroxy-1-piperidyl)ethyl]-2,3-dihydro-1,4-benzoxazepin-5-one |
| 259 | 4-[(2R)-3-(3,4-dihydro-1H-isoquinolin-2-yl)-2-hydroxypropyl]-8-[1-(4-methoxy-1-piperidyl)ethyl]-2,3-dihydro-1,4-benzoxazepin-5-one |
| 260 | 4-[(2R)-3-(3,4-dihydro-1H-isoquinolin-2-yl)-2-hydroxypropyl]-8-[1-(3-hydroxy-3-methyl-pyrrolidin-1-yl)ethyl]-2,3-dihydro-1,4-benzoxazepin-5-one |
| 261 | (2R)-4-[(2R)-3-(3,4-dihydro-1H-isoquinolin-2-yl)-2-hydroxy-propyl]-8-[[1-(2-hydroxyethyl)-4-piperidyl]oxy]-2-methyl-2,3-dihydro-1,4-benzoxazepin-5-one dihydrochloride |
| 262 | 4-[(2R)-3-(3,4-dihydro-1H-isoquinolin-2-yl)-2-hydroxy-propyl]-8-[[1-(2-methoxyethyl)-4-piperidyl]oxy]-2,2-dimethyl-3H-pyrido[3,2-f][1,4]oxazepin-5-one |
| 263 | 4-[(2R)-3-(3,4-dihydro-1H-isoquinolin-2-yl)-2-hydroxy-propyl]-8-[(3S)-1-(oxetan-3-yl)pyrrolidin-3-yl]oxy-2,3-dihydro-1,4-benzoxazepin-5-one |
| 264 | (2R)-4-[(2R)-3-(3,4-dihydro-1H-isoquinolin-2-yl)-2-hydroxy-propyl]-2-methyl-8-[(3S)-1-methylpyrrolidin-3-yl]oxy-2,3-dihydro-1,4-benzoxazepin-5-one |
| 265 | 4-[(2R)-3-(3,4-dihydro-1H-isoquinolinon-2-yl)-2-hydroxy-propyl]-8-[(3R)-tetrahydrofuran-3-yl]oxy-2,3-dihydro-1,4-benzoxazepin-5-one |
| 266 | 4-[(2R)-3-(3,4-dihydro-1H-isoquinolinon-2-yl)-2-hydroxy-propyl]-8-[(3S)-tetrahydrofuran-3-yl]oxy-2,3-dihydro-1,4-benzoxazepin-5-one |
| 267 | (2R)-4-[(2R)-3-(3,4-dihydro-1H-isoquinolin-2-yl)-2-hydroxy-propyl]-8-[[1-[(2S)-2-hydroxypropyl]-4-piperidyl]oxy]-2-methyl-2,3-dihydro-1,4-benzoxazepin-5-one |
| 268 | (2R)-4-[(2R)-3-(3,4-dihydro-1H-isoquinolin-2-yl)-2-hydroxy-propyl]-8-[[1-[(2R)-2-hydroxypropyl]-4-piperidyl]oxy]-2-methyl-2,3-dihydro-1,4-benzoxazepin-5-one |
| 269 | 8-[cyclopropyl(hydroxy)methyl]-4-[(2R)-3-(3,4-dihydro-1H-isoquinolin-2-yl)-2-hydroxy-propyl]-2,3-dihydro-1,4-benzoxazepin-5-one |
| 270 | 8-[cyclopentyl(hydroxy)methyl]-4-[(2R)-3-(3,4-dihydro-1H-isoquinolin-2-yl)-2-hydroxy-propyl]-2,3-dihydro-1,4-benzoxazepin-5-one |

TABLE 1-continued

| No. | Compound Name |
|---|---|
| 271 | 4-[(2R)-3-(3,4-dihydro-1H-isoquinolin-2-yl)-2-hydroxy-propyl]-8-[(3R)-1-(oxetan-3-yl)pyrrolidin-3-yl]oxy-2,3-dihydro-1,4-benzoxazepin-5-one |
| 272 | 4-[(2R)-3-(3,4-dihydro-1H-isoquinolin-2-yl)-2-hydroxy-propyl]-8-[(3R)-1-(2-methoxyethyl)pyrrolidin-3-yl]oxy-2,3-dihydro-1,4-benzoxazepin-5-one |
| 273 | (2R)-4-[(2R)-3-(3,4-dihydro-1H-isoquinolin-2-yl)-2-hydroxy-propyl]-2-methyl-8-[(3R)-1-methylpyrrolidin-3-yl]oxy-2,3-dihydro-1,4-benzoxazepin-5-one |
| 274 | (2R)-4-[(2R)-3-(3,4-dihydro-1H-isoquinolin-2-yl)-2-hydroxy-propyl]-8-[(3R)-1-(2-methoxyethyl)pyrrolidin-3-yl]oxy-2-methyl-2,3-dihydro-1,4-benzoxazepin-5-one |
| 275 | 4-[(2R)-3-(3,4-dihydro-1H-isoquinolin-2-)-2-hydroxy-propyl]-8-[[1-(3,3,3-trifluoro-2-hydroxy-propyl)-4-piperidyl]oxy]-2,3-dihydro-1,4-benzoxazepin-5-one |
| 276 | (2R)-4-[(2R)-3-(3,4-dihydro-1H-isoquinolin-2-)-2-hydroxy-propyl]-2-methyl-8-[[1-(3,3,3-trifluoro-2-hydroxy-propyl)-4-piperidyl]oxy]-2,3-dihydro-1,4-benzoxazepin-5-one |
| 277 | (2R)-4-[(2R)-3-(3,4-dihydro-1H-isoquinolin-2-yl)-2-hydroxypropyl]-2-methyl-8-[(3R)-1-(oxetan-3-yl)pyrrolidin-3-yl]oxy-2,3-dihydro-1,4-benzoxazepin-5-one |

Since the compounds according to the present invention may have an asymmetric carbon center and an asymmetric axis or an asymmetric plane, they may exist as substantially pure enantiomers, such as R and S enantiomers, as well as all optical and stereoisomeric forms including mixture racemates, and all isomers and compounds thereof are within the scope of the present invention. With respect to a pure enantiomer, the enantiomeric excess of such enantiomer and pharmaceutically acceptable salt thereof represented by Formula 1 may be preferably 60% ee or more, more preferably 95% ee ore more, and most preferably 98% ee or more.

The term "ee" refers to an enantiomeric excess. For example, one enantiomer in a particular compound is present as a mixture of enantiomers in the compound in a larger amount than the other enantiomers. Enantiomerically enriched forms may include enantiomeric compounds of a particular compound in which a single enantiomeric concentration in the enantiomeric mixture of the particular compound is at least 50%, more typically at least 60%, 70%, 80%, or 90%, or more (e.g., >95%, >97%, >98%, >99%, >99.5%) with respect to other enantiomers of the compound.

Herein, unless stated otherwise, the compound represented by Formula 1 is used as a meaning including all of compound represented by Formula 1, an optical isomer, a stereoisomer, an isotopic variant thereof, and a pharmaceutically acceptable salt thereof.

Herein the term "isotopic variant" refers to a compound that contains unnatural proportions of isotopes at one or more of the atoms that constitute such compound. For example, an isotopic variant of a compound may be radiolabeled; hydrogen atom may be selected from hydrogen, deuterium and tritium; and may contain carbon-13 ($^{13}C$), nitrogen-15 ($^{15}N$) or the like.

The compound of Formula 1, or an optical isomer, a stereoisomer or an isotopic variant thereof according to the present invention may form a pharmaceutically acceptable salt. The pharmaceutically acceptable salts include acid or base addition salts and their stereochemical isomers form. The salt may include any salt that maintains the activity of a parent compound in a subject to be administered and does not cause any undesirable effect, but is not limited thereto. The salts include inorganic salts and organic salts, and may be acid addition salts—for example, acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzenesulfonic acid, benzoic acid, stearic acid, ethanesulfonic acid, lactic acid, bicarbonic acid, bisulfuric acid, bitartaric acid, oxalic acid, butylic acid, calcium edatate, camsylic acid, carbonic acid, chlorobenzoic acid, citric acid, edetic acid, toluenesulfonic acid, edicylinic acid, ecylinic acid, fumaric acid, gluceptic acid, pamoic acid, gluconic acid, glycollarsanylic acid, methyl nitrate, polygalacturonic acid, hexyllisorcynonic acid, malonic acid, hydrabamic acid, hydrochlorinic acid, hydroiodic acid, hydroxynaphtholic acid, isethionic acid, lactobionic acid, mandelic acid, estolinic acid, mucic acid, naphthenic acid, muconic acid, p-nitromethanesulfonic acid, hexamic acid, pantothenic acid, monohydrogen phosphoric acid, dihydrogen phosphoric acid, salicylic acid, sulfamine acid, sulfanilic acid, methanesulfonic acid or theoclic acid. In addition, examples of basic salts include alkali and alkaline earth metal salts such as ammonium salts, lithium salts, sodium salts, potassium salts, magnesium salts, and calcium salts, salts having organic bases such as benzathine, N-methyl-D-glucamine, and hydrabamine salts, and salts having amino acids such as arginine and lysine. In addition, the salt form may be converted into a free form by treatment with an appropriate base or acid. As used herein, the term "additional salt" may be taken to include solvates obtainable from any of the compound represented by Formula 1 and salts thereof. Examples of these solvates are hydrates or alcoholates.

Terms and abbreviations used in the present specification have their original meanings unless stated otherwise.

The present invention also provides a method for preparing a compound of Formula 1. Hereinafter, a method of preparing the compound of Formula 1 will be described based on an exemplary reaction scheme for better understanding of the present invention. However, it should be construed that those of ordinary skill in the art may prepare the compound of Formula 1 by various methods using known compounds based on the structure of Formula 1 or compounds that may be easily prepared therefrom, and be construed that all the methods may be included in the scope of the present invention. That is, the compound of Formula 1 may be prepared by arbitrarily combining several synthesis methods described in the present specification or disclosed in the prior art, and thus the following description related to the method of preparing the compound of Formula 1 is merely illustrative, and if necessary, the order of unit operations may be selectively changed, and the scope of the method of preparing the present invention is not limited thereto.

[Reaction Scheme 1]

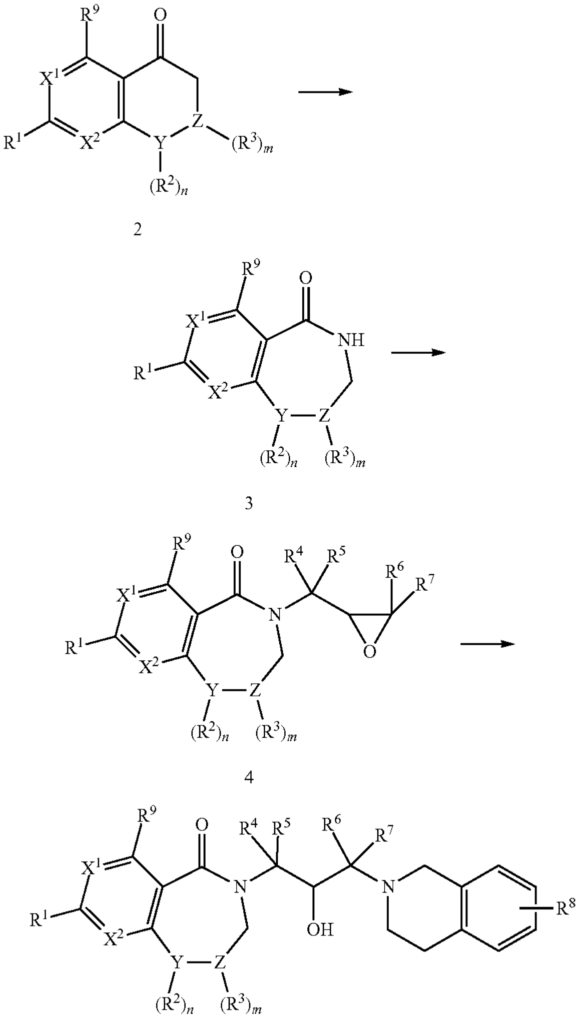

2

3

4

1a

In a general synthesis method, an intermediate 3 can be obtained from the starting material 2 by Schmidt reaction using sodium azide under an acidic condition. From this compound, an intermediate 4 into which oxirane has been introduced is obtained through a substitution reaction, and a final compound 1a can be obtained through addition reaction of tetrahydroisoquinoline.

[Reaction Scheme 2]

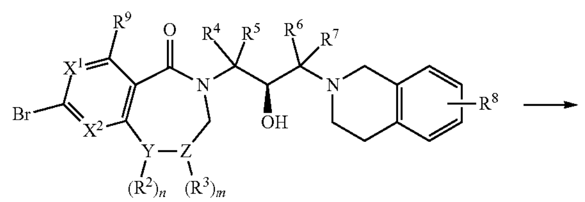

5

-continued

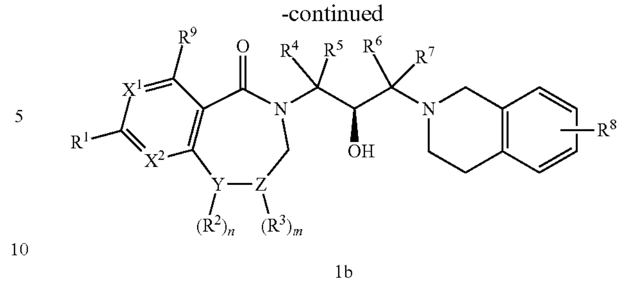

1b

As another synthesis method, a final compound 1b in which alkyl and alkenyl groups are substituted can be obtained by a Suzuki-coupling reaction under a palladium condition using compound 5 as a starting material.

[Reaction Scheme 3]

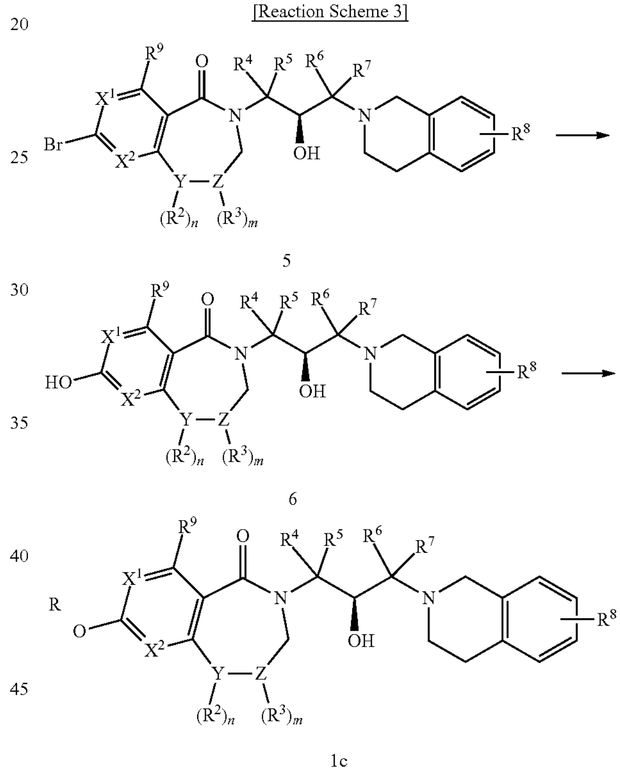

5

6

1c

In still another synthesis method, as in Scheme 3, compound 5 is used as a starting material and an intermediate 6 obtained by substituting a bromine group with a hydroxy group using potassium hydroxide under a palladium condition was obtained, and then a final compound 1c—in which the ether group was substituted through a substitution reaction—can be obtained.

According to another aspect of the present invention, there is provided a pharmaceutical composition for the prevention or treatment of a disease associated with PRMT5 inhibition comprising a therapeutically effective amount of the compound, or optical isomer, stereoisomer or isotopic variant thereof, or pharmaceutically acceptable salt thereof as an active ingredient, together with a pharmaceutically acceptable carrier. In addition, prodrugs having various forms that are converted to a compound of Formula 1 as desired in vivo are also within the scope of the present invention. The pharmaceutical composition may further include one or more additives selected from the group consisting of a pharmaceutically acceptable carrier, diluent and adjuvant.

As used herein, the term "treatment" refers to the interruption, delay or alleviation of disease progression when used in a subject having a symptom.

As used herein, the term "prevention" refers to reduce the possibility of disease or eliminate the possibility of disease.

As used herein, the term "pharmaceutical composition" may include other chemical components, such as carriers, diluents, excipients, and the like in addition to the active compounds according to the present invention. Accordingly, the pharmaceutical composition may include a pharmaceutically acceptable carrier, diluent, excipient, or a combination thereof, if necessary. The pharmaceutical composition facilitates administration of the active compound into the organism. A variety of techniques for administering pharmaceutical compositions comprising a compound are known, in which the techniques includes oral, injection, aerosol, parenteral, and topical administration, but not limited thereto. In addition, the pharmaceutical composition may be sterilized, may further include an adjuvant such as a preservative, a stabilizer, a hydrating or an emulsifying accelerator, a salt for osmotic pressure regulation, and/or a buffer, may further include other therapeutically useful substances, and may be formulated according to conventional methods of mixing, granulating or coating.

As used herein, the term "carrier" refers to a compound that facilitates injection of a compound into a cell or tissue. For example, dimethylsulfoxide (DMSO) is a common carrier for easy input of a large amount of organic compounds into cells or tissues of an organism.

As used herein, the term "diluent" refers to a compound that stabilizes the biologically active form of the compound of interest, and is diluted in water that dissolves the compound. The salt dissolved in the buffer is used as a diluent in the art. A commonly used buffer is phosphate-buffered saline that imitates the salt form of a human body solution. Since the buffer salt is capable of controlling the pH of the solution at low concentrations, the buffer diluent rarely modifies the biological activity of the compound.

As used herein, the term "pharmaceutically acceptable" refers to a property that does not damage biological activity and physical properties of a compound.

In addition, the pharmaceutical composition may be a composition for the prevention and/or treatment of diseases associated with PRMT5 inhibition. The diseases associated with the PRMT5 inhibition may be, for example, cancer, blood disease, autoimmune disease, inflammatory disease or neurodegenerative disease, and may include any disease known to be related to PRMT5.

The cancer includes, but is not limited to, acoustic neuroma, adenocarcinoma, adrenal cancer, anal cancer, angiosarcoma, benign monoclonal gammaglobulinopathy, cholangiocarcinoma, bladder cancer, breast cancer, brain cancer, lymphoma, multiple myeloma, lacrimal gland tumor, bronchial cancer, cervical cancer, craniopharyngioma, colorectal cancer, epithelial carcinoma, epithelial cell tumor, endothelial sarcoma, endometrial cancer, esophageal cancer, Barrett's adenocarcinoma, Ewing's sarcoma, eye cancer, gallbladder cancer, gastric cancer, gastrointestinal stromal tumor (GIST), head and neck cancer, oral cancer (oral squamous cell carcinoma, OSCC), throat cancer, hematopoietic cancer, hemangioblastoma, inflammatory myofibroblast tumor, immune cell amyloidosis, kidney cancer, liver cancer, lung cancer, myelodysplastic syndrome (MDS), mesothelioma, myeloproliferative disorder (MPD), chronic idiopathic myelofibrosis, chronic myelogenous leukemia (CML), chronic neutrophilic leukemia (CNL), neuroblastoma, neurofibroma, neuroendocrine cancer, osteosarcoma, ovarian cancer, papillary adenocarcinoma, pancreatic cancer, penile cancer, prostate cancer, rectal cancer, rhabdomyosarcoma, salivary gland cancer, skin cancer, small intestine cancer, soft tissue sarcoma, thyroid cancer, urethral cancer, vaginal cancer and vulvar cancer. The brain cancer may include, but is not limited to, meningioma, glioma, medulloblastoma, glioblastoma and brain metastasis cancer.

The blood disease may be hemoglobinemia or sickle cell anemia, but is not limited thereto.

The autoimmune disease may include, but is not limited to, rheumatoid arthritis, spinal arthritis, gouty arthritis, degenerative joint disease, osteoarthritis, systemic lupus erythematosus, multiple sclerosis, psoriatic arthritis, juvenile arthritis, asthma, atherosclerosis, osteoporosis, bronchitis, tendinitis, psoriasis, eczema, burns, dermatitis, pruritus, enuresis, eosinophilic disease, peptic ulcer, localized enteritis, diverticulitis, gastrointestinal bleeding, eosinophilic esophagitis, eosinophilic gastritis, eosinophilic gastroenteritis and eosinophilic colitis.

The inflammatory disease may include, but is not limited to, acne-related inflammation, aplastic anemia, hemolytic autoimmune anemia, rhinitis, asthma, polyarteritis, temporal arteritis, periarteritis nodosa, Takayasu's arteritis, crystalline arthritis, osteoarthritis, psoriatic arthritis, gouty arthritis, reactive arthritis, rheumatoid arthritis, amyotrophic lateral sclerosis, autoimmune disease, allergic or allergic reaction, atherosclerosis, bronchitis, bursitis, chronic prostatitis, conjunctivitis, chronic obstructive pulmonary disease, dermatitis, type I diabetes, type 2 diabetes, psoriasis, eczema, eczema hypersensitivity reaction, burn, dermatitis, pruritus, endometriosis, infection, ischemic heart disease, glomerulonephritis, gingivitis, irritability, migraine, tension headache, postoperative intestinal obstruction, intestinal obstruction during sepsis, idiopathic thrombocytopenia purpura, bladder pain syndrome, peptic ulcer, localized enteritis, diverticulitis, gastric bleeding, eosinophilic esophagitis, eosinophilic gastritis, eosinophilic gastroenteritis, eosinophilic colitis, gastritis, diarrhea, gastroesophageal reflux disease, Crohn's disease, ulcerative colitis, collagenous colitis, lymphocytic colitis, ischemic colitis, bypass colitis, Behcet's syndrome, indeterminate colitis, inflammatory bowel syndrome (IBS), lupus, ecchymosis, myasthenia gravis and myocardial ischemia.

The neurodegenerative disease may include, but is not limited to, motor neuron disease, Pick's disease, Alzheimer's disease, AIDS-related dementia, Parkinson's disease, amyotrophic lateral sclerosis, retinal pigmentation, spinal muscular atrophy and cerebellar degeneration.

The pharmaceutical composition may be formulated in various oral or parenteral dosage forms. For example, the pharmaceutical composition may be formulated into any dosage form for oral administration, such as tablets, pills, hard/soft capsules, solutions, suspensions, emulsifiers, syrups, granules or elixirs. The formulation for oral administration may include, for example, a pharmaceutically acceptable carrier, such as a diluent, such as lactose, dextrose, sucrose, mannitol, sorbitol, cellulose, and/or glycine, or a lubricant, such as silica, talc, stearic acid, magnesium or calcium salt thereof, and/or polyethylene glycol, in addition to the active ingredient, according to the typical configuration of each formulation.

In addition, when the formulation for oral administration is a tablet, the formulation may include a binder such as magnesium aluminum silicate, starch paste, gelatin, tragacanth, methylcellulose, sodium carboxymethyl cellulose, and/or polyvinylpyrrolidine, and optionally, may include a disintegrant such as starch, agar, alginic acid or a sodium salt thereof, a boiling mixture, and/or an absorbent, a colorant, a flavoring agent, or a sweetening agent.

When the pharmaceutical composition is formulated into a parenteral dosage form, the pharmaceutical composition may be administered by a parenteral administration method such as subcutaneous injection, intravenous injection, intramuscular injection or intrathoracic injection. The pharmaceutical composition may be prepared as a solution or a suspension by mixing an active ingredient—i.e., a compound of Formula 1, or an optical isomer, a stereoisomer or an isotopic variant thereof, or a pharmaceutically acceptable salt thereof, with a stabilizer or a buffer in water, and the solution or the suspension may be prepared as a unit dosage form of an ampoule or a vial.

In addition, the pharmaceutical composition may be sterilized or further include adjuvants such as preservatives, stabilizers, hydrating agents or emulsification accelerators, salts and/or buffers for controlling osmotic pressure, or other therapeutically useful agents, and may be formulated according to a conventional method of mixing, granulating or coating.

The active ingredient—i.e., a compound of Formula 1, or an optical isomer, a stereoisomer or an isotopic variant thereof, or a pharmaceutically acceptable salt thereof may be included in the pharmaceutical composition in an effective amount of 0.1 to 500 mg/kg (body weight), preferably 0.5 to 100 mg/kg (body weight) per day, with respect to mammals including humans, and the pharmaceutical composition may be divided once or twice a day and administered via an oral or parenteral route.

According to the present invention, there are provided compounds based on a 6-7 bicyclic ring which exhibit excellent PRMT5 inhibitory effect, or optical isomers, stereoisomers or isotopic variants thereof, or pharmaceutically acceptable salts thereof. Therefore, such compounds, or optical isomers, stereoisomers or isotopic variants thereof, or pharmaceutically acceptable salts thereof, can be effectively used to prevent or treat diseases associated with PRMT5 inhibition such as cancer, blood diseases, autoimmune diseases, inflammatory diseases or neurodegenerative diseases.

In addition, the compounds according to the present invention, or optical isomers, stereoisomers or isotopic variants thereof, or pharmaceutically acceptable salts thereof, may have improved blood-brain barrier permeability, superior efficacy or improved pharmacokinetic properties.

DETAILED DESCRIPTION

Hereinafter, the present invention is explained in more detail with the following examples. However, it must be understood that the protection scope of the present disclosure is not limited to the examples.

Example 1: Synthesis of 4-[3-(3,4-dihydro-1H-isoquinolin-2-yl)-2-hydroxy-propyl]-8-methoxy-2,3-dihydro-1,4-benzoxazepin-5-one

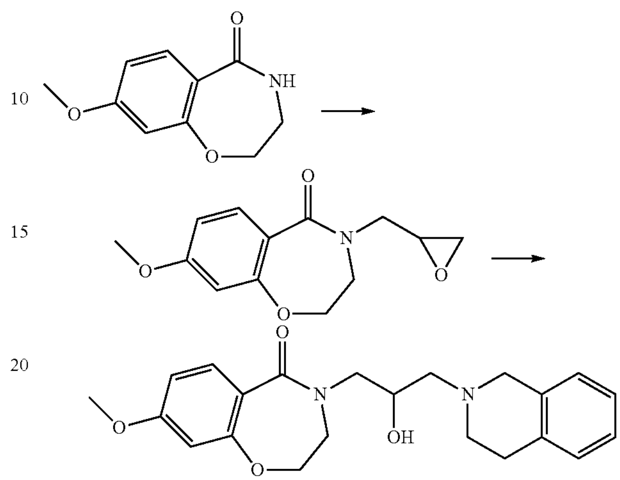

Example 1-1: Synthesis of 8-methoxy-4-(oxyran-2-ylmethyl)-2,3-dihydro-1,4-benzoxazepin-5-one 8-Methoxy-3,4-dihydro-2H-1,4-benzoxazepin-5-one (97 mg, 0.5 mmol) was dissolved in dimethylformamide, and 60% sodium hydride (30 mg, 0.75 mmol) was added thereto under ice bath. After the reaction solution was stirred at 0° C. for 30 minutes, epibromohydrin (0.056 mL, 0.65 mmol) was slowly added thereto, and the mixture was stirred at room temperature for 2 hours. The reaction was terminated by the addition of methanol. After adding ethyl acetate, the reaction mixture was washed with a saturated aqueous ammonium chloride solution and a saturated aqueous sodium chloride solution, and the organic layer was dried over anhydrous magnesium sulfate. The solvent was removed by evaporation under reduced pressure, and the obtained compound was used in the next reaction without additional purification.

Example 1-2: Synthesis of 4-[3-(3,4-dihydro-1H-isoquinolin-2-yl)-2-hydroxy-propyl]-8-methoxy-2,3-dihydro-1,4-benzo xazepin-5-one The starting material obtained in Example 1-1 was dissolved in 3 mL of isopropanol, and tetrahydroisoquinoline (0.06 mL, 0.5 mmol) was added thereto and stirred at 80° C. for 12 hours. The temperature was lowered to room temperature, and the oily liquid obtained by concentrating the solvent was purified by flash chromatography to obtain the transparent and sticky solid compound. NMR data about the obtained title compound are as follows:

$^1$H NMR (400 MHz, Methanol-$d_4$) δ 7.67 (d, J=8.8 Hz, 1H), 7.20-7.00 (m, 4H), 6.75 (dd, J=8.8, 2.5 Hz, 1H), 6.58 (d, J=2.5 Hz, 1H), 4.48 (t, J=5.0 Hz, 2H), 4.23 (q, J=8.2, 6.4 Hz, 1H), 3.98 (dd, J=13.9, 3.6 Hz, 1H), 3.84 (s, 3H), 3.81-3.68 (m, 4H), 3.42 (dd, J=13.9, 7.7 Hz, 1H), 2.97-2.85 (m, 4H), 2.69-2.60 (m, 2H).

Example 2: Synthesis of 2-[3-(3,4-dihydro-1H-isoquinolin-2-yl)-2-hydroxy-propyl]-7-methoxy-4,5-dihydro-3H-2-benzazepin-1-one

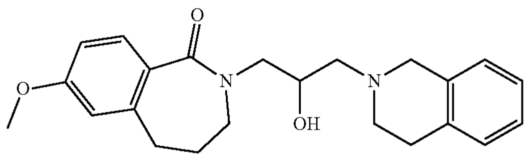 [SMILES: COc1ccc2c(c1)CCCN(CC(O)CN1CCc3ccccc3C1)C2=O]

7-Methoxy-2,3,4,5-tetrahydro-2-benzazepin-1-one as a starting material was used in the same manner as in Example 1 to obtained the title compound.

$^1$H NMR (400 MHz, Methanol-$d_4$) δ 7.42 (d, J=8.5 Hz, 1H), 6.99 (dd, J=20.3, 3.4 Hz, 4H), 6.78 (dd, J=8.7, 2.6 Hz, 1H), 6.69 (d, J=2.5 Hz, 1H), 4.17-4.08 (m, 1H), 3.79 (dd, J=13.9, 3.8 Hz, 1H), 3.73 (s, 3H), 3.71 (s, 2H), 3.35-3.23 (m, 3H), 2.88-2.79 (m, 4H), 2.68 (t, J=7.1 Hz, 2H), 2.64-2.52 (m, 2H), 2.02 (p, J=7.0 Hz, 2H).

Example 3: Synthesis of 2-[3-(3,4-dihydro-1H-isoquinolin-2-yl)-2-hydroxy-propyl]-7-hydroxy-4,5-dihydro-3H-2-benzazepin-1-one

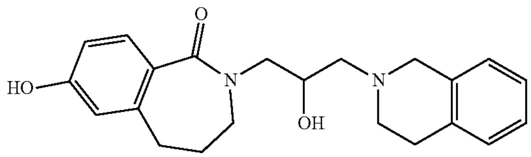 [SMILES: O=C1c2ccc(O)cc2CCCN1CC(O)CN1CCc2ccccc2C1]

(1-Oxo-2,3,4,5-tetrahydro-2-benzazepin-7-yl) acetate as a starting material was used in the same manner as in Example 1 to obtained the title compound.

$^1$H NMR (400 MHz, Methanol-$d_4$) δ 7.56 (d, J=8.5 Hz, 1H), 7.15-7.02 (m, 4H), 6.97 (dd, J=9.0, 1.9 Hz, 1H), 6.90 (d, J=2.0 Hz, 1H), 4.32-4.22 (m, 1H), 4.14 (dd, J=9.9, 4.1 Hz, 1H), 4.05 (dd, J=9.8, 6.0 Hz, 1H), 3.78 (s, 2H), 3.07 (t, J=6.5 Hz, 2H), 2.98-2.86 (m, 4H), 2.86-2.78 (m, 3H), 2.73 (dd, J=13.1, 7.5 Hz, 1H), 2.09-1.97 (m, 2H).

Example 4: Synthesis of 2-[3-(3,4-dihydro-1H-isoquinolin-2-yl)-2-hydroxy-propyl]-7-(trifluoromethoxy)-4,5-dihydro-3H-2-benzazepin-1-one

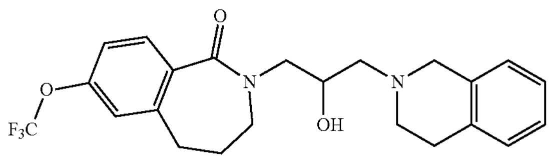 [SMILES: O=C1c2ccc(OC(F)(F)F)cc2CCCN1CC(O)CN1CCc2ccccc2C1]

6-(Trifluoromethoxy)tetralin-1-one as a starting material was used in the same manner as in Example 1 to obtained the title compound.

$^1$H NMR (400 MHz, Methanol-$d_4$) δ 7.63 (d, J=8.4 Hz, 1H), 7.21 (dd, J=8.5, 2.3 Hz, 1H), 7.13 (d, J=2.4 Hz, 1H), 7.10-6.96 (m, 4H), 4.23-4.13 (m, 1H), 3.88 (dd, J=13.8, 3.6 Hz, 1H), 3.70 (s, 2H), 3.41-3.29 (m, 2H), 3.30-3.20 (m, 1H), 2.92-2.84 (m, 2H), 2.84-2.73 (m, 4H), 2.64-2.52 (m, 2H), 2.15-2.04 (m, 2H).

Example 5: Synthesis of 4-[(2R)-3-(3,4-dihydro-1H-isoquinolin-2-yl)-2-hydroxy-propyl]-8-(trifluoromethyl)-2,3-dihydro-1,4-benzoxazepin-5-one

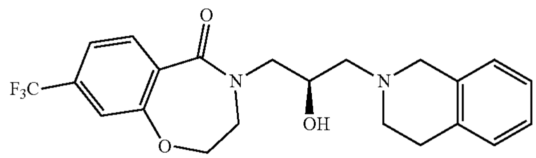 [SMILES: O=C1c2ccc(C(F)(F)F)cc2OCCN1C[C@H](O)CN1CCc2ccccc2C1]

The title compound was synthesized in the same manner as in Example 1, except that 7-(trifluoromethyl)chroman-4-one was used as a starting material and (R)-(−)-glycidyl nosylate was used instead of epibromohydrin in Example 1-1.

$^1$H NMR (400 MHz, Methanol-$d_4$) δ 7.90 (d, J=8.2 Hz, 1H), 7.48 (d, J=8.2 Hz, 1H), 7.36 (s, 1H), 7.16-7.03 (m, 4H), 4.56 (t, J=5.1 Hz, 2H), 4.25-4.22 (m, 1H), 4.02 (dd, J=13.9, 3.5 Hz, 1H), 3.76-3.74 (s, 4H), 3.47 (dd, J=14.0, 8.0 Hz, 1H), 2.99-2.83 (m, 4H), 2.73-2.60 (m, 2H).

Example 6: Synthesis of 2-[(2R)-3-(3,4-dihydro-1H-isoquinolin-2-yl)-2-hydroxy-propyl]-7-(trifluoromethoxy)-4,5-dihydro-3H-2-benzazepin-1-one

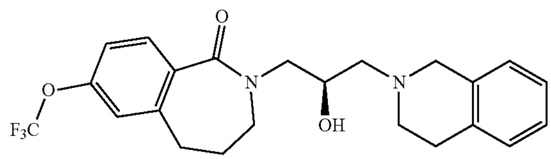 [SMILES: O=C1c2ccc(OC(F)(F)F)cc2CCCN1C[C@H](O)CN1CCc2ccccc2C1]

7-(Trifluoromethoxy)-2,3,4,5-tetrahydro-2-benzazepin-1-one as a starting material was used in the same manner as in Example 5 to obtained the title compound.

$^1$H NMR (400 MHz, Methanol-$d_4$) δ 7.68 (d, J=8.5 Hz, 1H), 7.27 (d, J=8.6 Hz, 1H), 7.20 (d, J=2.3 Hz, 1H), 7.16-7.02 (m, 4H), 4.29-4.20 (m, 1H), 3.94 (dd, J=13.8, 3.6 Hz, 1H), 3.78 (s, 2H), 3.48-3.34 (m, 2H), 3.37 (d, J=6.7 Hz, 1H), 2.99-2.82 (m, 6H), 2.72-2.59 (m, 2H), 2.18 (q, J=6.8 Hz, 2H).

Example 7: Synthesis of 2-[(2R)-3-(3,4-dihydro-1H-isoquinolin-2-yl)-2-hydroxy-propyl]-7-ethoxy-4,5-dihydro-3H-2-benzazepin-1-one

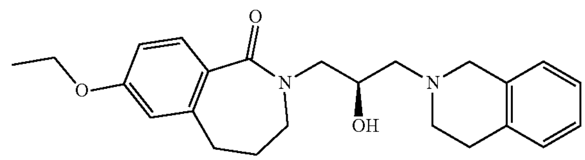 [SMILES: CCOc1ccc2c(c1)CCCN(C[C@H](O)CN1CCc3ccccc3C1)C2=O]

7-Ethoxy-2,3,4,5-tetrahydro-2-benzazepin-1-one as a starting material was used in the same manner as in Example 5 to obtained the title compound.

$^1H$ NMR (400 MHz, Methanol-$d_4$) δ 7.52 (d, J=8.5 Hz, 1H), 7.19-7.04 (m, 4H), 6.92-6.84 (m, 1H), 6.78 (s, 1H), 4.30-4.20 (m, 1H), 4.09 (q, J=7.1 Hz, 2H), 3.91 (dd, J=13.8, 3.8 Hz, 1H), 3.82 (s, 2H), 3.40 (td, J=13.6, 12.5, 7.2 Hz, 3H), 3.03-2.90 (m, 4H), 2.79 (t, J=7.1 Hz, 2H), 2.73-2.62 (m, 2H), 2.19-2.07 (m, 2H), 1.41 (t, J=7.0 Hz, 3H).

Example 8: Synthesis of [2-[(2R)-3-(3,4-dihydro-1H-isoquinolin-2-yl)-2-hydroxy-propyl]-1-oxo-4,5-dihydro-3H-2-benzazepin-7-yl] trifluoromethanesulfonate

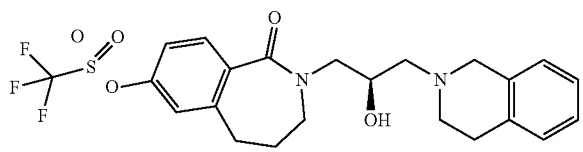

(1-Oxo-2,3,4,5-tetrahydro-2-benzazepin-7-yl) trifluoromethanesulfonate as a starting material was used in the same manner as in Example 5 to obtained the title compound.

$^1H$ NMR (400 MHz, Methanol-$d_4$) δ 7.74 (d, J=8.2 Hz, 1H), 7.38 (dd, J=8.5, 2.4 Hz, 1H), 7.32 (d, J=2.3 Hz, 1H), 7.18-6.99 (m, 4H), 4.30-4.19 (m, 1H), 3.94 (dd, J=13.8, 3.6 Hz, 1H), 3.78 (s, 2H), 3.46-3.3.4 (m, 3H), 2.98-2.83 (m, 6H), 2.71-2.62 (m, 2H), 2.18 (p, J=6.8 Hz, 2H).

Example 9: Synthesis of 2-[(2R)-3-(3,4-dihydro-1H-isoquinolin-2-yl)-2-hydroxy-propyl]-1-oxo-4,5-dihydro-3H-2-benzazepin-7-carbonitrile

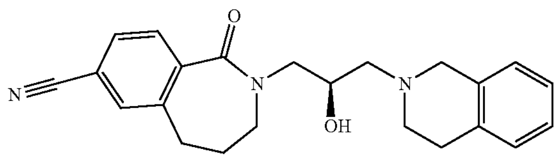 [SMILES: N#Cc1ccc2c(c1)CCCN(C[C@H](O)CN1CCc3ccccc3C1)C2=O]

7-Cyano-2,3,4,5-tetrahydro-2-benzazepin-1-one as a starting material was used in the same manner as in Example 5 to obtained the title compound.

$^1H$ NMR (400 MHz, Methanol-$d_4$) δ 7.73 (s, 2H), 7.66 (s, 1H), 7.21-7.02 (m, 4H), 4.31-4.17 (m, 1H), 3.94 (dd, J=13.9, 3.6 Hz, 1H), 3.77 (s, 2H), 3.57-3.34 (m, 3H), 3.01-2.81 (m, 6H), 2.70-2.61 (t, J=5.4 Hz, 2H), 2.17 (p, J=7.0 Hz, 2H).

Example 10: Synthesis of 4-[(2R)-3-(3,4-dihydro-1H-isoquinolin-2-yl)-2-hydroxy-propyl]-8-methyl-2,3-dihydro-1,4-benzoxazepin-5-one

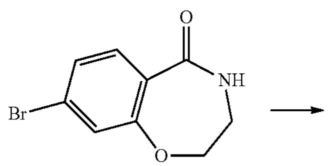

-continued

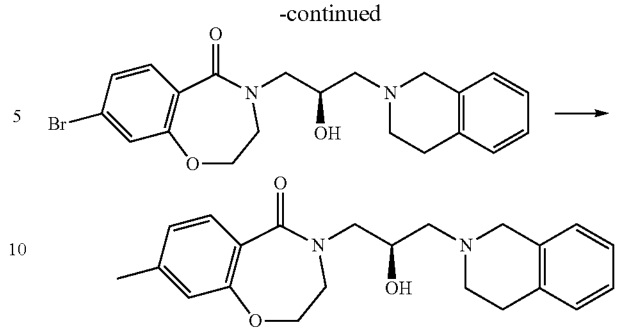

Example 10-1: Synthesis of 8-bromo-4-[(2R)-3-(3,4-dihydro-1H-isoquinolin-2-yl)-2-hydroxy-propyl]-2,3-dihydro-1,4-benzoxazepin-5-one 8-Bromo-3,4-dihydro-2H-1,4-benzoxazepin-5-one as a starting material was used in the same manner as in Example 5 to obtained the title compound.

Example 10-2: Synthesis of 4-[(2R)-3-(3,4-dihydro-1H-isoquinolin-2-yl)-2-hydroxy-propyl]-8-methyl-2,3-dihydro-1,4-benzoxazepin-5-one 8-Bromo-4-[(2R)-3-(3,4-dihydro-1H-isoquinolin-2-yl)-2-hydroxy-propyl]-2,3-dihydro-1,4-benzoxazepin-5-one (96 mg, 0.22 mmol), methylboronic acid (27 mg, 0.45 mmol), $Pd(dppf)Cl_2 \cdot CH_2Cl_2$ (18 mg, 0.022 mmol) and potassium carbonate (91 mg, 0.66 mg) were dissolved in 10 mL of 1,4-dioxane:distilled water (=3:1) solvent and stirred at 100° C. After confirming that the reaction was complete, the reaction solution was concentrated under reduced pressure and filtered with ethyl acetate. The filtrate was concentrated under reduced pressure and purified by flash column chromatography to obtain the title compound (11 mg).

$^1H$ NMR (400 MHz, Methanol-$d_4$) δ 7.59 (d, J=7.9 Hz, 1H), 7.18-6.98 (m, 5H), 6.88 (s, 1H), 4.45 (t, J=5.2 Hz, 2H), 4.23 (p, J=3.3 Hz, 1H), 3.98 (dd, J=13.9, 3.6 Hz, 1H), 3.76 (s, 2H), 3.69 (t, J=5.3 Hz, 2H), 3.43 (dd, J=13.9, 7.7 Hz, 1H), 2.98-2.83 (m, 4H), 2.71-2.59 (m, 2H), 2.36 (s, 3H).

Example 11: Synthesis of 4-[(2R)-3-(3,4-dihydro-1H-isoquinolin-2-yl)-2-hydroxy-propyl]-8-propyl-2,3-dihydro-1,4-benzoxazepin-5-one

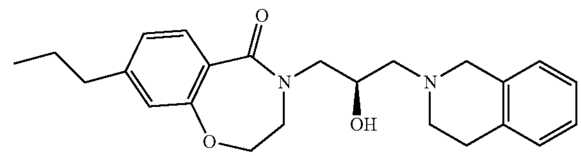 [SMILES: CCCc1ccc2c(c1)OCCN(C[C@H](O)CN1CCc3ccccc3C1)C2=O]

The title compound was synthesized in the same manner as in Example 10, except that propylboronic acid was used instead of methylboronic acid in Example 10-2.

$^1H$ NMR (400 MHz, Methanol-$d_4$) δ 7.61 (d, J=7.9 Hz, 1H), 7.16-6.99 (m, 5H), 6.88 (s, 1H), 4.46 (t, J=5.2 Hz, 2H), 4.25 (dd, J=8.3, 4.3 Hz, 1H), 3.98 (dd, J=13.9, 3.7 Hz, 1H), 3.78 (s, 2H), 3.70 (t, J=5.2 Hz, 2H), 3.45 (dd, J=13.9, 7.6 Hz, 1H), 2.97-2.88 (m, 4H), 2.73-2.65 (m, 2H), 2.62 (t, J=7.6 Hz, 2H), 1.67 (q, J=7.5 Hz, 2H), 0.97 (t, J=7.3 Hz, 3H).

Example 12: Synthesis of 4-[(2R)-3-(3,4-dihydro-1H-isoquinolin-2-yl)-2-hydroxy-propyl]-8-isobutyl-2,3-dihydro-1,4-benzoxazepin-5-one

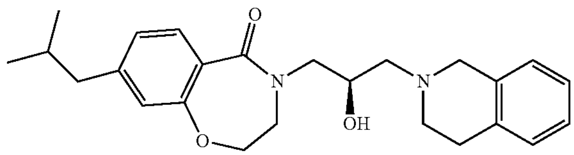 [SMILES: CC(C)Cc1ccc2c(c1)OCCN(C[C@H](O)CN1CCc3ccccc3C1)C2=O]

8-Bromo-4-[(2R)-3-(3,4-dihydro-1H-isoquinolin-2-yl)-2-hydroxy-propyl]-2,3-dihydro-1,4-benzoxazepin-5-one (100 mg, 0.23 mmol), isobutylboronic acid (47 mg, 0.46 mmol), $Pd(dppf)Cl_2$ (17 mg, 0.023 mmol) and potassium carbonate (95 mg, 0.69 mg) were dissolved in 2 mL of toluene and stirred at 120° C. for 2 hours. After confirming that the boronic acid reaction was complete, the reaction solution was concentrated under reduced pressure and filtered with ethyl acetate. The filtrate was concentrated under reduced pressure and purified by flash column chromatography to obtain the title compound (11 mg).

$^1$H NMR (400 MHz, Methanol-$d_4$) δ 7.62 (d, J=8.0 Hz, 1H), 7.16-7.03 (m, 4H), 7.00 (dd, J=7.9, 1.6 Hz, 1H), 6.85 (d, J=1.6 Hz, 1H), 4.46 (t, J=5.1 Hz, 2H), 4.28-4.20 (m, 1H), 3.99 (dd, J=13.9, 3.6 Hz, 1H), 3.76 (s, 2H), 3.70 (t, J=5.2 Hz, 2H), 3.44 (dd, J=13.9, 7.6 Hz, 1H), 2.97-2.84 (m, 4H), 2.69-2.59 (m, 2H), 2.51 (d, J=7.2 Hz, 2H), 1.96-1.83 (m, 1H), 0.93 (d, J=6.6 Hz, 6H).

Example 13: Synthesis of 4-[(2R)-3-(3,4-dihydro-1H-isoquinolin-2-yl)-2-hydroxy-propyl]-8-(3,3,3-trifluoropropyl)-2,3-dihydro-1,4-benzoxazepin-5-one

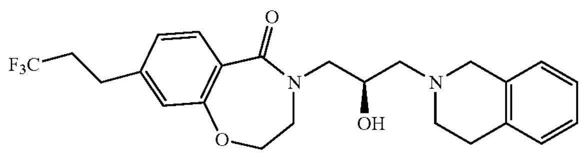 [SMILES: O=C1c2ccc(CCC(F)(F)F)cc2OCCN1C[C@H](O)CN1CCc2ccccc2C1]

The title compound was synthesized in the same manner as in Example 12, except that 3,3,3-trifluoropropylboronic acid was used instead of isobutylboronic acid at 100° C.

$^1$H NMR (400 MHz, Methanol-$d_4$) δ 7.66 (d, J=8.0 Hz, 1H), 7.19-7.05 (m, 5H), 6.97 (s, 1H), 4.48 (t, J=5.1 Hz, 2H), 4.28-4.25 (m, 1H), 3.98 (dd, J=13.8, 3.7 Hz, 1H), 3.81 (s, 2H), 3.71 (t, J=5.3 Hz, 2H), 3.46 (dd, J=13.9, 7.6 Hz, 1H), 2.96-2.89 (m, 6H), 2.76-2.64 (m, 2H), 2.59-2.44 (m, 2H).

Example 14: Synthesis of tert-butyl 4-[4-[(2R)-3-(3,4-dihydro-1H-isoquinolin-2-yl)-2-hydroxy-propyl]-5-oxo-2,3-dihydro-1,4-benzoxazepin-8-yl]-3,6-dihydro-2H-pyridine-1-carboxylate

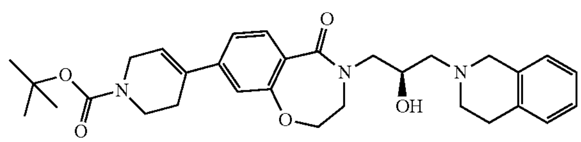 [SMILES: CC(C)(C)OC(=O)N1CC=C(c2ccc3c(c2)OCCN(C[C@H](O)CN2CCc4ccccc4C2)C3=O)CC1]

The title compound was synthesized in the same manner as in Example 10, except that tert-butyl 4-(4,4,5,5-tetramethyl-1,3,2-dioxaborolan-2-yl)-3,6-dihydro-2H-pyridine-1-carboxylate was used instead of methylboronic acid in Example 10-2.

$^1$H NMR (400 MHz, Methanol-$d_4$) δ 7.68 (d, J=8.3 Hz, 1H), 7.29 (d, J=8.2 Hz, 1H), 7.19-7.03 (m, 5H), 6.26 (s, 1H), 4.49 (t, J=5.2 Hz, 2H), 4.30-4.19 (m, 1H), 4.16-4.05 (m, 2H), 4.00 (dd, J=13.8, 3.8 Hz, 1H), 3.77 (s, 2H), 3.76-3.69 (m, 2H), 3.70-3.60 (m, 2H), 3.45 (dd, J=14.0, 7.7 Hz, 1H), 2.98-2.85 (m, 4H), 2.73-2.63 (m, 2H), 2.55 (s, 2H), 1.51 (s, 9H).

Example 15: Synthesis of 4-[(2R)-3-(3,4-dihydro-1H-isoquinolin-2-yl)-2-hydroxy-propyl]-8-(1,2,3,6-tetrahydropyridin-4-yl)-2,3-dihydro-1,4-benzoxazepin-5-one

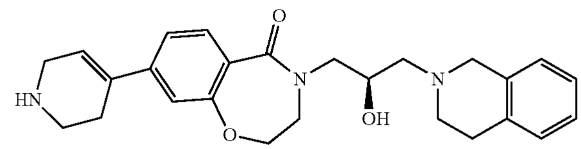 [SMILES: O=C1c2ccc(C3=CCNCC3)cc2OCCN1C[C@H](O)CN1CCc2ccccc2C1]

Tert-butyl 4-[4-[(2R)-3-(3,4-dihydro-1H-isoquinolin-2-yl)-2-hydroxy-propyl]-5-oxo-2,3-dihydro-1,4-benzoxazepin-8-yl]-3,6-dihydro-2H-pyridine-1-carboxylate obtained in Example 14 was dissolved in methanol, and 4 N hydrochloric acid solution dissolved in 1,4-dioxane was added thereto. The mixture was stirred at room temperature until the reaction was completed, diluted with ethyldiethyl ether, and filtered to obtain the title compound in the form of a white solid dihydrochloride. After addition of water, the title compound in the form of a dihydrochloride was washed with ethyl acetate 3 times. The obtained aqueous layer was basified with sodium hydroxide aqueous solution until the pH reached 14, and ethyl acetate was added again to extract 3 times. The combined organic layers were dried over anhydrous sodium sulfate, filtered, and concentrated under reduced pressure to obtain the title compound without additional purification.

$^1$H NMR (400 MHz, Methanol-$d_4$) δ 7.67 (d, J=8.2 Hz, 1H), 7.29 (d, J=8.3 Hz, 1H), 7.17-7.01 (m, 5H), 6.32 (s, 1H), 4.49 (t, J=5.1 Hz, 2H), 4.29-4.19 (m, 1H), 4.00 (dd, J=14.0, 3.6 Hz, 1H), 3.79-3.65 (m, 4H), 3.53 (d, J=3.2 Hz, 2H), 3.45 (dd, J=13.9, 7.7 Hz, 1H), 3.11 (t, J=5.8 Hz, 2H), 2.98-2.84 (m, 4H), 2.71-2.62 (m, 2H), 2.53 (bs, 2H).

Example 16: Synthesis of 8-(1-acetyl-3,6-dihydro-2H-pyridin-4-yl)-4-[(2R)-3-(3,4-dihydro-1H-isoquinolin-2-yl)-2-hydroxy-propyl]-2,3-dihydro-1,4-benzoxazepin-5-one

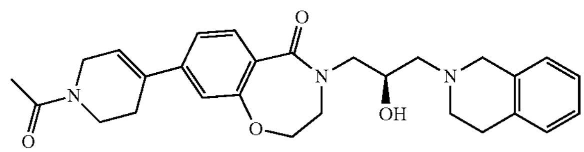 [SMILES: CC(=O)N1CC=C(c2ccc3c(c2)OCCN(C[C@H](O)CN2CCc4ccccc4C2)C3=O)CC1]

Dihydrochloride of 4-[(2R)-3-(3,4-dihydro-1H-isoquinolin-2-yl)-2-hydroxy-propyl]-8-(1,2,3,6-tetrahydropyridin-4- yl)-2,3-dihydro-1,4-benzoxazepin-5-one obtained in Example 15 (75 mg, 0.16 mmol) and potassium carbonate (66 mg, 0.48 mmol) were dissolved in 1.5 mL of acetone, and acetic anhydride (0.03 mLm 0.32 mmol) was slowly added thereto at room temperature. The reaction solution was stirred at room temperature and filtered after confirming that the reaction was complete. The filtrate was concentrated under reduced pressure and purified by flash column chromatography to obtain the title compound.

$^1$H NMR (400 MHz, Methanol-$d_4$) δ 7.69 (d, J=8.2 Hz, 1H), 7.29 (d, J=8.2 Hz, 1H), 7.19-7.02 (m, 5H), 6.28 (s, 1H), 4.49 (t, J=5.1 Hz, 2H), 4.31-4.19 (m, 3H), 3.98 (dd, J=13.9, 3.7 Hz, 1H), 3.88-3.78 (m, 3H), 3.80-3.67 (m, 3H), 3.47 (dd, J=13.9, 7.5 Hz, 1H), 3.02-2.90 (m, 4H), 2.77-2.68 (m, 2H), 2.64 (bs, 1H), 2.56 (bs, 1H), 2.18 (d, J=15.1 Hz, 3H).

Example 17: Synthesis of 8-(1-acetyl-4-piperidyl)-4-[(2R)-3-(3,4-dihydro-1H-isoquinolin-2-yl)-2-hydroxy-propyl]-2,3-dihydro-1,4-benzoxazepin-5-one

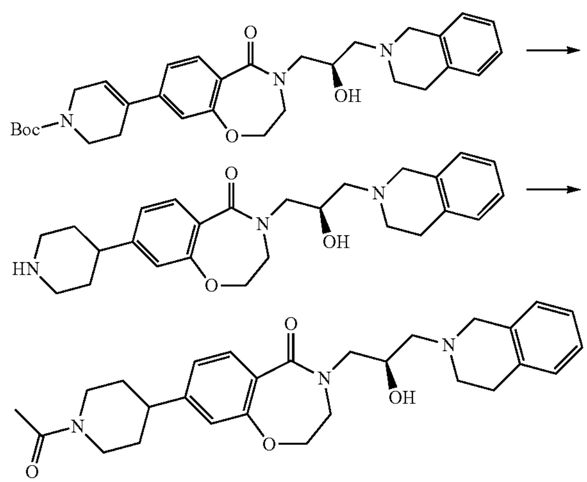

Example 17-1: Synthesis of 4-[(2R)-3-(3,4-dihydro-1H-isoquinolin-2-yl)-2-hydroxy-propyl]-8-(4-piperidyl)-2,3-dihydro-1,4-benzoxazepin-5-one Tert-butyl 4-[4-[(2R)-3-(3,4-dihydro-1H-isoquinolin-2-yl)-2-hydroxy-propyl]-5-oxo-2,3-dihydro-1,4-benzoxazepin-8-yl]-3,6-dihydro-2H-pyridine-1-carboxylate obtained in Example 14 was dissolved in methanol, and 5% palladium-charcoal in a catalytic amount was added thereto. The reaction solution was stirred under a hydrogen balloon and filtered through celite. The filtrate was concentrated under reduced pressure, dissolved in a small amount of methanol, and then 4 N hydrochloric acid dissolved in 1,4-dioxane was added thereto, followed by stirring at room temperature for 1 hour. After addition of distilled water, the reaction solution was washed with ethyl acetate. The obtained aqueous layer was basified with sodium hydroxide aqueous solution until the pH reached 14 and extracted with dichloromethane 3 times. The combined organic layers were dried over anhydrous sodium sulfate, filtered, and concentrated under reduced pressure to obtain the title compound without additional purification.

Example 17-2: Synthesis of 8-(1-acetyl-4-piperidyl)-4-[(2R)-3-(3,4-dihydro-1H-isoquinolin-2-yl)-2-hydroxy-propyl]-2,3-dihydro-1,4-benzoxazepin-5-one 4-[(2R)-3-(3,4-dihydro-1H-isoquinolin-2-yl)-2-hydroxy-propyl]-8-(4-piperidyl)-2,3-dihydro-1,4-benzoxazepin-5-one (50 mg, 0.11 mmol) obtained in Example 17-1 and potassium carbonate (46 mg, 0.33 mg) were dissolved in dichloromethane, and acetic anhydride (0.02 mL, 0.17 mmol) was slowly added thereto. The reaction solution was stirred at room temperature for one day, diluted with dichloromethane, filtered, and concentrated under reduced pressure. The obtained concentrate was purified by flash column chromatography to obtain the title compound (21 mg).

$^1$H NMR (400 MHz, Methanol-$d_4$) δ 7.65 (d, J=8.0 Hz, 1H), 7.18-7.02 (m, 5H), 6.95 (s, 1H), 4.69 (d, J=13.4 Hz, 1H), 4.47 (t, J=5.2 Hz, 2H), 4.29-4.18 (m, 1H), 4.03 (dd, J=27.3, 14.3 Hz, 2H), 3.80-3.65 (m, 4H), 3.44 (dd, J=14.0, 7.7 Hz, 1H), 3.29-3.20 (m, 1H), 2.98-2.82 (m, 4H), 2.80-2.60 (m, 3H), 2.16 (s, 3H), 1.98-1.85 (m, 2H), 1.78-1.50 (m, 3H).

Example 18: Synthesis of 4-[(2R)-3-(3,4-dihydro-1H-isoquinolin-2-yl)-2-hydroxy-propyl]-8-(1-ethyl-3,6-dihydro-2H-pyridin-4-yl)-2,3-dihydro-1,4-benzoxazepin-5-one

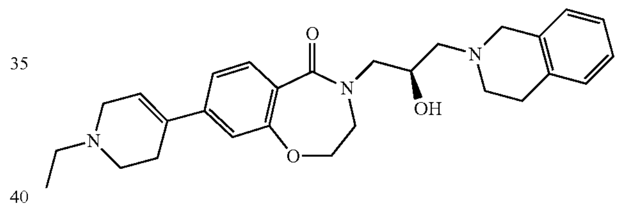

Dihydrochloride of 4-[(2R)-3-(3,4-dihydro-1H-isoquinolin-2-yl)-2-hydroxy-propyl]-8-(1,2,3,6-tetrahydropyridin-4-yl)-2,3-dihydro-1,4-benzoxazepin-5-one obtained in Example 15 (75 mg, 0.16 mmol) was dissolved in methanol, and an excess of acetaldehyde was added thereto. While stirring the reaction solution, an excess of sodium cyanoborohydride was added, followed by stirring at room temperature for one day. The reaction was terminated by adding saturated aqueous ammonium chloride solution to the reaction solution, and 1 N sodium hydroxide aqueous solution was added for basification. The reaction mixture was extracted with ethyl acetate 3 times and dried over anhydrous sodium sulfate. The oily liquid obtained by removing the solvent by evaporation under reduced pressure was purified by flash column chromatography to obtain the title compound (10 mg) as a white solid.

$^1$H NMR (400 MHz, Methanol-$d_4$) δ 7.68 (d, J=8.2 Hz, 1H), 7.30 (d, J=7.9 Hz, 1H), 7.09 (d, J=18.9 Hz, 5H), 6.30 (s, 1H), 4.49 (t, J=5.1 Hz, 2H), 4.29-4.18 (m, 1H), 4.00 (dd, J=13.7, 3.5 Hz, 1H), 3.77 (s, 2H), 3.73 (t, J=5.2 Hz, 2H), 3.45 (dd, J=13.8, 7.6 Hz, 1H), 3.27 (s, 2H), 2.99-2.85 (m, 4H), 2.83 (t, J=5.9 Hz, 2H), 2.71-2.59 (m, 6H), 1.21 (t, J=7.2 Hz, 3H).

Example 19: Synthesis of 4-[(2R)-3-(3,4-dihydro-1H-isoquinolin-2-yl)-2-hydroxy-propyl]-8-(1-isopropyl-3,6-dihydro-2H-pyridin-4-yl)-2,3-dihydro-1,4-benzoxazepin-5-one

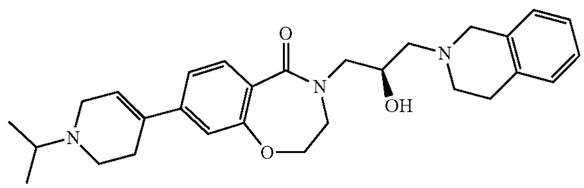 [SMILES: CC(C)N1CC=C(c2ccc3c(c2)OCCN(C[C@H](O)CN2CCc4ccccc4C2)C3=O)CC1]

The title compound was synthesized in the same manner as in Example 18, except that acetone was used instead of acetaldehyde.

$^1$H NMR (400 MHz, Methanol-$d_4$) δ 7.61 (d, J=8.2 Hz, 1H), 7.23 (d, J=8.2 Hz, 1H), 7.10-6.95 (m, 5H), 6.24 (s, 1H), 4.42 (t, J=5.2 Hz, 2H), 4.22-4.12 (m, 1H), 3.96-3.84 (m, 1H), 3.71 (s, 2H), 3.65 (t, J=5.2 Hz, 2H), 3.48-3.31 (m, 3H), 3.05-2.90 (m, 3H), 2.90-2.78 (m, 4H), 2.68-2.50 (m, 4H), 1.17 (d, J=6.5 Hz, 6H).

Example 20: Synthesis of 4-[(2R)-3-(3,4-dihydro-1H-isoquinolin-2-yl)-2-hydroxy-propyl]-8-(3,6-dihydro-2H-pyran-4-yl)-2,3-dihydro-1,4-benzoxazepin-5-one

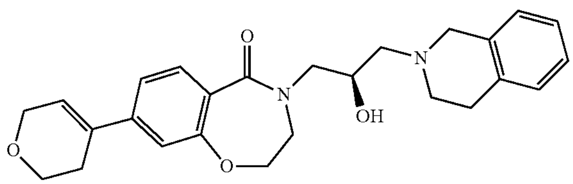 [SMILES: O=C1c2ccc(C3=CCOCC3)cc2OCCN1C[C@H](O)CN1CCc2ccccc2C1]

The title compound was synthesized in the same manner as in Example 10, except that 2-(3,6-dihydro-2H-pyran-4-yl)-4,4,5,5-tetramethyl-1,3,2-dioxaborolane was used instead of methylboronic acid.

$^1$H NMR (400 MHz, Methanol-$d_4$) δ 7.68 (d, J=8.2 Hz, 1H), 7.30 (d, J=8.3 Hz, 1H), 7.20-6.98 (m, 5H), 6.34 (s, 1H), 4.49 (t, J=5.1 Hz, 2H), 4.32 (d, J=3.3 Hz, 2H), 4.29-4.19 (m, 1H), 4.00 (dd, J=13.8, 3.6 Hz, 1H), 3.94 (t, J=5.5 Hz, 2H), 3.81-3.68 (m, 4H), 3.48-3.40 (m, 1H), 2.99-2.84 (m, 4H), 2.69-2.60 (m, 2H), 2.53 (bs, 2H).

Example 21: Synthesis of 4-[(2R)-3-(3,4-dihydro-1H-isoquinolin-2-yl)-2-hydroxy-propyl]-8-tetrahydropyran-4-yl-2,3-dihydro-1,4-benzoxazepin-5-one

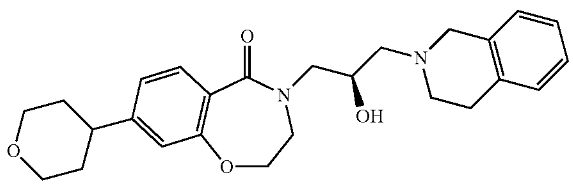 [SMILES: O=C1c2ccc(C3CCOCC3)cc2OCCN1C[C@H](O)CN1CCc2ccccc2C1]

4-[(2R)-3-(3,4-dihydro-1H-isoquinolin-2-yl)-2-hydroxy-propyl]-8-(3,6-dihydro-2H-pyran-4-yl)-2,3-dihydro-1,4-benzoxazepin-5-one obtained in Example 20 was dissolved in methanol, and 5% palladium-charcoal in a catalytic amount was added thereto. The reaction solution was stirred under a hydrogen balloon and filtered through celite. The filtrate was concentrated under reduced pressure and purified by flash chromatography to obtain the title compound as transparent oil.

$^1$H NMR (400 MHz, Methanol-$d_4$) δ 7.65 (d, J=8.1 Hz, 1H), 7.17-7.02 (m, 5H), 6.95 (s, 1H), 4.48 (t, J=5.2 Hz, 2H), 4.29-4.17 (m, 1H), 4.08-3.95 (m, 3H), 3.76 (s, 2H), 3.71 (t, J=5.3 Hz, 2H), 3.63-3.52 (m, 2H), 3.44 (dd, J=13.9, 7.7 Hz, 1H), 2.98-2.80 (m, 5H), 2.69-2.59 (m, 2H), 1.84-1.72 (m, 4H).

Example 22: Synthesis of 4-[(2R)-3-(3,4-dihydro-1H-isoquinolin-2-yl)-2-hydroxy-propyl]-8-(morpholinomethyl)-2,3-dihydro-1,4-benzoxazepin-5-one

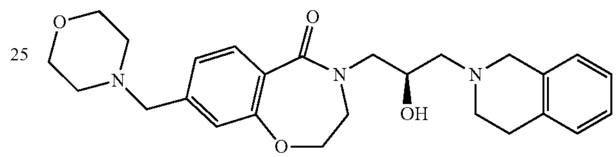

8-Bromo-4-[(2R)-3-(3,4-dihydro-1H-isoquinolin-2-yl)-2-hydroxy-propyl]-2,3-dihydro-1,4-benzoxazepin-5-one (160 mg, 0.37 mmol), potassium (morpholin-4-yl)methyltrifluoroborate (85 mg, 0.41 mg), palladium acetate (4 mg, 0.0185 mmol), XPhos (18 mg, 0.037 mmol) and cesium carbonate (362 mg, 1.11 mmol) were dissolved in 3 mL of tetrahydrofuran:distilled water (=10:1) solvent, and nitrogen was charged, followed by stirring at 80° C. for 16 hours. The reaction solution was cooled to room temperature, diluted with ethyl acetate, and filtered through celite. The obtained solution was concentrated under reduced pressure and purified by flash chromatography to obtain the white title compound (103 mg).

$^1$H NMR (400 MHz, Methanol-$d_4$) δ 7.67 (d, J=7.9 Hz, 1H), 7.19 (d, J=8.0 Hz, 1H), 7.16-7.03 (m, 5H), 4.48 (t, J=5.1 Hz, 2H), 4.30-4.19 (m, 1H), 3.99 (dd, J=13.9, 3.6 Hz, 1H), 3.77 (s, 2H), 3.71 (t, J=4.8 Hz, 6H), 3.55 (s, 2H), 3.46 (dd, J=13.9, 7.6 Hz, 1H), 2.99-2.85 (m, 4H), 2.72-2.60 (m, 2H), 2.48 (t, J=4.7 Hz, 4H).

Example 23: Synthesis of 4-[(2R)-3-(3,4-dihydro-1H-isoquinolin-2-yl)-2-hydroxy-propyl]-8-(1-piperidylmethyl)-2,3-dihydro-1,4-benzoxazepin-5-one

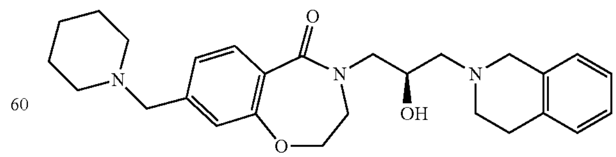

The title compound was synthesized in the same manner as in Example 22, except that potassium (piperidin-1-yl) methyltrifluoroborate was used instead of potassium (morpholin-4-yl)methyltrifluoroborate.

$^1$H NMR (400 MHz, Methanol-$d_4$) δ 7.67 (d, J=7.9 Hz, 1H), 7.17 (d, J=8.0 Hz, 1H), 7.15-7.02 (m, 5H), 4.49 (t, J=5.1 Hz, 2H), 4.29-4.20 (m, 1H), 4.00 (dd, J=13.8, 3.6 Hz, 1H), 3.76 (s, 2H), 3.72 (t, J=5.3 Hz, 2H), 3.53 (s, 2H), 3.45 (dd, J=13.8, 7.6 Hz, 1H), 2.96-2.86 (m, 4H), 2.71-2.59 (m, 2H), 2.46 (bs, 4H), 1.62 (q, J=5.6 Hz, 4H), 1.49 (bs, 2H).

Example 24: Synthesis of 4-[(2R)-3-(3,4-dihydro-1H-isoquinolin-2-yl)-2-hydroxy-propyl]-8-(pyrrolidin-1-ylmethyl)-2,3-dihydro-1,4-benzoxazepin-5-one

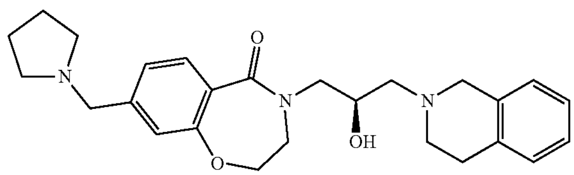 [SMILES: O=C1c2ccc(CN3CCCC3)cc2OCCN1C[C@H](O)CN1CCc2ccccc2C1]

The title compound was synthesized in the same manner as in Example 22, except that potassium 1-trifluoroboratomethylpyrrolidine was used instead of potassium (morpholin-4-yl)methyltrifluoroborate.

$^1$H NMR (400 MHz, Methanol-$d_4$) δ 7.69 (d, J=8.0 Hz, 1H), 7.20 (d, J=8.0 Hz, 1H), 7.15-7.03 (m, 5H), 4.49 (t, J=5.1 Hz, 2H), 4.27-4.24 (m, 1H), 4.00 (dd, J=13.9, 3.6 Hz, 1H), 3.81-3.67 (m, 6H), 3.46 (dd, J=13.9, 7.7 Hz, 1H), 2.95-2.88 (m, 4H), 2.66 (bs, 6H), 1.87 (bs, 4H).

Example 25: Synthesis of 4-[(2R)-3-(3,4-dihydro-1H-isoquinolin-2-yl)-2-hydroxy-propyl]-8-[(dimethylamino)methyl]-2,3-dihydro-1,4-benzoxazepin-5-one

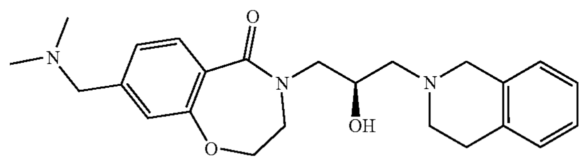 [SMILES: CN(C)Cc1ccc2c(c1)OCCN(C[C@H](O)CN1CCc3ccccc3C1)C2=O]

The title compound was synthesized in the same manner as in Example 22, except that potassium dimethylaminomethyltrifluoroboronate was used instead of potassium (morpholin-4-yl)methyltrifluoroborate.

$^1$H NMR (400 MHz, Chloroform-d) δ 7.75 (d, J=8.0 Hz, 1H), 7.18-7.07 (m, 4H), 7.06-6.95 (m, 2H), 4.51-4.39 (m, 2H), 4.17-4.06 (m, 2H), 3.93 (d, J=14.7 Hz, 1H), 3.83 (d, J=15.0 Hz, 1H), 3.74-3.66 (m, 2H), 3.63 (d, J=14.9 Hz, 1H), 3.56 (dd, J=14.2, 6.0 Hz, 1H), 3.42 (s, 2H), 3.00-2.87 (m, 3H), 2.77-2.70 (m, 1H), 2.69-2.63 (m, 1H), 2.56 (t, J=11.3 Hz, 1H), 2.25 (s, 6H).

Example 26: Synthesis of 8-(diethylaminomethyl)-4-[(2R)-3-(3,4-dihydro-1H-isoquinolin-2-yl)-2-hydroxy-propyl]-2,3-dihydro-1,4-benzoxazepin-5-one

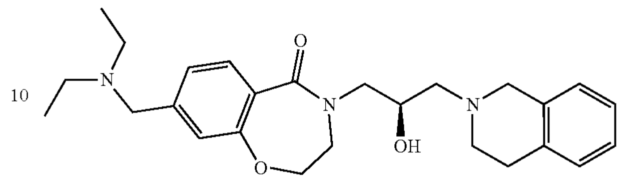

The title compound was synthesized in the same manner as in Example 22, except that potassium diethylaminomethyltrifluoroboronate was used instead of potassium (morpholin-4-yl)methyltrifluoroborate.

$^1$H NMR (400 MHz, Chloroform-d) δ 7.74 (d, J=7.9 Hz, 1H), 7.18-7.08 (m, 4H), 7.02 (bs, 2H), 4.45 (qt, J=10.8, 4.6 Hz, 2H), 4.16-4.06 (m, 1H), 3.93 (d, J=14.2 Hz, 1H), 3.83 (d, J=14.9 Hz, 1H), 3.75-3.66 (m, 2H), 3.63 (d, J=14.9 Hz, 1H), 3.57-3.54 (m, 3H), 3.00-2.87 (m, 3H), 2.74 (dd, J=10.7, 5.3 Hz, 1H), 2.67 (dd, J=12.5, 3.9 Hz, 1H), 2.61-2.47 (m, 5H), 1.04 (t, J=7.1 Hz, 6H).

Example 27: Synthesis of 4-[(2R)-3-(3,4-dihydro-1H-isoquinolin-2-yl)-2-hydroxy-propyl]-8-[(4-methyl-1-piperidyl)methyl]-2,3-dihydro-1,4-benzoxazepin-5-one

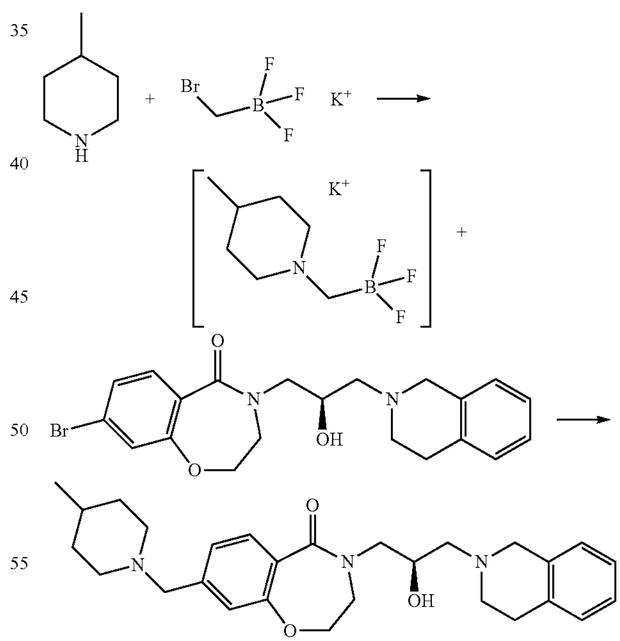

4-Methyl piperidine (0.054 mL, 0.46 mmol) and potassium (bromomethyl)trifluoroborate (92 mg, 0.46 mmol) were dissolved in 2 mL of tetrahydrofuran, and stirred at 80° C. for 12 hours. The reaction mixture was cooled to room temperature, and 8-bromo-4-[(2R)-3-(3,4-dihydro-1H-isoquinolin-2-yl)-2-hydroxy-propyl]-2,3-dihydro-1,4-benzoxazepin-5-one (100 mg, 0.23 mmol), palladium acetate (3 mg, 0.011 mmol), XPhos (11 mg, 0.023 mmol), cesium carbonate (225 mg, 0.69 mmol) and 2 mL of tetrahydrofuran:distilled water (=10:1) were added thereto, followed by charging a reaction vessel with nitrogen. The reaction solution was stirred at 80° C. for 16 hours, diluted with ethyl acetate, and filtered through celite. The obtained solution was concentrated under reduced pressure and purified by flash chromatography to obtain the white title compound (70 mg).

$^1$H NMR (400 MHz, Methanol-$d_4$) δ 7.67 (d, J=8.0 Hz, 1H), 7.17 (d, J=8.0 Hz, 1H), 7.14-7.02 (m, 5H), 4.49 (t, J=5.1 Hz, 2H), 4.29-4.19 (m, 1H), 4.00 (dd, J=13.9, 3.6 Hz, 1H), 3.76 (s, 2H), 3.72 (t, J=5.2 Hz, 2H), 3.54 (s, 2H), 3.46 (dd, J=13.8, 7.7 Hz, 1H), 2.98-2.83 (m, 6H), 2.72-2.60 (m, 2H), 2.07 (d, J=11.6 Hz, 1H), 1.66 (d, J=13.0 Hz, 2H), 1.41 (bs, 1H), 1.34-1.19 (m, 2H), 0.96 (d, J=6.4 Hz, 3H).

Example 28: Synthesis of 4-[(2R)-3-(3,4-dihydro-1H-isoquinolin-2-yl)-2-hydroxy-propyl]-8-(2-oxa-6-azaspiro[3.3]heptan-6-ylmethyl)-2,3-dihydro-1,4-benzoxazepin-5-one

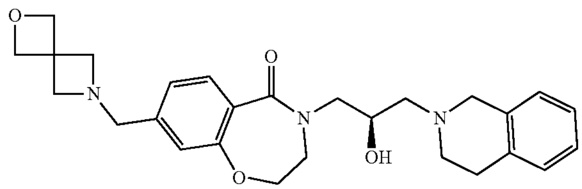 [SMILES: O=C1c2ccc(CN3CC4(COC4)C3)cc2OCCN1C[C@H](O)CN1CCc2ccccc2C1]

The title compound was synthesized in the same manner as in Example 27, except that 4 equivalents of potassium carbonate was added, and 2-oxa-6-azaspiro[3.3]heptane oxalate was used instead of 4-methyl piperidine.

$^1$H NMR (400 MHz, Methanol-$d_4$) δ 7.67 (d, J=7.9 Hz, 1H), 7.18-7.03 (m, 5H), 6.98 (s, 1H), 4.75 (s, 4H), 4.48 (t, J=5.1 Hz, 2H), 4.30-4.19 (m, 1H), 3.99 (dd, J=14.0, 3.6 Hz, 1H), 3.78 (s, 2H), 3.71 (t, J=5.3 Hz, 2H), 3.62 (s, 2H), 3.47-3.43 (m, 5H), 2.95-2.89 (m, 4H), 2.74-2.61 (m, 2H).

Example 29: Synthesis of 4-[(2R)-3-(3,4-dihydro-1H-isoquinolin-2-yl)-2-hydroxy-propyl]-8-[(3-methoxyazetidin-1-yl)methyl]-2,3-dihydro-1,4-benzoxazepin-5-one

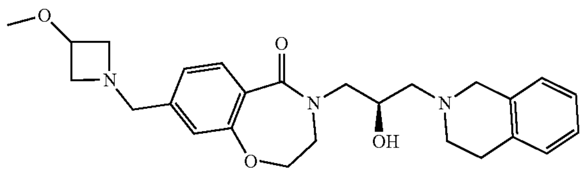 [SMILES: COC1CN(Cc2ccc3c(c2)OCCN(C[C@H](O)CN2CCc4ccccc4C2)C3=O)C1]

3-Methoxyazetidine hydrochloride (57 mg, 0.46 mmol), potassium (bromomethyl)trifluoroborate (92 mg, 0.46 mmol) and potassium carbonate (127 mg, 0.92 mmol) were dissolved in tetrahydrofuran:distilled water (10:1), and stirred at 80° C. for 12 hours. The reaction mixture was cooled to room temperature, and 8-bromo-4-[(2R)-3-(3,4-dihydro-1H-isoquinolin-2-yl)-2-hydroxy-propyl]-2,3-dihydro-1,4-benzoxazepin-5-one (100 mg, 0.23 mmol), palladium acetate (3 mg, 0.011 mmol), XPhos (11 mg, 0.023 mmol), cesium carbonate (225 mg, 0.69 mmol) and tetrahydrofuran:distilled water (=10:1) were added thereto, followed by charging a reaction vessel with nitrogen. The reaction solution was stirred at 80° C. for 16 hours, diluted with ethyl acetate, and filtered through celite. The obtained solution was concentrated under reduced pressure and purified by flash chromatography to obtain the white title compound (16 mg).

$^1$H NMR (400 MHz, Methanol-$d_4$) δ 7.67 (d, J=8.0 Hz, 1H), 7.16-7.04 (m, 5H), 7.00 (s, 1H), 4.48 (t, J=5.1 Hz, 2H), 4.28-4.19 (m, 1H), 4.11-4.04 (m, 1H), 3.99 (dd, J=13.9, 3.7 Hz, 1H), 3.77 (s, 2H), 3.74-3.67 (m, 3H), 3.61 (t, J=7.3 Hz, 2H), 3.45 (dd, J=14.0, 7.6 Hz, 1H), 3.27 (s, 3H), 3.08 (t, J=7.1 Hz, 2H), 3.00-2.84 (m, 4H), 2.71-2.61 (m, 2H).

Example 30: Synthesis of 4-[(2R)-3-(3,4-dihydro-1H-isoquinolin-2-yl)-2-hydroxy-propyl]-8-[(2-methylmorpholin-4-yl)methyl]-2,3-dihydro-1,4-benzoxazepin-5-one

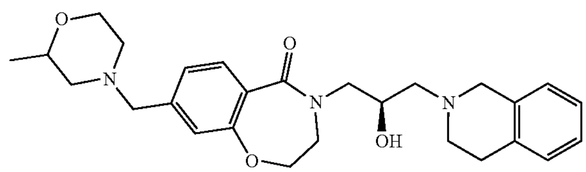 [SMILES: CC1CN(Cc2ccc3c(c2)OCCN(C[C@H](O)CN2CCc4ccccc4C2)C3=O)CCO1]

The title compound was synthesized in the same manner as in Example 29, except that 2-methylmorpholine was used instead of 3-methoxyazetidine hydrochloride.

$^1$H NMR (400 MHz, Methanol-$d_4$) δ 7.67 (d, J=7.9 Hz, 1H), 7.18 (d, J=8.0 Hz, 1H), 7.15-7.03 (m, 5H), 4.49 (t, J=5.1 Hz, 2H), 4.30-4.17 (m, 1H), 3.99 (dd, J=13.8, 3.7 Hz, 1H), 3.88-3.79 (m, 1H), 3.77 (s, 2H), 3.75-3.61 (m, 4H), 3.54 (s, 2H), 3.46 (dd, J=13.8, 7.6 Hz, 1H), 2.98-2.84 (m, 4H), 2.76 (d, J=11.4 Hz, 1H), 2.72-2.62 (m, 3H), 2.21-2.11 (m, 1H), 1.86 (t, J=10.6 Hz, 1H), 1.12 (d, J=6.3 Hz, 3H).

Example 31: Synthesis of 8-[(4,4-difluoro-1-piperidyl)methyl]-4-[(2R)-3-(3,4-dihydro-1H-isoquinolin-2-yl)-2-hydroxy-propyl]-2,3-dihydro-1,4-benzoxazepin-5-one

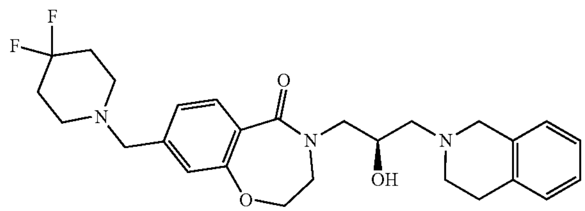 [SMILES: O=C1c2ccc(CN3CCC(F)(F)CC3)cc2OCCN1C[C@H](O)CN1CCc2ccccc2C1]

The title compound was synthesized in the same manner as in Example 29, except that 4,4-difluoropiperidine hydrochloride was used instead of 3-methoxyazetidine hydrochloride.

$^1$H NMR (400 MHz, Methanol-$d_4$) δ 7.68 (d, J=7.9 Hz, 1H), 7.19 (d, J=8.0 Hz, 1H), 7.15-7.03 (m, 4H), 4.49 (t, J=5.1 Hz, 2H), 4.29-4.19 (m, 1H), 4.00 (dd, J=13.8, 3.6 Hz, 1H), 3.77 (s, 2H), 3.72 (t, J=5.2 Hz, 2H), 3.60 (s, 2H), 3.46 (dd, J=13.8, 7.6 Hz, 1H), 2.99-2.84 (m, 4H), 2.71-2.64 (m, 2H), 2.59 (t, J=5.8 Hz, 4H), 2.01 (ddt, J=19.4, 12.4, 5.6 Hz, 4H).

Example 32: Synthesis of 4-[(2R)-3-(3,4-dihydro-1H-isoquinolin-2-yl)-2-hydroxy-propyl]-8-[(4-fluoro-1-piperidyl)methyl]-2,3-dihydro-1,4-benzoxazepin-5-one

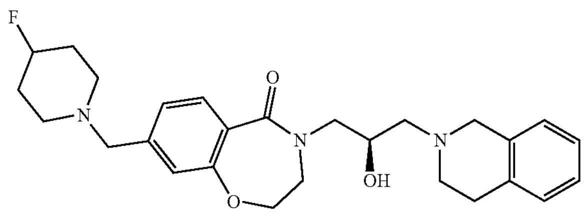 [SMILES: O=C1c2ccc(CN3CCC(F)CC3)cc2OCCN1C[C@H](O)CN1CCc2ccccc2C1]

The title compound was synthesized in the same manner as in Example 29, except that 4-fluoropiperidine hydrochloride was used instead of 3-methoxyazetidine hydrochloride.

$^1$H NMR (400 MHz, Methanol-$d_4$) δ 7.67 (d, J=7.9 Hz, 1H), 7.18 (d, J=8.0 Hz, 1H), 7.14-7.01 (m, 5H), 4.67 (d, J=48.8 Hz, 1H), 4.48 (t, J=5.1 Hz, 2H), 4.29-4.17 (m, 1H), 3.99 (dd, J=13.8, 3.6 Hz, 1H), 3.81-3.67 (m, 4H), 3.55 (s, 2H), 3.45 (dd, J=13.9, 7.7 Hz, 1H), 2.99-2.83 (m, 4H), 2.72-2.54 (m, 4H), 2.50-2.35 (m, 2H), 2.00-1.76 (m, 4H).

Example 33: Synthesis of 4-[(2R)-3-(3,4-dihydro-1H-isoquinolin-2-yl)-2-hydroxy-propyl]-8-[(3,5-dimethyl-1-piperidyl)methyl]-2,3-dihydro-1,4-benzoxazepin-5-one

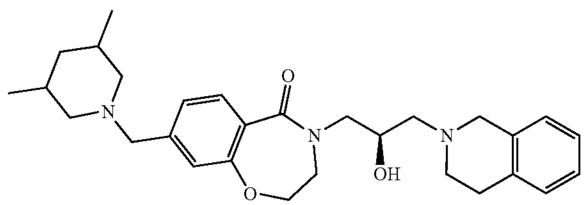 [SMILES: CC1CC(C)CN(Cc2ccc3c(c2)OCCN(C[C@H](O)CN2CCc4ccccc4C2)C3=O)C1]

The title compound was synthesized in the same manner as in Example 29, except that 3,5-dimethylpiperidine was used instead of 3-methoxyazetidine hydrochloride.

$^1$H NMR (400 MHz, Methanol-$d_4$) δ 7.68 (d, J=7.9 Hz, 1H), 7.17 (d, J=8.0 Hz, 1H), 7.16-6.95 (m, 4H), 4.49 (t, J=5.2 Hz, 2H), 4.25 (s, 1H), 4.00 (dd, J=14.0, 3.6 Hz, 1H), 3.75 (d, J=16.5 Hz, 2H), 3.55 (s, 2H), 3.46 (dd, J=13.7, 7.7 Hz, 1H), 3.01-2.81 (m, 5H), 2.67 (d, J=5.2 Hz, 2H), 1.75 (d, J=13.2 Hz, 3H), 1.55 (t, J=11.0 Hz, 2H), 0.87 (d, J=6.3 Hz, 6H).

Example 34: Synthesis of 8-(3,3a,4,5,6,6a-hexahydro-1H-cyclopenta[c]pyrrol-2-ylmethyl)-4-[(2R)-3-(3,4-dihydro-1H-isoquinolin-2-yl)-2-hydroxy-propyl]-2,3-dihydro-1,4-benzoxazepin-5-one

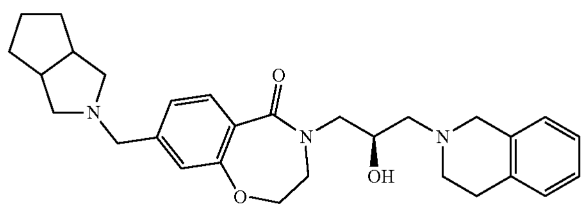 [SMILES: O=C1c2ccc(CN3CC4CCCC4C3)cc2OCCN1C[C@H](O)CN1CCc2ccccc2C1]

The title compound was synthesized in the same manner as in Example 29, except that 1,2,3,3a,4,5,6,6a-octahydrocyclopenta[c]pyrrole hydrochloride was used instead of 3-methoxyazetidine hydrochloride.

$^1$H NMR (400 MHz, Methanol-$d_4$) δ 7.67 (d, J=8.0 Hz, 1H), 7.18 (s, OH), 7.14-7.02 (m, 4H), 4.48 (t, J=5.1 Hz, 2H), 4.24 (s, 1H), 4.00 (dd, J=13.9, 3.6 Hz, 1H), 3.77 (s, 2H), 3.72 (t, J=5.1 Hz, 2H), 3.60 (s, 2H), 3.46 (dt, J=13.8, 7.6 Hz, 1H), 2.94 (d, J=5.5 Hz, 2H), 2.89 (d, J=6.2 Hz, 3H), 2.76-2.59 (m, 4H), 2.08 (dd, J=9.4, 5.4 Hz, 2H), 1.62 (d, J=41.3 Hz, 4H), 1.47 (s, 2H).

Example 35: Synthesis of 4-[(2R)-3-(3,4-dihydro-1H-isoquinolin-2-yl)-2-hydroxy-propyl]-8-[(3-hydroxypyrrolidin-1-yl)methyl]-2,3-dihydro-1,4-benzoxazepin-5-one

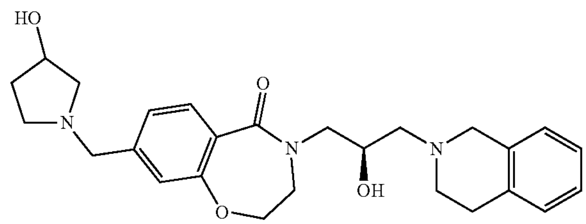 [SMILES: O=C1c2ccc(CN3CCC(O)C3)cc2OCCN1C[C@H](O)CN1CCc2ccccc2C1]

The title compound was synthesized in the same manner as in Example 29, except that pyrrolidin-3-ol was used instead of 3-methoxyazetidine hydrochloride.

$^1$H NMR (400 MHz, Methanol-$d_4$) δ 7.67 (d, J=7.9 Hz, 1H), 7.19 (d, J=8.0 Hz, 1H), 7.12 (d, J=4.2 Hz, 3H), 7.08 (s, 2H), 4.48 (t, J=5.2 Hz, 2H), 4.37 (s, 1H), 4.24 (s, 1H), 4.00 (dd, J=13.7, 3.6 Hz, 1H), 3.77 (s, 2H), 3.75-3.68 (m, 3H), 3.65 (d, J=13.0 Hz, 1H), 3.46 (dt, J=13.8, 7.4 Hz, 1H), 2.94 (d, J=5.6 Hz, 2H), 2.89 (d, J=5.4 Hz, 2H), 2.84-2.74 (m, 2H), 2.75-2.63 (m, 2H), 2.61-2.48 (m, 2H), 2.16 (dt, J=14.3, 7.0 Hz, 1H).

Example 36: Synthesis of 4-[(2R)-3-(3,4-dihydro-1H-isoquinolin-2-yl)-2-hydroxy-propyl]-8-[[(2R)-2-methylpyrrolidin-1-yl]methyl]-2,3-dihydro-1,4-benzoxazepin-5-one

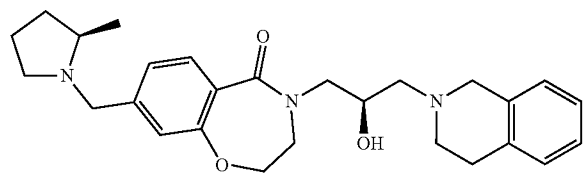 [SMILES: C[C@@H]1CCCN1Cc1ccc2c(c1)OCCN(C[C@H](O)CN1CCc3ccccc3C1)C2=O]

The title compound was synthesized in the same manner as in Example 29, except that (2R)-2-methylpyrrolidine was used instead of 3-methoxyazetidine hydrochloride.

$^1$H NMR (400 MHz, Methanol-$d_4$) δ 7.67 (d, J=7.9 Hz, 1H), 7.19 (d, J=8.0 Hz, 1H), 7.12 (d, J=4.3 Hz, 3H), 7.07 (s, 2H), 4.49 (t, J=5.2 Hz, 2H), 4.24 (s, OH), 4.11-3.93 (m, 2H), 3.76 (s, 2H), 3.72 (t, J=5.3 Hz, 2H), 3.46 (dt, J=13.9, 7.7 Hz, 1H), 3.24 (d, J=12.9 Hz, 1H), 2.94 (d, J=5.7 Hz, 3H), 2.89 (d, J=5.7 Hz, 2H), 2.71-2.62 (m, 2H), 2.57-2.45 (m, 1H), 2.24 (d, J=9.2 Hz, 1H), 2.03 (dq, J=14.6, 7.3 Hz, 1H), 1.74 (p, J=8.1 Hz, 2H), 1.49 (dt, J=17.6, 8.9 Hz, 1H), 1.21 (d, J=6.1 Hz, 3H).

Example 37: Synthesis of 4-[(2R)-3-(3,4-dihydro-1H-isoquinolin-2-yl)-2-hydroxy-propyl]-8-[[3-(hydroxymethyl)-1-piperidyl]methyl]-2,3-dihydro-1,4-benzoxazepin-5-one

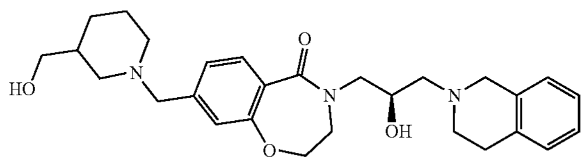 [SMILES: O=C1c2ccc(CN3CCCC(CO)C3)cc2OCCN1C[C@H](O)CN1CCc2ccccc2C1]

The title compound was synthesized in the same manner as in Example 29, except that 3-piperidylmethanol was used instead of 3-methoxyazetidine hydrochloride.

$^1$H NMR (400 MHz, Methanol-$d_4$) δ 7.67 (d, J=8.0 Hz, 1H), 7.18 (d, J=8.0 Hz, 1H), 7.12 (d, J=4.2 Hz, 3H), 7.06 (s, 2H), 4.49 (t, J=5.1 Hz, 2H), 4.24 (s, 1H), 3.99 (dd, J=14.0, 3.6 Hz, 1H), 3.77 (s, 2H), 3.72 (t, J=5.0 Hz, 2H), 3.65-3.53 (m, 2H), 3.54-3.41 (m, 1H), 3.00 (d, J=7.1 Hz, 1H), 2.94 (d, J=5.4 Hz, 2H), 2.88 (t, J=10.9 Hz, 3H), 2.73-2.61 (m, 2H), 2.16-1.95 (m, 1H), 1.76 (d, J=18.7 Hz, 2H), 1.63 (d, J=12.4 Hz, 1H).

Example 38: Synthesis of 4-[(2R)-3-(3,4-dihydro-1H-isoquinolin-2-yl)-2-hydroxy-propyl]-8-[(4-methoxy-1-piperidyl)methyl]-2,3-dihydro-1,4-benzoxazepin-5-one

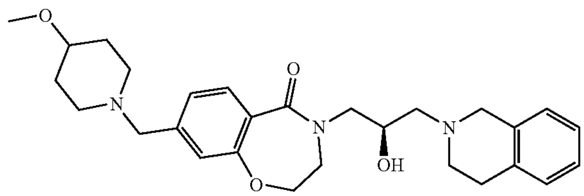 [SMILES: COC1CCN(Cc2ccc3c(c2)OCCN(C[C@H](O)CN2CCc4ccccc4C2)C3=O)CC1]

The title compound was synthesized in the same manner as in Example 29, except that 4-methoxypiperidine was used instead of 3-methoxyazetidine hydrochloride.

$^1$H NMR (400 MHz, Methanol-$d_4$) δ 7.67 (d, J=8.0 Hz, 1H), 7.17 (d, J=8.0 Hz, 1H), 7.15-7.01 (m, 5H), 4.49 (t, J=5.2 Hz, 2H), 4.31-4.19 (m, 1H), 4.00 (dd, J=13.8, 3.6 Hz, 1H), 3.77 (s, 2H), 3.72 (t, J=4.8 Hz, 2H), 3.55 (s, 2H), 3.46 (dd, J=13.8, 7.7 Hz, 1H), 3.34 (s, 3H), 3.31-3.24 (m, 1H), 2.98-2.85 (m, 4H), 2.76 (dd, J=11.1, 3.9 Hz, 2H), 2.71-2.62 (m, 2H), 2.25 (t, J=10.8 Hz, 2H), 1.99-1.87 (m, 2H), 1.67-1.52 (m, 2H).

Example 39: Synthesis of 4-[(2R)-3-(3,4-dihydro-1H-isoquinolin-2-yl)-2-hydroxy-propyl]-8-(1,4-oxazepan-4-ylmethyl)-2,3-dihydro-1,4-benzoxazepin-5-one

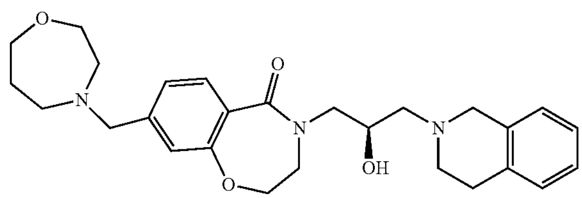 [SMILES: O=C1c2ccc(CN3CCCOCC3)cc2OCCN1C[C@H](O)CN1CCc2ccccc2C1]

The title compound was synthesized in the same manner as in Example 29, except that 1,4-oxazepane hydrochloride was used instead of 3-methoxyazetidine hydrochloride.

$^1$H NMR (400 MHz, Methanol-$d_4$) δ 7.67 (d, J=8.0 Hz, 1H), 7.21 (d, J=8.0 Hz, 1H), 7.15-7.03 (m, 5H), 4.48 (t, J=5.1 Hz, 2H), 4.29-4.19 (m, 1H), 3.99 (dd, J=13.7, 3.6 Hz, 1H), 3.83 (t, J=6.1 Hz, 2H), 3.79-3.65 (m, 8H), 3.46 (dd, J=13.8, 7.6 Hz, 1H), 2.98-2.84 (m, 4H), 2.78-2.68 (m, 4H), 2.69-2.61 (m, 2H), 1.93 (p, J=5.8 Hz, 2H).

Example 40: Synthesis of 4-[(2R)-3-(3,4-dihydro-1H-isoquinolin-2-yl)-2-hydroxy-propyl]-8-[(3-hydroxy-3-methyl-pyrrolidin-1-yl)methyl]-2,3-dihydro-1,4-benzoxazepin-5-one

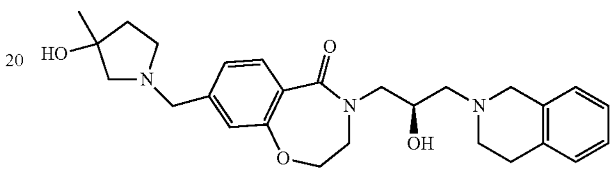

The title compound was synthesized in the same manner as in Example 29, except that 3-methylpyrrolidin-3-ol was used instead of 3-methoxyazetidine hydrochloride.

$^1$H NMR (400 MHz, Methanol-$d_4$) δ 7.67 (d, J=8.0 Hz, 1H), 7.20 (d, J=8.0 Hz, 1H), 7.16-7.01 (m, 5H), 4.48 (t, J=5.1 Hz, 2H), 4.30-4.19 (m, 1H), 4.00 (dd, J=14.0, 3.6 Hz, 1H), 3.77 (s, 2H), 3.75-3.61 (m, 4H), 3.46 (dd, J=13.9, 7.6 Hz, 1H), 2.94 (d, J=5.6 Hz, 2H), 2.92-2.80 (m, 4H), 2.73-2.60 (m, 4H), 2.55 (d, J=10.1 Hz, 1H), 1.95-1.85 (m, 2H), 1.36 (s, 3H).

Example 41: Synthesis of 4-[(2R)-3-(3,4-dihydro-1H-isoquinolin-2-yl)-2-hydroxy-propyl]-8-[[2-(hydroxymethyl)-1-piperidyl]methyl]-2,3-dihydro-1,4-benzoxazepin-5-one

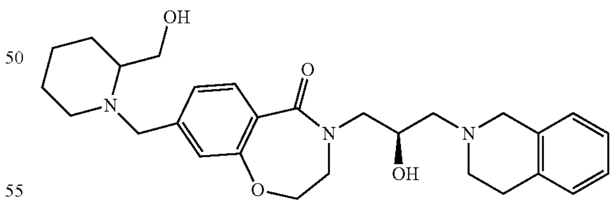

The title compound was synthesized in the same manner as in Example 29, except that morpholin-3-ylmethanol was used instead of 3-methoxyazetidine hydrochloride.

$^1$H NMR (400 MHz, Methanol-$d_4$) δ 7.66 (d, J=7.9 Hz, 1H), 7.21 (d, J=8.1 Hz, 1H), 7.15-7.04 (m, 5H), 4.48 (t, J=5.1 Hz, 2H), 4.29-4.19 (m, 1H), 4.14 (d, J=13.3 Hz, 1H), 3.99 (dd, J=14.0, 3.5 Hz, 1H), 3.91-3.84 (m, 1H), 3.83-3.75 (m, 3H), 3.75-3.63 (m, 4H), 3.64-3.50 (m, 2H), 3.46 (dd, J=13.8, 7.6 Hz, 1H), 3.39 (d, J=13.9 Hz, 1H), 2.99-2.85 (m, 4H), 2.72-2.63 (m, 3H), 2.53 (s, 1H), 2.29 (d, J=9.3 Hz, 1H).

Example 42: Synthesis of 8-[(3,3-difluoro-1-piperidyl)methyl]-4-[(2R)-3-(3,4-dihydro-1H-isoquinolin-2-yl)-2-hydroxy-propyl]-2,3-dihydro-1,4-benzoxazepin-5-one

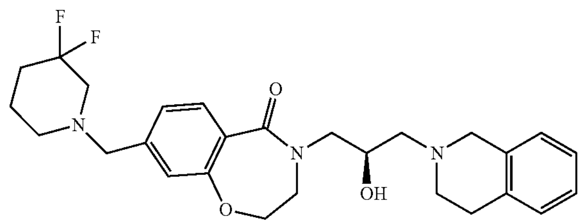 [SMILES: O=C1c2ccc(CN3CCCC(F)(F)C3)cc2OCCN1C[C@H](O)CN1CCc2ccccc2C1]

The title compound was synthesized in the same manner as in Example 29, except that 3,3-difluoropiperidine hydrochloride was used instead of 3-methoxyazetidine hydrochloride.

$^1$H NMR (400 MHz, Methanol-$d_4$) δ 7.68 (d, J=7.9 Hz, 1H), 7.18 (d, J=8.0 Hz, 1H), 7.09 (dd, J=21.4, 4.6 Hz, 4H), 4.49 (t, J=5.2 Hz, 2H), 4.31-4.20 (m, 1H), 3.99 (dd, J=14.0, 3.6 Hz, 1H), 3.78 (s, 2H), 3.72 (t, J=5.3 Hz, 2H), 3.63 (s, 2H), 3.46 (dd, J=13.9, 7.9 Hz, 1H), 3.00-2.83 (m, 4H), 2.74-2.58 (m, 4H), 2.55-2.44 (m, 2H), 1.97-1.83 (m, 2H), 1.82-1.72 (m, 2H).

Example 43: Synthesis of 4-[(2R)-3-(3,4-dihydro-1H-isoquinolin-2-yl)-2-hydroxy-propyl]-8-[(3-fluoro-1-piperidyl)meth yl]-2,3-dihydro-1,4-benzoxazepin-5-one

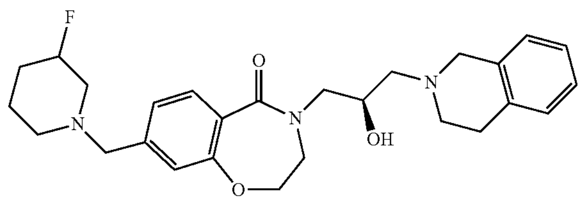 [SMILES: O=C1c2ccc(CN3CCCC(F)C3)cc2OCCN1C[C@H](O)CN1CCc2ccccc2C1]

The title compound was synthesized in the same manner as in Example 29, except that 3-fluoropiperidine hydrochloride was used instead of 3-methoxyazetidine hydrochloride.

$^1$H NMR (400 MHz, Methanol-$d_4$) δ 7.67 (d, J=7.9 Hz, 1H), 7.18 (d, J=8.0 Hz, 1H), 7.15-7.02 (m, 5H), 4.63 (d, J=48.0 Hz, 1H), 4.49 (t, J=5.1 Hz, 2H), 4.30-4.19 (m, 1H), 4.00 (dd, J=14.0, 3.6 Hz, 1H), 3.77 (s, 2H), 3.72 (t, J=5.3 Hz, 2H), 3.58 (s, 2H), 3.46 (dd, J=13.9, 7.7 Hz, 1H), 3.00-2.82 (m, 4H), 2.81-2.58 (m, 3H), 2.55-2.41 (m, 2H), 2.38 (t, J=9.9 Hz, 1H), 1.94-1.78 (m, 2H), 1.70-1.51 (m, 2H).

Example 44: Synthesis of 4-[(2R)-3-(3,4-dihydro-1H-isoquinolin-2-yl)-2-hydroxy-propyl]-8-[(3-hydroxy-1-piperidyl)methyl]-2,3-dihydro-1,4-benzoxazepin-5-one

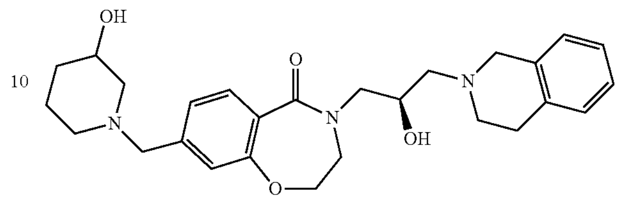

The title compound was synthesized in the same manner as in Example 29, except that piperidin-3-ol hydrochloride was used instead of 3-methoxyazetidine hydrochloride.

$^1$H NMR (400 MHz, Methanol-$d_4$) δ 7.67 (d, J=8.0 Hz, 1H), 7.18 (d, J=8.0 Hz, 1H), 7.16-7.01 (m, 5H), 4.48 (t, J=5.1 Hz, 2H), 4.30-4.19 (m, 1H), 3.99 (dd, J=13.7, 3.6 Hz, 1H), 3.78 (s, 2H), 3.75-3.63 (m, 3H), 3.63-3.50 (m, 2H), 3.46 (dd, J=13.9, 7.7 Hz, 1H), 3.00-2.82 (m, 5H), 2.77-2.61 (m, 3H), 2.12-2.04 (m, 1H), 1.99-1.88 (m, 2H), 1.82-1.70 (m, 1H), 1.65-1.50 (m, 1H).

Example 45: Synthesis of 4-[(2R)-3-(3,4-dihydro-1H-isoquinolin-2-yl)-2-hydroxy-propyl]-8-[(4-hydroxy-1-piperidyl)methyl]-2,3-dihydro-1,4-benzoxazepin-5-one

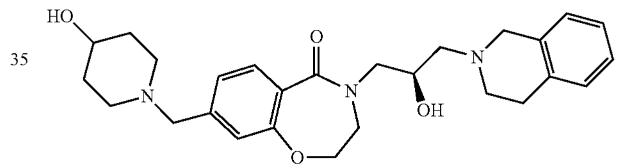

The title compound was synthesized in the same manner as in Example 29, except that piperidin-4-ol was used instead of 3-methoxyazetidine hydrochloride.

$^1$H NMR (400 MHz, Methanol-$d_4$) δ 7.67 (d, J=7.9 Hz, 1H), 7.18 (d, J=8.0 Hz, 1H), 7.15-7.03 (m, 5H), 4.49 (t, J=5.0 Hz, 2H), 4.29-4.20 (m, 1H), 4.02-3.96 (m, 1H), 3.77 (s, 2H), 3.76-3.70 (m, 2H), 3.68-3.59 (m, 1H), 3.55 (s, 2H), 3.46 (dd, J=13.8, 7.5 Hz, 1H), 2.98-2.86 (m, 4H), 2.86-2.76 (m, 2H), 2.70-2.63 (m, 2H), 2.28-2.15 (m, 2H), 1.92-1.82 (m, 2H), 1.66-1.53 (m, 2H).

Example 46: Synthesis of 4-[(2R)-3-(3,4-dihydro-1H-isoquinolin-2-yl)-2-hydroxy-propyl]-8-[[(2S)-2-(hydroxymethyl)pyrrolidin-1-yl]methyl]-2,3-dihydro-1,4-benzoxazepin-5-one

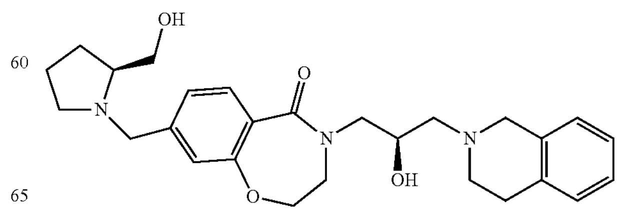

The title compound was synthesized in the same manner as in Example 29, except that [(2S)-pyrrolidin-2-yl]methanol was used instead of 3-methoxyazetidine hydrochloride.

$^1$H NMR (400 MHz, Methanol-$d_4$) δ 7.66 (d, J=7.9 Hz, 1H), 7.21 (d, J=8.0 Hz, 1H), 7.16-7.03 (m, 5H), 4.48 (t, J=5.1 Hz, 2H), 4.29-4.19 (m, 1H), 4.13 (d, J=12.8 Hz, 1H), 4.00 (dd, J=14.1, 3.6 Hz, 1H), 3.77 (s, 2H), 3.72 (t, J=5.4 Hz, 2H), 3.60 (dd, J=11.1, 4.6 Hz, 1H), 3.56-3.41 (m, 3H), 3.02-2.85 (m, 5H), 2.79-2.62 (m, 3H), 2.39-2.25 (m, 1H), 2.03-1.93 (m, 1H), 1.82-1.66 (m, 3H).

Example 47: Synthesis of 4-[(2R)-3-(3,4-dihydro-1H-isoquinolin-2-yl)-2-hydroxy-propyl]-8-[[(2R)-2-(hydroxymethyl)pyrrolidin-1-yl]methyl]-2,3-dihydro-1,4-benzoxazepin-5-one

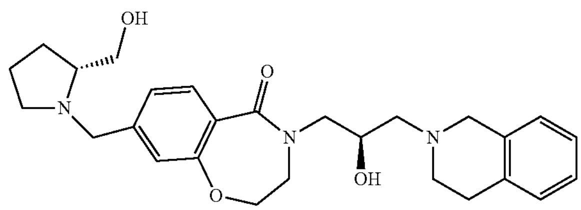 [SMILES: O=C1c2ccc(CN3CCC[C@@H]3CO)cc2OCCN1C[C@H](O)CN1CCc2ccccc2C1]

The title compound was synthesized in the same manner as in Example 29, except that [(2R)-pyrrolidin-2-yl]methanol was used instead of 3-methoxyazetidine hydrochloride.

$^1$H NMR (400 MHz, Methanol-$d_4$) δ 7.66 (d, J=8.0 Hz, 1H), 7.21 (d, J=8.0 Hz, 1H), 7.17-7.02 (m, 5H), 4.48 (t, J=5.2 Hz, 2H), 4.24 (s, 1H), 4.14 (d, J=13.2 Hz, 1H), 3.99 (dd, J=13.8, 3.5 Hz, 1H), 3.77 (s, 2H), 3.72 (t, J=4.9 Hz, 2H), 3.60 (dd, J=11.0, 4.6 Hz, 1H), 3.57-3.41 (m, 3H), 3.02-2.84 (m, 5H), 2.79-2.68 (m, 1H), 2.69-2.61 (m, 2H), 2.38-2.27 (m, 1H), 2.05-1.92 (m, 1H), 1.83-1.66 (m, 3H).

Example 48: Synthesis of 4-[(2R)-3-(3,4-dihydro-1H-isoquinolin-2-yl)-2-hydroxy-propyl]-8-[(2-ethylpyrrolidin-1-yl)methyl]-2,3-dihydro-1,4-benzoxazepin-5-one

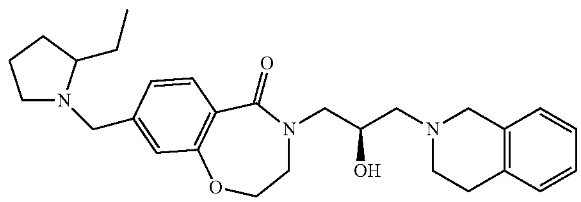 [SMILES: CCC1CCCN1Cc1ccc2c(c1)OCCN(C[C@H](O)CN1CCc3ccccc3C1)C2=O]

The title compound was synthesized in the same manner as in Example 29, except that 2-ethylpyrrolidine hydrochloride was used instead of 3-methoxyazetidine hydrochloride.

$^1$H NMR (400 MHz, Methanol-$d_4$) δ 7.67 (d, J=8.0 Hz, 1H), 7.18 (d, J=8.0 Hz, 1H), 7.16-7.02 (m, 5H), 4.48 (t, J=5.2 Hz, 2H), 4.29-4.19 (m, 1H), 4.07 (d, J=13.2 Hz, 1H), 4.00 (dd, J=14.1, 3.5 Hz, 1H), 3.76 (s, 2H), 3.74-3.67 (m, 2H), 3.45 (dd, J=13.9, 7.7 Hz, 1H), 3.25 (d, J=12.9 Hz, 1H), 2.99-2.81 (m, 5H), 2.70-2.60 (m, 2H), 2.41-2.29 (m, 1H), 2.27-2.15 (m, 1H), 2.09-1.99 (m, 1H), 1.91-1.80 (m, 1H), 1.79-1.65 (m, 2H), 1.57-1.45 (m, 1H), 1.43-1.26 (m, 2H), 0.96 (t, J=7.5 Hz, 3H).

Example 49: Synthesis of 4-[(2R)-3-(3,4-dihydro-1H-isoquinolin-2-yl)-2-hydroxy-propyl]-8-[[(2S)-2-(methoxymethyl)pyrrolidin-1-yl]methyl]-2,3-dihydro-1,4-benzoxazepin-5-one

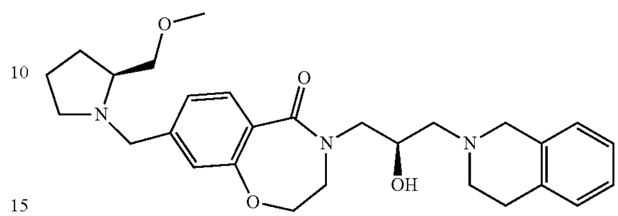

The title compound was synthesized in the same manner as in Example 29, except that (2S)-2-(methoxymethyl)pyrrolidine was used instead of 3-methoxyazetidine hydrochloride.

$^1$H NMR (400 MHz, Methanol-$d_4$) δ 7.66 (d, J=7.9 Hz, 1H), 7.19 (d, J=8.0 Hz, 1H), 7.16-7.03 (m, 5H), 4.48 (t, J=5.3 Hz, 2H), 4.24 (dd, J=9.6, 5.5 Hz, 1H), 4.16 (d, J=13.1 Hz, 1H), 4.00 (d, J=11.2 Hz, 1H), 3.77 (s, 2H), 3.72 (t, J=6.2 Hz, 2H), 3.52-3.42 (m, 3H), 3.43-3.36 (m, 1H), 3.36 (s, 3H), 2.99-2.85 (m, 5H), 2.84-2.74 (m, 1H), 2.71-2.60 (m, 2H), 2.35-2.24 (m, 1H), 2.02-1.88 (m, 1H), 1.80-1.69 (m, 2H), 1.67-1.57 (m, 1H).

Example 50: Synthesis of 4-[(2R)-3-(3,4-dihydro-1H-isoquinolin-2-yl)-2-hydroxy-propyl]-8-[[(2R)-2-(methoxymethyl)pyrrolidin-1-yl]methyl]-2,3-dihydro-1,4-benzoxazepin-5-one

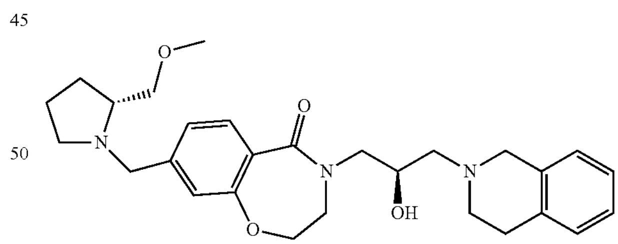

The title compound was synthesized in the same manner as in Example 29, except that (2R)-2-(methoxymethyl) pyrrolidine was used instead of 3-methoxyazetidine hydrochloride.

$^1$H NMR (400 MHz, Methanol-$d_4$) δ 7.66 (d, J=7.9 Hz, 1H), 7.19 (d, J=7.9 Hz, 1H), 7.15-7.02 (m, 5H), 4.48 (t, J=5.2 Hz, 2H), 4.30-4.19 (m, 1H), 4.15 (d, J=13.4 Hz, 1H), 4.00 (dd, J=13.9, 3.5 Hz, 1H), 3.76 (s, 2H), 3.72 (t, J=5.2 Hz, 2H), 3.51-3.41 (m, 3H), 3.41-3.37 (m, 1H), 3.36 (s, 3H), 2.98-2.84 (m, 5H), 2.83-2.74 (m, 1H), 2.71-2.60 (m, 2H), 2.35-2.22 (m, 1H), 2.02-1.89 (m, 1H), 1.80-1.68 (m, 2H), 1.68-1.54 (m, 1H).

Example 51: Synthesis of 4-[(2R)-3-(3,4-dihydro-1H-isoquinolin-2-yl)-2-hydroxy-propyl]-8-[(3-fluoropyrrolidin-1-yl)methyl]-2,3-dihydro-1,4-benzoxazepin-5-one

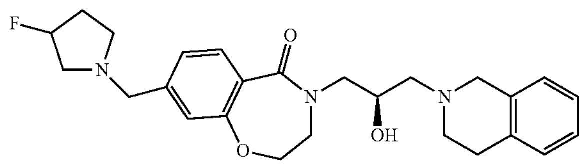 [SMILES: O=C1c2ccc(CN3CCC(F)C3)cc2OCCN1C[C@H](O)CN1CCc2ccccc2C1]

The title compound was synthesized in the same manner as in Example 29, except that 3-fluoropyrrolidine hydrochloride was used instead of 3-methoxyazetidine hydrochloride.

$^1$H NMR (400 MHz, Methanol-$d_4$) δ 7.68 (d, J=8.0 Hz, 1H), 7.20 (d, J=8.0 Hz, 1H), 7.16-7.04 (m, 5H), 5.30-5.22 (m, 1H), 5.16-5.08 (m, 1H), 4.49 (t, J=5.2 Hz, 2H), 4.30-4.19 (m, 1H), 4.00 (dd, J=13.7, 3.6 Hz, 1H), 3.77 (s, 2H), 3.74-3.62 (m, 4H), 3.46 (dd, J=13.9, 7.7 Hz, 1H), 2.98-2.89 (m, 4H), 2.71-2.62 (m, 2H), 2.47 (q, J=8.0 Hz, 1H), 2.32-2.13 (m, 2H), 2.10-1.91 (m, 2H).

Example 52: Synthesis of 8-[(3,3-difluoropyrrolidin-1-yl)methyl]-4-[(2R)-3-(3,4-dihydro-1H-isoquinolin-2-yl)-2-hydroxy-propyl]-2,3-dihydro-1,4-benzoxazepin-5-one

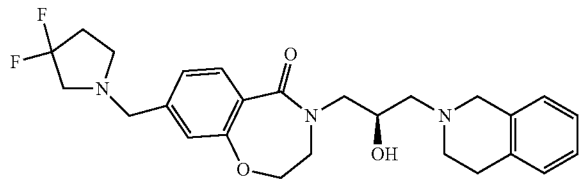 [SMILES: O=C1c2ccc(CN3CCC(F)(F)C3)cc2OCCN1C[C@H](O)CN1CCc2ccccc2C1]

The title compound was synthesized in the same manner as in Example 29, except that 3,3-difluoropyrrolidine was used instead of 3-methoxyazetidine hydrochloride.

$^1$H NMR (400 MHz, Methanol-$d_4$) δ 7.68 (d, J=7.9 Hz, 1H), 7.19 (d, J=8.0 Hz, 1H), 7.15-7.02 (m, 5H), 4.49 (t, J=5.0 Hz, 2H), 4.29-4.19 (m, 1H), 4.00 (dd, J=14.0, 3.6 Hz, 1H), 3.77 (s, 2H), 3.72 (t, J=4.9 Hz, 2H), 3.68 (s, 2H), 3.46 (dd, J=14.0, 7.7 Hz, 1H), 3.00-2.91 (m, 3H), 2.92-2.85 (m, 3H), 2.79 (t, J=7.0 Hz, 2H), 2.71-2.62 (m, 2H), 2.36-2.23 (m, 2H).

Example 53: Synthesis of 8-[(4-acetylpiperazin-1-yl)methyl]-4-[(2R)-3-(3,4-dihydro-1H-isoquinolin-2-yl)-2-hydroxy-propyl]-2,3-dihydro-1,4-benzoxazepin-5-one

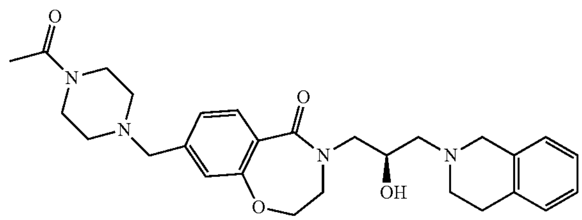 [SMILES: CC(=O)N1CCN(Cc2ccc3c(c2)OCCN(C[C@H](O)CN2CCc4ccccc4C2)C3=O)CC1]

The title compound was synthesized in the same manner as in Example 29, except that 1-piperazin-1-yl-ethanone was used instead of 3-methoxyazetidine hydrochloride.

$^1$H NMR (400 MHz, Methanol-$d_4$) δ 7.68 (d, J=7.9 Hz, 1H), 7.20 (d, J=8.0 Hz, 1H), 7.13 (d, J=4.4 Hz, 3H), 7.07 (s, 2H), 4.49 (t, J=5.1 Hz, 2H), 4.25 (s, 1H), 3.99 (dd, J=13.9, 3.7 Hz, 1H), 3.79 (s, 2H), 3.72 (t, J=5.3 Hz, 2H), 3.59 (dq, J=10.4, 5.0 Hz, 7H), 3.47 (dd, J=13.9, 7.6 Hz, 1H), 2.93 (dd, J=14.0, 4.7 Hz, 4H), 2.74-2.63 (m, 2H), 2.48 (dt, J=19.1, 5.1 Hz, 5H), 2.11 (s, 3H).

Example 54: Synthesis of 4-[(2R)-3-(3,4-dihydro-1H-isoquinolin-2-yl)-2-hydroxy-propyl]-8-[(4-methylpiperazin-1-yl)methyl]-2,3-dihydro-1,4-benzoxazepin-5-one

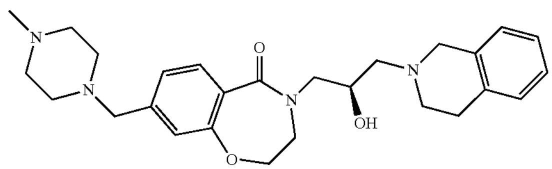 [SMILES: CN1CCN(Cc2ccc3c(c2)OCCN(C[C@H](O)CN2CCc4ccccc4C2)C3=O)CC1]

Example 54-1: Synthesis of tert-butyl 4-[[4-[(2R)-3-(3,4-dihydro-1H-isoquinolin-2-yl)-2-hydroxy-propyl]-5-oxo-2,3-dihydro-1,4-benzoxazepin-8-yl]methyl]piperazin-1-carboxylate The title compound was synthesized in the same manner as in Example 29, except that tert-butyl piperazin-1-carboxylate was used instead of 3-methoxyazetidine hydrochloride.

Example 54-2: Synthesis of 4-[(2R)-3-(3,4-dihydro-1H-isoquinolin-2-yl)-2-hydroxy-propyl]-8-(piperazin-1-ylmethyl)-2,3-dihydro-1,4-benzoxazepin-5-one dihydrochloride Tert-butyl 4-[[4-[(2R)-3-(3,4-dihydro-1H-isoquinolin-2-yl)-2-hydroxy-propyl]-5-oxo-2,3-dihydro-1,4-benzoxazepin-8-yl]methyl]piperazin-1-carboxylate obtained in Example 54-1 was dissolved in methanol, and 4 M hydrochloric acid solution dissolved in 1,4-dioxane was slowly added thereto. The reaction solution was stirred at room temperature, diluted with diethyl ether, and filtered to obtain the title compound as a white solid.

Example 54-3: Synthesis of 4-[(2R)-3-(3,4-dihydro-1H-isoquinolin-2-yl)-2-hydroxy-propyl]-8-[(4-methylpiperazin-1-yl)methyl]-2,3-dihydro-1,4-benzoxazepin-5-one The obtained hydrochloride was dissolved in methanol, and an excess of paraformaldehyde and sodium cyanoborohydride were added thereto, followed by stirring at room temperature for 12 hours. The reaction was terminated by adding a saturated aqueous ammonium chloride solution to the reaction solution, and 1 N sodium hydroxide aqueous solution was added for basification. The mixture was extracted with ethyl acetate 3 times and dried over anhydrous sodium sulfate. The pale yellow oily liquid obtained by removing the solvent by evaporation under reduced pressure was purified by flash chromatography to obtain the title compound.

$^1$H NMR (400 MHz, Methanol-$d_4$) δ 7.67 (d, J=7.9 Hz, 1H), 7.18 (d, J=8.0 Hz, 1H), 7.09 (dd, J=23.3, 5.1 Hz, 5H), 4.48 (t, J=5.3 Hz, 2H), 4.28-4.19 (m, 1H), 4.00 (d, J=13.6 Hz, 1H), 3.79-3.67 (m, 4H), 3.56 (s, 2H), 3.45 (dd, J=13.8, 7.6 Hz, 1H), 2.98-2.84 (m, 4H), 2.66 (d, J=6.5 Hz, 2H), 2.53 (bs, 6H), 2.31 (s, 3H).

Example 55: Synthesis of 4-[(2R)-3-(3,4-dihydro-1H-isoquinolin-2-yl)-2-hydroxy-propyl]-8-(2-oxa-5-azabicyclo[2.2.1]heptan-5-ylmethyl)-2,3-dihydro-1,4-benzoxazepin-5-one

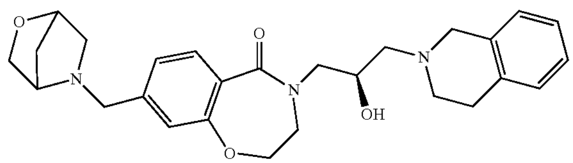 [SMILES: O=C1c2ccc(CN3CC4CC3CO4)cc2OCCN1C[C@H](O)CN1CCc2ccccc2C1]

The title compound was synthesized in the same manner as in Example 29, except that 2-oxa-5-azabicyclo[2.2.1]heptane hydrochloride was used instead of 3-methoxyazetidine hydrochloride.

$^1$H NMR (400 MHz, Methanol-$d_4$) δ 7.67 (d, J=8.0 Hz, 1H), 7.21 (d, J=8.0 Hz, 1H), 7.16-7.02 (m, 5H), 4.47 (dd, J=11.9, 6.9 Hz, 3H), 4.29-4.19 (m, 2H), 4.11 (d, J=7.8 Hz, 1H), 3.99 (dd, J=14.0, 3.6 Hz, 1H), 3.81 (d, J=6.1 Hz, 2H), 3.77 (s, 2H), 3.72 (t, J=5.3 Hz, 2H), 3.65 (d, J=7.9 Hz, 1H), 3.54 (s, 1H), 3.46 (dd, J=13.9, 7.6 Hz, 1H), 2.98-2.83 (m, 5H), 2.73-2.59 (m, 3H), 2.00-1.93 (m, 1H), 1.76 (d, J=10.2 Hz, 1H).

Example 56: Synthesis of 4-[(2R)-3-(3,4-dihydro-1H-isoquinolin-2-yl)-2-hydroxy-propyl]-8-(3-pyridylmethoxy)-2,3-dihydro-1,4-benzoxazepin-5-one

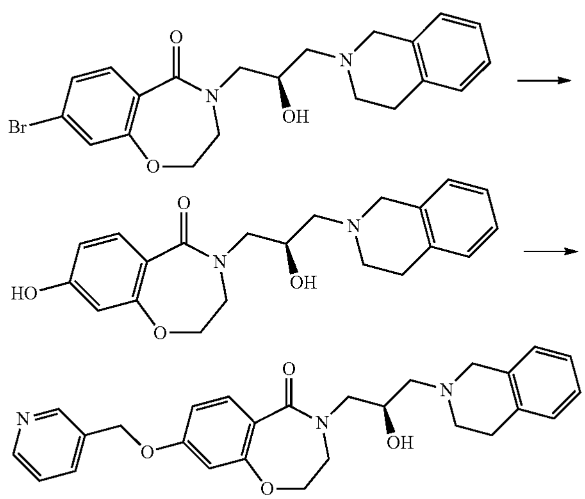

Example 56-1: Synthesis of 4-[(2R)-3-(3,4-dihydro-1H-isoquinolin-2-yl)-2-hydroxy-propyl]-8-hydroxy-2,3-dihydro-1,4-benzoxazepin-5-one 8-Bromo-4-[(2R)-3-(3,4-dihydro-1H-isoquinolin-2-yl)-2-hydroxy-propyl]-2,3-dihydro-1,4-benzoxazepin-5-one (9.0 g, 21 mmol), hydroxypotassium (4.68 g, 83 mmol), $Pd(dba)_2$ (180 mg, 0.315 mmol) and tBuXPhos (270 mg, 0.63 mmol) were dissolved in 80 mL of 1,4-dioxane:distilled water (=1:1) solution, and a reaction vessel was charged with nitrogen. The reaction solution was stirred at 100° C. for 3 hours, and a hydrochloric acid aqueous solution was added under an ice bath to acidify the reaction solution to pH~1. The aqueous layer was washed with ethyl acetate 3 times, and sodium hydroxide aqueous solution was added under an ice bath to basify to pH 14, followed by extraction with ethyl acetate 3 times. The combined organic layers were dried over anhydrous magnesium sulfate and concentrated under reduced pressure to obtain the title compound as a white solid without additional purification.

Example 56-2: Synthesis of 4-[(2R)-3-(3,4-dihydro-1H-isoquinolin-2-yl)-2-hydroxy-propyl]-8-(3-pyridylmethoxy)-2,3-dihydro-1,4-benzoxazepin-5-one 4-[(2R)-3-(3,4-dihydro-1H-isoquinolin-2-yl)-2-hydroxy-propyl]-8-hydroxy-2,3-dihydro-1,4-benzoxazepin-5-one (100 mg, 0.27 mmol) obtained in Example 56-1 was dissolved in dimethylformamide, and 60% sodium hydride (33 mg, 0.81 mmol) and 3-(chloromethyl)pyridine hydrochloride (66 mg, 0.41 mmol) were added thereto at room temperature. The reaction solution was stirred at room temperature for 3 hours and extracted by adding ethyl acetate and distilled water. The oily liquid obtained by drying the organic layer over anhydrous sodium sulfate and concentrated under reduced pressure was purified by flash chromatography to obtain the title compound (64 mg) as a sticky white solid.

$^1$H NMR (400 MHz, Methanol-$d_4$) δ 8.66 (s, 1H), 8.54 (d, J=4.9 Hz, 1H), 7.98 (d, J=8.0 Hz, 1H), 7.71 (d, J=8.8 Hz, 1H), 7.50 (t, J=6.6 Hz, 1H), 7.18-7.02 (m, 4H), 6.86 (d, J=8.8 Hz, 1H), 6.70 (d, J=2.9 Hz, 1H), 5.22 (s, 2H), 4.49 (t, J=5.0 Hz, 2H), 4.29-4.17 (m, 1H), 3.98 (dd, J=13.8, 3.2 Hz, 1H), 3.83-3.67 (m, 4H), 3.43 (dd, J=13.9, 7.6 Hz, 1H), 2.99-2.83 (m, 4H), 2.71-2.59 (m, 2H).

Example 57: Synthesis of 4-[(2R)-3-(3,4-dihydro-1H-isoquinolin-2-yl)-2-hydroxy-propyl]-8-(4-pyridylmethoxy)-2,3-dihydro-1,4-benzoxazepin-5-one

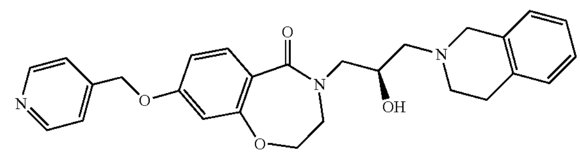 [SMILES: O=C1c2ccc(OCc3ccncc3)cc2OCCN1C[C@H](O)CN1CCc2ccccc2C1]

The title compound was synthesized in the same manner as in Example 56, except that 4-(chloromethyl)pyridine hydrochloride was used instead of 3-(chloromethyl)pyridine hydrochloride in Example 56-2.

$^1$H NMR (400 MHz, Methanol-$d_4$) δ 8.60-8.51 (m, 2H), 7.71 (d, J=8.8 Hz, 1H), 7.54 (d, J=5.2 Hz, 2H), 7.18-7.00 (m, 4H), 6.86 (d, J=9.0 Hz, 1H), 6.68 (d, J=2.4 Hz, 1H), 5.25 (s, 2H), 4.48 (t, J=4.9 Hz, 2H), 4.27-4.18 (m, 1H), 3.98 (dd, J=14.0, 3.6 Hz, 1H), 3.81-3.67 (m, 4H), 3.43 (dd, J=13.9, 7.7 Hz, 1H), 2.99-2.83 (m, 4H), 2.71-2.60 (m, 2H).

Example 58: Synthesis of 4-[(2R)-3-(3,4-dihydro-1H-isoquinolin-2-yl)-2-hydroxy-propyl]-8-[(2-fluoro-4-pyridyl)methoxy]-2,3-dihydro-1,4-benzoxazepin-5-one

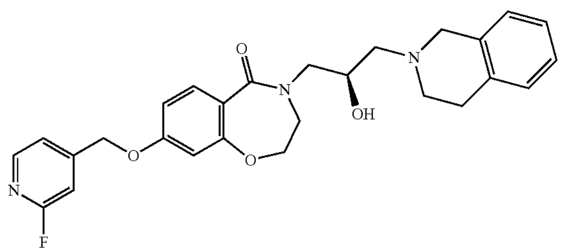 [SMILES: O=C1c2ccc(OCc3ccnc(F)c3)cc2OCCN1C[C@H](O)CN1CCc2ccccc2C1]

The title compound was synthesized in the same manner as in Example 56, except that (2-fluoro-4-pyridyl)methyl methanesulfonate was used instead of 3-(chloromethyl)pyridine hydrochloride in Example 56-2.

$^1$H NMR (400 MHz, Methanol-$d_4$) δ 8.22 (d, J=5.3 Hz, 1H), 7.71 (dd, J=8.8, 2.0 Hz, 1H), 7.40 (d, J=5.2 Hz, 1H), 7.18 (s, 1H), 7.12 (t, J=2.6 Hz, 3H), 7.06 (d, J=6.8 Hz, 1H), 6.87 (dd, J=8.9, 2.4 Hz, 1H), 6.69 (d, J=2.5 Hz, 1H), 5.27 (s, 2H), 4.49 (t, J=5.1 Hz, 2H), 4.24 (s, 1H), 3.97 (dd, J=13.7, 3.3 Hz, 1H), 3.79 (s, 2H), 3.74 (t, J=4.7 Hz, 2H), 3.44 (dd, J=13.9, 7.7 Hz, 1H), 2.93 (dd, J=11.6, 4.7 Hz, 4H), 2.68 (d, J=6.4 Hz, 2H).

Example 59: Synthesis of 8-[(2,6-dichloro-4-pyridyl)methoxy]-4-[(2R)-3-(3,4-dihydro-1H-isoquinolin-2-yl)-2-hydroxy-propyl]-2,3-dihydro-1,4-benzoxazepin-5-one

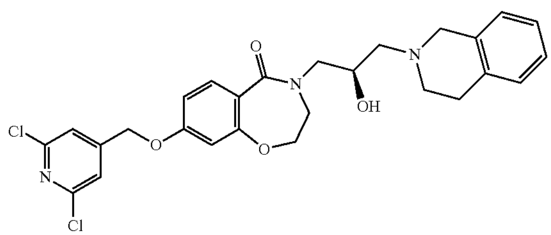 [SMILES: O=C1c2ccc(OCc3cc(Cl)nc(Cl)c3)cc2OCCN1C[C@H](O)CN1CCc2ccccc2C1]

The title compound was synthesized in the same manner as in Example 56, except that 2,6-dichloro-4-ethyl-pyridine hydrochloride was used instead of 3-(chloromethyl)pyridine hydrochloride in Example 56-2.

$^1$H NMR (400 MHz, Methanol-$d_4$) δ 7.72 (d, J=8.8 Hz, 1H), 7.53 (s, 2H), 7.23-7.06 (m, 2H), 7.06 (s, 1H), 6.86 (d, J=8.7 Hz, 1H), 6.69 (d, J=3.1 Hz, 1H), 5.23 (s, 2H), 4.64 (s, 2H), 4.50 (d, J=5.6 Hz, 2H), 4.23 (s, 1H), 4.00 (s, 1H), 3.75 (s, 4H), 3.55-3.37 (m, 1H), 2.93 (d, J=5.7 Hz, 2H), 2.88 (d, J=5.5 Hz, 2H), 2.64 (d, J=6.2 Hz, 2H).

Example 60: Synthesis of 8-[(2,3-difluoro-4-pyridyl)methoxy]-4-[(2R)-3-(3,4-dihydro-1H-isoquinolin-2-yl)-2-hydroxy-propyl]-2,3-dihydro-1,4-benzoxazepin-5-one

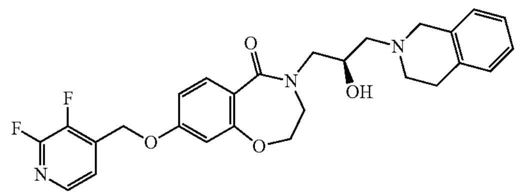 [SMILES: O=C1c2ccc(OCc3ccnc(F)c3F)cc2OCCN1C[C@H](O)CN1CCc2ccccc2C1]

The title compound was synthesized in the same manner as in Example 56, except that (2,3-difluoro-4-pyridyl)methyl methanesulfonate was used instead of 3-(chloromethyl)pyridine hydrochloride in Example 56-2.

$^1$H NMR (400 MHz, Methanol-$d_4$) δ 8.02 (d, J=5.0 Hz, 1H), 7.83-7.66 (m, 1H), 7.51 (d, J=5.3 Hz, 1H), 7.26-7.06 (m, 3H), 7.06 (d, J=6.5 Hz, 1H), 6.89-6.84 (m, 1H), 6.71 (d, J=2.9 Hz, 1H), 5.34 (s, 2H), 4.48 (d, J=5.4 Hz, 2H), 4.23 (d, J=7.0 Hz, 1H), 4.05-3.92 (m, 1H), 3.75 (d, J=10.7 Hz, 4H), 3.43 (dd, J=14.0, 7.7 Hz, 1H), 2.98-2.92 (m, 2H), 2.89 (d, J=5.3 Hz, 2H), 2.66 (d, J=6.1 Hz, 2H).

Example 61: Synthesis of 4-[(2R)-3-(3,4-dihydro-1H-isoquinolin-2-yl)-2-hydroxy-propyl]-8-[(6-fluoro-3-pyridyl)methoxy]-2,3-dihydro-1,4-benzoxazepin-5-one

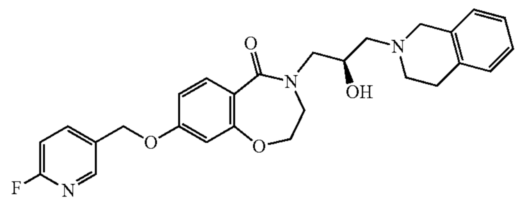 [SMILES: O=C1c2ccc(OCc3ccc(F)nc3)cc2OCCN1C[C@H](O)CN1CCc2ccccc2C1]

The title compound was synthesized in the same manner as in Example 56, except that (6-fluoro-3-pyridyl)methyl methanesulfonate was used instead of 3-(chloromethyl)pyridine hydrochloride in Example 56-2.

$^1$H NMR (400 MHz, Methanol-$d_4$) δ 8.32 (s, 1H), 8.07 (t, J=8.3 Hz, 1H), 7.70 (dd, J=8.8, 2.2 Hz, 1H), 7.20-7.03 (m, 5H), 6.85 (d, J=8.9 Hz, 1H), 6.69 (d, J=2.7 Hz, 1H), 5.18 (s, 2H), 4.48 (t, J=5.3 Hz, 2H), 4.23 (s, 1H), 3.98 (d, J=13.9 Hz, 1H), 3.75 (d, J=15.5 Hz, 4H), 3.43 (dd, J=14.0, 7.8 Hz, 1H), 3.03-2.82 (m, 4H), 2.66 (d, J=6.1 Hz, 2H).

Example 62: Synthesis of 4-[(2R)-3-(3,4-dihydro-1H-isoquinolin-2-yl)-2-hydroxy-propyl]-8-[(3-fluoro-4-pyridyl)methoxy]-2,3-dihydro-1,4-benzoxazepin-5-one

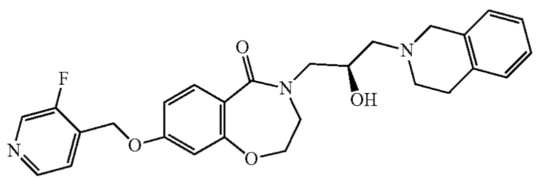 [SMILES: O=C1c2ccc(OCc3ccncc3F)cc2OCCN1C[C@H](O)CN1CCc2ccccc2C1]

The title compound was synthesized in the same manner as in Example 56, except that (3-fluoro-4-pyridyl)methyl methanesulfonate was used instead of 3-(chloromethyl)pyridine hydrochloride in Example 56-2.

$^1$H NMR (400 MHz, Methanol-$d_4$) δ 8.50 (s, 1H), 8.44 (d, J=5.0 Hz, 1H), 7.72 (d, J=8.8 Hz, 1H), 7.65 (t, J=5.7 Hz, 1H), 7.16-7.02 (m, 4H), 6.87 (d, J=9.3 Hz, 1H), 6.70 (d, J=2.9 Hz, 1H), 5.32 (s, 2H), 4.49 (t, J=5.0 Hz, 2H), 4.27-4.18 (m, 1H), 3.98 (dd, J=13.7, 3.1 Hz, 1H), 3.79-3.67 (m, 4H), 3.43 (dd, J=13.9, 7.6 Hz, 1H), 2.97-2.83 (m, 4H), 2.69-2.59 (m, 2H).

Example 63: Synthesis of 4-[(2R)-3-(3,4-dihydro-1H-isoquinolin-2-yl)-2-hydroxy-propyl]-8-[(5-fluoro-2-pyridyl)methoxy]-2,3-dihydro-1,4-benzoxazepin-5-one

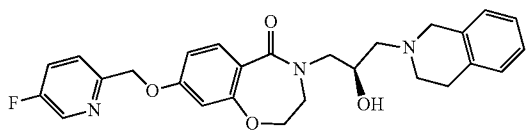 [SMILES: O=C1c2ccc(OCc3ccc(F)cn3)cc2OCCN1C[C@H](O)CN1CCc2ccccc2C1]

The title compound was synthesized in the same manner as in Example 56, except that (5-fluoro-2-pyridyl)methyl methanesulfonate was used instead of 3-(chloromethyl)pyridine hydrochloride in Example 56-2.

$^1$H NMR (400 MHz, Methanol-$d_4$) δ 8.49 (s, 1H), 7.68 (dd, J=15.0, 6.3 Hz, 3H), 7.16-7.03 (m, 4H), 6.85 (d, J=8.9 Hz, 1H), 6.67 (s, 1H), 5.22 (s, 2H), 4.48 (t, J=5.0 Hz, 2H), 4.28-4.16 (m, 1H), 3.98 (d, J=15.0 Hz, 1H), 3.78-3.69 (m, 4H), 3.43 (dd, J=13.9, 7.7 Hz, 1H), 3.00-2.83 (m, 4H), 2.70-2.61 (m, 2H).

Example 64: Synthesis of 4-[(2R)-3-(3,4-dihydro-1H-isoquinolin-2-yl)-2-hydroxy-propyl]-8-tetrahydropyran-4-yloxy-2,3-dihydro-1,4-benzoxazepin-5-one

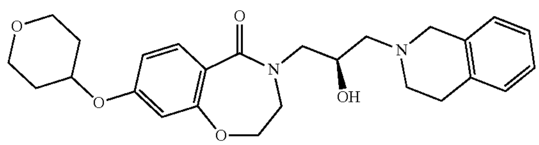 [SMILES: O=C1c2ccc(OC3CCOCC3)cc2OCCN1C[C@H](O)CN1CCc2ccccc2C1]

4-[(2R)-3-(3,4-dihydro-1H-isoquinolin-2-yl)-2-hydroxy-propyl]-8-hydroxy-2,3-dihydro-1,4-benzoxazepin-5-one (100 mg, 0.27 mmol) obtained in Example 56-1, potassium carbonate (112 mg, 0.81 mmol) and 4-chlorotetrahydropyran (0.12 mL, 0.81 mmol) were dissolved in dimethylformamide, and stirred at 150° C. for 12 hours or longer. The reaction solution was cooled to room temperature, and distilled water was added thereto, followed by extraction with ethyl acetate 3 times. The oily liquid obtained by drying the combined organic layers over anhydrous sodium sulfate and concentrated under reduced pressure was purified by flash chromatography to obtain the title compound as a sticky white solid.

$^1$H NMR (400 MHz, Methanol-$d_4$) δ 7.67 (d, J=8.7 Hz, 1H), 7.17-7.02 (m, 4H), 6.78 (d, J=8.9 Hz, 1H), 6.61 (s, 1H), 4.69-4.61 (m, 1H), 4.48 (t, J=5.0 Hz, 2H), 4.27-4.19 (m, 1H), 4.02-3.91 (m, 3H), 3.78 (s, 2H), 3.77-3.70 (m, 2H), 3.62 (t, J=10.0 Hz, 2H), 3.43 (dd, J=13.5, 7.5 Hz, 1H), 2.99-2.82 (m, 4H), 2.72-2.60 (m, 2H), 2.11-2.01 (m, 2H), 1.79-1.67 (m, 2H).

Example 65: Synthesis of 4-[(2R)-3-(3,4-dihydro-1H-isoquinolin-2-yl)-2-hydroxy-propyl]-8-(tetrahydropyran-2-ylmethoxy)-2,3-dihydro-1,4-benzoxazepin-5-one

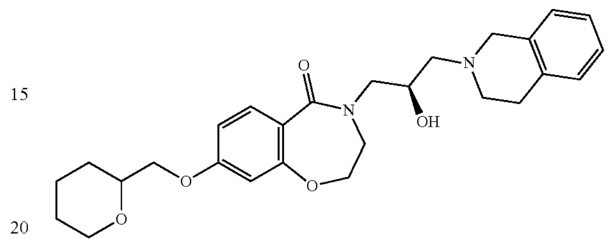

The title compound was synthesized in the same manner as in Example 64, except that tetrahydropyran-2-ylmethyl methanesulfonate was used instead of 4-chlorotetrahydropyran.

$^1$H NMR (400 MHz, Methanol-$d_4$) δ 7.65 (d, J=8.7 Hz, 1H), 7.12 (d, J=4.1 Hz, 3H), 7.06 (d, J=6.6 Hz, 1H), 6.73 (d, J=8.9 Hz, 1H), 6.55 (s, 1H), 4.47 (t, J=5.1 Hz, 2H), 4.23 (s, 1H), 4.05-3.94 (m, 1H), 3.89-3.67 (m, 76H), 3.43 (dd, J=13.9, 7.6 Hz, 1H), 2.92 (dd, J=17.2, 5.3 Hz, 4H), 2.66 (d, J=6.2 Hz, 2H), 1.89 (d, J=13.1 Hz, 2H), 1.84-1.66 (m, 4H), 1.49-1.19 (m, 4H), 1.11 (q, J=12.1 Hz, 2H).

Example 66: Synthesis of 8-(cyclohexylmethoxy)-4-[(2R)-3-(3,4-dihydro-1H-isoquinolin-2-yl)-2-hydroxy-propyl]-2,3-dihydro-1,4-benzoxazepin-5-one

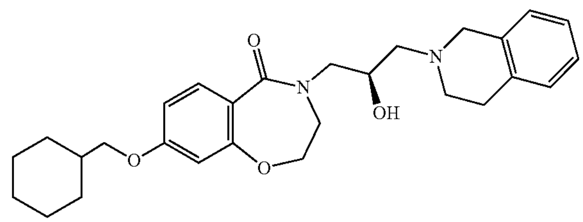 [SMILES: O=C1c2ccc(OCC3CCCCC3)cc2OCCN1C[C@H](O)CN1CCc2ccccc2C1]

The title compound was synthesized in the same manner as in Example 64, except that cyclohexylmethyl methanesulfonate was used instead of 4-chlorotetrahydropyran.

$^1$H NMR (400 MHz, Methanol-$d_4$) δ 7.67 (d, J=8.7 Hz, 1H), 7.13 (d, J=5.0 Hz, 4H), 7.06 (d, J=6.8 Hz, 1H), 6.76 (d, J=8.9 Hz, 1H), 6.59 (s, 1H), 4.46 (d, J=5.2 Hz, 2H), 4.28-4.17 (m, 1H), 3.99 (dd, J=14.1, 9.2 Hz, 4H), 3.88-3.66 (m, 6H), 3.53 (td, J=10.8, 3.5 Hz, 1H), 3.43 (dd, J=14.0, 7.6 Hz, 1H), 2.94 (dd, J=9.6, 4.6 Hz, 4H), 2.74-2.57 (m, 2H), 1.92 (d, J=6.5 Hz, 1H), 1.69 (t, J=14.9 Hz, 1H), 1.61 (d, J=10.2 Hz, 3H), 1.51-1.41 (m, 1H).

Example 67: Synthesis of 4-[(2R)-3-(3,4-dihydro-1H-isoquinolin-2-yl)-2-hydroxy-propyl]-8-(tetrahydrofuran-2-ylmethoxy)-2,3-dihydro-1,4-benzoxazepin-5-one

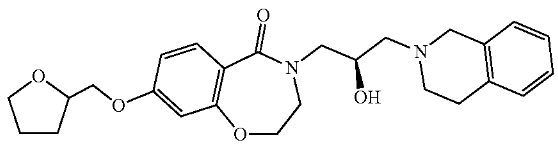 [SMILES: O=C1c2ccc(OCC3CCCO3)cc2OCCN1C[C@H](O)CN1CCc2ccccc2C1]

The title compound was synthesized in the same manner as in Example 64, except that tetrahydrofuran-2-ylmethyl methanesulfonate was used instead of 4-chlorotetrahydropyran.

$^1$H NMR (400 MHz, Chloroform-d) δ 7.79 (d, J=8.7 Hz, 1H), 7.20-7.10 (m, 3H), 7.04 (d, J=6.7 Hz, 1H), 6.74 (d, J=8.8 Hz, 1H), 6.55 (s, 1H), 4.46 (q, J=5.4 Hz, 2H), 4.30 (t, J=6.2 Hz, 1H), 4.13 (d, J=8.1 Hz, 1H), 4.06-3.90 (m, 4H), 3.86 (dd, J=15.1, 8.3 Hz, 2H), 3.77-3.60 (m, 3H), 3.53 (dd, J=14.1, 6.2 Hz, 1H), 3.02-2.87 (m, 4H), 2.84-2.51 (m, 3H), 2.31-2.05 (m, 1H), 1.98 (q, J=6.9 Hz, 2H), 1.79 (dt, J=12.0, 7.2 Hz, 1H), 1.35-1.22 (m, 1H).

Example 68: Synthesis of 4-[(2R)-3-(3,4-dihydro-1H-isoquinolin-2-yl)-2-hydroxy-propyl]-8-[(1-methyl-3-piperidyl)oxy]-2,3-dihydro-1,4-benzoxazepin-5-one

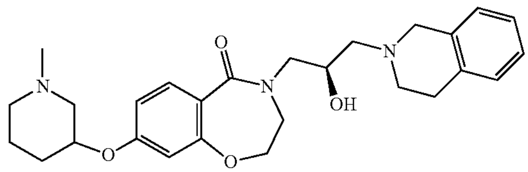 [SMILES: CN1CCCC(Oc2ccc3c(c2)OCCN(C[C@H](O)CN2CCc4ccccc4C2)C3=O)C1]

The title compound was synthesized in the same manner as in Example 64, except that (1-methyl-3-piperidyl) methanesulfonate was used instead of 4-chlorotetrahydropyran.

$^1$H NMR (400 MHz, Methanol-d$_4$) δ 7.68 (dd, J=8.8, 1.9 Hz, 1H), 7.12 (d, J=2.9 Hz, 3H), 7.06 (d, J=6.6 Hz, 1H), 6.78 (d, J=8.7 Hz, 1H), 6.61 (d, J=2.9 Hz, 1H), 4.69-4.42 (m, 3H), 4.24 (s, 1H), 3.97 (dd, J=14.5, 3.4 Hz, 1H), 3.78 (s, 2H), 3.74 (d, J=5.5 Hz, 2H), 3.43 (dd, J=14.0, 7.6 Hz, 1H), 3.03-2.84 (m, 5H), 2.67 (d, J=6.6 Hz, 3H), 2.37 (d, J=2.0 Hz, 3H), 2.05 (d, J=9.8 Hz, 2H), 1.91 (d, J=16.4 Hz, 3H), 1.66 (d, J=20.3 Hz, 3H), 0.93 (q, J=16.5, 10.6 Hz, 2H).

Example 69: Synthesis of 4-[(2R)-3-(3,4-dihydro-1H-isoquinolin-2-yl)-2-hydroxy-propyl]-8-[(1-ethyl-3-piperidyl)oxy]-2,3-dihydro-1,4-benzoxazepin-5-one

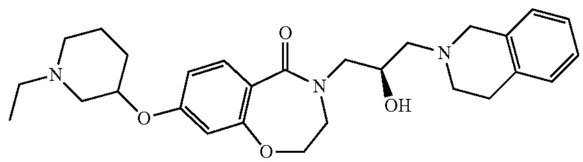 [SMILES: CCN1CCCC(Oc2ccc3c(c2)OCCN(C[C@H](O)CN2CCc4ccccc4C2)C3=O)C1]

The title compound was synthesized in the same manner as in Example 64, except that (1-ethyl-3-piperidyl) methanesulfonate was used instead of 4-chlorotetrahydropyran.

$^1$H NMR (400 MHz, Methanol-d$_4$) δ 7.68 (d, J=8.8 Hz, 1H), 7.17-7.02 (m, 4H), 6.78 (dd, J=8.5, 2.5 Hz, 1H), 6.61 (d, J=2.4 Hz, 1H), 4.48 (t, J=5.0 Hz, 2H), 4.28-4.17 (m, 1H), 4.11-3.94 (m, 3H), 3.79-3.68 (m, 4H), 3.43 (dd, J=13.8, 7.6 Hz, 1H), 3.26 (bs, 1H), 3.18-3.09 (m, 1H), 3.04 (bs, 1H), 2.99-2.91 (m, 2H), 2.92-2.84 (m, 2H), 2.71-2.59 (m, 2H), 2.54 (bs, 1H), 2.44 (bs, 1H), 2.16-2.05 (m, 1H), 1.89 (dd, J=16.4, 8.7 Hz, 2H), 1.81-1.71 (m, 1H), 1.20 (t, J=7.3 Hz, 3H).

Example 70: Synthesis of 8-[(1-acetyl-4-piperidyl)methoxy]-4-[(2R)-3-(3,4-dihydro-1H-isoquinolin-2-yl)-2-hydroxy-propyl]-2,3-dihydro-1,4-benzoxazepin-5-one

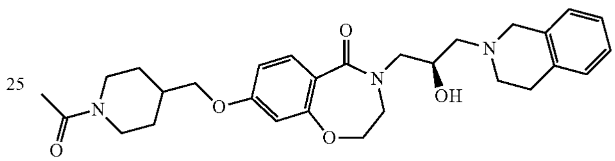

The title compound was synthesized in the same manner as in Example 64, except that (1-acetyl-4-piperidyl)methyl methanesulfonate was used instead of 4-chlorotetrahydropyran.

$^1$H NMR (400 MHz, Methanol-d$_4$) δ 7.66 (d, J=8.8 Hz, 1H), 7.17-7.01 (m, 4H), 6.79-6.71 (m, 1H), 6.58 (s, 1H), 4.59 (d, J=13.3 Hz, 1H), 4.53-4.41 (m, 2H), 4.27-4.17 (m, 1H), 3.98 (d, J=13.6 Hz, 2H), 3.91 (d, J=6.3 Hz, 2H), 3.83-3.64 (m, 4H), 3.42 (dd, J=13.9, 7.6 Hz, 1H), 3.21-3.12 (m, 1H), 2.98-2.82 (m, 4H), 2.75-2.60 (m, 3H), 2.13 (s, 3H), 1.92 (dd, J=25.3, 14.0 Hz, 2H), 1.45-1.21 (m, 3H).

Example 71: Synthesis of 4-[(2R)-3-(3,4-dihydro-1H-isoquinolin-2-yl)-2-hydroxy-propyl]-8-(2,2,2-trifluoroethoxy)-2,3-dihydro-1,4-benzoxazepin-5-one

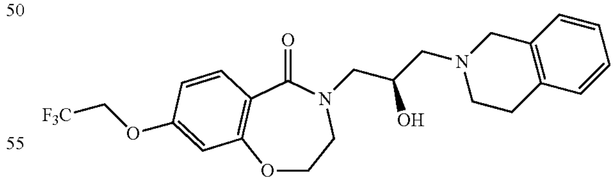

The title compound was synthesized in the same manner as in Example 64, except that 2,2,2-trifluoroethyl methanesulfonate was used instead of 4-chlorotetrahydropyran.

$^1$H NMR (400 MHz, Methanol-d$_4$) δ 7.73 (d, J=8.8 Hz, 1H), 7.19-6.99 (m, 4H), 6.84 (d, J=9.0 Hz, 1H), 6.69 (s, 1H), 4.61 (q, J=8.4 Hz, 2H), 4.50 (t, J=5.1 Hz, 2H), 4.27-4.17 (m, 1H), 3.99 (d, J=13.6 Hz, 1H), 3.81-3.67 (m, 4H), 3.43 (dd, J=13.9, 7.4 Hz, 1H), 3.00-2.82 (m, 4H), 2.65 (d, J=6.2 Hz, 2H).

Example 72: Synthesis of 4-[(2R)-3-(3,4-dihydro-1H-isoquinolin-2-yl)-2-hydroxy-propyl]-8-[2-(dimethylamino)ethoxy]-2,3-dihydro-1,4-benzoxazepin-5-one

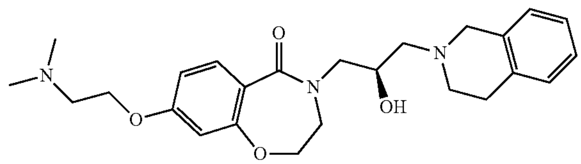 [SMILES: CN(C)CCOc1ccc2c(c1)OCCN(C[C@H](O)CN1CCc3ccccc3C1)C2=O]

The title compound was synthesized in the same manner as in Example 64, except that 2-chloro-N,N-dimethyl-ethanamine hydrochloride was used instead of 4-chlorotetrahydropyran.

$^1$H NMR (400 MHz, Methanol-$d_4$) δ 7.68 (d, J=8.6 Hz, 1H), 7.19-7.01 (m, 4H), 6.79 (d, J=9.0 Hz, 1H), 6.62 (s, 1H), 4.48 (t, J=5.0 Hz, 2H), 4.28-4.19 (m, 1H), 4.16 (t, J=5.5 Hz, 2H), 3.98 (d, J=13.8 Hz, 1H), 3.82-3.69 (m, 4H), 3.43 (dd, J=13.8, 7.8 Hz, 1H), 2.99-2.85 (m, 4H), 2.86-2.77 (m, 2H), 2.69-2.60 (m, 2H), 2.38 (s, 6H).

Example 73: Synthesis of 4-[(2R)-3-(3,4-dihydro-1H-isoquinolin-2-yl)-2-hydroxy-propyl]-8-(2-morpholinoethoxy)-2,3-dihydro-1,4-benzoxazepin-5-one

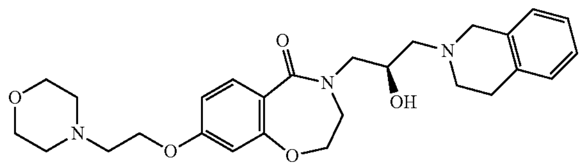 [SMILES: O=C1c2ccc(OCCN3CCOCC3)cc2OCCN1C[C@H](O)CN1CCc2ccccc2C1]

The title compound was synthesized in the same manner as in Example 64, except that 4-(2-chloroethyl)morpholine hydrochloride was used instead of 4-chlorotetrahydropyran.

$^1$H NMR (400 MHz, Chloroform-d) δ 7.78 (d, J=8.7 Hz, 1H), 7.13 (dd, J=9.7, 5.6 Hz, 3H), 7.01 (d, J=6.7 Hz, 1H), 6.69 (d, J=8.7 Hz, 1H), 6.50 (s, 1H), 4.45 (d, J=4.7 Hz, 2H), 4.12 (t, J=5.6 Hz, 3H), 3.93 (d, J=14.1 Hz, 1H), 3.83 (d, J=14.9 Hz, 1H), 3.73 (d, J=4.8 Hz, 6H), 3.63 (d, J=14.8 Hz, 1H), 3.51 (dd, J=14.1, 6.2 Hz, 1H), 2.93 (dq, J=13.3, 5.5 Hz, 3H), 2.81 (t, J=5.7 Hz, 3H), 2.77-2.71 (m, 1H), 2.66 (dd, J=12.3, 4.0 Hz, 1H), 2.57 (q, J=6.0, 5.3 Hz, 5H), 1.31-1.20 (m, 1H).

Example 74: Synthesis of 4-[(2R)-3-(3,4-dihydro-1H-isoquinolin-2-yl)-2-hydroxy-propyl]-8-[2-(2-oxopyrrolidin-1-yl)ethoxy]-2,3-dihydro-1,4-benzoxazepin-5-one

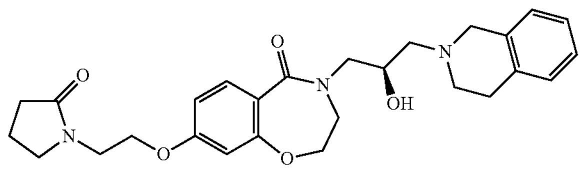 [SMILES: O=C1CCCN1CCOc1ccc2c(c1)OCCN(C[C@H](O)CN1CCc3ccccc3C1)C2=O]

The title compound was synthesized in the same manner as in Example 64, except that 2-(2-oxopyrrolidin-1-yl)ethyl methanesulfonate was used instead of 4-chlorotetrahydropyran.

$^1$H NMR (400 MHz, Chloroform-d) δ 7.79 (d, J=8.7 Hz, 1H), 7.13 (d, J=9.0 Hz, 3H), 7.01 (d, J=7.0 Hz, 1H), 6.67 (d, J=8.9 Hz, 1H), 6.48 (s, 1H), 4.46 (d, J=4.8 Hz, 3H), 4.12 (d, J=5.3 Hz, 4H), 3.88 (dd, J=41.5, 14.5 Hz, 2H), 3.79-3.43 (m, 8H), 2.93 (d, J=16.8 Hz, 3H), 2.70 (dd, J=32.9, 9.3 Hz, 2H), 2.60-2.48 (m, 1H), 2.39 (t, J=8.1 Hz, 2H), 2.12-1.97 (m, 3H), 1.26 (s, 1H).

Example 75: Synthesis of 2-[[4-[(2R)-3-(3,4-dihydro-1H-isoquinolin-2-yl)-2-hydroxy-propyl]-5-oxo-2,3-dihydro-1,4-benzoxazepin-8-yl]oxy]-N,N-diethyl-acetamide

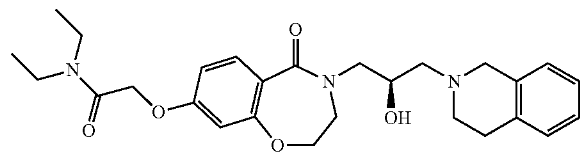 [SMILES: CCN(CC)C(=O)COc1ccc2c(c1)OCCN(C[C@H](O)CN1CCc3ccccc3C1)C2=O]

The title compound was synthesized in the same manner as in Example 64, except that [2-(diethylamino)-2-oxo-ethyl] methanesulfonate was used instead of 4-chlorotetrahydropyran.

$^1$H NMR (400 MHz, Chloroform-d) δ 7.79 (d, J=8.7 Hz, 1H), 7.13 (d, J=8.9 Hz, 3H), 7.02 (d, J=6.8 Hz, 1H), 6.74 (d, J=8.9 Hz, 1H), 6.55 (s, 1H), 4.69 (s, 2H), 4.53-4.42 (m, 2H), 4.12 (d, J=7.8 Hz, 1H), 3.93 (d, J=14.1 Hz, 1H), 3.83 (d, J=14.9 Hz, 1H), 3.76-3.57 (m, 3H), 3.52 (dd, J=14.1, 6.1 Hz, 1H), 3.39 (dq, J=14.6, 7.0 Hz, 4H), 2.93 (d, J=16.7 Hz, 3H), 2.74 (d, J=5.6 Hz, 1H), 2.66 (d, J=12.4 Hz, 1H), 2.55 (t, J=11.3 Hz, 1H), 2.05 (s, 1H), 1.30-1.20 (m, 3H), 1.15 (t, J=7.2 Hz, 3H).

Example 76: Synthesis of 4-[(2R)-3-(3,4-dihydro-1H-isoquinolin-2-yl)-2-hydroxy-propyl]-8-[(6-oxo-3-piperidyl)oxy]-2,3-dihydro-1,4-benzoxazepin-5-one

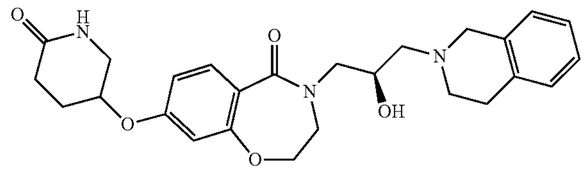 [SMILES: O=C1CCC(Oc2ccc3c(c2)OCCN(C[C@H](O)CN2CCc4ccccc4C2)C3=O)CN1]

The title compound was synthesized in the same manner as in Example 64, except that (6-oxo-3-piperidyl) methanesulfonate was used instead of 4-chlorotetrahydropyran.

$^1$H NMR (400 MHz, Methanol-$d_4$) δ 7.68 (d, J=8.8 Hz, 1H), 7.17-7.02 (m, 4H), 6.82-6.75 (m, 1H), 6.62 (s, 1H), 4.48 (t, J=5.0 Hz, 2H), 4.28-4.17 (m, 1H), 4.13-4.02 (m, 2H), 4.02-3.92 (m, 2H), 3.79-3.67 (m, 4H), 3.42 (dd, J=13.8, 7.6 Hz, 1H), 2.98-2.84 (m, 4H), 2.70-2.59 (m, 2H), 2.54-2.43 (m, 1H), 2.38 (dd, J=17.1, 13.5 Hz, 2H), 2.08-1.97 (m, 1H).

Example 77: Synthesis of tert-butyl 4-[[4-[(2R)-3-(3,4-dihydro-1H-isoquinolin-2-yl)-2-hydroxy-propyl]-5-oxo-2,3-dihydro-1,4-benzoxazepin-8-yl]oxy]piperidine-1-carboxylate

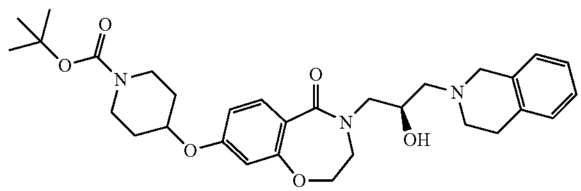 [SMILES: CC(C)(C)OC(=O)N1CCC(Oc2ccc3c(c2)OCCN(C[C@H](O)CN2CCc4ccccc4C2)C3=O)CC1]

The title compound was synthesized in the same manner as in Example 64, except that tert-butyl 4-methylsulfonyloxypiperidine-1-carboxylate was used instead of 4-chlorotetrahydropyran.

$^1$H NMR (400 MHz, Methanol-$d_4$) δ 7.67 (d, J=8.7 Hz, 1H), 7.09 (d, J=19.7 Hz, 4H), 6.79 (d, J=9.0 Hz, 1H), 6.62 (s, 1H), 4.70-4.60 (m, 1H), 4.51-4.44 (m, 2H), 4.27-4.19 (m, 1H), 3.98 (d, J=14.4 Hz, 1H), 3.85-3.64 (m, 6H), 3.45 (d, J=7.4 Hz, 1H), 2.98-2.92 (m, 2H), 2.93-2.86 (m, 2H), 2.71-2.62 (m, 2H), 2.04-1.89 (m, 3H), 1.76-1.60 (m, 2H), 1.49 (s, 9H).

Example 78: Synthesis of 8-[(1-acetyl-4-piperidyl)oxy]-4-[(2R)-3-(3,4-dihydro-1H-isoquinolin-2-yl)-2-hydroxy-propyl]-2,3-dihydro-1,4-benzoxazepin-5-one

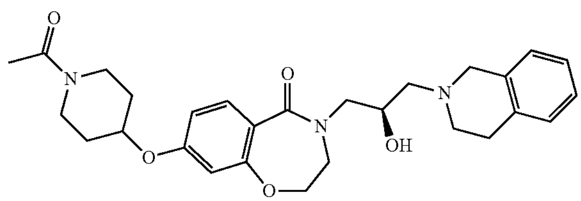 [SMILES: CC(=O)N1CCC(Oc2ccc3c(c2)OCCN(C[C@H](O)CN2CCc4ccccc4C2)C3=O)CC1]

Example 78-1: Synthesis of 4-[(2R)-3-(3,4-dihydro-1H-isoquinolin-2-yl)-2-hydroxy-propyl]-8-(4-piperidyloxy)-2,3-dihydro-1,4-benzoxazepin-5-one dihydrochloride Tert-butyl 4-[[4-[(2R)-3-(3,4-dihydro-1H-isoquinolin-2-yl)-2-hydroxy-propyl]-5-oxo-2,3-dihydro-1,4-benzoxazepin-8-yl]oxy]piperidine-1-carboxylate obtained in Example 77 was dissolved in methanol, and 4 M hydrochloric acid solution dissolved in 1,4-dioxane was slowly added thereto. The reaction solution was stirred at room temperature, diluted with diethyl ether and filtered to obtain the title compound as a white solid.

Example 78-2: Synthesis of 8-[(1-acetyl-4-piperidyl)oxy]-4-[(2R)-3-(3,4-dihydro-1H-isoquinolin-2-yl)-2-hydroxy-propyl]-2,3-dihydro-1,4-benzoxazepin-5-one 4-[(2R)-3-(3,4-dihydro-1H-isoquinolin-2-yl)-2-hydroxy-propyl]-8-(4-piperidyloxy)-2,3-dihydro-1,4-benzoxazepin-5-one dihydrochloride obtained in Example 78-1 was dissolved in dichloromethane, and trimethylamine and acetic anhydride were added thereto, followed by stirring at room temperature for 3 hours. To the reaction mixture, saturated aqueous ammonium chloride solution was added and extracted with ethyl acetate 3 times. The oily liquid obtained by drying the combined organic layers over anhydrous sodium sulfate and concentrated under reduced pressure was purified by flash chromatography to obtain the title compound as a white solid.

$^1$H NMR (400 MHz, Methanol-$d_4$) δ 7.58 (d, J=8.8 Hz, 1H), 7.27-7.05 (m, 4H), 6.70 (dd, J=9.0, 2.4 Hz, 1H), 6.54 (d, J=1.9 Hz, 1H), 4.65-4.49 (m, 2H), 4.47-4.28 (m, 4H), 3.81-3.57 (m, 7H), 3.48-3.33 (m, 3H), 3.33-3.23 (m, 2H), 3.12 (q, J=7.4 Hz, 2H), 2.03 (s, 3H), 1.97-1.80 (m, 3H), 1.77-1.54 (m, 2H).

Example 79: Synthesis of 8-[(1-acetyl-3-piperidyl)oxy]-4-[(2R)-3-(3,4-dihydro-1H-isoquinolin-2-yl)-2-hydroxy-propyl]-2,3-dihydro-1,4-benzoxazepin-5-one

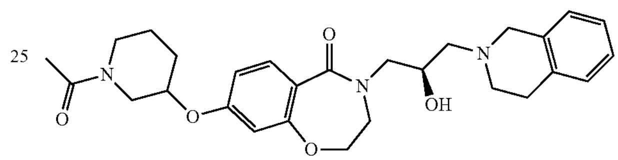

The title compound was synthesized in the same manner as in Example 64, except that (1-acetyl-3-piperidyl) methanesulfonate was used instead of 4-chlorotetrahydropyran.

$^1$H NMR (diastereomeric mixture, 400 MHz, Methanol-$d_4$) δ 7.72-7.65 (m, 2H), 7.17-7.02 (m, 8H), 6.83-6.74 (m, 2H), 6.61 (s, 2H), 4.68-4.59 (m, 1H), 4.48 (q, J=4.6 Hz, 5H), 4.23 (s, 2H), 4.10-3.93 (m, 4H), 3.86 (dd, J=14.3, 4.8 Hz, 1H), 3.81-3.68 (m, 8H), 3.66-3.48 (m, 4H), 3.43 (dd, J=14.0, 7.7 Hz, 2H), 3.20 (t, J=11.3 Hz, 1H), 2.99-2.84 (m, 8H), 2.71-2.59 (m, 4H), 2.17-1.95 (m, 9H), 1.93-1.77 (m, 3H), 1.70-1.52 (m, 2H).

Example 80: Synthesis of 8-(1-acetylpyrrolidin-3-yl)oxy-4-[(2R)-3-(3,4-dihydro-1H-isoquinolin-2-yl)-2-hydroxy-propyl]-2,3-dihydro-1,4-benzoxazepin-5-one

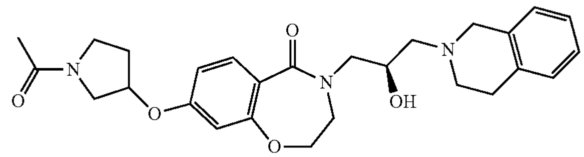 [SMILES: CC(=O)N1CCC(Oc2ccc3c(c2)OCCN(C[C@H](O)CN2CCc4ccccc4C2)C3=O)C1]

The title compound was synthesized in the same manner as in Example 64, except that tert-butyl 4-methylsulfonyloxypyrrolidine-1-carboxylate was used instead of 4-chlorotetrahydropyran.

$^1$H NMR (400 MHz, Methanol-$d_4$) δ 7.70 (dd, J=8.8, 3.8 Hz, 1H), 7.18-7.00 (m, 4H), 6.77 (t, J=8.6 Hz, 1H), 6.60 (dd, J=5.8, 2.3 Hz, 1H), 5.19-5.04 (m, 1H), 4.48 (t, J=5.0 Hz, 2H), 4.30-4.18 (m, 1H), 3.97 (dd, J=14.0, 3.5 Hz, 1H), 3.92-3.59 (m, 7H), 3.54-3.37 (m, 2H), 3.00-2.84 (m, 4H), 2.73-2.59 (m, 2H), 2.35-2.23 (m, 1H), 2.25-2.15 (m, 1H), 2.09 (d, J=15.8 Hz, 3H).

Example 81: Synthesis of 8-[(3R)-1-acetylpyrrolidin-3-yl]oxy-4-[(2R)-3-(3,4-dihydro-1H-isoquinolin-2-yl)-2-hydroxy-propyl]-2,3-dihydro-1,4-benzoxazepin-5-one

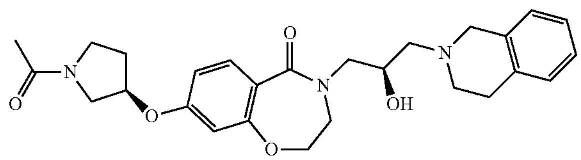 [SMILES: CC(=O)N1CC[C@@H](Oc2ccc3c(c2)OCCN(C[C@H](O)CN2CCc4ccccc4C2)C3=O)C1]

The title compound was synthesized in the same manner as in Example 80, except that tert-butyl (3S)-3-methylsulfonyloxypyrrolidine-1-carboxylate was used instead of tert-butyl 4-methylsulfonyloxypyrrolidine-1-carboxylate.

$^1$H NMR (400 MHz, Methanol-$d_4$) δ 7.70 (d, J=8.8 Hz, 1H), 7.09 (d, J=20.4 Hz, 4H), 6.81-6.72 (m, 1H), 6.61 (d, J=5.8 Hz, 1H), 5.13 (d, J=22.4 Hz, 1H), 4.52-4.44 (m, 2H), 4.29-4.18 (m, 1H), 3.98 (d, J=14.1 Hz, 1H), 3.83-3.62 (m, 8H), 3.43 (dd, J=14.2, 7.5 Hz, 1H), 2.99-2.81 (m, 4H), 2.70-2.59 (m, 2H), 2.36-2.27 (m, 1H), 2.27-2.16 (m, 1H), 2.09 (d, J=15.7 Hz, 3H).

Example 82: Synthesis of 8-[(3S)-1-acetylpyrrolidin-3-yl]oxy-4-[(2R)-3-(3,4-dihydro-1H-isoquinolin-2-yl)-2-hydroxy-propyl]-2,3-dihydro-1,4-benzoxazepin-5-one

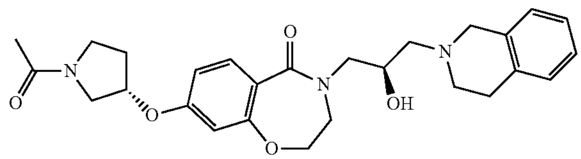 [SMILES: CC(=O)N1CC[C@H](Oc2ccc3c(c2)OCCN(C[C@H](O)CN2CCc4ccccc4C2)C3=O)C1]

The title compound was synthesized in the same manner as in Example 80, except that tert-butyl (3R)-3-methylsulfonyloxypyrrolidine-1-carboxylate was used instead of tert-butyl 4-methylsulfonyloxypyrrolidine-1-carboxylate.

$^1$H NMR (400 MHz, Methanol-$d_4$) δ 7.69 (d, J=8.6 Hz, 1H), 7.17-7.02 (m, 4H), 6.77 (t, J=7.5 Hz, 1H), 6.61 (d, J=4.8 Hz, 1H), 5.13 (d, J=22.4 Hz, 1H), 4.53-4.43 (m, 2H), 4.22 (dd, J=12.1, 5.5 Hz, 1H), 3.98 (d, J=13.4 Hz, 1H), 3.91-3.61 (m, 8H), 3.43 (dd, J=13.9, 7.9 Hz, 1H), 2.99-2.82 (m, 4H), 2.70-2.58 (m, 2H), 2.37-2.26 (m, 1H), 2.26-2.16 (m, 1H), 2.09 (d, J=15.6 Hz, 3H).

Example 83: Synthesis of 8-(1-acetylazetidin-3-yl)oxy-4-[(2R)-3-(3,4-dihydro-1H-isoquinolin-2-yl)-2-hydroxy-propyl]-2,3-dihydro-1,4-benzoxazepin-5-one

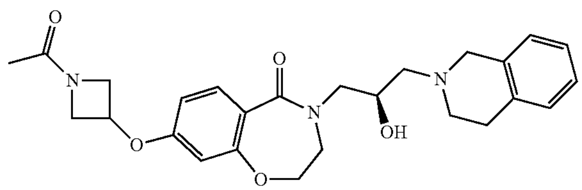 [SMILES: CC(=O)N1CC(Oc2ccc3c(c2)OCCN(C[C@H](O)CN2CCc4ccccc4C2)C3=O)C1]

Example 83-1: Synthesis of 8-(azetidin-3-yloxy)-4-[(2R)-3-(3,4-dihydro-1H-isoquinolin-2-yl)-2-hydroxy-propyl]-2,3-dihydro-1,4-benzoxazepin-5-one dihydrochloride The material, which is obtained by changing 4-chlorotetrahydropyrane to tert-butyl 3-methylsulfonyloxyazetidine-1-carboxylate in Example 64, as a starting material was used in the same manner as in Example 78-1 to obtain the title compound.

Example 83-2: Synthesis of 8-(1-acetylazetidin-3-yl)oxy-4-[(2R)-3-(3,4-dihydro-1H-isoquinolin-2-yl)-2-hydroxy-propyl]-2,3-dihydro-1,4-benzoxazepin-5-one 8-(Azetidin-3-yloxy)-4-[(2R)-3-(3,4-dihydro-1H-isoquinolin-2-yl)-2-hydroxy-propyl]-2,3-dihydro-1,4-benzoxazepin-5-one dihydrochloride obtained in Example 83-1 as a starting material was used in the same manner as in Example 78-2 to obtain the title compound.

$^1$H NMR (400 MHz, Methanol-$d_4$) δ 7.71 (d, J=8.7 Hz, 1H), 7.19-7.00 (m, 4H), 6.69 (dd, J=8.7, 2.2 Hz, 1H), 6.49 (d, J=2.3 Hz, 1H), 5.09 (dt, J=12.0, 6.5 Hz, 1H), 4.69-4.61 (m, 1H), 4.49 (t, J=5.0 Hz, 2H), 4.42 (dd, J=11.0, 6.6 Hz, 1H), 4.29-4.18 (m, 2H), 4.04-3.91 (m, 2H), 3.82-3.67 (m, 4H), 3.43 (dd, J=13.7, 7.7 Hz, 1H), 3.00-2.83 (m, 4H), 2.72-2.58 (m, 2H), 1.93 (s, 3H).

Example 84: Synthesis of 4-[(2R)-3-(3,4-dihydro-1H-isoquinolin-2-yl)-2-hydroxy-propyl]-8-(1-propanoylazetidin-3-yl)oxy-2,3-dihydro-1,4-benzoxazepin-5-one

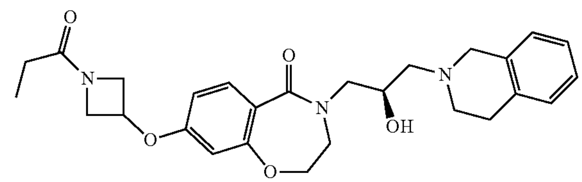 [SMILES: CCC(=O)N1CC(Oc2ccc3c(c2)OCCN(C[C@H](O)CN2CCc4ccccc4C2)C3=O)C1]

8-(Azetidin-3-yloxy)-4-[(2R)-3-(3,4-dihydro-1H-isoquinolin-2-yl)-2-hydroxy-propyl]-2,3-dihydro-1,4-benzoxazepin-5-one dihydrochloride obtained in Example 83-1 as a starting material was used in the same manner as in Example 78-2 to obtain the title compound, except that propanoyl chloride was used instead of acetic anhydride.

$^1$H NMR (400 MHz, Methanol-$d_4$) δ 7.71 (d, J=8.7 Hz, 1H), 7.21-7.01 (m, 4H), 6.72-6.65 (m, 1H), 6.49 (d, J=2.4 Hz, 1H), 5.15-5.05 (m, 1H), 4.69-4.59 (m, 1H), 4.49 (t, J=5.0 Hz, 2H), 4.46-4.38 (m, 1H), 4.28-4.17 (m, 2H), 4.03-3.90 (m, 2H), 3.85-3.68 (m, 4H), 3.44 (dd, J=13.9, 7.7 Hz, 1H), 3.02-2.82 (m, 4H), 2.75-2.62 (m, 2H), 2.21 (q, J=7.5 Hz, 2H), 1.12 (t, J=7.5 Hz, 3H).

Example 85: Synthesis of 8-[1-(cyclopropanecarbonyl)azetidin-3-yl]oxy-4-[(2R)-3-(3,4-dihydro-1H-isoquinolin-2-yl)-2-hydroxy-propyl]-2,3-dihydro-1,4-benzoxazepin-5-one

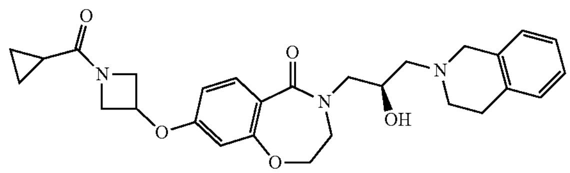 [SMILES: O=C1c2ccc(OC3CN(C(=O)C4CC4)C3)cc2OCCN1C[C@H](O)CN1CCc2ccccc2C1]

8-(Azetidin-3-yloxy)-4-[(2R)-3-(3,4-dihydro-1H-isoquinolin-2-yl)-2-hydroxy-propyl]-2,3-dihydro-1,4-benzoxazepin-5-one dihydrochloride obtained in Example 83-1 as a starting material was used in the same manner as in Example 78-2 to obtain the title compound, except that cyclopropanecarbonyl chloride was used instead of acetic anhydride.

$^1$H NMR (400 MHz, Methanol-$d_4$) δ 7.71 (d, J=8.7 Hz, 1H), 7.20-7.02 (m, 4H), 6.71 (d, J=8.4 Hz, 1H), 6.50 (s, 1H), 5.19-5.08 (m, 1H), 4.82-4.74 (m, 1H), 4.49 (t, J=5.1 Hz, 2H), 4.45-4.37 (m, 1H), 4.33 (d, J=9.9 Hz, 1H), 4.29-4.16 (m, 1H), 3.97 (d, J=12.2 Hz, 2H), 3.84-3.68 (m, 4H), 3.44 (dd, J=13.9, 7.7 Hz, 1H), 3.00-2.84 (m, 4H), 2.74-2.61 (m, 2H), 1.67-1.56 (m, 1H), 0.93-0.78 (m, 4H).

Example 86: Synthesis of methyl 3-[[4-[(2R)-3-(3,4-dihydro-1H-isoquinolin-2-yl)-2-hydroxy-propyl]-5-oxo-2,3-dihydro-1,4-benzoxazepin-8-yl]oxy]azetidin-1-carboxylate

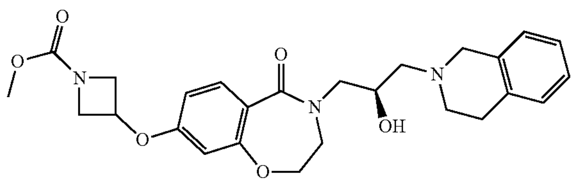 [SMILES: COC(=O)N1CC(Oc2ccc3c(c2)OCCN(C[C@H](O)CN2CCc4ccccc4C2)C3=O)C1]

8-(Azetidin-3-yloxy)-4-[(2R)-3-(3,4-dihydro-1H-isoquinolin-2-yl)-2-hydroxy-propyl]-2,3-dihydro-1,4-benzoxazepin-5-one dihydrochloride obtained in Example 83-1 as a starting material was used in the same manner as in Example 78-2 to obtain the title compound, except that methyl chloroformate was used instead of acetic anhydride.

$^1$H NMR (400 MHz, Methanol-$d_4$) δ 7.70 (d, J=8.8 Hz, 1H), 7.16-7.00 (m, 4H), 6.66 (d, J=8.7 Hz, 1H), 6.46 (s, 1H), 5.10-5.00 (m, 1H), 4.54-4.35 (m, 4H), 4.28-4.16 (m, 1H), 4.06-3.90 (m, 3H), 3.78-3.70 (m, 4H), 3.69 (s, 3H), 3.41 (dd, J=14.0, 7.7 Hz, 1H), 2.98-2.81 (m, 4H), 2.69-2.58 (m, 2H).

Example 87: Synthesis of 4-[(2R)-3-(3,4-dihydro-1H-isoquinolin-2-yl)-2-hydroxy-propyl]-8-[(1-methyl-4-piperidyl)oxy]-2,3-dihydro-1,4-benzoxazepin-5-one

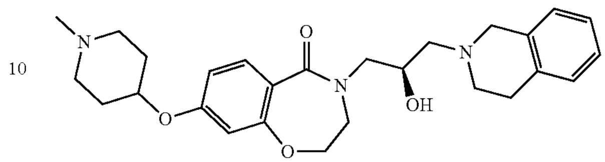

4-[(2R)-3-(3,4-dihydro-1H-isoquinolin-2-yl)-2-hydroxy-propyl]-8-(4-piperidyloxy)-2,3-dihydro-1,4-benzoxazepin-5-one dihydrochloride (100 mg, 0.19 mmol) obtained in Example 78-1 was dissolved in methanol, and paraformaldehyde (57 mg, 1.9 mmol) and sodium cyanoborohydride (36 mg, 0.57 mmmol) were added thereto. The reaction solution was stirred at room temperature until the reaction was completed, a saturated aqueous ammonium chloride solution was added, stirred for 30 minutes, and then 1 N sodium hydroxide aqueous solution was added for basification. The mixture was extracted with ethyl acetate 3 times and dried over anhydrous sodium sulfate. The pale yellow oily liquid obtained by removing the solvent by evaporation under reduced pressure was purified by flash chromatography to obtain the title compound as a white solid.

$^1$H NMR (400 MHz, Methanol-$d_4$) δ 7.66 (d, J=8.8 Hz, 1H), 7.16-7.00 (m, 4H), 6.76 (dd, J=8.8, 2.4 Hz, 1H), 6.58 (d, J=2.4 Hz, 1H), 4.56-4.41 (m, 3H), 4.27-4.16 (m, 1H), 3.97 (dd, J=13.9, 3.5 Hz, 1H), 3.79-3.63 (m, 4H), 3.41 (dd, J=13.9, 7.7 Hz, 1H), 2.98-2.88 (m, 2H), 2.90-2.80 (m, 2H), 2.79-2.68 (m, 2H), 2.68-2.56 (m, 2H), 2.49-2.36 (m, 2H), 2.32 (s, 3H), 2.10-2.01 (m, 3H), 1.90-1.76 (m, 2H).

Example 88: Synthesis of 4-[(2R)-3-(3,4-dihydro-1H-isoquinolin-2-yl)-2-hydroxy-propyl]-8-[(1-ethyl-4-piperidyl)oxy]-2,3-dihydro-1,4-benzoxazepin-5-one

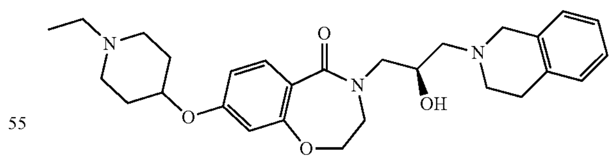

The title compound was synthesized in the same manner as in Example 87, except that acetaldehyde was used instead of paraformaldehyde.

$^1$H NMR (400 MHz, Methanol-$d_4$) δ 7.67 (d, J=8.7 Hz, 1H), 7.17-7.03 (m, 4H), 6.81-6.74 (m, 1H), 6.60 (s, 1H), 4.61-4.51 (m, 1H), 4.47 (t, J=5.0 Hz, 2H), 4.28-4.16 (m, 1H), 4.02-3.92 (m, 1H), 3.82-3.68 (m, 4H), 3.43 (dd, J=13.9, 7.7 Hz, 1H), 3.01-2.80 (m, 6H), 2.74-2.51 (m, 6H), 2.15-2.02 (m, 2H), 1.96-1.78 (m, 2H), 1.19 (t, J=7.2 Hz, 3H).

Example 89: Synthesis of 4-[(2R)-3-(3,4-dihydro-1H-isoquinolin-2-yl)-2-hydroxy-propyl]-8-[(1-isopropyl-4-piperidyl)oxy]-2,3-dihydro-1,4-benzoxazepin-5-one

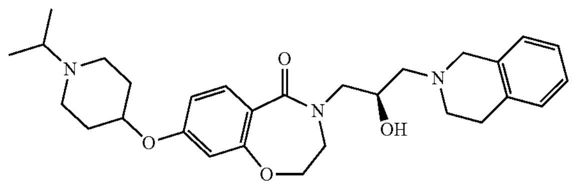 [SMILES: CC(C)N1CCC(Oc2ccc3c(c2)OCCN(C[C@H](O)CN2CCc4ccccc4C2)C3=O)CC1]

The title compound was synthesized in the same manner as in Example 87, except that acetone was used instead of paraformaldehyde.

$^1$H NMR (400 MHz, Methanol-$d_4$) δ 7.68 (d, J=8.7 Hz, 1H), 7.16-7.01 (m, 4H), 6.78 (d, J=8.8 Hz, 1H), 6.61 (s, 1H), 4.63-4.51 (m, 1H), 4.47 (t, J=4.9 Hz, 2H), 4.22 (dd, J=7.8, 4.4 Hz, 1H), 3.97 (d, J=13.9 Hz, 1H), 3.81-3.66 (m, 4H), 3.43 (dd, J=13.9, 7.6 Hz, 1H), 3.10-2.98 (m, 2H), 2.98-2.82 (m, 4H), 2.83-2.70 (m, 2H), 2.69-2.58 (m, 2H), 2.18-1.98 (m, 3H), 1.95-1.82 (m, 2H), 1.21 (d, J=6.5 Hz, 6H).

Example 90: Synthesis of 8-[(1-cyclopropyl-4-piperidyl)oxy]-4-[(2R)-3-(3,4-dihydro-1H-isoquinolin-2-yl)-2-hydroxy-propyl]-2,3-dihydro-1,4-benzoxazepin-5-one

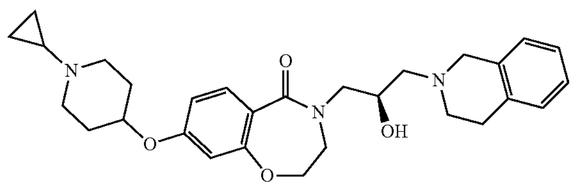 [SMILES: O=C1c2ccc(OC3CCN(C4CC4)CC3)cc2OCCN1C[C@H](O)CN1CCc2ccccc2C1]

The title compound was synthesized in the same manner as in Example 87 at 60° C., except that (1-ethoxycyclopropoxy)trimethylsilane was used instead of paraformaldehyde.

$^1$H NMR (400 MHz, Methanol-$d_4$) δ 7.67 (d, J=9.0 Hz, 1H), 7.18-7.02 (m, 4H), 6.76 (d, J=8.8 Hz, 1H), 6.59 (s, 1H), 4.58-4.41 (m, 3H), 4.28-4.17 (m, 1H), 3.97 (dd, J=14.0, 3.6 Hz, 1H), 3.83-3.66 (m, 4H), 3.42 (dd, J=14.0, 7.7 Hz, 1H), 3.01-2.78 (m, 6H), 2.73-2.51 (m, 4H), 2.10-1.96 (m, 2H), 1.86-1.66 (m, 3H), 0.59-0.39 (m, 4H).

Example 91: Synthesis of 8-[(1-cyclobutyl-4-piperidyl)oxy]-4-[(2R)-3-(3,4-dihydro-1H-isoquinolin-2-yl)-2-hydroxy-propyl]-2,3-dihydro-1,4-benzoxazepin-5-one

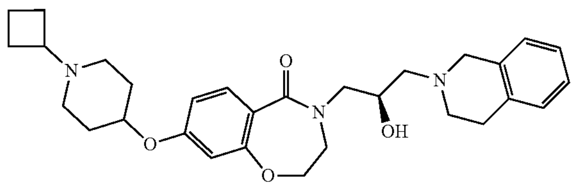 [SMILES: O=C1c2ccc(OC3CCN(C4CCC4)CC3)cc2OCCN1C[C@H](O)CN1CCc2ccccc2C1]

The title compound was synthesized in the same manner as in Example 87, except that cyclobutanone was used instead of paraformaldehyde.

$^1$H NMR (400 MHz, Methanol-$d_4$) δ 7.67 (d, J=8.8 Hz, 1H), 7.10 (d, J=21.0 Hz, 4H), 6.77 (d, J=8.9 Hz, 1H), 6.60 (s, 1H), 4.63-4.50 (m, 2H), 4.47 (d, J=5.3 Hz, 2H), 4.29-4.18 (m, 1H), 3.97 (d, J=14.5 Hz, 1H), 3.80 (s, 2H), 3.77-3.67 (m, 2H), 3.44 (dd, J=14.0, 7.5 Hz, 1H), 3.05-2.88 (m, 5H), 2.86-2.74 (m, 2H), 2.71-2.63 (m, 2H), 2.56-2.35 (m, 3H), 2.22-2.11 (m, 2H), 2.11-1.93 (m, 4H), 1.92-1.74 (m, 4H).

Example 92: Synthesis of 4-[(2R)-3-(3,4-dihydro-1H-isoquinolin-2-yl)-2-hydroxy-propyl]-8-[[1-(oxetan-3-yl)-4-piperidyl]oxy]-2,3-dihydro-1,4-benzoxazepin-5-one

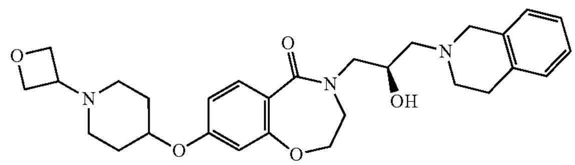 [SMILES: O=C1c2ccc(OC3CCN(C4COC4)CC3)cc2OCCN1C[C@H](O)CN1CCc2ccccc2C1]

The title compound was synthesized in the same manner as in Example 87, except that oxetan-3-one was used instead of paraformaldehyde.

$^1$H NMR (400 MHz, Methanol-$d_4$) δ 7.75-7.56 (m, 1H), 7.12 (d, J=3.1 Hz, 3H), 7.06 (d, J=6.7 Hz, 1H), 6.76 (d, J=8.8 Hz, 1H), 6.58 (d, J=2.1 Hz, 1H), 4.71 (t, J=6.7 Hz, 2H), 4.62 (t, J=6.3 Hz, 2H), 4.54-4.41 (m, 3H), 4.23 (s, 1H), 4.02-3.91 (m, 1H), 3.79 (s, 2H), 3.73 (s, 2H), 3.55 (t, J=6.5 Hz, 1H), 3.43 (dd, J=14.0, 7.6 Hz, H), 2.93 (dd, J=11.3, 4.6 Hz, 4H), 2.68 (d, J=6.6 Hz, 2H), 2.61 (s, 2H), 2.28 (t, J=10.0 Hz, 2H), 2.04 (d, J=10.2 Hz, 2H), 1.89 (d, J=36.1 Hz, 2H).

Example 93: Synthesis of 4-[(2R)-3-(3,4-dihydro-1H-isoquinolin-2-yl)-2-hydroxy-propyl]-8-(1-methylazetidin-3-yl)oxy-2,3-dihydro-1,4-benzoxazepin-5-one

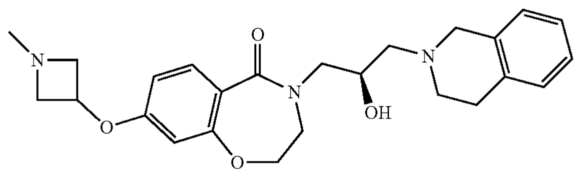 [SMILES: CN1CC(Oc2ccc3c(c2)OCCN(C[C@H](O)CN2CCc4ccccc4C2)C3=O)C1]

The material obtained in Example 83-1 as a starting material was used in the same manner as in Example 87 to obtain the title compound.

$^1$H NMR (400 MHz, Methanol-$d_4$) δ 7.68 (d, J=8.5 Hz, 1H), 7.09 (d, J=19.7 Hz, 4H), 6.65 (d, J=8.9 Hz, 1H), 6.44 (s, 1H), 4.86 (t, J=5.6 Hz, 3H), 4.47 (t, J=5.2 Hz, 2H), 4.29-4.17 (m, 1H), 3.98 (dd, J=13.7, 2.5 Hz, 1H), 3.83 (t, J=7.5 Hz, 2H), 3.78-3.69 (m, 4H), 3.42 (dd, J=13.9, 7.8 Hz, 1H), 3.28 (dd, J=8.6, 5.1 Hz, 3H), 2.98-2.82 (m, 4H), 2.70-2.58 (m, 2H), 2.44 (s, 3H).

Example 94: Synthesis of 4-[(2R)-3-(3,4-dihydro-1H-isoquinolin-2-yl)-2-hydroxy-propyl]-8-(1-ethylazetidin-3-yl)oxy-2,3-dihydro-1,4-benzoxazepin-5-one

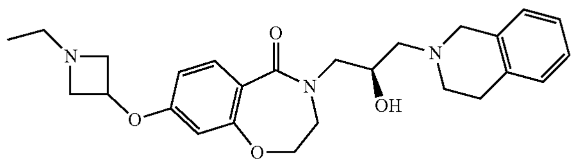 [SMILES: CCN1CC(Oc2ccc3c(c2)OCCN(C[C@H](O)CN2CCc4ccccc4C2)C3=O)C1]

The material obtained in Example 83-1 as a starting material was used in the same manner as in Example 87 to obtain the title compound, except that acetaldehyde was used instead of paraformaldehyde.

$^1$H NMR (400 MHz, Methanol-$d_4$) δ 7.57 (d, J=8.7 Hz, 1H), 7.05-6.91 (m, 4H), 6.55 (d, J=8.7 Hz, 1H), 6.34 (d, J=2.9 Hz, 1H), 4.36 (t, J=5.0 Hz, 2H), 4.15-4.04 (m, 1H), 3.90-3.80 (m, 1H), 3.73 (t, J=7.7 Hz, 2H), 3.66 (s, 2H), 3.61 (t, J=5.2 Hz, 2H), 3.31 (dd, J=13.9, 7.7 Hz, 1H), 3.17 (dd, J=8.8, 4.9 Hz, 4H), 2.87-2.73 (m, 4H), 2.60-2.47 (m, 4H), 1.96-1.85 (m, 3H), 0.92 (t, J=7.2 Hz, 3H).

Example 95: Synthesis of 4-[(2R)-3-(3,4-dihydro-1H-isoquinolin-2-yl)-2-hydroxy-propyl]-8-(1-isopropylazetidin-3-yl)oxy-2,3-dihydro-1,4-benzoxazepin-5-one

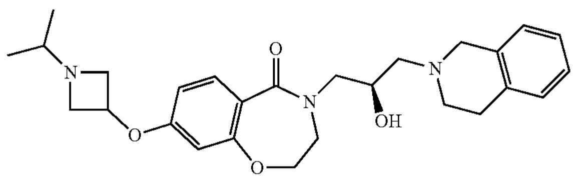 [SMILES: CC(C)N1CC(Oc2ccc3c(c2)OCCN(C[C@H](O)CN2CCc4ccccc4C2)C3=O)C1]

The material obtained in Example 83-1 as a starting material was used in the same manner as in Example 87 to obtain the title compound, except that acetone was used instead of paraformaldehyde.

$^1$H NMR (400 MHz, Methanol-$d_4$) δ 7.68 (d, J=8.7 Hz, 1H), 7.18-7.01 (m, 4H), 6.67 (d, J=8.9 Hz, 1H), 6.46 (s, 1H), 4.88-4.78 (m, 1H), 4.48 (t, J=5.2 Hz, 2H), 4.28-4.17 (m, 1H), 4.02-3.93 (m, 1H), 3.86-3.65 (m, 6H), 3.42 (dd, J=13.9, 7.7 Hz, 1H), 3.24 (t, J=7.0 Hz, 2H), 3.00-2.83 (m, 4H), 2.72-2.60 (m, 2H), 2.57-2.46 (m, 1H), 1.01 (d, J=6.2 Hz, 6H).

Example 96: Synthesis of 4-[(2R)-3-(3,4-dihydro-1H-isoquinolin-2-yl)-2-hydroxy-propyl]-8-[1-(oxetan-3-ylyl)azetidin-3-yl]oxy-2,3-dihydro-1,4-benzoxazepin-5-one

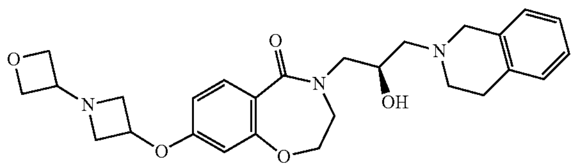 [SMILES: O=C1c2ccc(OC3CN(C4COC4)C3)cc2OCCN1C[C@H](O)CN1CCc2ccccc2C1]

The material obtained in Example 83-1 as a starting material was used in the same manner as in Example 87 to obtain the title compound, except that oxetan-3-one was used instead of paraformaldehyde.

$^1$H NMR (400 MHz, Methanol-$d_4$) δ 7.69 (d, J=8.7 Hz, 1H), 7.19-7.02 (m, 4H), 6.67 (d, J=8.7 Hz, 1H), 6.47 (s, 1H), 4.77 (t, J=6.9 Hz, 2H), 4.50 (dt, J=15.6, 5.6 Hz, 4H), 4.25 (d, J=6.3 Hz, 1H), 4.01-3.83 (m, 4H), 3.82 (s, 2H), 3.73 (d, J=5.0 Hz, 2H), 3.44 (dd, J=13.9, 7.5 Hz, 1H), 2.95 (s, 4H), 2.69 (d, J=6.7 Hz, 2H).

Example 97: Synthesis of 4-[(2R)-3-(3,4-dihydro-1H-isoquinolin-2-yl)-2-hydroxy-propyl]-8-[(1-ethylazetidin-3-yl)meth oxy]-2,3-dihydro-1,4-benzoxazepin-5-one

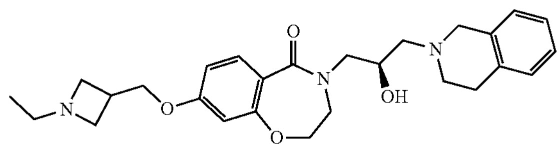 [SMILES: CCN1CC(COc2ccc3c(c2)OCCN(C[C@H](O)CN2CCc4ccccc4C2)C3=O)C1]

The material obtained by changing tert-butyl 3-methylsulfonyloxyazetidin-1-carboxylate to tert-butyl 3-(methylsulfonyloxymethyl)azetidin-1-carboxylate in Example 83-1 as a starting material was used in the same manner as in Example 87 to obtain the title compound, except that acetaldehyde was used instead of paraformaldehyde.

$^1$H NMR (400 MHz, Methanol-$d_4$) δ 7.68 (d, J=8.7 Hz, 1H), 7.17-7.01 (m, 4H), 6.76 (d, J=8.8 Hz, 1H), 6.60 (s, 1H), 4.48 (t, J=5.0 Hz, 2H), 4.27-4.17 (m, 1H), 4.14 (d, J=6.4 Hz, 2H), 3.98 (dd, J=13.7, 3.5 Hz, 1H), 3.80-3.67 (m, 4H), 3.53-3.37 (m, 3H), 3.15 (t, J=7.2 Hz, 2H), 3.01-2.89 (m, 3H), 2.90-2.80 (m, 2H), 2.70-2.61 (m, 2H), 2.57 (q, J=7.4 Hz, 2H), 1.00 (t, J=7.2 Hz, 3H).

Example 98: Synthesis of 4-[(2R)-3-(3,4-dihydro-1H-isoquinolin-2-yl)-2-hydroxy-propyl]-8-(1-methylpyrrolidin-3-yl)oxy-2,3-dihydro-1,4-benzoxazepin-5-one

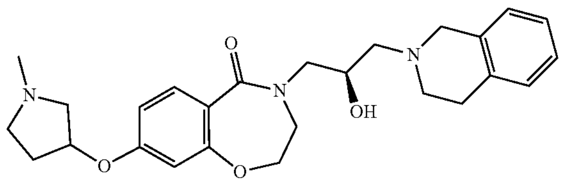 [SMILES: CN1CCC(Oc2ccc3c(c2)OCCN(C[C@H](O)CN2CCc4ccccc4C2)C3=O)C1]

The material obtained by changing tert-butyl 3-methylsulfonyloxyazetidin-1-carboxylate to tert-butyl 4-methylsulfonyloxypyrrolidin-1-carboxylate in Example 83-1 as a starting material was used in the same manner as in Example 87 to obtain the title compound.

$^1$H NMR (400 MHz, Methanol-$d_4$) δ 7.67 (dd, J=8.7, 2.0 Hz, 1H), 7.11 (d, J=3.3 Hz, 3H), 7.05 (d, J=6.7 Hz, 1H), 6.72 (dd, J=8.8, 2.4 Hz, 1H), 6.53 (d, J=2.4 Hz, 1H), 4.95 (d, J=6.9 Hz, 1H), 4.47 (t, J=5.3 Hz, 2H), 4.22 (d, J=6.3 Hz, 1H), 3.98 (dd, J=14.0, 3.4 Hz, 1H), 3.74 (d, J=9.3 Hz, 4H), 3.42 (dd, J=14.0, 7.7 Hz, 1H), 3.00-2.81 (m, 8H), 2.64 (d, J=6.2 Hz, 2H), 2.53-2.45 (m, 1H), 2.41 (s, 3H), 2.07-1.93 (m, 2H), 1.32 (d, J=6.0 Hz, 1H).

Example 99: Synthesis of 4-[(2R)-3-(3,4-dihydro-1H-isoquinolin-2-yl)-2-hydroxy-propyl]-8-[(3R)-1-ethylpyrrolidin-3-yl]oxy-2,3-dihydro-1,4-benzoxazepin-5-one

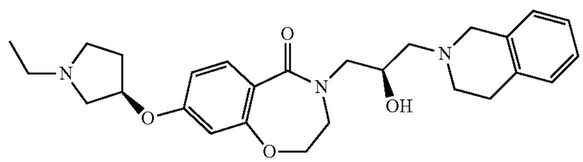 [SMILES: CCN1CC[C@@H](Oc2ccc3c(c2)OCCN(C[C@H](O)CN2CCc4ccccc4C2)C3=O)C1]

The material obtained by changing tert-butyl 3-methylsulfonyloxyazetidin-1-carboxylate to tert-butyl (3S)-3-methylsulfonyloxypyrrolidin-1-carboxylate in Example 83-1 as a starting material was used in the same manner as in Example 87 to obtain the title compound, except that acetaldehyde was used instead of paraformaldehyde.

$^1$H NMR (400 MHz, Methanol-$d_4$) δ 7.61 (d, J=8.7 Hz, 1H), 7.10-6.95 (m, 4H), 6.66 (d, J=8.9 Hz, 1H), 6.48 (s, 1H), 4.94 (s, 1H), 4.41 (t, J=5.0 Hz, 2H), 4.21-4.11 (m, 1H), 3.90 (d, J=16.4 Hz, 1H), 3.72 (s, 2H), 3.66 (t, J=5.1 Hz, 2H), 3.37 (dd, J=14.0, 7.5 Hz, 1H), 3.03-2.77 (m, 7H), 2.72-2.53 (m, 5H), 2.40-2.29 (m, 1H), 1.98 (dd, J=10.0, 7.6 Hz, 2H), 1.13 (t, J=7.3 Hz, 3H).

Example 100: Synthesis of 4-[(2R)-3-(3,4-dihydro-1H-isoquinolin-2-yl)-2-hydroxy-propyl]-8-(2-pyridyloxy)-2,3-dihydro-1,4-benzoxazepin-5-one

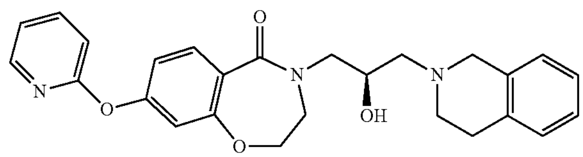 [SMILES: O=C1c2ccc(Oc3ccccn3)cc2OCCN1C[C@H](O)CN1CCc2ccccc2C1]

The title compound was synthesized in the same manner as in Example 64, except that cesium carbonate was used instead of potassium carbonate, and 2-fluoropyridine was used instead of 4-chlorotetrahydropyran.

$^1$H NMR (400 MHz, Chloroform-d) δ 8.26 (d, J=5.2 Hz, 1H), 7.75 (t, J=7.7 Hz, 1H), 7.38 (d, J=8.6 Hz, 1H), 7.22-6.94 (m, 7H), 6.73 (d, J=2.2 Hz, 1H), 6.56 (d, J=8.7 Hz, 1H), 4.16-4.01 (m, 1H), 3.91-3.77 (m, 1H), 3.69 (t, J=14.7 Hz, 2H), 3.52 (d, J=14.5 Hz, 1H), 3.06-2.87 (m, 3H), 2.80 (d, J=8.8 Hz, 1H), 2.68-2.53 (m, 2H), 2.05 (d, J=11.5 Hz, 1H), 1.63 (d, J=6.0 Hz, 1H), 1.01-0.73 (m, 1H).

Example 101: Synthesis of 4-[(2R)-3-(3,4-dihydro-1H-isoquinolin-2-yl)-2-hydroxy-propyl]-8-[[(2S)-1-isopropylpyrrolidin-2-yl]methoxy]-2,3-dihydro-1,4-benzoxazepin-5-one

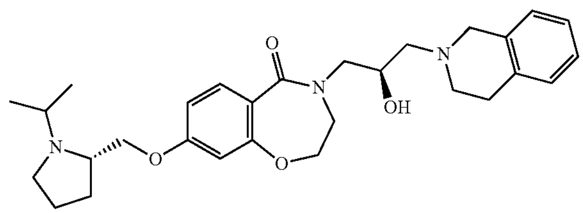 [SMILES: CC(C)N1CCC[C@H]1COc1ccc2c(c1)OCCN(C[C@H](O)CN1CCc3ccccc3C1)C2=O]

The material obtained by changing tert-butyl 3-methylsulfonyloxyazetidine-1-carboxylate to tert-butyl (2R)-2-(methylsulfonyloxymethyl)pyrrolidine-1-carboxylate in Example 83-1 as a starting material was used in the same manner as in Example 87 to obtain the title compound, except that acetone was used instead of paraformaldehyde.

$^1$H NMR (400 MHz, Methanol-$d_4$) δ 7.62 (d, J=8.7 Hz, 1H), 7.08-7.03 (m, 3H), 6.98 (d, J=6.7 Hz, 1H), 6.78-6.69 (m, 1H), 6.56 (d, J=2.4 Hz, 1H), 4.41 (t, J=5.1 Hz, 2H), 4.16 (s, 1H), 4.03 (d, J=5.7 Hz, 2H), 3.94-3.85 (m, 1H), 3.73-3.62 (m, 4H), 3.37 (dd, J=13.7, 7.6 Hz, 2H), 3.22-3.15 (m, 1H), 2.95 (d, J=9.3 Hz, 1H), 2.89-2.80 (m, 4H), 2.60 (d, J=6.4 Hz, 2H), 2.08 (t, J=9.4 Hz, 1H), 1.98-1.79 (m, 5H), 1.24 (d, J=6.7 Hz, 5H), 1.19 (d, J=6.5 Hz, 3H).

Example 102: Synthesis of 4-[(2R)-3-(3,4-dihydro-1H-isoquinolin-2-yl)-2-hydroxy-propyl]-8-[(1-methyl-4-piperidyl)methoxy]-2,3-dihydro-1,4-benzoxazepin-5-one

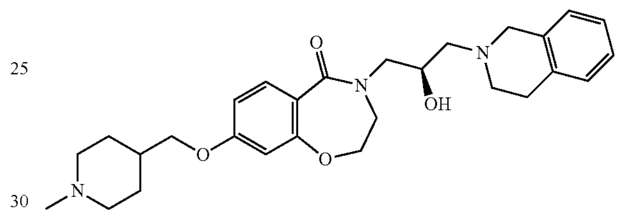 [SMILES: CCN1CCC(COc2ccc3c(c2)OCCN(C[C@H](O)CN2CCc4ccccc4C2)C3=O)CC1]

The material obtained by changing tert-butyl 3-methylsulfonyloxyazetidin-1-carboxylate to tert-butyl 4-(methylsulfonyloxymethyl)piperidine-1-carboxylate in Example 83-1 as a starting material was used in the same manner as in Example 87 to obtain the title compound.

$^1$H NMR (400 MHz, Methanol-$d_4$) δ 7.59 (d, J=8.7 Hz, 1H), 7.06 (d, J=5.1 Hz, 3H), 7.00 (d, J=7.0 Hz, 1H), 6.80-6.60 (m, 1H), 6.51 (d, J=2.6 Hz, 1H), 5.42 (d, J=1.7 Hz, 1H), 4.39 (t, J=5.2 Hz, 2H), 4.29-4.07 (m, 1H), 4.01-3.74 (m, 5H), 3.65 (t, J=5.0 Hz, 2H), 3.47 (d, J=7.2 Hz, 2H), 3.32 (d, J=12.1 Hz, 2H), 3.25 (p, J=1.7 Hz, 3H), 2.90 (s, 4H), 2.76 (t, J=12.5 Hz, 2H), 2.71-2.57 (m, 6H), 2.05-1.92 (m, 4H), 1.55 (d, J=12.9 Hz, 2H), 1.11 (t, J=7.0 Hz, 1H).

Example 103: Synthesis of 4-[(2R)-3-(3,4-dihydro-1H-isoquinolin-2-yl)-2-hydroxy-propyl]-8-[(1-ethyl-4-piperidyl)methoxy]-2,3-dihydro-1,4-benzoxazepin-5-one

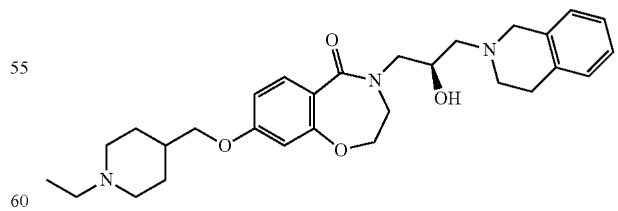

The material obtained by changing tert-butyl 3-methylsulfonyloxyazetidine-1-carboxylate to tert-butyl 4-(methylsulfonyloxymethyl)piperidine-1-carboxylate in Example 83-1 as a starting material was used in the same manner as in Example 87 to obtain the title compound, except that acetaldehyde was used instead of paraformaldehyde.

$^1$H NMR (400 MHz, Methanol-$d_4$) δ 7.60 (d, J=8.8 Hz, 1H), 7.07 (d, J=4.4 Hz, 4H), 7.00 (d, J=6.0 Hz, 1H), 6.69 (d, J=8.9 Hz, 1H), 6.52 (d, J=2.5 Hz, 1H), 4.40 (t, J=5.1 Hz, 2H), 4.18 (s, 1H), 3.89 (d, J=5.2 Hz, 3H), 3.79 (s, 2H), 3.66 (t, J=5.1 Hz, 2H), 3.44 (ddt, J=21.3, 13.9, 6.9 Hz, 4H), 3.29 (s, 1H), 3.02 (q, J=7.4 Hz, 2H), 2.91 (s, 4H), 2.81 (t, J=12.8 Hz, 2H), 2.66 (d, J=7.8 Hz, 2H), 2.03 (d, J=14.1 Hz, 4H), 1.59 (d, J=13.0 Hz, 1H), 1.26 (t, J=7.3 Hz, 5H)

Example 104: Synthesis of 4-[(2R)-3-(3,4-dihydro-1H-isoquinolin-2-yl)-2-hydroxy-propyl]-8-[(4-methylmorpholin-2-yl) methoxy]-2,3-dihydro-1,4-benzoxazepin-5-one

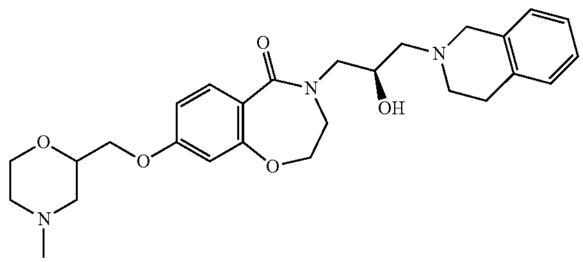 [SMILES: CN1CCOC(COc2ccc3c(c2)OCCN(C[C@H](O)CN2CCc4ccccc4C2)C3=O)C1]

The material obtained by changing tert-butyl 3-methylsulfonyloxyazetidine-1-carboxylate to tert-butyl 2-(methylsulfonyloxymethyl)morpholine-4-carboxylate in Example 83-1 as a starting material was used in the same manner as in Example 87 to obtain the title compound.

$^1$H NMR (400 MHz, Methanol-$d_4$) δ 7.67 (d, J=8.8 Hz, 1H), 7.12 (d, J=4.0 Hz, 3H), 7.06 (s, 1H), 6.77 (d, J=8.9 Hz, 1H), 6.60 (s, 1H), 4.48 (t, J=4.9 Hz, 2H), 4.23 (s, 1H), 4.12-3.86 (m, 5H), 3.80-3.66 (m, 5H), 3.56-3.35 (m, 1H), 2.91 (dd, J=20.1, 6.0 Hz, 5H), 2.74 (d, J=11.8 Hz, 1H), 2.67-2.56 (m, 2H), 2.35 (s, 3H), 2.26-2.16 (m, 1H), 2.07 (q, J=9.9, 8.9 Hz, 2H).

Example 105: Synthesis of 4-[(2R)-3-(3,4-dihydro-1H-isoquinolin-2-yl)-2-hydroxy-propyl]-8-[(4-ethylmorpholin-2-yl)methoxy]-2,3-dihydro-1,4-benzoxazepin-5-one

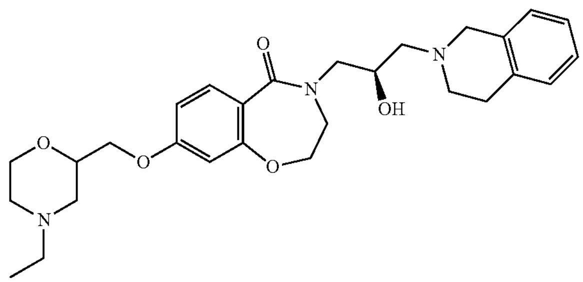 [SMILES: CCN1CCOC(COc2ccc3c(c2)OCCN(C[C@H](O)CN2CCc4ccccc4C2)C3=O)C1]

The material obtained by changing tert-butyl 3-methylsulfonyloxyazetidine-1-carboxylate to tert-butyl 2-(methylsulfonyloxymethyl)morpholine-4-carboxylate in Example 83-1 as a starting material was used in the same manner as in Example 87 to obtain the title compound, except that acetaldehyde was used instead of paraformaldehyde.

$^1$H NMR (400 MHz, Methanol-$d_4$) δ 7.68 (d, J=8.8 Hz, 1H), 7.12 (s, 3H), 7.07 (s, 1H), 6.77 (d, J=9.0 Hz, 1H), 6.60 (s, 1H), 4.48 (s, 2H), 4.24 (s, 1H), 4.13-3.86 (m, 5H), 3.75 (d, J=22.3 Hz, 5H), 3.51-3.37 (m, 2H), 2.93 (td, J=30.3, 29.0, 11.6 Hz, 6H), 2.68 (s, 2H), 2.51 (q, J=7.3 Hz, 2H), 2.20 (d, J=11.2 Hz, 2H), 2.05 (d, J=10.7 Hz, 4H), 1.30 (d, J=9.4 Hz, 4H), 1.15 (t, J=7.3 Hz, 3H).

Example 106: Synthesis of 4-[(2R)-3-(3,4-dihydro-1H-isoquinolin-2-yl)-2-hydroxy-propyl]-8-[(1-methylpyrrolidin-3-yl)methoxy]-2,3-dihydro-1,4-benzoxazepin-5-one

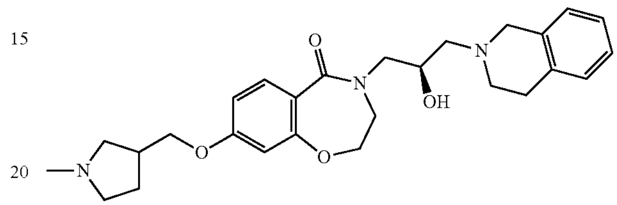

The material obtained by changing tert-butyl 3-methylsulfonyloxyazetidine-1-carboxylate to tert-butyl 3-(methylsulfonyloxymethyl)pyrrolidine-1-carboxylate in Example 83-1 as a starting material was used in the same manner as in Example 87 to obtain the title compound.

$^1$H NMR (400 MHz, Methanol-$d_4$) δ 7.67 (d, J=8.7 Hz, 1H), 7.11 (d, J=3.6 Hz, 3H), 7.06 (s, 1H), 6.75 (d, J=8.9 Hz, 1H), 6.58 (s, 1H), 4.47 (t, J=5.2 Hz, 2H), 4.23 (s, 1H), 3.97 (t, J=7.8 Hz, 3H), 3.74 (d, J=11.0 Hz, 4H), 3.42 (dd, J=14.0, 7.7 Hz, 1H), 2.93 (d, J=5.7 Hz, 2H), 2.89-2.82 (m, 3H), 2.74-2.62 (m, 4H), 2.54 (t, J=8.2 Hz, 1H), 2.43 (s, 3H), 2.12 (t, J=11.3 Hz, 1H), 2.05 (d, J=9.8 Hz, 1H), 1.69 (dd, J=13.2, 6.7 Hz, 1H).

Example 107: Synthesis of 4-[(2R)-3-(3,4-dihydro-1H-isoquinolin-2-yl)-2-hydroxy-propyl]-8-[(1-methyl-3-piperidyl)methoxy]-2,3-dihydro-1,4-benzoxazepin-5-one

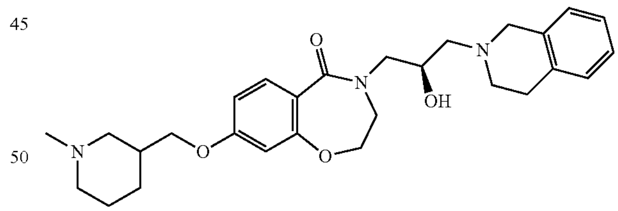

The material obtained by changing tert-butyl 3-methylsulfonyloxyazetidin-1-carboxylate to tert-butyl 3-(methylsulfonyloxymethyl)piperidine-1-carboxylate in Example 83-1 as a starting material was used in the same manner as in Example 87 to obtain the title compound.

$^1$H NMR (400 MHz, Methanol-$d_4$) δ 7.66 (d, J=8.7 Hz, 1H), 7.16-7.09 (m, 3H), 7.05 (d, J=6.7 Hz, 1H), 6.75 (dd, J=8.8, 2.4 Hz, 1H), 6.57 (d, J=2.3 Hz, 1H), 4.47 (t, J=5.1 Hz, 2H), 4.22 (s, 1H), 3.96 (ddd, J=15.0, 11.6, 4.5 Hz, 3H), 3.86 (d, J=7.7 Hz, 1H), 3.76-3.69 (m, 4H), 3.42 (dd, J=13.9, 7.7 Hz, 1H), 3.04 (d, J=11.3 Hz, 1H), 2.93 (d, J=6.0 Hz, 3H), 2.87 (d, J=5.6 Hz, 3H), 2.68-2.59 (m, 2H), 2.31 (d, J=8.8 Hz, 4H), 2.02 (td, J=11.9, 11.4, 6.9 Hz, 2H), 1.93-1.74 (m, 4H), 1.66 (d, J=13.3 Hz, 1H), 1.20-1.09 (m, 1H).

Example 108: Synthesis of 4-[(2R)-3-(3,4-dihydro-1H-isoquinolin-2-yl)-2-hydroxy-propyl]-6-fluoro-8-(morpholinomethyl)-2,3-dihydro-1,4-benzoxazepin-5-one

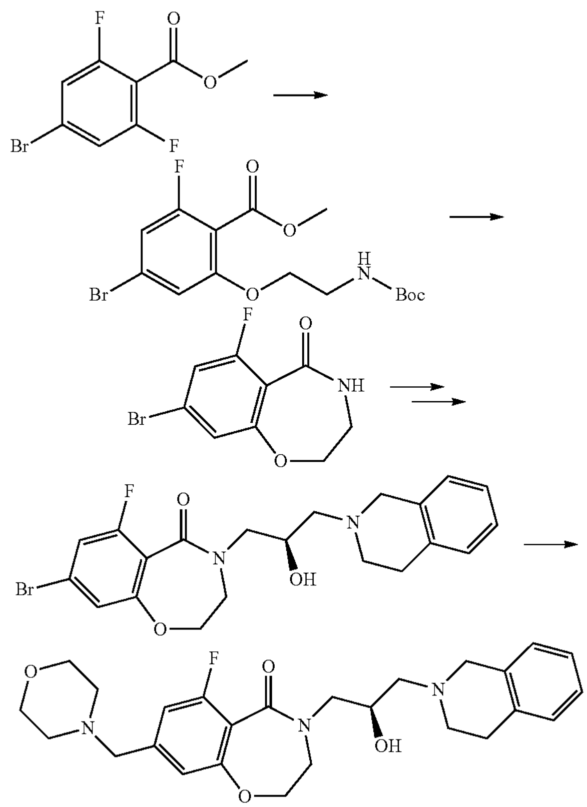

Example 108-1: Synthesis of methyl 4-bromo-2-[2-(tert-butoxycarbonylamino)ethoxy]-6-fluoro-benzoate Methyl 4-bromo-2,6-difluoro-benzoate (5.0 g, 19.9 mmol) was dissolved in 50 mL of tetrahydrofura, and 60% sodium hydride (1.03 g, 25.8 mmol) and tert-butyl N-(2-hydroxyethyl)carbamate (3.7 mL, 23.9 mmol) were slowly added thereto at 0° C., followed by stirring at the same temperature. To the reaction solution saturated aqueous chloroammonium solution and extracted with ethyl acetate 3 times. The oily liquid obtained by drying the combined organic layers over anhydrous magnesium sulfate and concentrating was purified by flash chromatography to obtain the title compound (5.07 g) as transparent liquid.

Example 108-2: Synthesis of 8-bromo-6-fluoro-3,4-dihydro-2H-1,4-benzoxazepin-5-one Methyl 4-bromo-2-[2-(tert-butoxycarbonylamino) ethoxy]-6-fluoro-benzoate (5.07 g, 12.9 mmol) obtained in Example 108-1 was dissolved in 20 mL of methanol, and 4 M hydrochloric acid solution dissolved in 1,4-dioxane (20 mL, 80 mmol) was added thereto. The reaction solution was stirred at room temperature, and sodium hydroxide aqueous solution was added under an ice bath to basify, followed by extraction with ethyl acetate 3 times. The oily liquid obtained by drying the combined organic layers over anhydrous magnesium sulfate and concentrating under reduced pressure was purified by flash chromatography to obtain the solid title compound (870 mg).

Example 108-3: Synthesis of 8-bromo-4-[(2R)-3-(3,4-dihydro-1H-isoquinolin-2-yl)-2-hydroxy-propyl]-6-fluoro-2,3-dihydro-1,4-benzoxazepin-5-one 8-Bromo-6-fluoro-3,4-dihydro-2H-1,4-benzoxazepin-5-one obtained in Example 108-2 as a starting material was used in the same manner as in Example 5 to obtain the title compound.

Example 108-4: Synthesis of 4-[(2R)-3-(3,4-dihydro-1H-isoquinolin-2-yl)-2-hydroxy-propyl]-6-fluoro-8-(morpholinomethyl)-2,3-dihydro-1,4-benzoxazepin-5-one 8-Bromo-4-[(2R)-3-(3,4-dihydro-1H-isoquinolin-2-yl)-2-hydroxy-propyl]-6-fluoro-2,3-dihydro-1,4-benzoxazepin-5-one obtained in Example 108-3 as a starting material was used in the same manner as in Example 22 to obtain the title compound.

$^1$H NMR (400 MHz, Methanol-$d_4$) δ 7.12 (d, J=3.8 Hz, 3H), 7.06 (d, J=9.8 Hz, 2H), 6.95 (s, 1H), 4.43 (t, J=5.6 Hz, 2H), 4.29-4.20 (m, 1H), 4.03-3.94 (m, 1H), 3.85-3.76 (m, 2H), 3.76-3.65 (m, 6H), 3.54 (s, 2H), 3.52-3.44 (m, 1H), 3.02-2.86 (m, 4H), 2.74-2.63 (m, 2H), 2.54-2.42 (m, 4H).

Example 109: Synthesis of 4-[(2R)-3-(3,4-dihydro-1H-isoquinolin-2-yl)-2-hydroxy-propyl]-6-fluoro-8-[(1-methyl-4-piperidyl)oxy]-2,3-dihydro-1,4-benzoxazepin-5-one

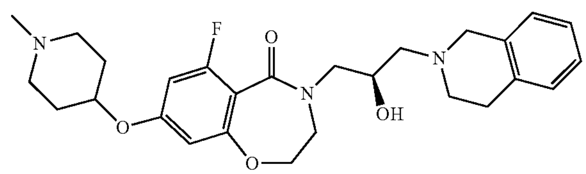 [SMILES: CN1CCC(Oc2cc(F)c3c(c2)OCCN(C[C@H](O)CN2CCc4ccccc4C2)C3=O)CC1]

Example 109-1: Synthesis of 4-[(2R)-3-(3,4-dihydro-1H-isoquinolin-2-yl)-2-hydroxy-propyl]-6-fluoro-8-hydroxy-2,3-dihydro-1,4-benzoxazepin-5-one 8-Bromo-4-[(2R)-3-(3,4-dihydro-1H-isoquinolin-2-yl)-2-hydroxy-propyl]-6-fluoro-2,3-dihydro-1,4-benzoxazepin-5-one obtained in Example 108-3 as a starting material was used in the same manner as in Example 56-1 to obtain the title compound.

Example 109-2: Synthesis of 4-[(2R)-3-(3,4-dihydro-1H-isoquinolin-2-yl)-2-hydroxy-propyl]-6-fluoro-8-[(1-methyl-4-piperidyl)oxy]-2,3-dihydro-1,4-benzoxazepin-5-one 4-[(2R)-3-(3,4-dihydro-1H-isoquinolin-2-yl)-2-hydroxy-propyl]-6-fluoro-8-hydroxy-2,3-dihydro-1,4-benzoxazepin-5-one as a starting material was used in the same manner as in Examples 77, 78-1 and 87 to obtain the title compound.

$^1$H NMR (400 MHz, Methanol-$d_4$) δ 7.09 (d, J=19.1 Hz, 4H), 6.65 (d, J=12.2 Hz, 1H), 6.51 (s, 1H), 4.57-4.46 (m, 1H), 4.41 (t, J=5.7 Hz, 2H), 4.28-4.16 (m, 1H), 3.97 (d, J=12.0 Hz, 1H), 3.77 (s, 2H), 3.71 (t, J=5.6 Hz, 2H), 3.45 (dd, J=13.8, 7.6 Hz, 1H), 3.00-2.83 (m, 4H), 2.81-2.70 (m, 2H), 2.70-2.59 (m, 2H), 2.51-2.38 (m, 2H), 2.35 (s, 3H), 2.12-1.99 (m, 2H), 1.92-1.76 (m, 2H).

Example 110: Synthesis of 4-[(2R)-3-(3,4-dihydro-1H-isoquinolin-2-yl)-2-hydroxy-propyl]-8-[(1-ethyl-4-piperidyl)oxy]-2,2-dimethyl-3H-1,4-benzoxazepin-5-one

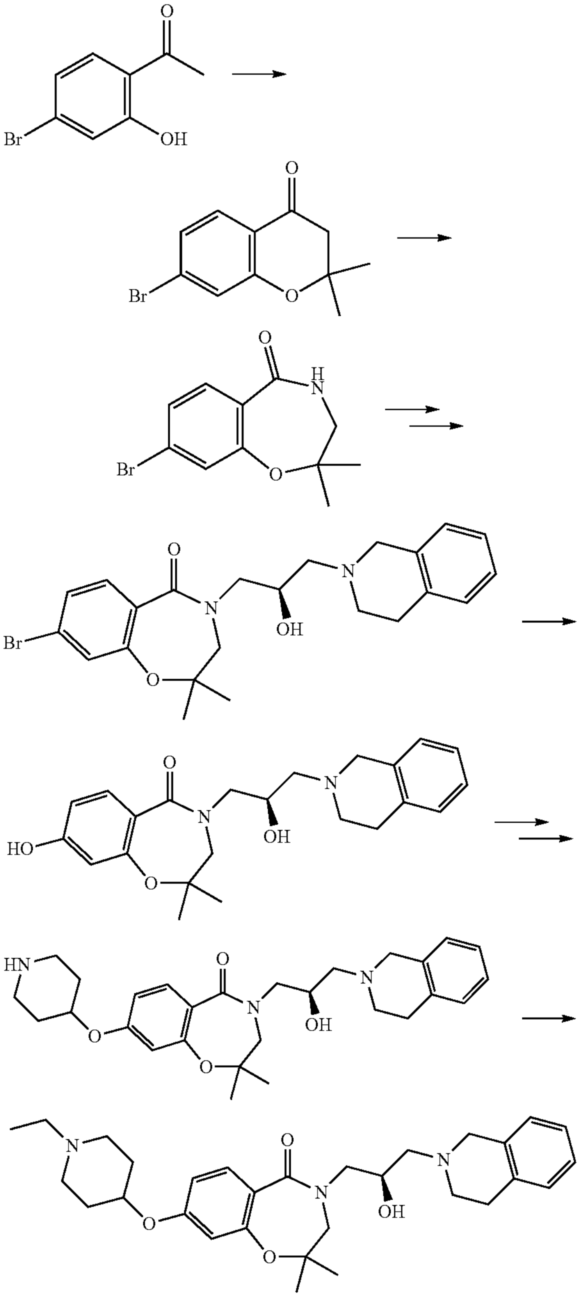

Example 110-1: Synthesis of 7-bromo-2,2-dimethyl-chroman-4-one 1-(4-Bromo-2-hydroxyphenyl)ethanone (5.0 g, 23.2 mmol) was dissolved in 20 mL of methanol, and pyrrolidine (5 mL, 60.9 mmol) was added thereto and stirred for 30 minutes under an ice bath. To the reaction solution acetone (2.5 mL, 33.7 mmol) was added, heated to reflux for 4 hours, and water was added to terminate the reaction, followed by extraction with ethyl acetate 3 times. The combined organic layers were dried over anhydrous magnesium sulfate, concentrated, dissolved in ethyl acetate, and filtered through a small amount of silica. The solution was concentrated under reduced pressure to obtain the title compound (4.7 g) as a crystalline solid without additional purification.

Example 110-2: Synthesis of 8-bromo-2,2-dimethyl-3,4-dihydro-1,4-benzoxazepin-5-one 7-Bromo-2,2-dimethyl-chroman-4-one (4.7 g, 18.6 mmol) obtained in Example 110-1 was dissolved in 25 mL of methanesulfonic acid, and sodium azide (1.81 g, 27.9 mmol) was slowly added thereto under an ice bath. The reaction solution was stirred at room temperature for 5 hours, and 1 M sodium hydroxide aqueous solution was slowly added while maintaining at 0° C. under an ice bath. After basifying the reaction solution to pH 10 or more, ethyl acetate was added thereto and extracted 3 times. The combined organic layers were dried over anhydrous magnesium sulfate, the solvent was removed by evaporation under reduced pressure, and then recrystallized from dichloromethane and hexane to obtain the solid title compound.

Example 110-3: Synthesis of 8-bromo-4-[(2R)-3-(3,4-dihydro-1H-isoquinolin-2-yl)-2-hydroxy-propyl]-2,2-dimethyl-3H-1,4-benzoxazepin-5-one 8-Bromo-2,2-dimethyl-3,4-dihydro-1,4-benzoxazepin-5-one obtained in Example 110-2 as a starting material was used in the same manner as in Example 5 to obtain the title compound.

Example 110-4: Synthesis of 4-[(2R)-3-(3,4-dihydro-1H-isoquinolin-2-yl)-2-hydroxy-propyl]-8-hydroxy-2,2-dimethyl-3H-1,4-benzoxazepin-5-one 8-Bromo-4-[(2R)-3-(3,4-dihydro-1H-isoquinolin-2-yl)-2-hydroxy-propyl]-2,2-dimethyl-3H-1,4-benzoxazepin-5-one obtained in Example 110-3 as a starting material was used in the same manner as in Example 56-1 to obtain the title compound.

Example 110-5: Synthesis of 4-[(2R)-3-(3,4-dihydro-1H-isoquinolin-2-yl)-2-hydroxy-propyl]-2,2-dimethyl-8-(4-piperidyloxy)-3H-1,4-benzoxazepin-5-one dihydrochloride The material obtained in Example 110-4 as a starting material was used in the same manner as in Examples 77 and 78-1 to obtain the title compound.

Example 110-6: Synthesis of 4-[(2R)-3-(3,4-dihydro-1H-isoquinolin-2-yl)-2-hydroxy-propyl]-8-[(1-ethyl-4-piperidyl)oxy]-2,2-dimethyl-3H-1,4-benzoxazepin-5-one The material obtained in Example 110-5 as a starting material was used in the same manner as in Example 87 to obtain the title compound, except that acetaldehyde was used instead of paraformaldehyde.

$^1$H NMR (400 MHz, Methanol-$d_4$) δ 7.58 (d, J=8.0 Hz, 1H), 7.09 (d, J=19.8 Hz, 4H), 6.81 (d, J=8.9 Hz, 1H), 6.52 (s, 1H), 4.58-4.48 (m, 1H), 4.32-4.22 (m, 1H), 4.03 (d, J=13.7 Hz, 1H), 3.76 (s, 2H), 3.50 (s, 2H), 3.41 (dd, J=10.0, 3.2 Hz, 1H), 2.97-2.90 (m, 2H), 2.91-2.76 (m, 4H), 2.71-2.59 (m, 2H), 2.59-2.41 (m, 4H), 2.14-1.98 (m, 2H), 1.94-1.78 (m, 2H), 1.43 (s, 3H), 1.34 (s, 3H), 1.16 (t, J=7.2 Hz, 3H).

Example 111: Synthesis of 4-[(2R)-3-(3,4-dihydro-1H-isoquinolin-2-yl)-2-hydroxy-propyl]-2,2-dimethyl-8-(morpholino methyl)-3H-1,4-benzoxazepin-5-one

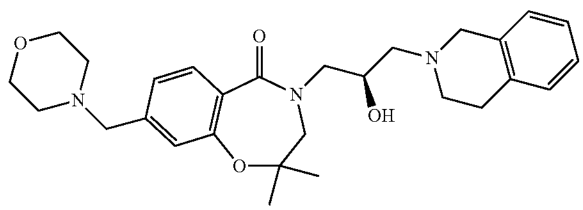 [SMILES: CC1(C)CN(C[C@H](O)CN2CCc3ccccc3C2)C(=O)c2ccc(CN3CCOCC3)cc2O1]

8-Bromo-4-[(2R)-3-(3,4-dihydro-1H-isoquinolin-2-yl)-2-hydroxy-propyl]-2,2-dimethyl-3H-1,4-benzoxazepin-5-one as a starting material was used in the same manner as in Example 22 to obtain the title compound.

$^1$H NMR (400 MHz, Methanol-$d_4$) δ 7.61 (d, J=7.8 Hz, 1H), 7.22 (d, J=7.9 Hz, 1H), 7.17-7.02 (m, 4H), 7.00 (s, 1H), 4.34-4.24 (m, 1H), 4.06 (dd, J=13.7, 2.6 Hz, 1H), 3.78 (s, 2H), 3.71 (t, J=4.7 Hz, 4H), 3.56 (s, 2H), 3.53-3.38 (m, 3H), 2.99-2.81 (m, 4H), 2.72-2.58 (m, 2H), 2.48 (t, J=4.8 Hz, 4H), 1.43 (s, 3H), 1.33 (s, 3H).

Example 112: Synthesis of 4-[(2R)-3-(3,4-dihydro-1H-isoquinolin-2-yl)-2-hydroxy-propyl]-2,2-dimethyl-8-[(1-methyl-4-piperidyl)oxy]-3H-1,4-benzoxazepin-5-one

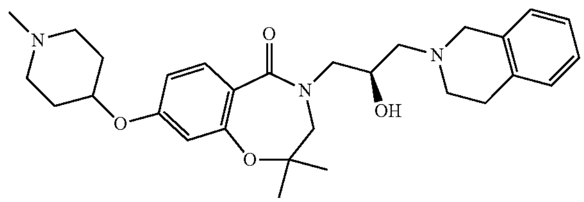 [SMILES: CN1CCC(Oc2ccc3c(c2)OC(C)(C)CN(C[C@H](O)CN2CCc4ccccc4C2)C3=O)CC1]

The material obtained in Example 110-5 as a starting material was used in the same manner as in Example 87 to obtain the title compound.

$^1$H NMR (400 MHz, Methanol-$d_4$) δ 7.57 (d, J=8.6 Hz, 1H), 7.17-7.02 (m, 4H), 6.81 (d, J=8.7 Hz, 1H), 6.52 (s, 1H), 4.56-4.46 (m, 1H), 4.33-4.21 (m, 1H), 4.03 (d, J=13.3 Hz, 1H), 3.75 (s, 2H), 3.50 (s, 2H), 3.40 (dd, J=14.0, 8.1 Hz, 1H), 2.98-2.81 (m, 4H), 2.80-2.66 (m, 2H), 2.66-2.54 (m, 2H), 2.51-2.39 (m, 2H), 2.34 (s, 3H), 2.10-1.98 (m, 2H), 1.89-1.76 (m, 2H), 1.43 (s, 3H), 1.34 (s, 3H).

Example 113: Synthesis of 4-[(2R)-3-(3,4-dihydro-1H-isoquinolin-2-yl)-2-hydroxy-propyl]-2,2-dimethyl-8-(4-pyridylmethoxy)-3H-1,4-benzoxazepin-5-one

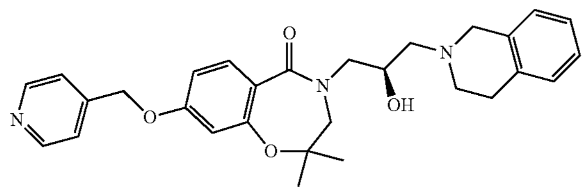 [SMILES: CC1(C)CN(C[C@H](O)CN2CCc3ccccc3C2)C(=O)c2ccc(OCc3ccncc3)cc2O1]

The material obtained in Example 110-4 as a starting material was used in the same manner as in Example 56-2 to obtain the title compound, except that 4-(chloromethyl)pyridine hydrochloride was used instead of 3-(chloromethyl)pyridine hydrochloride.

$^1$H NMR (400 MHz, Methanol-$d_4$) δ 8.56 (d, J=5.2 Hz, 2H), 7.61 (d, J=8.6 Hz, 1H), 7.54 (d, J=5.1 Hz, 2H), 7.17-7.00 (m, 4H), 6.90 (d, J=8.8 Hz, 1H), 6.62 (s, 1H), 5.25 (s, 2H), 4.32-4.22 (m, 1H), 4.03 (d, J=13.8 Hz, 1H), 3.76 (s, 2H), 3.50 (s, 2H), 3.41 (dd, J=13.9, 8.2 Hz, 1H), 2.97-2.82 (m, 4H), 2.66-2.57 (m, 2H), 1.42 (s, 3H), 1.32 (s, 3H).

Example 114: Synthesis of 8-(1-acetylazetidin-3-yl)oxy-4-[(2R)-3-(3,4-dihydro-1H-isoquinolin-2-yl)-2-hydroxy-propyl]-2,2-dimethyl-3H-1,4-benzoxazepin-5-one

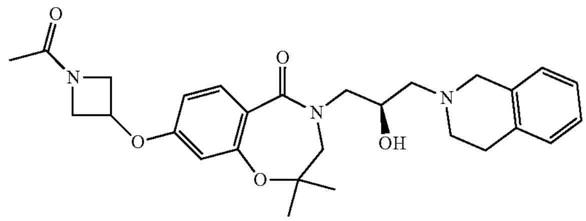 [SMILES: CC(=O)N1CC(Oc2ccc3c(c2)OC(C)(C)CN(C[C@H](O)CN2CCc4ccccc4C2)C3=O)C1]

The material obtained in Example 110-4 as a starting material was used in the same manner as in Example 83 to obtain the title compound.

$^1$H NMR (400 MHz, Methanol-$d_4$) δ 7.61 (d, J=8.6 Hz, 1H), 7.16-7.02 (m, 4H), 6.72 (d, J=8.1 Hz, 1H), 6.44 (s, 1H), 5.15-5.05 (m, 1H), 4.69-4.59 (m, 1H), 4.47-4.37 (m, 1H), 4.33-4.19 (m, 2H), 4.10-4.00 (m, 1H), 4.01-3.92 (m, 1H), 3.76 (s, 2H), 3.50 (s, 2H), 3.40-3.33 (m, 1H), 2.99-2.81 (m, 4H), 2.67-2.58 (m, 2H), 1.93 (s, 3H), 1.43 (s, 3H), 1.34 (s, 3H).

Example 115: Synthesis of 4-[(2R)-3-(3,4-dihydro-1H-isoquinolin-2-yl)-2-hydroxy-propyl]-1-methyl-8-(morpholinomethyl)-2,3-dihydro-1,4-benzodiazepin-5-one

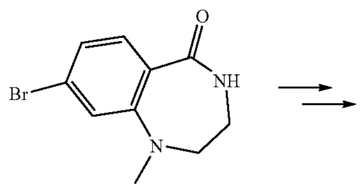

-continued

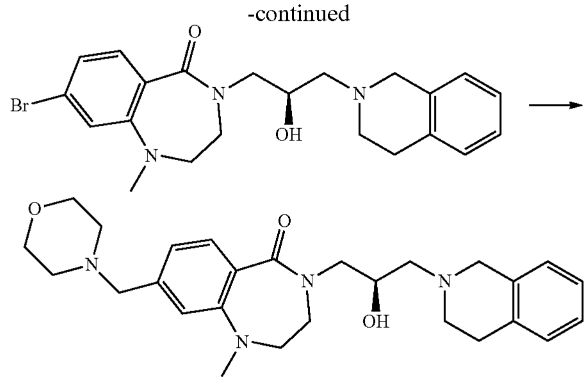

Example 115-1: Synthesis of 8-bromo-4-[(2R)-3-(3,4-dihydro-1H-isoquinolin-2-yl)-2-hydroxy-propyl]-1-methyl-2,3-dihydro-1,4-benzodiazepin-5-one 8-Bromo-1-methyl-3,4-dihydro-2H-1,4-benzodiazepin-5-one as a starting material was used in the same manner as in Example 5 to obtain the title compound.

Example 115-2: Synthesis of 4-[(2R)-3-(3,4-dihydro-1H-isoquinolin-2-yl)-2-hydroxy-propyl]-1-methyl-8-(morpholinomethyl)-2,3-dihydro-1,4-benzodiazepin-5-one 8-Bromo-4-[(2R)-3-(3,4-dihydro-1H-isoquinolin-2-yl)-2-hydroxy-propyl]-1-methyl-2,3-dihydro-1,4-benzodiazepin-5-one as a starting material was used in the same manner as in Example 22 to obtain the title compound.

$^1$H NMR (400 MHz, Methanol-$d_4$) δ 7.49 (d, J=8.0 Hz, 1H), 7.15-7.08 (m, 2H), 7.09-7.03 (m, 1H), 7.01 (d, J=7.0 Hz, 2H), 4.29-4.20 (m, 1H), 3.94 (dd, J=14.0, 4.0 Hz, 1H), 3.78 (s, 2H), 3.72 (t, J=4.7 Hz, 4H), 3.65-3.57 (m, 2H), 3.55 (s, 2H), 3.50 (t, J=7.4 Hz, 1H), 3.48-3.36 (m, 3H), 3.00-2.88 (m, 4H), 2.86 (s, 3H), 2.69 (t, J=5.4 Hz, 2H), 2.49 (s, 4H).

Example 116: Synthesis of 4-[(2R)-3-(3,4-dihydro-1H-isoquinolin-2-yl)-2-hydroxy-propyl]-1-methyl-8-(3,3,3-trifluoropropyl)-2,3-dihydro-1,4-benzodiazepin-5-one

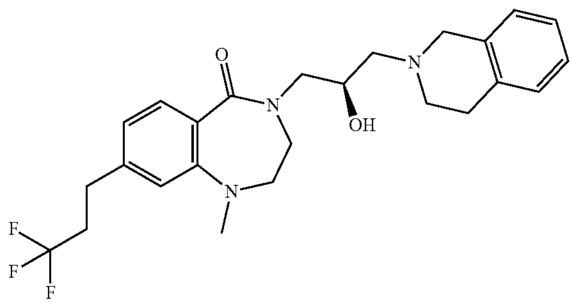 [SMILES: CN1CCN(C[C@H](O)CN2CCc3ccccc3C2)C(=O)c2ccc(CCC(F)(F)F)cc21]

8-Bromo-4-[(2R)-3-(3,4-dihydro-1H-isoquinolin-2-yl)-2-hydroxy-propyl]-1-methyl-2,3-dihydro-1,4-benzodiazepin-5-one as a starting material was used in the same manner as in Example 10 to obtain the title compound, except that 3,3,3-trifluoropropylboronic acid was used instead of methylboronic acid.

$^1$H NMR (400 MHz, Chloroform-d) δ 7.59 (d, J=7.8 Hz, 1H), 7.14 (q, J=5.6, 5.1 Hz, 3H), 7.09-6.91 (m, 1H), 6.82 (d, J=7.8 Hz, 1H), 6.67 (s, 1H), 4.11 (s, 1H), 3.98-3.76 (m, 2H), 3.73-3.48 (m, 4H), 3.41 (dt, J=11.8, 6.0 Hz, 1H), 3.30 (dt, J=10.8, 5.3 Hz, 1H), 2.94 (d, J=11.3 Hz, 2H), 2.87 (d, J=8.0 Hz, 5H), 2.84 (s, 1H), 2.75 (s, 1H), 2.68 (dd, J=12.5, 4.2 Hz, 1H), 2.65-2.56 (m, 1H), 2.39 (dq, J=20.0, 10.5 Hz, 2H), 1.00-0.78 (m, 2H).

Example 117: Synthesis of 8-(cyclohexylmethyl)-4-[(2R)-3-(3,4-dihydro-1H-isoquinolin-2-yl)-2-hydroxy-propyl]-1-meth yl-2,3-dihydro-1,4-benzodiazepin-5-one

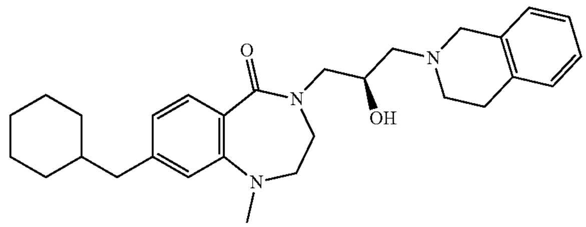 [SMILES: CN1CCN(C[C@H](O)CN2CCc3ccccc3C2)C(=O)c2ccc(CC3CCCCC3)cc21]

8-Bromo-4-[(2R)-3-(3,4-dihydro-1H-isoquinolin-2-yl)-2-hydroxy-propyl]-1-methyl-2,3-dihydro-1,4-benzodiazepin-5-one as a starting material was used in the same manner as in Example 10 to obtain the title compound, except that cyclohexylmethylboronic acid was used instead of methylboronic acid.

$^1$H NMR (400 MHz, Chloroform-d) δ 7.53 (d, J=7.8 Hz, 1H), 7.24-7.04 (m, 3H), 7.02 (d, J=6.7 Hz, 1H), 6.78 (d, J=7.8 Hz, 1H), 6.61 (s, 1H), 4.12 (s, 1H), 3.85 (dd, J=17.6, 14.1 Hz, 2H), 3.74-3.52 (m, 4H), 3.39 (dt, J=11.7, 5.9 Hz, 1H), 3.33-3.21 (m, 1H), 2.95 (s, 1H), 2.82 (s, 2H), 2.77 (d, J=9.0 Hz, 1H), 2.71-2.59 (m, 2H), 2.46 (d, J=7.1 Hz, 2H), 1.68 (d, J=11.4 Hz, 5H), 1.32-1.13 (m, 5H), 0.93 (q, J=13.8, 12.4 Hz, 3H).

Example 118: Synthesis of 8-(cyclohexen-1-yl)-4-[(2R)-3-(3,4-dihydro-1H-isoquinolin-2-yl)-2-hydroxy-propyl]-1-methyl-2,3-dihydro-1,4-benzodiazepin-5-one

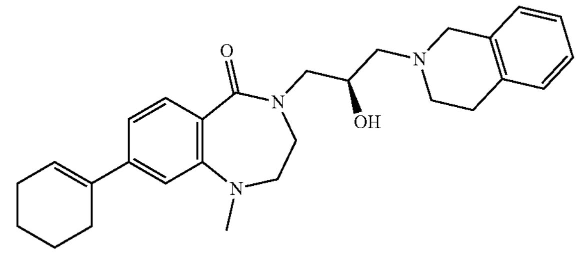 [SMILES: CN1CCN(C[C@H](O)CN2CCc3ccccc3C2)C(=O)c2ccc(C3=CCCCC3)cc21]

8-Bromo-4-[(2R)-3-(3,4-dihydro-1H-isoquinolin-2-yl)-2-hydroxy-propyl]-1-methyl-2,3-dihydro-1,4-benzodiazepin-5-one as a starting material was used in the same manner as in Example 10 to obtain the title compound, except that 2-(cyclohexen-1-yl)-4,4,5,5-tetramethyl-1,3,2-dioxaborolane was used instead of methylboronic acid.

$^1$H NMR (400 MHz, Chloroform-d) δ 7.57 (d, J=8.0 Hz, 1H), 7.19-7.07 (m, 3H), 7.01 (t, J=6.2 Hz, 2H), 6.86 (s, 1H), 6.17 (s, 1H), 4.12 (d, J=7.3 Hz, 1H), 3.97-3.76 (m, 2H), 3.70-3.44 (m, 4H), 3.38 (dt, J=11.9, 6.1 Hz, 1H), 3.27 (dt, J=10.6, 5.2 Hz, 1H), 2.91 (d, J=5.3 Hz, 4H), 2.85 (s, 3H), 2.75 (t, J=7.8 Hz, 1H), 2.70-2.56 (m, 2H), 2.40 (s, 2H), 2.25-2.18 (m, 2H), 2.17 (s, 1H), 2.05 (s, 1H), 1.78 (q, J=6.2, 5.3 Hz, 2H), 1.67 (t, J=5.8 Hz, 2H), 1.30-1.20 (m, 1H).

Example 119: Synthesis of 4-[(2R)-3-(3,4-dihydro-1H-isoquinolin-2-yl)-2-hydroxy-propyl]-1-methyl-8-[4-(trifluoromethyl)cyclohexen-1-yl]-2,3-dihydro-1,4-benzodiazepin-5-one

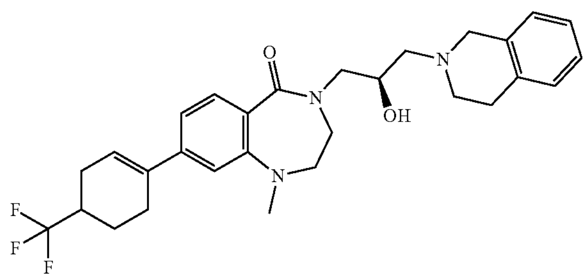 [SMILES: CN1CCN(C[C@H](O)CN2CCc3ccccc3C2)C(=O)c2ccc(C3=CCC(C(F)(F)F)CC3)cc21]

8-Bromo-4-[(2R)-3-(3,4-dihydro-1H-isoquinolin-2-yl)-2-hydroxy-propyl]-1-methyl-2,3-dihydro-1,4-benzodiazepin-5-one as a starting material was used in the same manner as in Example 10 to obtain the title compound, except that 4,4,5,5-tetramethyl-2-[4-(trifluoromethyl)cyclohexen-1-yl]-1,3,2-dioxaborolane was used instead of methylboronic acid.

$^1$H NMR (400 MHz, Chloroform-d) δ 7.59 (d, J=7.9 Hz, 1H), 7.19-7.07 (m, 3 Hz), 7.00 (dd, J=13.6, 7.3 Hz, 2H), 6.84 (s, 1H), 6.11 (d, J=5.1 Hz, 1H), 4.11 (t, J=7.1 Hz, 2H), 3.95-3.76 (m, 2H), 3.65 (s, 1H), 3.60 (dd, J=10.0, 4.6 Hz, 3H), 3.39 (dt, J=10.4, 5.1 Hz, 1H), 3.29 (dq, J=10.4, 5.2 Hz, 1H), 2.92 (q, J=8.0, 6.0 Hz, 4H), 2.85 (s, 3H), 2.75 (dd, J=10.8, 5.0 Hz, 1H), 2.69-2.58 (m, 2H), 2.57-2.43 (m, 2H), 2.42-2.24 (m, 1H), 2.23-2.14 (m, 1H), 2.05 (s, 1H), 1.69 (qd, J=11.9, 5.8 Hz, 1H), 1.43-1.18 (m, 1H).

Example 120: Synthesis of tert-butyl 4-[4-[(2R)-3-(3,4-dihydro-1H-isoquinolin-2-yl)-2-hydroxy-propyl]-1-methyl-5-oxo-2,3-dihydro-1,4-benzodiazepin-8-yl]-3,6-dihydro-2H-pyridine-1-carboxylate

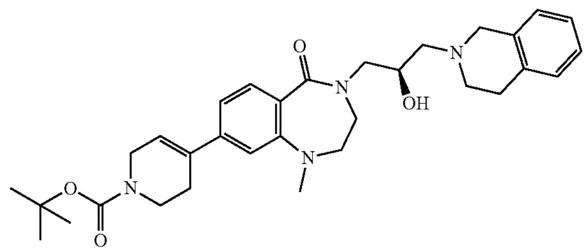 [SMILES: CN1CCN(C[C@H](O)CN2CCc3ccccc3C2)C(=O)c2ccc(C3=CCN(C(=O)OC(C)(C)C)CC3)cc21]

8-Bromo-4-[(2R)-3-(3,4-dihydro-1H-isoquinolin-2-yl)-2-hydroxy-propyl]-1-methyl-2,3-dihydro-1,4-benzodiazepin-5-one as a starting material was used in the same manner as in Example 10 to obtain the title compound, except that 4-(4,4,5,5-tetramethyl-1,3,2-dioxaborolan-2-yl)-3,6-dihydro-2H-pyridine-1-carboxylate was used instead of methylboronic acid.

$^1$H NMR (400 MHz, Chloroform-d) δ 7.60 (d, J=8.0 Hz, 1H), 7.18-7.08 (m, 3H), 7.01 (t, J=8.8 Hz, 2H), 6.84 (s, 1H), 6.08 (s, 1H), 4.21-4.04 (m, 3H), 4.01-3.75 (m, 2H), 3.74-3.52 (m, 5H), 3.48-3.35 (m, 1H), 3.36-3.24 (m, 1H), 2.92 (s, 2H), 2.85 (s, 3H), 2.74 (s, 1H), 2.72-2.56 (m, 2H), 2.52 (s, 2H), 2.05 (s, 1H), 1.49 (s, 7H), 1.31-1.21 (m, 2H).

Example 121: Synthesis of 8-[(1-acetyl-4-piperidyl)oxy]-4-[(2R)-3-(3,4-dihydro-1H-isoquinolin-2-yl)-2-hydroxy-propyl]-1-methyl-2,3-dihydro-1,4-benzodiazepin-5-one

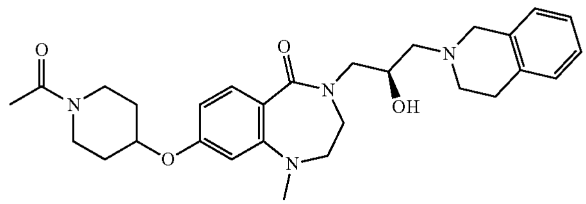 [SMILES: CC(=O)N1CCC(Oc2ccc3c(c2)N(C)CCN(C[C@H](O)CN2CCc4ccccc4C2)C3=O)CC1]

Example 121-1: Synthesis of 4-[(2R)-3-(3,4-dihydro-1H-isoquinolin-2-yl)-2-hydroxy-propyl]-8-hydroxy-1-methyl-2,3-dihydro-1,4-benzodiazepin-5-one 8-Bromo-4-[(2R)-3-(3,4-dihydro-1H-isoquinolin-2-yl)-2-hydroxy-propyl]-1-methyl-2,3-dihydro-1,4-benzodiazepin-5-one as a starting material was used in the same manner as in Example 56-1 to obtain the title compound Example 121-2: Synthesis of 8-[(1-acetyl-4-piperidyl)oxy]-4-[(2R)-3-(3,4-dihydro-1H-isoquinolin-2-yl)-2-hydroxy-propyl]-1-methyl-2,3-dihydro-1,4-benzodiazepin-5-one The title compound was synthesized in the same manner as in Example 64, except that (1-acetyl-4-piperidyl) methanesulfonate was used instead of 4-chlorotetrahydropyran.

$^1$H NMR (400 MHz, Chloroform-d) δ 7.61 (d, J=8.5 Hz, 1H), 7.13 (d, J=8.2 Hz, 3H), 7.02 (d, J=6.7 Hz, 1H), 6.51 (d, J=8.6 Hz, 1H), 6.38 (s, 1H), 4.59 (s, 1H), 4.11 (t, J=7.1 Hz, 2H), 3.99-3.81 (m, 1H), 3.84-3.72 (m, 2H), 3.74-3.56 (m, 6H), 3.42 (dd, J=11.6, 5.8 Hz, 2H), 3.36-3.25 (m, 1H), 2.91 (d, J=8.7 Hz, 3H), 2.81 (s, 3H), 2.75 (s, 1H), 2.69-2.53 (m, 2H), 2.13 (d, J=1.5 Hz, 3H), 2.05 (d, J=1.5 Hz, 1H), 1.98-1.77 (m, 5H), 1.44-1.15 (m, 2H), 1.09-0.81 (m, 1H).

Example 122: Synthesis of 8-(1-acetylazetidin-3-yl)oxy-4-[(2R)-3-(3,4-dihydro-1H-isoquinolin-2-yl)-2-hydroxy-propyl]-1-methyl-2,3-dihydro-1,4-benzodiazepin-5-one

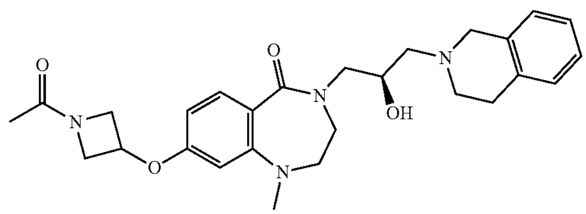 [SMILES: CC(=O)N1CC(Oc2ccc3c(c2)N(C)CCN(C[C@H](O)CN2CCc4ccccc4C2)C3=O)C1]

The material obtained in Example 121-1 as a starting material was used in the same manner as in Example 83 to obtain the title compound.

$^1$H NMR (400 MHz, Chloroform-d) δ 7.61 (d, J=8.4 Hz, 1H), 7.19-7.07 (m, 3H), 7.02 (d, J=6.7 Hz, 1H), 6.44-6.16 (m, 2H), 4.97 (t, J=5.7 Hz, 1H), 4.49 (t, J=8.0 Hz, 1H), 4.39 (dd, J=10.9, 6.6 Hz, 1H), 4.28-3.99 (m, 4H), 3.95-3.72 (m, 2H), 3.75-3.50 (m, 4H), 3.52-3.26 (m, 2H), 2.93 (q, J=9.0, 6.9 Hz, 3H), 2.81 (s, 3H), 2.78-2.54 (m, 3H), 2.05 (s, 1H), 1.92 (s, 3H), 1.26 (t, J=7.2 Hz, 1H).

Example 123: Synthesis of 8-[(3R)-1-acetylpyrrolidin-3-yl]oxy-4-[(2R)-3-(3,4-dihydro-1H-isoquinolin-2-yl)-2-hydroxy-propyl]-1-methyl-2,3-dihydro-1,4-benzodiazepin-5-one

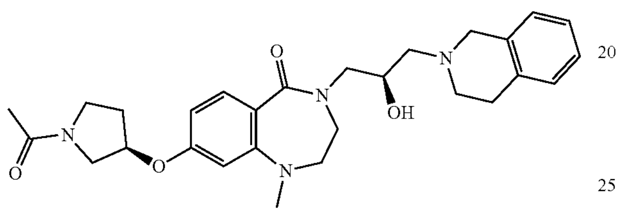

The material obtained in Example 121-1 as a starting material and the intermediate obtained by changing 4-chlorotetrahydropyran to tert-butyl (3S)-3-methylsulfonyloxy-pyrrolidin-1-carboxylate in Example 64 were used in the same manner as in Example 78 to obtain the title compound.

$^1$H NMR (400 MHz, Methanol-$d_4$) δ 7.51 (dd, J=8.7, 3.2 Hz, 1H), 7.29-7.03 (m, 4H), 6.68-6.34 (m, 2H), 5.15 (d, J=22.7 Hz, 1H), 4.27 (s, 1H), 3.99-3.84 (m, 3H), 3.79-3.57 (m, 6H), 3.55-3.39 (m, 2H), 3.01 (d, J=8.8 Hz, 4H), 2.81 (d, J=15.8 Hz, 5H), 2.40-2.14 (m, 2H), 2.16-1.90 (m, 5H), 1.31 (s, 3H).

Example 124: Synthesis of 8-[(3S)-1-acetylpyrrolidin-3-yl]oxy-4-[(2R)-3-(3,4-dihydro-1H-isoquinolin-2-yl)-2-hydroxy-propyl]-1-methyl-2,3-dihydro-1,4-benzodiazepin-5-one

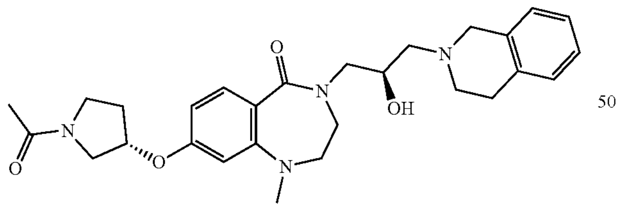

The material obtained in Example 121-1 as a starting material and the intermediate obtained by changing 4-chlorotetrahydropyran to tert-butyl (3R)-3-methylsulfonyloxy-pyrrolidin-1-carboxylate in Example 64 were used in the same manner as in Example 78 to obtain the title compound.

$^1$H NMR (400 MHz, Methanol-$d_4$) δ 7.57-7.45 (m, 1H), 7.15 (d, J=4.5 Hz, 3H), 7.09 (s, 1H), 6.60 (d, J=7.9 Hz, 1H), 6.48 (d, J=5.6 Hz, 1H), 5.15 (d, J=22.7 Hz, 1H), 4.27 (s, 1H), 3.90 (d, J=14.7 Hz, 3H), 3.79-3.58 (m, 5H), 3.59-3.41 (m, 2H), 2.99 (s, 4H), 2.80 (d, J=23.3 Hz, 5H), 2.31 (s, 1H), 2.23 (s, 1H), 2.18-1.98 (m, 4H), 1.96 (s, 1H), 1.28 (d, J=20.7 Hz, 2H).

Example 125: Synthesis of 4-[(2R)-3-(3,4-dihydro-1H-isoquinolin-2-yl)-2-hydroxy-propyl]-1-methyl-8-[(1-methyl-4-piperidyl)oxy]-2,3-dihydro-1,4-benzodiazepin-5-one

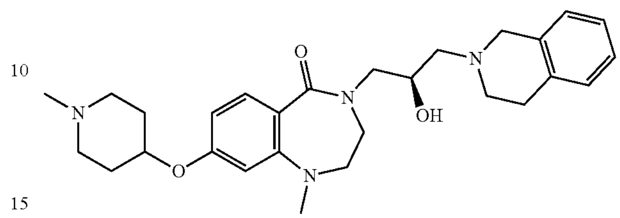 [SMILES: CCN1CCC(Oc2ccc3c(c2)N(C)CCN(C[C@H](O)CN2CCc4ccccc4C2)C3=O)CC1]

Example 125-1: Synthesis of 4-[(2R)-3-(3,4-dihydro-1H-isoquinolin-2-yl)-2-hydroxy-propyl]-1-methyl-8-(4-piperidyloxy)-2,3-dihydro-1,4-benzodiazepin-5-one dihydrochloride The material obtained in Example 121-1 as a starting material was used in the same manner as in Examples 77 and 78-1 to obtain the title compound.

Example 125-2: Synthesis of 4-[(2R)-3-(3,4-dihydro-1H-isoquinolin-2-yl)-2-hydroxy-propyl]-1-methyl-8-[(1-methyl-4-piperidyl)oxy]-2,3-dihydro-1,4-benzodiazepin-5-one The material obtained in Example 125-1 as a starting material was used in the same manner as in Example 87 to obtain the title compound.

$^1$H NMR (400 MHz, Methanol-$d_4$) δ 7.49 (d, J=8.4 Hz, 1H), 7.13 (d, J=4.4 Hz, 3H), 7.08 (s, 1H), 6.62 (d, J=8.7 Hz, 1H), 6.50 (s, 1H), 4.25 (s, 1H), 4.00-3.78 (m, 3H), 3.61 (d, J=5.7 Hz, 2H), 3.52-3.38 (m, 2H), 2.89 (d, J=52.2 Hz, 8H), 2.73 (s, 3H), 2.49 (s, 3H), 2.05 (d, J=11.4 Hz, 3H), 1.94 (s, 2H).

Example 126: Synthesis of 4-[(2R)-3-(3,4-dihydro-1H-isoquinolin-2-yl)-2-hydroxy-propyl]-8-[(1-ethyl-4-piperidyl)oxy]-1-methyl-2,3-dihydro-1,4-benzodiazepin-5-one

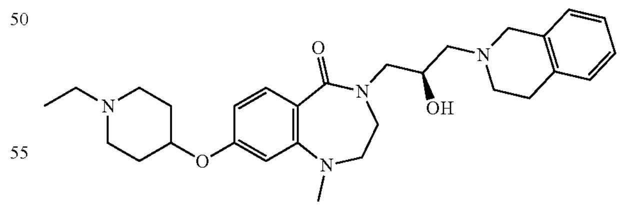

The material obtained in Example 125-1 as a starting material was used in the same manner as in Example 87 to obtain the title compound, except that acetaldehyde was used instead of paraformaldehyde.

$^1$H NMR (400 MHz, Methanol-$d_4$) δ 7.50 (d, J=8.6 Hz, 1H), 7.13 (d, J=3.0 Hz, 3H), 7.07 (d, J=6.9 Hz, 1H), 6.63 (d, J=8.8 Hz, 1H), 6.51 (s, 1H), 4.65 (d, J=9.6 Hz, 1H), 4.25 (s, 1H), 3.91 (dd, J=13.9, 3.9 Hz, 1H), 3.84 (s, 2H), 3.62 (t, J=5.8 Hz, 2H), 3.51-3.36 (m, 3H), 3.18-3.04 (m, 2H), 2.96

(s, 4H), 2.85 (d, J=12.9 Hz, 6H), 2.73 (t, J=5.5 Hz, 2H), 2.14 (s, 2H), 2.09-1.93 (m, 3H), 1.35-1.10 (m, 5H).

Example 127: Synthesis of 8-[(1-cyclobutyl-4-piperidyl)oxy]-4-[(2R)-3-(3,4-dihydro-1H-isoquinolin-2-yl)-2-hydroxy-propyl]-1-methyl-2,3-dihydro-1,4-benzodiazepin-5-one

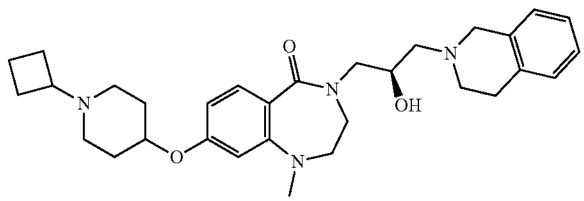 [SMILES: CN1CCN(C[C@H](O)CN2CCc3ccccc3C2)C(=O)c2ccc(OC3CCN(C4CCC4)CC3)cc21]

The material obtained in Example 125-1 as a starting material was used in the same manner as in Example 87 to obtain the title compound, except that cyclobutanone was used instead of paraformaldehyde.

$^1$H NMR (400 MHz, Methanol-$d_4$) δ 7.41 (d, J=8.5 Hz, 1H), 7.05 (d, J=3.0 Hz, 3H), 6.99 (s, 1H), 6.53 (d, J=8.6 Hz, 1H), 6.41 (s, 1H), 4.47 (s, 1H), 4.15 (d, J=6.7 Hz, 1H), 3.85 (d, J=14.6 Hz, 1H), 3.71 (s, 2H), 3.54 (s, 2H), 3.37 (dt, J=11.7, 6.3 Hz, 2H), 2.92-2.81 (m, 4H), 2.75 (s, 3H), 2.68-2.54 (m, 4H), 2.32 (s, 2H), 2.06 (s, 2H), 1.97 (d, J=8.7 Hz, 4H), 1.88 (d, J=9.6 Hz, 1H), 1.79-1.62 (m, 4H).

Example 128: Synthesis of 4-[(2R)-3-(3,4-dihydro-1H-isoquinolin-2-yl)-2-hydroxy-propyl]-1-methyl-8-[(1-tetrahydrofuran-3-yl-4-piperidyl)oxy]-2,3-dihydro-1,4-benzodiazepin-5-one

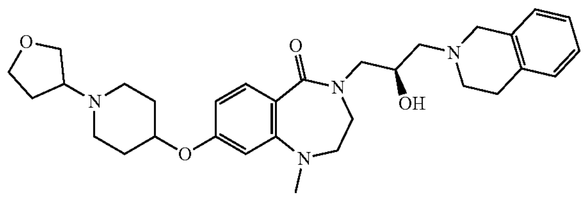 [SMILES: CN1CCN(C[C@H](O)CN2CCc3ccccc3C2)C(=O)c2ccc(OC3CCN(C4CCOC4)CC3)cc21]

The material obtained in Example 125-1 as a starting material was used in the same manner as in Example 87 to obtain the title compound, except that tetrahydrofuran-3-one was used instead of paraformaldehyde.

$^1$H NMR (400 MHz, Methanol-$d_4$) δ 7.48 (d, J=8.6 Hz, 1H), 7.12 (d, J=4.2 Hz, 3H), 7.06 (s, 1H), 6.60 (d, J=8.6 Hz, 1H), 6.47 (s, 1H), 4.51 (d, J=7.7 Hz, 1H), 4.23 (t, J=5.9 Hz, 1H), 3.93 (tt, J=12.0, 4.8 Hz, 6H), 3.78 (s, 5H), 3.69-3.51 (m, 5H), 3.48-3.36 (m, 2H), 3.06 (t, J=7.3 Hz, 1H), 2.94 (d, J=5.3 Hz, 2H), 2.90 (d, J=4.6 Hz, 2H), 2.82 (s, 3H), 2.74-2.64 (m, 3H), 2.51 (t, J=10.1 Hz, 1H), 2.41 (t, J=9.8 Hz, 1H), 2.16 (dd, J=13.1, 6.9 Hz, 2H), 2.04 (d, J=9.5 Hz, 3H), 1.94-1.71 (m, 5H).

Example 129: Synthesis of 4-[(2R)-3-(3,4-dihydro-1H-isoquinolin-2-yl)-2-hydroxy-propyl]-1-methyl-8-[[1-(oxetan-3-yl)-4-piperidyl]oxy]-2,3-dihydro-1,4-benzodiazepin-5-one

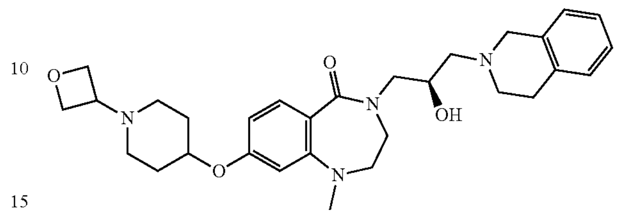

The material obtained in Example 125-1 as a starting material was used in the same manner as in Example 87 to obtain the title compound, except that oxetan-3-one was used instead of paraformaldehyde.

$^1$H NMR (400 MHz, Methanol-$d_4$) δ 7.55-7.37 (m, 1H), 7.12 (d, J=5.1 Hz, 3H), 7.06 (d, J=6.8 Hz, 1H), 6.60 (d, J=8.6 Hz, 1H), 6.47 (s, 1H), 4.71 (t, J=6.7 Hz, 2H), 4.62 (t, J=6.2 Hz, 2H), 4.53 (s, 1H), 4.23 (s, 1H), 3.94 (s, 1H), 3.79 (s, 2H), 3.69 (d, J=4.9 Hz, 1H), 3.64-3.51 (m, 3H), 3.44 (dt, J=13.1, 6.7 Hz, 2H), 2.93 (dd, J=11.8, 4.7 Hz, 4H), 2.82 (s, 3H), 2.68 (d, J=7.8 Hz, 2H), 2.62 (d, J=12.0 Hz, 2H), 2.29 (t, J=9.8 Hz, 2H), 2.04 (d, J=10.2 Hz, 2H), 1.85 (s, 2H).

Example 130: Synthesis of 4-[(2R)-3-(3,4-dihydro-1H-isoquinolin-2-yl)-2-hydroxy-propyl]-1-methyl-8-[(1-methyl-3-piperidyl)oxy]-2,3-dihydro-1,4-benzodiazepin-5-one

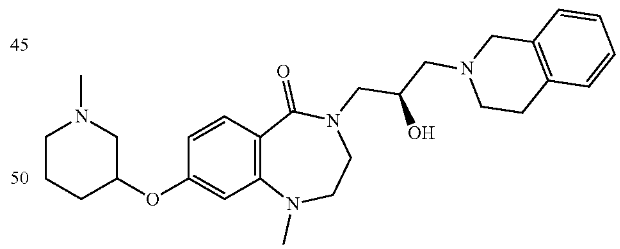

The material obtained in Example 121-1 as a starting material was used in the same manner as in Example 68 to obtain the title compound.

$^1$H NMR (400 MHz, Methanol-$d_4$) δ 7.50 (dd, J=8.6, 1.7 Hz, 1H), 7.12 (t, J=2.5 Hz, 3H), 7.06 (d, J=6.6 Hz, 1H), 6.61 (dd, J=8.5, 2.5 Hz, 1H), 6.51 (d, J=2.4 Hz, 1H), 4.28-4.20 (m, 1H), 4.08 (d, J=5.3 Hz, 2H), 3.92 (dd, J=14.2, 3.9 Hz, 1H), 3.78 (s, 2H), 3.62 (dt, J=8.6, 4.5 Hz, 2H), 3.42 (ddd, J=21.1, 15.3, 6.7 Hz, 2H), 3.17 (dt, J=10.1, 4.3 Hz, 1H), 2.99-2.87 (m, 5H), 2.87-2.81 (m, 3H), 2.67 (t, J=4.7 Hz, 2H), 2.57 (d, J=1.8 Hz, 3H), 2.47 (q, J=8.9 Hz, 1H), 2.14 (dd, J=12.4, 8.3 Hz, 1H), 2.05 (d, J=10.0 Hz, 2H), 1.93-1.73 (m, 4H), 1.31 (s, 3H).

Example 131: Synthesis of 4-[(2R)-3-(3,4-dihydro-1H-isoquinolin-2-yl)-2-hydroxy-propyl]-1-methyl-8-[(1-methylpyrrolidin-3-yl)methoxy]-2,3-dihydro-1,4-benzodiazepin-5-one

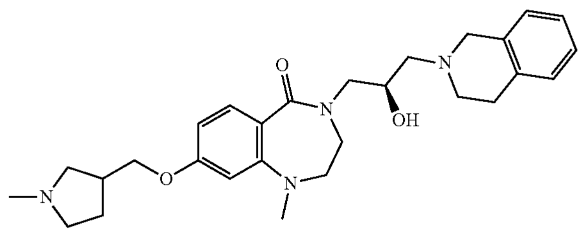 [SMILES: CN1CCC(COc2ccc3c(c2)N(C)CCN(C[C@H](O)CN2CCc4ccccc4C2)C3=O)C1]

The material obtained in Example 121-1 as a starting material was used in the same manner as in Example 106 to obtain the title compound.

$^1$H NMR (400 MHz, Methanol-$d_4$) δ 7.49 (d, J=8.5 Hz, 1H), 7.11 (s, 3H), 7.06 (s, 1H), 6.58 (d, J=8.7 Hz, 1H), 6.48 (s, 1H), 4.23 (s, 1H), 4.07-3.87 (m, 3H), 3.76 (s, 2H), 3.61 (s, 2H), 3.51-3.40 (m, 2H), 2.91 (dd, J=19.1, 5.4 Hz, 5H), 2.84 (s, 3H), 2.68 (d, J=8.9 Hz, 5H), 2.56 (d, J=8.0 Hz, 1H), 2.43 (d, J=2.1 Hz, 3H), 2.05 (d, J=9.6 Hz, 3H), 1.71 (d, J=7.2 Hz, 1H), 1.57 (s, 1H), 0.91 (s, 2H).

Example 132: Synthesis of 4-[(2R)-3-(3,4-dihydro-1H-isoquinolin-2-yl)-2-hydroxy-propyl]-1-methyl-8-(1-methylpyrrolidin-3-yl)oxy-2,3-dihydro-1,4-benzodiazepin-5-one

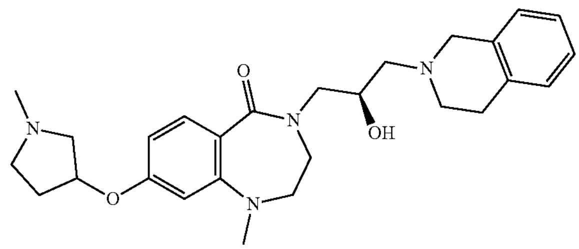 [SMILES: CN1CCC(Oc2ccc3c(c2)N(C)CCN(C[C@H](O)CN2CCc4ccccc4C2)C3=O)C1]

The material obtained in Example 121-1 as a starting material was used in the same manner as in Example 98 to obtain the title compound.

$^1$H NMR (400 MHz, Methanol-$d_4$) δ 7.49 (d, J=8.5 Hz, 1H), 7.11 (s, 3H), 7.07 (s, 1H), 6.53 (d, J=8.6 Hz, 1H), 6.44 (s, 1H), 4.98 (s, 1H), 4.23 (s, 1H), 3.93 (d, J=13.8 Hz, 1H), 3.77 (s, 2H), 3.62 (s, 2H), 3.44 (dd, J=14.5, 7.2 Hz, 2H), 2.91 (dd, J=18.9, 6.2 Hz, 6H), 2.83 (s, 3H), 2.66 (d, J=7.7 Hz, 2H), 2.49 (d, J=8.0 Hz, 1H), 2.42 (s, 3H), 2.05 (d, J=10.2 Hz, 3H), 1.31 (s, 4H).

Example 133: Synthesis of 4-[(2R)-3-(3,4-dihydro-1H-isoquinolin-2-yl)-2-hydroxy-propyl]-1-methyl-8-[(1-methyl-3-piperidyl) methoxy]-2,3-dihydro-1,4-benzodiazepin-5-one

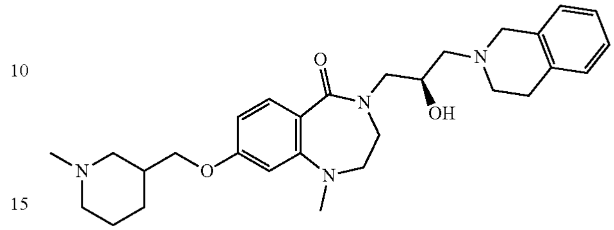

The material obtained in Example 121-1 as a starting material was used in the same manner as in Example 107 to obtain the title compound.

$^1$H NMR (400 MHz, Methanol-$d_4$) δ 7.48 (d, J=8.5 Hz, 1H), 7.11 (d, J=4.7 Hz, 3H), 7.06 (s, 1H), 6.57 (d, J=8.6 Hz, 1H), 6.47 (s, 1H), 4.22 (s, 1H), 4.00-3.84 (m, 4H), 3.76 (s, 2H), 3.61 (d, J=5.4 Hz, 2H), 3.44 (dd, J=14.2, 7.8 Hz, 2H), 3.05 (d, J=12.9 Hz, 1H), 2.93 (d, J=6.0 Hz, 5H), 2.85 (d, J=16.2 Hz, 6H), 2.65 (d, J=7.2 Hz, 2H), 2.30 (dd, J=10.2, 1.7 Hz, 5H), 2.14 (s, 2H), 2.09-1.81 (m, 4H), 1.77 (s, 1H).

Example 134: Synthesis of 4-[(2R)-3-(3,4-dihydro-1H-isoquinolin-2-yl)-2-hydroxy-propyl]-8-[(3-fluoro-4-pyridyl)methoxy]-1-methyl-2,3-dihydro-1,4-benzodiazepin-5-one

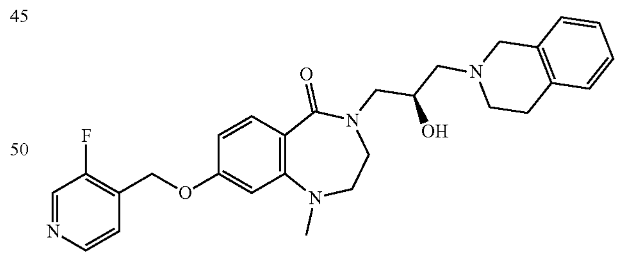

The material obtained in Example 121-1 as a starting material was used in the same manner as in Example 56-2 to obtain the title compound, except that (3-fluoro-4-pyridyl)methyl methanesulfonate was used instead of 3-(chloromethyl)pyridine hydrochloride.

$^1$H NMR (400 MHz, Methanol-$d_4$) δ 8.50 (s, 1H), 8.44 (d, J=5.0 Hz, 1H), 7.67 (t, J=5.8 Hz, 1H), 7.52 (dd, J=8.7, 2.0 Hz, 1H), 7.20-7.00 (m, 4H), 6.68 (dd, J=8.7, 2.6 Hz, 1H), 6.60 (d, J=2.8 Hz, 1H), 5.33 (s, 2H), 4.23 (s, 1H), 3.95-3.87 (m, 1H), 3.77 (s, 2H), 3.62 (s, 2H), 3.49-3.37 (m, 3H), 2.92 (dd, J=15.9, 5.2 Hz, 4H), 2.84 (d, J=2.0 Hz, 3H), 2.74-2.62 (m, 2H), 1.31 (s, 1H).

Example 135: Synthesis of 4-[(2R)-3-(3,4-dihydro-1H-isoquinolin-2-yl)-2-hydroxy-propyl]-8-[(3-fluoro-4-piperidyl)oxy]-1-methyl-2,3-dihydro-1,4-benzodiazepin-5-one; dihydrochloride

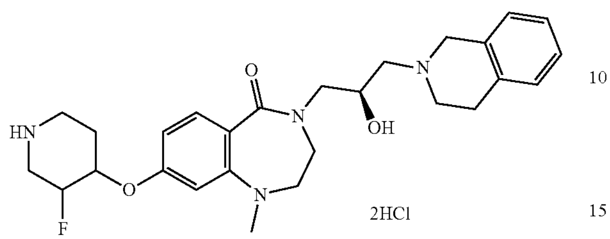

The intermediate in which Boc is substituted was synthesized by using the material obtained in Example 121-1 as a starting material and changing 4-chlorotetrahydropyran to tert-butyl 3-fluoro-4-methylsulfonyloxy-piperidine-1-carboxylate in Example 64. The obtained intermediate was dissolved in methanol, and 4 N hydrochloric acid solution dissolved in 1,4-dioxane was added thereto. The reaction solution was stirred at room temperature until the reaction was terminated, diluted with ethyldiethyl ether and filtered to obtain the title compound as a white solid in the form of dihydrochloride.

$^1$H NMR (400 MHz, Methanol-$d_4$) δ 7.63 (d, J=8.5 Hz, 1H), 7.31 (q, J=7.5 Hz, 3H), 7.24 (t, J=7.6 Hz, 1H), 6.94 (d, J=8.8 Hz, 1H), 6.89 (s, 1H), 5.06 (d, J=44.3 Hz, 2H), 4.74-4.58 (m, 1H), 4.49 (td, J=15.4, 14.0, 7.3 Hz, 2H), 3.93-3.86 (m, 1H), 3.80 (d, J=9.6 Hz, 1H), 3.74-3.63 (m, 6H), 3.60 (s, 1H), 3.52 (d, J=15.3 Hz, 2H), 3.44-3.35 (m, 2H), 3.25-3.14 (m, 1H), 3.02 (s, 3H), 2.44-2.30 (m, 1H), 2.19 (d, J=15.7 Hz, 1H).

Example 136: Synthesis of 4-[(2R)-3-(3,4-dihydro-1H-isoquinolin-2-yl)-2-hydroxy-propyl]-8-[(1-ethyl-3-fluoro-4-piperid yl)oxy]-1-methyl-2,3-dihydro-1,4-benzodiazepin-5-one

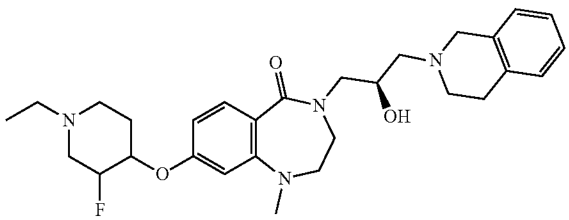 [SMILES: CCN1CCC(Oc2ccc3c(c2)N(C)CCN(C[C@H](O)CN2CCc4ccccc4C2)C3=O)C(F)C1]

The material obtained in Example 135 as a starting material was used in the same manner as in Example 87 to obtain the title compound, except that acetaldehyde was used instead of paraformaldehyde.

$^1$H NMR (400 MHz, Methanol-$d_4$) δ 7.49 (dd, J=8.6, 1.9 Hz, 1H), 7.12 (d, J=3.1 Hz, 3H), 7.06 (d, J=6.7 Hz, 1H), 6.65 (d, J=8.6 Hz, 1H), 6.53 (d, J=2.6 Hz, 1H), 4.67 (d, J=48.8 Hz, 1H), 4.52 (s, 1H), 4.23 (s, 1H), 3.92 (dd, J=13.7, 3.8 Hz, 1H), 3.78 (s, 2H), 3.62 (s, 2H), 3.45 (dd, J=14.4, 7.6 Hz, 2H), 3.14-3.02 (m, 1H), 2.94 (d, J=5.2 Hz, 3H), 2.90 (d, J=4.6 Hz, 2H), 2.83 (d, J=1.8 Hz, 3H), 2.68 (t, J=5.4 Hz, 2H), 2.55 (d, J=7.2 Hz, 1H), 2.46 (d, J=8.2 Hz, OH), 2.34 (t, J=10.8 Hz, 1H), 2.21 (s, 1H), 1.77 (dd, J=12.9, 8.8 Hz, 1H), 1.19-1.11 (m, 3H).

Example 137: Synthesis of 4-[(2R)-3-(3,4-dihydro-1H-isoquinolin-2-yl)-2-hydroxy-propyl]-8-[(8-ethyl-8-azabicyclo[3.2.1]octan-3-yl)oxy]-1-methyl-2,3-dihydro-1,4-benzodiazepin-5-one

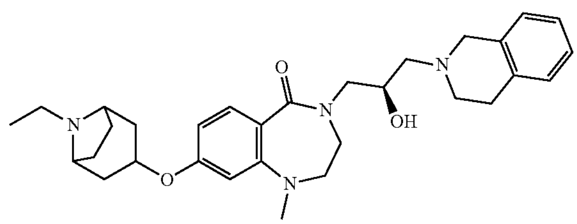 [SMILES: CCN1C2CCC1CC(Oc1ccc3c(c1)N(C)CCN(C[C@H](O)CN1CCc4ccccc4C1)C3=O)C2]

Example 137-1: Synthesis of 8-(8-azabicyclo[3.2.1]octan-3-yloxy)-4-[(2R)-3-(3,4-dihydro-1H-isoquinolin-2-yl)-2-hydroxy-propyl]-1-methyl-2,3-dihydro-1,4-benzodiazepin-5-one dihydrochloride The intermediate in which Boc is substituted was synthesized by using the material obtained in Example 121-1 as a starting material and changing 4-chlorotetrahydropyran to tert-butyl 3-methylsulfonyloxy-8-azabicyclo [3.2.1]octane-8-carboxylate in Example 64. The obtained intermediate was dissolved in methanol, and 4 N hydrochloric acid solution dissolved in 1,4-dioxane was added thereto. The reaction solution was stirred at room temperature until the reaction was terminated, diluted with ethyldiethyl ether and filtered to obtain the title compound as a white solid in the form of dihydrochloride.

Example 137-2: Synthesis of 4-[(2R)-3-(3,4-dihydro-1H-isoquinolin-2-yl)-2-hydroxy-propyl]-8-[(8-ethyl-8-azabicyclo[3.2.1]octan-3-yl)oxy]-1-methyl-2,3-dihydro-1,4-benzodiazepin-5-one The material obtained in Example 137-1 as a starting material was used in the same manner as in Example 87 to obtain the title compound, except that acetaldehyde was used instead of paraformaldehyde.

$^1$H NMR (400 MHz, Methanol-$d_4$) δ 7.66-7.39 (m, 1H), 7.12 (d, J=4.9 Hz, 3H), 7.05 (d, J=6.7 Hz, 1H), 6.63 (d, J=8.6 Hz, 1H), 6.45 (d, J=2.4 Hz, 1H), 4.80 (dq, J=10.7, 5.6, 4.9 Hz, 1H), 4.22 (d, J=8.0 Hz, 1H), 3.94-3.87 (m, 1H), 3.77 (s, 2H), 3.69 (s, 2H), 3.61 (dd, J=7.5, 3.6 Hz, 2H), 3.43 (dt, J=11.7, 6.2 Hz, 2H), 2.93 (d, J=5.5 Hz, 2H), 2.89 (d, J=5.3 Hz, 2H), 2.82 (s, 4H), 2.71-2.54 (m, 2H), 2.30-2.13 (m, 4H), 2.03 (d, J=1.6 Hz, 1H), 1.97-1.84 (m, 5H), 1.24 (t, J=7.1 Hz, 4H).

Example 138: Synthesis of 4-[(2R)-3-(3,4-dihydro-1H-isoquinolin-2-yl)-2-hydroxy-propyl]-1-methyl-8-[(2-methyl-4-piperidyl)oxy]-2,3-dihydro-1,4-benzodiazepin-5-one; dihydrochloride

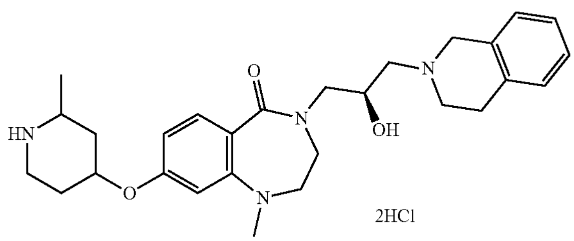 [SMILES: CC1CC(Oc2ccc3c(c2)N(C)CCN(C[C@H](O)CN2CCc4ccccc4C2)C3=O)CCN1 ; "2HCl"]

The intermediate in which Boc is substituted was synthesized by using the material obtained in Example 121-1 as a starting material and changing 4-chlorotetrahydropyran to tert-butyl 2-methyl-4-methylsulfonyloxy-piperidine-1-carboxylate in Example 64. The obtained intermediate was dissolved in methanol, and 4 N hydrochloric acid solution dissolved in 1,4-dioxane was added thereto. The reaction solution was stirred at room temperature until the reaction was terminated, diluted with ethyldiethyl ether and filtered to obtain the title compound as a white solid in the form of dihydrochloride.

$^1$H NMR (400 MHz, Methanol-$d_4$) δ 7.60 (d, J=8.6 Hz, 1H), 7.32 (q, J=7.7, 7.1 Hz, 3H), 7.23 (d, J=7.7 Hz, 1H), 6.87 (d, J=8.9 Hz, 1H), 6.76 (s, 1H), 4.75 (d, J=11.8 Hz, 1H), 4.74-4.62 (m, 1H), 4.49 (td, J=15.2, 12.9, 6.6 Hz, 2H), 3.89 (s, 1H), 3.84-3.75 (m, 1H), 3.73-3.61 (m, 3H), 3.51 (t, J=17.0 Hz, 3H), 3.44-3.36 (m, 2H), 3.20 (q, J=13.8 Hz, 2H), 3.00 (s, 3H), 2.42 (t, J=13.0 Hz, 1H), 1.80 (q, J=11.8, 10.8 Hz, 1H), 1.68-1.57 (m, 1H), 1.42 (d, J=6.4 Hz, 2H), 1.37 (d, J=6.5 Hz, 1H).

Example 139: Synthesis of 4-[(2R)-3-(3,4-dihydro-1H-isoquinolin-2-yl)-2-hydroxy-propyl]-8-[(5-fluoro-2-pyridyl)methoxy]-1-methyl-2,3-dihydro-1,4-benzodiazepin-5-one

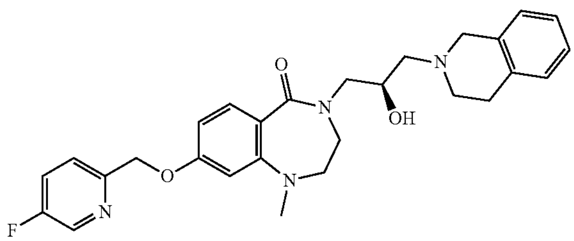 [SMILES: CN1CCN(C[C@H](O)CN2CCc3ccccc3C2)C(=O)c2ccc(OCc3ccc(F)cn3)cc21]

The material obtained in Example 121-1 as a starting material was used in the same manner as in Example 56-2 to obtain the title compound, except that (5-fluoro-2-pyridyl)methyl methanesulfonate was used instead of 3-(chloromethyl)pyridine hydrochloride.

$^1$H NMR (400 MHz, Methanol-$d_4$) δ 8.49 (s, 1H), 7.80-7.62 (m, 2H), 7.50 (d, J=8.5 Hz, 1H), 7.11 (d, J=3.6 Hz, 3H), 7.06 (s, 1H), 6.65 (d, J=8.7 Hz, 1H), 6.59 (s, 1H), 5.23 (s, 2H), 4.23 (s, 1H), 3.92 (d, J=13.8 Hz, 1H), 3.77 (s, 2H), 3.62 (d, J=5.4 Hz, 2H), 3.44 (dd, J=13.3, 6.9 Hz, 2H), 2.94 (d, J=5.5 Hz, 2H), 2.89 (d, J=5.2 Hz, 2H), 2.82 (s, 3H), 2.71-2.60 (m, 2H).

Example 140: Synthesis of 4-[(2R)-3-(3,4-dihydro-1H-isoquinolin-2-yl)-2-hydroxypropyl]-2-methyl-8-(4-piperidyloxy)-2,3-dihydro-1,4-benzoxazepin-5-one dihydrochloride

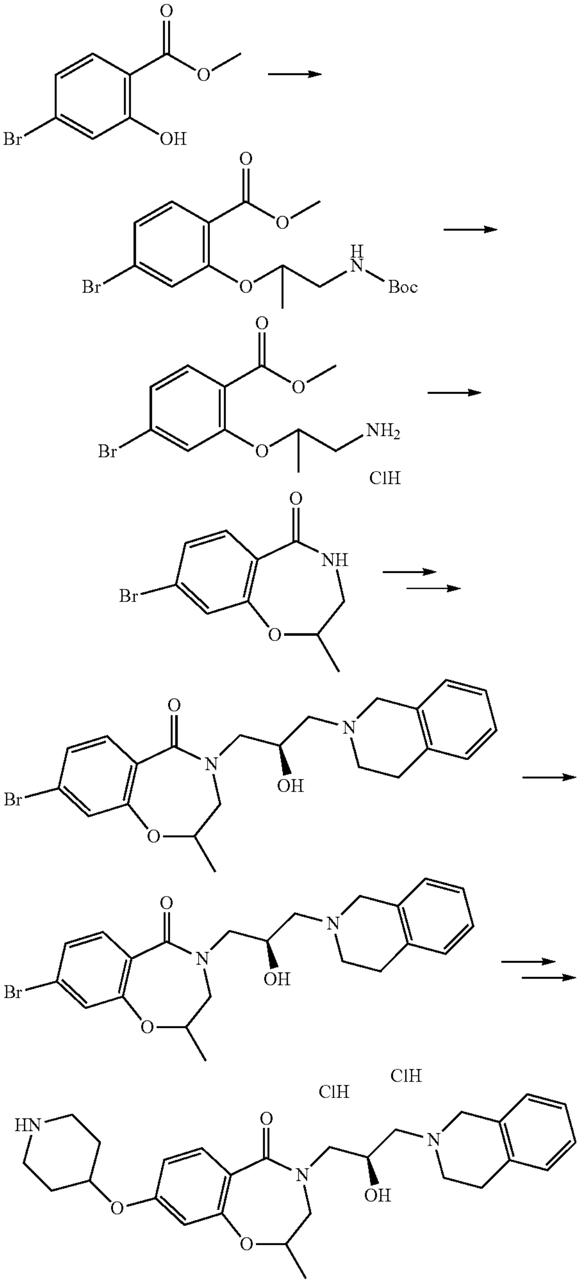

Example 140-1: Synthesis of methyl 4-bromo-2-[2-(tert-butoxycarbonylamino)propoxy]benzoate Methyl 4-bromo-2-hydroxy-benzoate (3 g, 12.98 mmol), $Cs_2CO_3$ (12.7 g, 51.95 mmol) and [2-(tert-butoxycarbonylamino)-1-methyl-ethyl] methanesulfonate (7 mL, 25.98 mmol) were dissolved in acetonitrile, stirred for one day and heated to reflux. The reaction solution was cooled to room temperature, and distilled water was added thereto, followed by dilution with ethyl acetate. The combined organic layers were dried over anhydrous magnesium sulfate, concentrated and purified by flash chromatography to obtain the title compound.

Example 140-2: Synthesis of methyl 2-(2-aminopropoxy)-4-bromo-benzoate hydrochloride The material obtained in Example 140-1 as a starting material was dissolved in methanol, and 4 N hydrochloric acid solution dissolved in 1,4-dioxane was added thereto, followed by stirring at room temperature. The reaction solution was concentrated under reduced pressure to obtain the title compound without additional purification.

Example 140-3: Synthesis of 8-bromo-2-methyl-3,4-dihydro-2H-1,4-benzoxazepin-5-one The material (2.3 g, 8.01 mmol) obtained in Example 140-2 was dissolved in toluene, and triethylamine was added thereto. The reaction solution was stirred and heated to reflux. After confirming that the reaction was complete, the reaction solution was cooled to room temperature, and the solvent was removed under reduced pressure. The concentrate was purified by flash chromatography to obtain the title compound.

Example 140-4: Synthesis of 8-bromo-4-[(2R)-3-(3,4-dihydro-1H-isoquinolin-2-yl)-2-hydroxypropyl]-2-methyl-2,3-dihydro-1,4-benzoxazepin-5-one The material obtained in Example 140-3 as a starting material was used in the same manner as in Example 5 to obtain the title compound.

Example 140-5: Synthesis of 4-[(2R)-3-(3,4-dihydro-1H-isoquinolin-2-yl)-2-hydroxypropyl]-8-hydroxy-2-methyl-2,3-dihydro-1,4-benzoxazepin-5-one The material obtained in Example 140-4 as a starting material was used in the same manner as in Example 56-1 to obtain the title compound.

Example 140-6: Synthesis of 4-[(2R)-3-(3,4-dihydro-1H-isoquinolin-2-yl)-2-hydroxypropyl]-2-methyl-8-(4-piperidyloxy)-2,3-dihydro-1,4-benzoxazepin-5-one dihydrochloride The material obtained in Example 140-5 as a starting material was used in the same manner as in Examples 77 and 78-1 to obtain the title compound.

$^1$H NMR (400 MHz, Methanol-$d_4$) δ 7.66 (d, J=8.5 Hz, 1H), 7.32 (d, J=8.4 Hz, 3H), 7.23 (s, 1H), 6.93-6.84 (m, 1H), 6.67 (s, 1H), 4.82 (s, 2H), 4.68 (d, J=16.0 Hz, 1H), 4.48 (d, J=10.0 Hz, 2H), 4.01-3.83 (m, 3H), 3.70 (d, J=15.8 Hz, 2H), 3.58-3.36 (m, 8H), 3.26 (d, J=13.3 Hz, 3H), 3.08 (d, J=26.7 Hz, 1H), 2.21 (s, 2H), 2.05 (d, J=14.1 Hz, 3H), 1.76 (s, 1H), 1.34 (dd, J=14.1, 6.4 Hz, 3H).

Example 141: Synthesis of 4-[(2R)-3-(3,4-dihydro-1H-isoquinolin-2-yl)-2-hydroxypropyl]-2-methyl-8-[(1-methyl-4-piperidyl)oxy]-2,3-dihydro-1,4-benzoxazepin-5-one

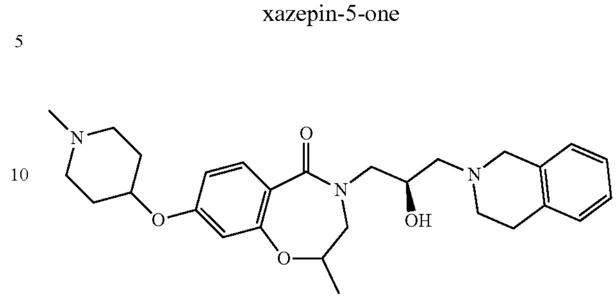

The material obtained in Example 140 as a starting material was used in the same manner as in Example 87 to obtain the title compound.

$^1$H NMR (400 MHz, Methanol-$d_4$) δ 7.62 (d, J=8.8 Hz, 1H), 7.10 (d, J=21.1 Hz, 3H), 6.80 (s, 1H), 6.57 (s, 1H), 4.55 (s, 1H), 4.25 (s, 1H), 4.15 (d, J=14.1 Hz, 1H), 3.79 (s, 2H), 3.63 (d, J=14.6 Hz, 1H), 3.49 (q, J=7.6, 6.7 Hz, 1H), 3.27-3.15 (m, 1H), 2.93 (d, J=13.9 Hz, 3H), 2.84 (s, 2H), 2.71-2.61 (m, 2H), 2.56 (s, 2H), 2.42 (s, 2H), 2.06 (s, 2H), 1.88 (s, 2H), 1.31 (dd, J=16.5, 6.5 Hz, 3H).

Example 142: Synthesis of (2R)-8-(1-acetylazetidin-3-yl)oxy-4-[(2R)-3-(3,4-dihydro-1H-isoquinolin-2-yl)-2-hydroxypropyl]-2-methyl-2,3-dihydro-1,4-benzoxazepin-5-one

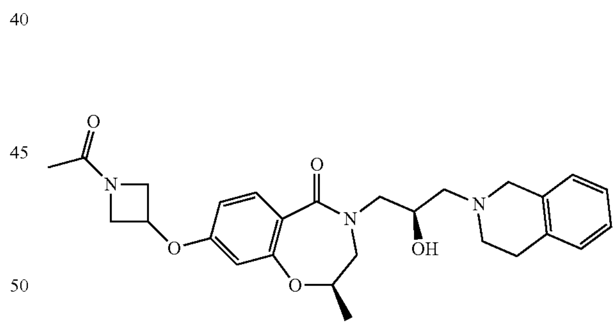

The material obtained by changing [2-(tert-butoxycarbonylamino)-1-methyl-ethyl]methanesulfonate to [(1S)-2-(tert-butoxycarbonylamino)-1-methyl-ethyl] methanesulfonate in Example 140 as a starting material was used in the same manner as in Example 83 to obtain the title compound.

$^1$H NMR (400 MHz, Methanol-$d_4$) δ 7.66 (d, J=8.6 Hz, 1H), 7.19-7.02 (m, 4H), 6.70 (d, J=8.7 Hz, 1H), 6.47 (s, 1H), 5.10 (t, J=5.4 Hz, 1H), 4.80 (s, 1H), 4.65 (t, J=8.5 Hz, 1H), 4.42 (dd, J=11.1, 6.7 Hz, 1H), 4.23 (d, J=10.2 Hz, 2H), 4.14 (d, J=13.8 Hz, 1H), 3.97 (d, J=11.3 Hz, 1H), 3.81 (s, 2H), 3.64 (d, J=15.5 Hz, 1H), 3.50 (dd, J=15.9, 7.5 Hz, 1H), 3.29-3.20 (m, 1H), 2.95 (s, 4H), 2.68 (t, J=6.9 Hz, 2H), 1.93 (s, 3H), 1.34 (d, J=6.3 Hz, 4H).

Example 143: Synthesis of (2R)-4-[(2R)-3-(3,4-dihydro-1H-isoquinolin-2-yl)-2-hydroxypropyl]-2-methyl-8-[(1-methyl-4-piperidyl)oxy]-2,3-dihydro-1,4-benzoxazepin-5-one

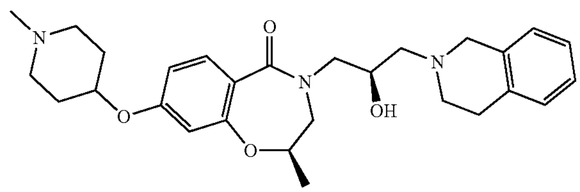 [SMILES: C[C@@H]1CN(C[C@H](O)CN2CCc3ccccc3C2)C(=O)c2ccc(OC3CCN(C)CC3)cc2O1]

The material obtained by changing [2-(tert-butoxycarbonylamino)-1-methyl-ethyl]methanesulfonate to [(1S)-2-(tert-butoxycarbonylamino)-1-methyl-ethyl] methanesulfonate in Example 140 as a starting material was used in the same manner as in Example 141 to obtain the title compound.

$^1$H NMR (400 MHz, Methanol-$d_4$) δ 7.63 (d, J=8.8 Hz, 1H), 7.17-7.02 (m, 4H), 6.79 (d, J=8.8 Hz, 1H), 6.57 (s, 1H), 4.79 (s, 1H), 4.56 (s, 1H), 4.24 (s, 1H), 4.14 (d, J=12.2 Hz, 1H), 3.79 (s, 2H), 3.69-3.59 (m, 1H), 3.50 (dd, J=15.6, 7.6 Hz, 1H), 3.24 (dd, J=13.8, 8.1 Hz, 1H), 2.98-2.80 (m, 6H), 2.63 (dt, J=24.4, 8.0 Hz, 4H), 2.05 (d, J=13.3 Hz, 2H), 1.92 (d, J=18.6 Hz, 2H), 1.33 (d, J=6.4 Hz, 3H).

Example 144: Synthesis of 4-[(2R)-3-(3,4-dihydro-1H-isoquinolin-2-yl)-2-hydroxypropyl]-2-methyl-8-[(1-methyl-4-piperidyl)oxy]-2,3-dihydropyrido[3,2-f][1,4]oxazepin-5-one

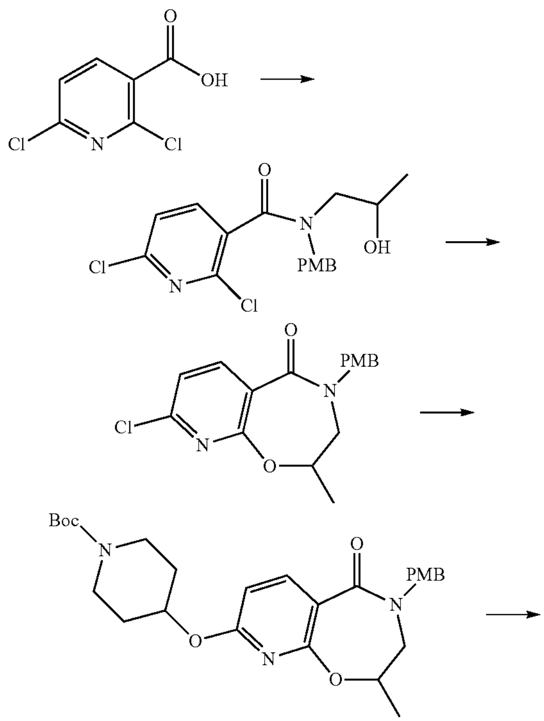

-continued

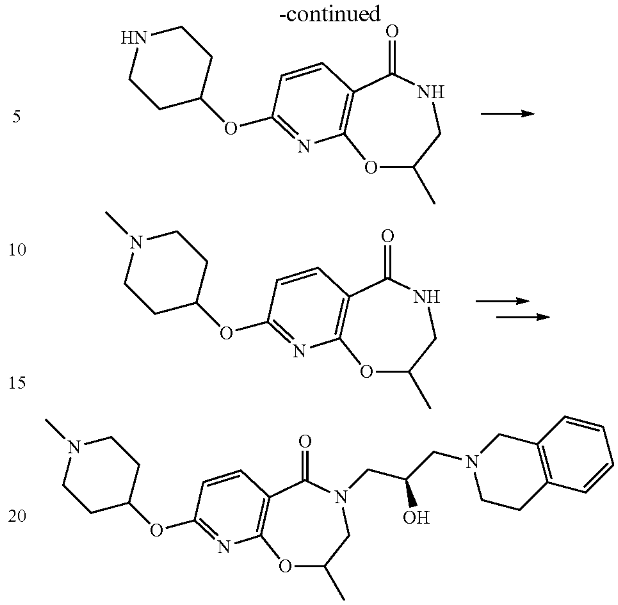

Example 144-1: Synthesis of 2,6-dichloro-N-(2-hydroxypropyl)-N-[(4-methoxyphenyl)methyl]pyridine-3-carboxamide 2,6-Dichloropyridine-3-carboxylic acid (5.0 g, 26 mmol) was dissolved in dichloromethane, and oxalyl chloride (3.3 mL, 39 mmol) and a catalytic amount of dimethylformamide were added thereto. The reaction solution was stirred at room temperature and concentrated under reduced pressure to obtain 2,6-dichloropyridine-3-carbonyl chloride without additional purification. 1-[(4-Methoxyphenyl)methylamino]propan-2-ol (1.3 g, 7.2 mmol) and $K_2CO_3$ (2.2 g, 15.8 mmol) were dissolved in dichloromethane, and 2,6-dichloropyridine-3-carbonyl chloride (1.6 g, 7.6 mmol) dissolved in dichloromethane was slowly added thereto under an ice bath. The reaction solution was stirred at the same temperature for 1 hour, and the reaction was termination by adding water. The reaction solution was extracted with dichloromethane, dried over anhydrous magnesium sulfate and concentrated under reduced pressure to obtain the title compound (2.64 g) as a sticky liquid.

Example 144-2: Synthesis of 8-chloro-4-[(4-methoxyphenyl)methyl]-2-methyl-2,3-dihydropyrido[3,2-f][1,4]oxazepin-5-one 2,6-Dichloro-N-(2-hydroxypropyl)-N-[(4-methoxyphenyl)methyl]pyridine-3-carboxamide (2.64 g) obtained in Example 144-1 was dissolved in tetrahydrofuran, and 60% sodium hydride (630 mg, 15.8 mmol) was slowly added thereto under an ice bath. The reaction solution was slowly heated to room temperature, stirred until the starting material completely disappeared, and methanol was added to terminate the reaction. To the reaction mixture, saturated sodium chloride aqueous solution was added, extracted with ethyl acetate, dried over anhydrous magnesium sulfate and concentrated under reduced pressure. The concentrate was purified by flash chromatography to obtain the title compound (1.35 g) as a sticky liquid.

Example 144-3: Synthesis of tert-butyl 4-[[4-[(4-methoxyphenyl)methyl]-2-methyl-5-oxo-2,3-dihydropyrido[3,2-f][1,4]oxazepin-8-yl]oxy]piperidine-1-carboxylate The material (500 mg, 1.51 mmol) obtained in Example 144-2, tert-butyl 4-hydroxypiperidine-1-carboxylate (460 mg, 2.26 mmol) and 60% sodium hydride (180 mg, 4.5 mmol) were dissolved in 20 mL of tetrahydrofuran and stirred at 60° C. for one day. The reaction solution was extracted with saturated aqueous sodium chloride solution and ethyl acetate, and purified by flash chromatography to obtain the title compound (540 mg).

Example 144-4: Synthesis of 2-methyl-8-(4-piperidyloxy)-3,4-dihydro-2H-pyrido[3,2-f][1,4]oxazepin-5-one The material (540 mg) obtained in Example 144-3 was dissolved in 4 mL of trifluoroacetic acid, and the reaction was carried out by the use of a microwave at 120° C. for 30 minutes. The reaction solution was diluted with ethyl acetate under an ice bath and basified with $K_2CO_3$ aqueous solution. The reaction mixture was washed with ethyl acetate 3 times, and KOH was added to the aqueous layer to basify the pH to 9 or higher, followed by extraction with ethyl acetate. The extracted organic layer was dried over anhydrous sodium sulfate and concentrated to obtain the title compound.

Example 144-5: Synthesis of 2-methyl-8-[(1-methyl-4-piperidyl)oxy]-3,4-dihydro-2H-pyrido[3,2-f][1,4]oxazepin-5-one The material obtained in Example 144-4 as a starting material was used in the same manner as in Example 87 to obtain the title compound.

Example 144-6: Synthesis of 4-[(2R)-3-(3,4-dihydro-1H-isoquinolin-2-yl)-2-hydroxypropyl]-2-methyl-8-[(1-methyl-4-piperidyl)oxy]-2,3-dihydropyrido[3,2-f][1,4]oxazepin-5-one The material obtained in Example 144-5 as a starting material was used in the same manner as in Example 5 to obtain the title compound.

$^1$H NMR (400 MHz, Methanol-$d_4$) (diastereomeric mixture) δ 8.18 (t, J=7.4 Hz, 2H), 7.17-7.01 (m, 8H), 6.57 (dd, J=9.0, 3.9 Hz, 2H), 5.10 (s, 2H), 4.83 (d, J=7.4 Hz, 3H), 4.29-4.16 (m, 2H), 4.12 (d, J=14.1 Hz, 1H), 3.85 (d, J=14.1 Hz, 1H), 3.78-3.66 (m, 8H), 3.68-3.53 (m, 3H), 3.21 (dd, J=13.9, 8.7 Hz, 1H), 2.98-2.85 (m, 9H), 2.85-2.73 (m, 4H), 2.69-2.56 (m, 4H), 2.46 (s, 4H), 2.36 (s, 6H), 2.12-2.02 (m, 4H), 1.93-1.78 (m, 4H), 1.44 (t, J=6.7 Hz, 6H).

Example 145: Synthesis of 4-[(2R)-3-(3,4-dihydro-1H-isoquinolin-2-yl)-2-hydroxypropyl]-2,2-dimethyl-8-[(1-methyl-4-piperidyl)oxy]-3H-pyrido[3,2-f][1,4]oxazepin-5-one

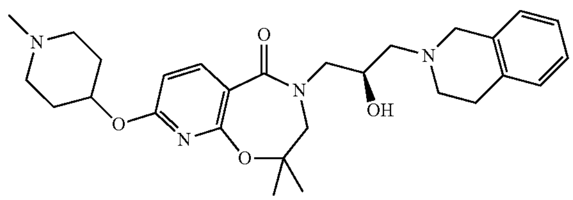 [SMILES: CN1CCC(Oc2ccc3c(n2)OC(C)(C)CN(C[C@H](O)CN2CCc4ccccc4C2)C3=O)CC1]

The title compound was synthesized in the same manner as in Example 144, except that 1-[(4-methoxyphenyl)methylamino]-2-methyl-propan-2-ol was used instead of 1-[(4-methoxyphenyl)methylamino]propan-2-ol.

$^1$H NMR (400 MHz, Methanol-$d_4$) δ 8.04 (d, J=8.0 Hz, 1H), 7.17-7.02 (m, 4H), 6.62 (d, J=8.3 Hz, 1H), 5.17-5.03 (m, 1H), 4.32-4.21 (m, 1H), 4.03 (d, J=14.1 Hz, 1H), 3.76 (s, 2H), 3.71-3.57 (m, 2H), 3.41 (dd, J=13.8, 8.1 Hz, 1H), 2.97-2.84 (m, 4H), 2.85-2.73 (m, 2H), 2.71-2.58 (m, 3H), 2.55-2.41 (m, 2H), 2.37 (s, 3H), 2.13-2.01 (m, 2H), 1.91-1.80 (m, 2H), 1.45 (d, J=18.4 Hz, 6H).

Example 146: Synthesis of (2S)-4-[(2R)-3-(3,4-dihydro-1H-isoquinolin-2-yl)-2-hydroxypropyl]-2-methyl-8-[(1-methyl-4-piperidyl)oxy]-2,3-dihydro-1,4-benzoxazepin-5-one

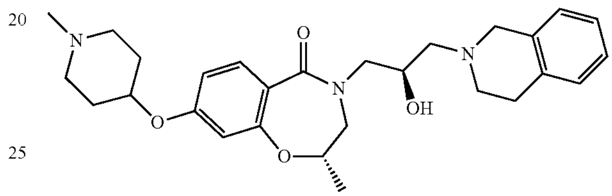

The material obtained by changing [2-(tert-butoxycarbonylamino)-1-methyl-ethyl]methanesulfonate to [(1R)-2-(tert-butoxycarbonylamino)-1-methyl-ethyl] methanesulfonate in Example 140 as a starting material was used in the same manner as in Example 141 to obtain the title compound.

$^1$H NMR (400 MHz, Methanol-$d_4$) δ 7.62 (d, J=8.5 Hz, 1H), 7.18-7.04 (m, 4H), 6.81 (d, J=8.8 Hz, 1H), 6.58 (d, J=2.8 Hz, 1H), 4.83 (s, 1H), 4.57 (s, 1H), 4.32 (d, J=2.0 Hz, 3H), 4.25 (s, 1H), 3.79 (d, J=13.0 Hz, 3H), 3.68-3.58 (m, 2H), 3.47 (dd, J=15.6, 9.2 Hz, 1H), 2.92 (d, J=23.0 Hz, 5H), 2.70 (d, J=6.3 Hz, 2H), 2.63 (s, 2H), 2.46 (d, J=2.0 Hz, 3H), 2.08 (s, 2H), 1.95-1.87 (m, 2H), 1.29 (d, J=6.5 Hz, 3H).

Example 147: Synthesis of 4-[3-(3,4-dihydro-1H-isoquinolin-2-yl)-2-hydroxy-propyl]-2,3-dihydro-1,4-benzoxazepin-5-one

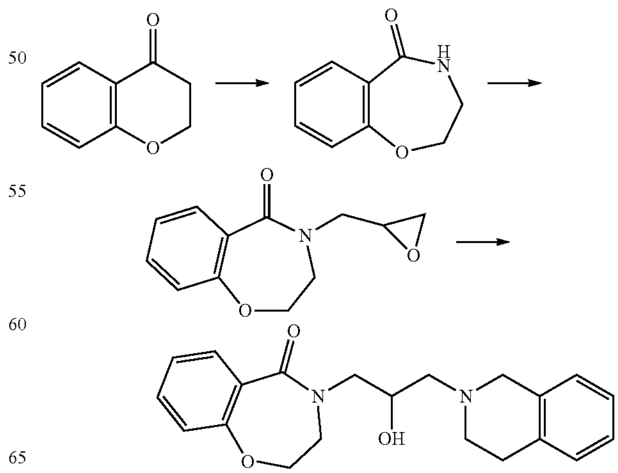

Example 147-1: Synthesis of 3,4-dihydro-2H-1,4-benzoxazepin-5-one

Chroman-4-one (2.0 g, 14 mmol) was dissolved in 10 mL of concentrated sulfuric acid, and sodium azide (1.1 g, 18 mmol) was slowly added thereto at 0° C. The reaction mixture was slowly heated to room temperature and stirred for 12 hours. The reaction mixture was maintained at 0° C. under an ice bath, and 1 M sodium hydroxide aqueous solution was slowly added thereto. After basifying the reaction solution to pH 10 or more, ethyl acetate was added and extracted 3 times. The combined organic layers were dried over anhydrous magnesium sulfate, the solvent was removed by evaporating under reduced pressure, and recrystallized with dichloromethane and hexane to obtain the title compound as a white solid.

Example 147-2: Synthesis of 4-(oxyran-2-ylmethyl)-2,3-dihydro-1,4-benzoxazepin-5-one 3,4-Dihydro-2H-1,4-benzoxazepin-5-one (163 mg, 1 mmol) obtained in Example 147-1 was dissolved in dimethylformamide, and sodium hydride (52 mg, 1.3 mmol) was added thereto under an ice bath. The reaction solution was stirred at 0° C. for 30 minutes, and epibromohydrin (0.1 mL, 1.2 mmol) was slowly added thereto and stirred at room temperature for 2 hours. Methanol was added to the reaction mixture to terminate the reaction, and ethyl acetate was added, and washed with a saturated aqueous ammonium chloride solution and a saturated aqueous sodium chloride solution. The organic layer was dried over anhydrous magnesium sulfate. The solvent was removed by evaporating under reduced pressure, and the obtained title compound was used in the next reaction without additional purification.

Example 147-3: Synthesis of 4-[3-(3,4-dihydro-1H-isoquinolin-2-yl)-2-hydroxy-propyl]-2,3-dihydro-1,4-benzoxazepin-5-one 4-(Oxyran-2-ylmethyl)-2,3-dihydro-1,4-benzoxazepin-5-one obtained in Example 147-2 was dissolved in isopropanol, and tetrahydroisoquinoline (0.13 mL, 1.0 mmol) was added thereto and stirred at 80° C. for 12 hours. The temperature was lowered to room temperature temperature, and the oily liquid obtained by concentrating the solvent was purified by flash chromatography to obtain the transparent and sticky solid compound. NMR data about the obtained title compound are as follows.

$^1$H NMR (400 MHz, Methanol-$d_4$) δ 7.69 (dd, J=7.9, 1.7 Hz, 1H), 7.48 (td, J=7.8, 1.7 Hz, 1H), 7.20 (t, J=7.5 Hz, 1H), 7.15-6.99 (m, 5H), 4.46 (t, J=5.2 Hz, 2H), 4.29-4.18 (m, 1H), 3.99 (dd, J=13.9, 3.6 Hz, 1H), 3.68 (td, J=5.1, 1.6 Hz, 2H), 3.44 (dd, J=13.8, 7.7 Hz, 1H), 2.92 (d, J=5.6 Hz, 2H), 2.86 (t, J=6.2 Hz, 2H), 2.70-2.59 (m, 2H).

Example 148: Synthesis of 2-[3-(3,4-dihydro-1H-isoquinolin-2-yl)-2-hydroxy-propyl]-4,5-dihydro-3H-2-benzazepin-1-one

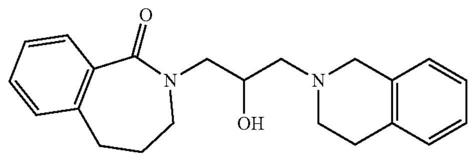 [SMILES: O=C1c2ccccc2CCCN1CC(O)CN1CCc2ccccc2C1]

Tetralin-1-one (1.9 g, 14 mmol) as a starting material was used in the same manner as in Example 147 to obtain the title compound, except that 35% hydrochloric acid aqueous solution (30 mL) was used instead of concentrated sulfuric acid in Example 147-1.

$^1$H NMR (400 MHz, Methanol-$d_4$) δ 7.58 (d, J=7.9 Hz, 1H), 7.45 (t, J=7.4 Hz, 1H), 7.36 (t, J=7.5 Hz, 1H), 7.25 (d, J=7.4 Hz, 1H), 7.17-7.02 (m, 4H), 4.25 (dt, J=7.8, 3.7 Hz, 1H), 3.95 (dd, J=13.8, 3.7 Hz, 1H), 3.48-3.36 (m, 3H), 2.94 (d, J=5.5 Hz, 3H), 2.91-2.86 (m, 2H), 2.82 (t, J=7.1 Hz, 2H), 2.66 (h, J=7.6 Hz, 2H), 2.14 (p, J=6.8 Hz, 2H).

Example 149: Synthesis of 4-[(2R)-3-(3,4-dihydro-1H-isoquinolin-2-yl)-2-hydroxy-propyl]-2,3-dihydro-1,4-benzoxazepin-5-one

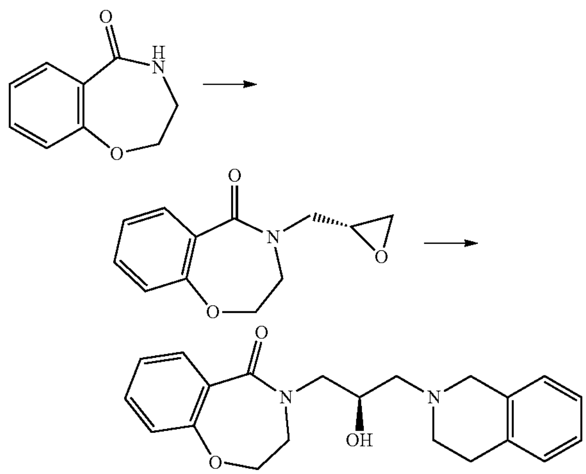

Example 149-1: Synthesis of 4-[[(2R)-oxyran-2-yl]methyl]-2,3-dihydro-1,4-benzoxazepin-5-one 3,4-Dihydro-2H-1,4-benzoxazepin-5-one (163 mg, 1 mmol) obtained in Example 147-1 was dissolved in 5 mL of dimethylformamide, and sodium hydride (48 mg, 1.2 mmol) was added thereto under an ice bath. The reaction solution was stirred at 0° C. for 30 minutes, and (R)-(−)-glycidyl nosylate (298 mg, 1.15 mmol) was slowly added thereto and stirred at room temperature for 2 hours. Methanol was added to the reaction mixture to terminate the reaction, and ethyl acetate was added, and washed with a saturated aqueous ammonium chloride solution and a saturated aqueous sodium chloride solution. The organic layer was dried over anhydrous magnesium sulfate. The solvent was removed by evaporating under reduced pressure, and the obtained title compound was used in the next reaction without additional purification.

Example 149-2: Synthesis of 4-[(2R)-3-(3,4-dihydro-1H-isoquinolin-2-yl)-2-hydroxy-propyl]-2,3-dihydro-1,4-benzoxazepin-5-one 4-[[(2R)-oxyran-2-yl]methyl]-2,3-dihydro-1,4-benzoxazepin-5-one obtained in Example 149-1 was used in the same manner as in Example 147-3 to obtain the title compound.

$^1$H NMR (400 MHz, Methanol-$d_4$) δ 7.69 (dd, J=7.9, 1.7 Hz, 1H), 7.48 (td, J=7.8, 1.8 Hz, 1H), 7.20 (t, J=7.5 Hz, 1H), 7.15-7.02 (m, 5H), 4.46 (t, J=5.2 Hz, 2H), 4.29-4.19 (m, 1H), 3.99 (dd, J=13.9, 3.6 Hz, 1H), 3.75 (d, J=2.2 Hz, 2H), 3.74-3.63 (m, 2H), 3.44 (dd, J=13.9, 7.7 Hz, 1H), 2.97-2.90 (m, 2H), 2.91-2.83 (m, 2H), 2.70-2.60 (m, 2H).

Example 150: Synthesis of 4-[(2R)-3-(3,4-dihydro-1H-isoquinolin-2-yl)-2-hydroxy-propyl]-8-fluoro-2,3-dihydro-1,4-benzoxazepin-5-one

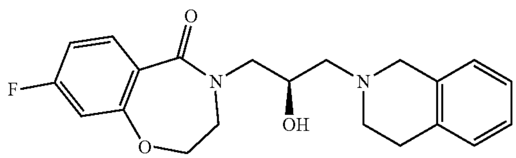 [SMILES: O=C1c2ccc(F)cc2OCCN1C[C@H](O)CN1CCc2ccccc2C1]

7-Fluorochroman-4-one as a starting material was used in the same manner as in Examples 147-1 and 149 to obtain the title compound.

$^1$H NMR (400 MHz, Methanol-$d_4$) δ 7.81-7.73 (m, 1H), 7.16-7.02 (m, 4H), 6.94 (td, J=8.5, 2.6 Hz, 1H), 6.81 (dd, J=9.9, 2.6 Hz, 1H), 4.52 (t, J=5.0 Hz, 2H), 4.27-4.20 (m, 1H), 3.99 (dd, J=13.9, 3.6 Hz, 1H), 3.81-3.71 (m, 4H), 3.44 (dd, J=13.9, 7.8 Hz, 1H), 2.98-2.84 (m, 4H), 2.69-2.61 (m, 2H).

Example 151: Synthesis of 8-bromo-4-[(2R)-3-(3,4-dihydro-1H-isoquinolin-2-yl)-2-hydroxy-propyl]-2,3-dihydro-1,4-benzoxazepin-5-one

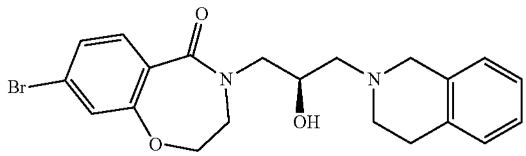 [SMILES: O=C1c2ccc(Br)cc2OCCN1C[C@H](O)CN1CCc2ccccc2C1]

7-Bromochroman-4-one as a starting material was used in the same manner as in Examples 147-1 and 149 to obtain the title compound.

$^1$H NMR (400 MHz, Methanol-$d_4$) δ 7.63 (d, J=8.4 Hz, 1H), 7.35 (dd, J=8.4, 1.7 Hz, 1H), 7.26 (d, J=1.6 Hz, 1H), 7.16-7.01 (m, 4H), 4.51 (t, J=5.0 Hz, 2H), 4.27-4.17 (m, 1H), 3.99 (dd, J=13.7, 3.5 Hz, 1H), 3.74 (d, J=6.5 Hz, 4H), 3.44 (dd, J=13.9, 7.8 Hz, 1H), 2.97-2.83 (m, 4H), 2.69-2.59 (m, 2H).

Example 152: Synthesis of 4-[(2R)-3-(3,4-dihydro-1H-isoquinolin-2-yl)-2-hydroxy-propyl]-2,3-dihydropyrido[4,3-f][1,4]oxazepin-5-one

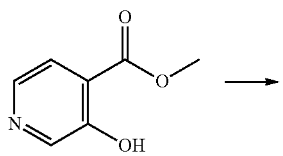

-continued

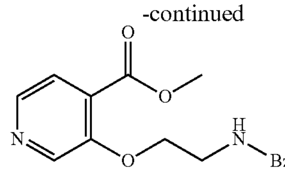

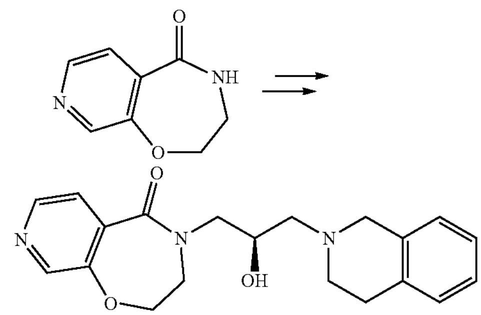

Example 152-1: Synthesis of methyl 3-[2-(benzyloxycarbonylamino)ethoxy]pyridine-4-carboxylate Methyl 3-hydroxypyridine-4-carboxylate (1.0 g, 6.53 mmol), benzyl N-(2-hydroxyethyl)carbamate (1.53 g, 7.84 mmol) and triphenylphosphine (2.06 g) were dissolved in tetrahydrofuran, and diisopropyl azodicarboxylate was slowly added thereto at 0° C. The reaction solution was stirred at room temperature for 12 hours, and the solvent was removed under reduced pressure. The concentrate was purified by flash chromatography under the solvent condition of hexane and ethyl acetate to obtain the title compound.

Example 152-2: Synthesis of 3,4-dihydro-2H-pyrido[4,3-f][1,4]oxazepin-5-one

Methyl 3-[2-(benzyloxycarbonylamino)ethoxy]pyridine-4-carboxylate obtained in Example 152-1 was dissolved in ethanol at room temperature, and 5% palladium-charcoal was added thereto, followed by stirring under a hydrogen balloon for 24 hours. The reaction solution was filtered through celite and washed with ethanol. The obtained solution was concentrated under reduced pressure and purified by flash chromatography to obtain the title compound (548 mg) as a white crystalline solid.

Example 152-3: Synthesis of 4-[(2R)-3-(3,4-dihydro-1H-isoquinolin-2-yl)-2-hydroxy-propyl]-2,3-dihydropyrido[4,3-f][1,4]oxazepin-5-one 3,4-Dihydro-2H-pyrido[4,3-f][1,4]oxazepin-5-one obtained in Example 152-2 as a starting material was used in the same manner as in Example 149 to obtain the title compound.

$^1$H NMR (400 MHz, Methanol-$d_4$) δ 8.36 (s, 1H), 8.31 (d, J=5.1 Hz, 1H), 7.75 (d, J=5.1 Hz, 1H), 7.17-7.02 (m, 4H), 4.62 (t, J=4.7 Hz, 2H), 4.30-4.20 (m, 1H), 4.02 (dd, J=13.9, 3.5 Hz, 1H), 3.82 (t, J=4.6 Hz, 2H), 3.76 (s, 2H), 3.45 (dd, J=13.9, 8.0 Hz, 1H), 2.98-2.90 (m, 2H), 2.91-2.83 (m, 2H), 2.69-2.60 (m, 2H).

Example 153: Synthesis of 8-chloro-4-[(2R)-3-(3,4-dihydro-1H-isoquinolin-2-yl)-2-hydroxy-propyl]-2,3-dihydropyrido[3,2-f][1,4]oxazepin-5-one

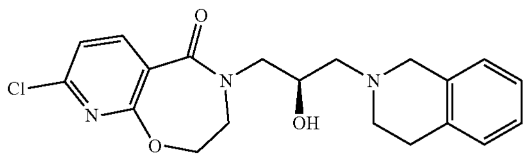 [SMILES: O=C1c2ccc(Cl)nc2OCCN1C[C@H](O)CN1CCc2ccccc2C1]

8-Chloro-3,4-dihydro-2H-pyrido[3,2-f][1,4]oxazepin-5-one as a starting material was used in the same manner as in Example 149 to obtain the title compound.

$^1$H NMR (400 MHz, Methanol-$d_4$) δ 8.36 (dd, J=8.1, 1.4 Hz, 1H), 7.26 (dd, J=8.2, 1.4 Hz, 1H), 7.17-7.00 (m, 4H), 4.70-4.67 (m, 2H), 4.24 (q, J=9.0, 8.0 Hz, 1H), 3.99 (dd, J=13.9, 3.5 Hz, 1H), 3.89 (t, J=4.3 Hz, 2H), 3.76 (s, 2H), 3.42 (dd, J=13.8, 8.1 Hz, 1H), 2.94-2.86 (dd, J=17.3, 5.4 Hz, 4H), 2.65 (d, J=6.3 Hz, 2H).

Example 154: Synthesis of 7-chloro-2-[(2R)-3-(3,4-dihydro-1H-isoquinolin-2-yl)-2-hydroxy-propyl]-4,5-dihydro-3H-2-benzazepin-1-one

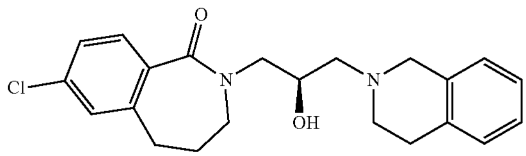 [SMILES: O=C1c2ccc(Cl)cc2CCCN1C[C@H](O)CN1CCc2ccccc2C1]

7-Chloro-2,3,4,5-tetrahydro-2-benzazepin-1-one as a starting material was used in the same manner as in Example 149 to obtain the title compound.

$^1$H NMR (400 MHz, Methanol-$d_4$) δ 7.55 (d, J=8.2 Hz, 1H), 7.35 (dd, J=8.3, 1.9 Hz, 1H), 7.27 (d, J=2.1 Hz, 1H), 7.15-7.00 (m, 4H), 4.27-4.18 (m, 1H), 3.91 (dd, J=13.8, 3.6 Hz, 1H), 3.75 (s, 2H), 3.44-3.33 (m, 2H), 3.32-3.23 (m, 1H), 2.97-2.89 (m, 2H), 2.90-2.82 (m, 2H), 2.78 (t, J=7.1 Hz, 2H), 2.68-2.59 (m, 2H), 2.11 (p, J=6.8 Hz, 2H).

Example 155: Synthesis of 7-bromo-2-[(2R)-3-(3,4-dihydro-1H-isoquinolin-2-yl)-2-hydroxy-propyl]-4,5-dihydro-3H-2-benzazepin-1-one

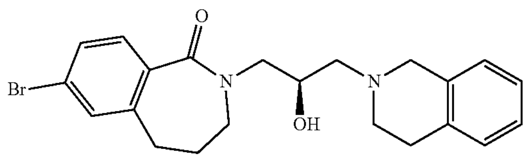

7-Bromo-2,3,4,5-tetrahydro-2-benzazepin-1-one as a starting material was used in the same manner as in Example 149 to obtain the title compound.

$^1$H NMR (400 MHz, Methanol-$d_4$) δ 7.55-7.51 (m, 1H), 7.51-7.45 (m, 2H), 7.16-7.01 (m, 4H), 4.29-4.19 (m, 1H), 3.92 (dd, J=13.8, 3.6 Hz, 1H), 3.78 (s, 2H), 3.47-3.38 (m, 2H), 3.36-3.34 (m, 1H), 2.99-2.91 (m, 2H), 2.93-2.85 (m, 2H), 2.80 (t, J=7.1 Hz, 2H), 2.71-2.61 (m, 2H), 2.14 (p, J=6.9 Hz, 2H).

Example 156: Synthesis of 8-bromo-4-[(2R)-3-(3,4-dihydro-1H-isoquinolin-2-yl)-2-hydroxy-propyl]-1-methyl-2,3-dihydro-1,4-benzodiazepin-5-one

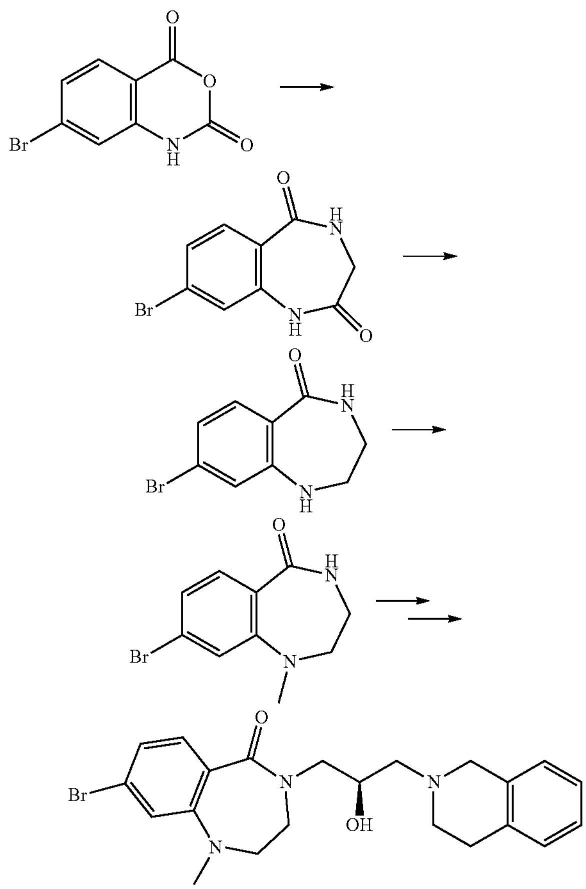

Example 156-1: Synthesis of 8-bromo-3,4-dihydro-1H-1,4-benzodiazepin-2,5-dione

7-Bromo-1H-3,1-benzoxazine-2,4-dione (550 g, 2.27 mol) was dissolved in 2.5 L of distilled water, and triethylamine (230 g, 2.27 mol) and glycine (239 g, 3.18 mol) were added thereto. The reaction solution was stirred at room temperature for 4 hours, concentrated, dissolved again in 3 L of acetic acid, and the mixture was stirred at 140° C. for 8 hours. The reaction solution was diluted with petroleum ether and filtered to obtain the title compound (866 g, 74.7%) as a white solid.

Example 156-2: Synthesis of 8-bromo-1,2,3,4-tetrahydro-1,4-benzodiazepin-5-one

8-Bromo-3,4-dihydro-1H-1,4-benzodiazepin-2,5-dione (200 g, 784 mmol) obtained in Example 156-1 was dissolved in 4 L of tetrahydrofuran, and LAH (50.6 g, 1.33 mol) was slowly added thereto at 0° C. The reaction solution was stirred at 70° C. for 3 hours, and after cooling, 100 mL of distilled water, 100 mL of 15% sodium hydroxide aqueous solution, and additional 100 mL of distilled water were slowly added to terminate the reaction. The mixture solution was dried over anhydrous sodium sulfate, filtered with hot tetrahydrofuran, the solvent was removed under reduced pressure, and recrystallized by adding 500 mL of ethyl acetate to obtain the title compound (177 g, 46.8%) as a white solid.

Example 156-3: Synthesis of 8-bromo-1-methyl-3,4-dihydro-2H-1,4-benzodiazepin-5-one 8-Bromo-1,2,3,4-tetrahydro-1,4-benzodiazepin-5-one (177 g, 734 mmol) obtained in Example 156-2 was dissolved in 1.2 L of methanol, and paraformaldehyde (200 g, 3.67 mol) dissolved in 1.2 L of acetic acid was added thereto. The reaction solution was stirred at 50° C. for 1 hour. Sodium cyanoborohydride (231 g, 3.67 mol) was added to the reaction solution, stirred at 50° C. for 4 hours, and concentrated by removing the solvent under reduced pressure. The mixture was diluted with 4 L of distilled water and extracted with dichloromethane 2 times. The combined organic layers were washed with saturated aqueous sodium chloride solution 2 times, dried over anhydrous sodium sulfate, filtered, and concentrated under reduced pressure. Methanol was added to the obtained concentrate and recrystallized to obtain the title compound (yield: 78%) as a white solid.

Example 156-4: Synthesis of 8-bromo-4-[(2R)-3-(3,4-dihydro-1H-isoquinolin-2-yl)-2-hydroxy-propyl]-1-methyl-2,3-dihydro-1,4-benzodiazepin-5-one 8-Bromo-1-methyl-3,4-dihydro-2H-1,4-benzodiazepin-5-one obtained in Example 156-3 as a starting material was used in the same manner as in Example 149 to obtain the title compound.

$^1$H NMR (400 MHz, Methanol-$d_4$) δ 7.42 (d, J=7.7 Hz, 1H), 7.20-7.02 (m, 6H), 4.23 (m, 1H), 3.94 (dd, J=13.8, 3.9 Hz, 1H), 3.76 (s, 2H), 3.63 (q, J=4.9 Hz, 2H), 3.52-3.37 (m, 3H), 2.93 (d, J=5.7 Hz, 2H), 2.92-2.80 (m, 5H), 2.73-2.59 (m, 2H).

Example 157: Synthesis of 8-bromo-4-[(2R)-3-(3,4-dihydro-1H-isoquinolin-2-yl)-2-hydroxy-propyl]-1-ethyl-2,3-dihydro-1,4-benzodiazepin-5-one

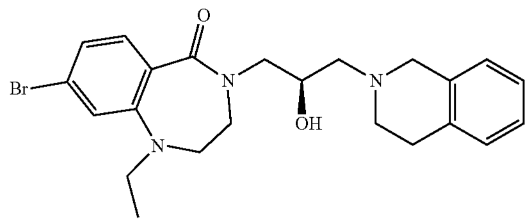 [SMILES: CCN1CCN(C[C@H](O)CN2CCc3ccccc3C2)C(=O)c2ccc(Br)cc21]

Example 157-1: Synthesis of 8-bromo-1-ethyl-3,4-dihydro-2H-1,4-benzodiazepin-5-one 8-Bromo-1,2,3,4-tetrahydro-1,4-benzodiazepin-5-one (100 mg, 0.41 mmol) obtained in Example 156-2 and potassium carbonate (170 mg, 1.23 mmol) were dissolved in dimethylformamide, and iodoethane (0.07 mL, 0.82 mmol) was added thereto. The reaction solution was stirred at 60° C. for one day. The reaction mixture was cooled to room temperature, diluted with distilled water and extracted with ethyl acetate 3 times. The combined organic layers were washed with saturated aqueous sodium chloride solution 2 times, dried over anhydrous magnesium sulfate, filtered, and concentrated under reduced pressure. The obtained concentrate was purified by flash chromatography to obtain the solid title compound.

Example 157-2: Synthesis of 8-bromo-4-[(2R)-3-(3,4-dihydro-1H-isoquinolin-2-yl)-2-hydroxy-propyl]-1-ethyl-2,3-dihydro-1,4-benzodiazepin-5-one The material obtained in Example 157-1 as a starting material was used in the same manner as in Example 149 to obtain the title compound.

$^1$H NMR (400 MHz, Methanol-$d_4$) δ 7.42 (d, J=8.6 Hz, 1H), 7.17-7.09 (m, 5H), 7.06 (d, J=5.6 Hz, 1H), 4.23 (dt, J=12.4, 6.4 Hz, 1H), 3.90 (dd, J=13.8, 4.0 Hz, 1H), 3.79 (s, 2H), 3.61 (d, J=5.9 Hz, 2H), 3.49 (dd, J=14.4, 6.8 Hz, 2H), 3.41 (t, J=5.4 Hz, 2H), 3.22 (dt, J=11.9, 6.8 Hz, 2H), 2.95-2.88 (m, 4H), 2.76-2.63 (m, 2H), 1.20 (t, J=7.1 Hz, 3H).

Example 158: Synthesis of 8-bromo-4-[(2R)-3-(3,4-dihydro-1H-isoquinolin-2-yl)-2-hydroxy-propyl]-1-ethyl-3H-1,4-benzodiazepin-2,5-dione

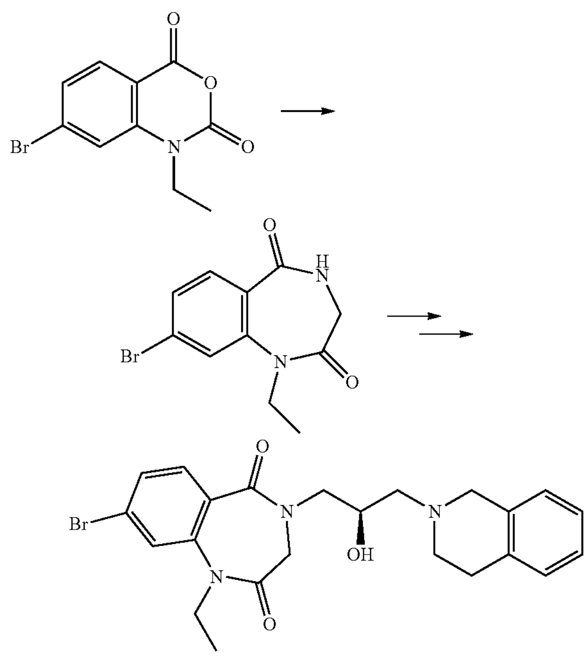

Example 158-1: Synthesis of 8-bromo-1-ethyl-3,4-dihydro-1,4-benzodiazepin-2,5-dione 7-Bromo-1-ethyl-3,1-benzoxazine-2,4-dione (262 mg, 0.97 mmol) and glycine (73 mg, 0.97 mmol) were dissolved in acetic acid, and heated to reflux for 4 hours. The reaction mixture was cooled to room temperature, diluted with distilled water and filtered. The obtained solid was washed with diethyl ether to obtain the solid title compound (100 mg) without additional purification.

Example 158-2: Synthesis of 8-bromo-4-[(2R)-3-(3,4-dihydro-1H-isoquinolin-2-yl)-2-hydroxy-propyl]-1-ethyl-3H-1,4-benzodiazepin-2,5-dione The material obtained in Example 158-1 as a starting material was used in the same manner as in Example 149 to obtain the title compound.

$^1$H NMR (400 MHz, Methanol-$d_4$) δ 7.72-7.69 (m, 2H), 7.55 (d, J=8.5 Hz, 1H), 7.17-6.99 (m, 4H), 4.24 (p, J=7.4 Hz, 2H), 4.15 (dd, J=14.9, 6.0 Hz, 1H), 4.01-3.95 (m, 2H), 3.85-3.67 (m, 4H), 3.53-3.45 (m, 1H), 2.93-2.86 (m, 4H), 2.63 (d, J=7.0 Hz, 2H), 1.19-1.09 (m, 3H).

Example 159: Synthesis of 2-[4-[[4-(2R)-3-(3,4-dihydro-1H-isoquinolin-2-yl)-2-hydroxy-propyl]-5-oxo-2,3-dihydro-1,4-benzoxazepin-8-yl]-1-piperidyl]acetonitrile

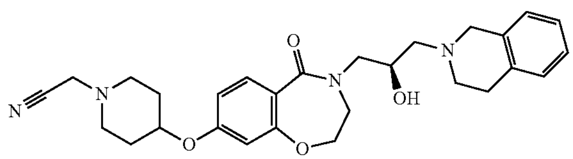 [SMILES: N#CCN1CCC(Oc2ccc3c(c2)OCCN(C[C@H](O)CN2CCc4ccccc4C2)C3=O)CC1]

4-[(2R)-3-(3,4-dihydro-1H-isoquinolin-2-yl)-2-hydroxy-propyl]-8-(4-piperidyloxy)-2,3-dihydro-1,4-benzoxazepin-5-one dihydrochloride obtained in Example 78-1 was dissolved in acetonitrile, potassium carbonate and 2-bromoacetonitrile were added thereto, followed by stirring at 90° C. for 1 hour. To the reaction mixture, saturated aqueous ammonium chloride aqueous solution was added and extracted with ethyl acetate 3 times. The oily liquid obtained by drying the combined organic layers over anhydrous sodium sulfate and concentrating under reduced pressure was purified by flash chromatography to obtain the title compound as a white solid.

$^1$H NMR (400 MHz, Methanol-$d_4$) δ 7.69 (dd, J=8.7, 2.2 Hz, 1H), 7.16-7.09 (m, 3H), 7.06 (d, J=6.6 Hz, 1H), 6.81 (dd, J=8.8, 2.7 Hz, 1H), 6.64 (d, J=2.6 Hz, 1H), 4.76 (dq, J=7.2, 3.8 Hz, 1H), 4.47 (d, J=5.4 Hz, 2H), 4.23 (s, 1H), 4.17-4.07 (m, 1H), 3.97 (dt, J=13.8, 3.2 Hz, 1H), 3.86-3.65 (m, 6H), 3.61 (t, J=11.6 Hz, 1H), 3.43 (dd, J=14.2, 7.6 Hz, 1H), 2.97-2.86 (m, 4H), 2.67 (d, J=6.1 Hz, 2H), 2.04 (t, J=6.5 Hz, 3H), 1.87 (ddd, J=23.5, 11.9, 4.2 Hz, 2H), 1.26 (td, J=7.4, 2.2 Hz, 1H).

Example 160: Synthesis of 8-[[1-(2,2-difluoro-acetyl)-4-piperidyl]oxy]-4-[(2R)-3-(3,4-dihydro-1H-isoquinolin-2-yl)-2-hydroxy-propyl]-2,3-dihydro-1,4-benzoxazepin-5-one

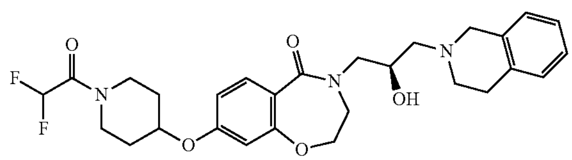 [SMILES: O=C1c2ccc(OC3CCN(C(=O)C(F)F)CC3)cc2OCCN1C[C@H](O)CN1CCc2ccccc2C1]

The title compound was synthesized in the same manner as in Example 78 except that difluoro-acetic anhydride was used instead of acetic anhydride in Example 78-2.

$^1$H NMR (400 MHz, Methanol-$d_4$) δ 7.67 (dd, J=8.8, 2.1 Hz, 1H), 7.14 (h, J=5.8 Hz, 3H), 7.07 (d, J=7.0 Hz, 1H), 6.77 (dd, J=8.8, 2.9 Hz, 1H), 6.60 (d, J=2.3 Hz, 1H), 4.52 (s, 1H), 4.47 (d, J=5.4 Hz, 2H), 4.26 (s, 1H), 3.95 (dd, J=13.9, 3.4 Hz, 1H), 3.86 (s, 2H), 3.77-3.65 (m, 4H), 3.46 (dd, J=14.0, 7.5 Hz, 1H), 2.98 (s, 3H), 2.88-2.67 (m, 4H), 2.58 (t, J=9.5 Hz, 2H), 2.08-2.00 (m, 2H), 1.86 (d, J=11.8 Hz, 2H).

Example 161: Synthesis of 8-[[1-(2,2-difluoro-acetyl)azetidin-3-yl]oxy-4-[(2R)-3-(3,4-dihydro-1H-isoquinolin-2-yl)-2-hydroxy-propyl]-2,3-dihydro-1,4-benzoxazepin-5-one

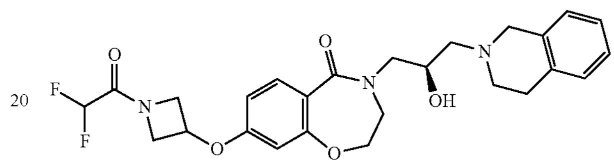

8-(Azetidin-3-yloxy)-4-[(2R)-3-(3,4-dihydro-1H-isoquinolin-2-yl)-2-hydroxy-propyl]-2,3-dihydro-1,4-benzoxazepin-5-one dihydrochloride obtained in Example 83-1 as a starting material was used in the same manner as in Example 160 to obtain the title compound.

$^1$H NMR (400 MHz, Methanol-$d_4$) δ 7.72 (dd, J=8.7, 2.0 Hz, 1H), 7.14 (d, J=5.7 Hz, 3H), 7.07 (d, J=6.9 Hz, 1H), 6.69 (d, J=8.6 Hz, 1H), 6.49 (d, J=2.3 Hz, 1H), 5.21-5.14 (m, 1H), 4.88-4.77 (m, 1H), 4.60-4.37 (m, 4H), 4.25 (d, J=7.2 Hz, 1H), 4.11 (td, J=11.8, 10.3, 5.3 Hz, 2H), 3.96 (dd, J=13.9, 3.2 Hz, 1H), 3.85 (s, 2H), 3.72 (h, J=7.3, 6.4 Hz, 2H), 3.46 (dd, J=14.1, 7.6 Hz, 1H), 2.97 (s, 3H), 2.80-2.69 (m, 2H).

Example 162: Synthesis of 4-[(2R)-3-(3,4-dihydro-1H-isoquinolin-2-yl)-2-hydroxy-propyl]-8-[[1-(2-hydroxyethyl)-4-piperidyl]oxy]-2,3-dihydro-1,4-benzoxazepin-5-one

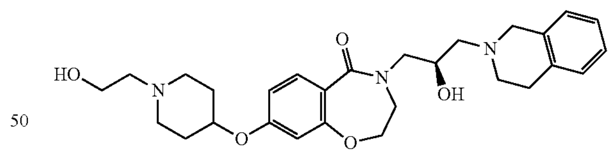

4-[(2R)-3-(3,4-dihydro-1H-isoquinolin-2-yl)-2-hydroxy-propyl]-8-(4-piperidyloxy)-2,3-dihydro-1,4-benzoxazepin-5-one dihydrochloride (100 mg, 0.19 mmol) obtained in Example 78-1, potassium carbonate (79 mg, 0.57 mmol) and 2-iodoethanol (15 μL, 0.19 mmol) were dissolved in acetonitrile and stirred. After completion of the reaction, the reaction solution was concentrated and purified by flash chromatography to obtain the title compound.

$^1$H NMR (400 MHz, Methanol-$d_4$) δ 7.66 (d, J=8.9 Hz, 1H), 7.11-7.03 (m, 4H), 6.76 (d, J=8.9 Hz, 1H), 6.59 (s, 1H), 4.51-4.46 (m, 3H), 4.18 (s, 1H), 3.98 (d, J=13.9 Hz, 1H), 3.76-3.71 (m, 6H), 3.42 (dd, J=14.0, 7.9 Hz, 1H), 3.02-2.79 (m, 6H), 2.71-2.58 (m, 4H), 2.58-2.43 (m, 2H), 2.04 (t, J=7.4 Hz, 2H), 1.91-1.75 (m, 2H).

Example 163: Synthesis of 4-[(2R)-3-(3,4-dihydro-1H-isoquinolin-2-yl)-2-hydroxy-propyl]-8-[[1-(2-fluoroethyl)-4-piperidyl]oxy]-2,3-dihydro-1,4-benzoxazepin-5-one

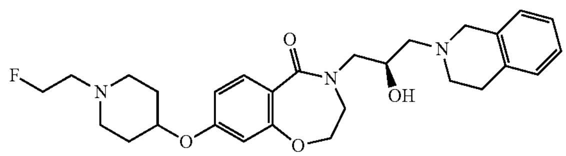 [SMILES: O=C1c2ccc(OC3CCN(CCF)CC3)cc2OCCN1C[C@H](O)CN1CCc2ccccc2C1]

The title compound was synthesized in the same manner as in Example 162 except that 2-fluoroethyl 4-methylbenzenesulfonate was used instead of 2-iodoethanol at 90° C.

$^1$H NMR (400 MHz, Methanol-$d_4$) δ 7.66 (d, J=8.7 Hz, 1H), 7.17-7.01 (m, 4H), 6.76 (d, J=8.9 Hz, 1H), 6.58 (s, 1H), 4.66 (t, J=5.0 Hz, 1H), 4.59-4.42 (m, 4H), 4.23 (s, 1H), 3.97 (d, J=13.4 Hz, 1H), 3.84-3.66 (m, 4H), 3.42 (dd, J=13.9, 7.6 Hz, 1H), 3.02-2.76 (m, 7H), 2.75-2.59 (m, 3H), 2.51 (t, J=10.2 Hz, 2H), 2.13-2.00 (m, 2H), 1.93-1.75 (m, 2H).

Example 164: Synthesis of 4-[(2R)-3-(3,4-dihydro-1H-isoquinolin-2-yl)-2-hydroxy-propyl]-8-[[1-(2-fluoroethyl)-4-piperidyl]oxy]-2,3-dihydropyrido[3,2-f][1,4]oxazepin-5-one

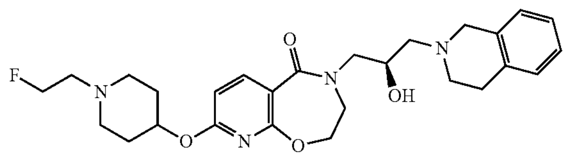 [SMILES: O=C1c2ccc(OC3CCN(CCF)CC3)nc2OCCN1C[C@H](O)CN1CCc2ccccc2C1]

4-[(2R)-3-(3,4-dihydro-1H-isoquinolin-2-yl)-2-hydroxy-propyl]-8-(4-piperidyloxy)-2,3-dihydropyrido[3,2-f][1,4]oxazepin-5-one dihydrochloride as a starting material was used in the same manner as in Example 163 to obtain the title compound.

$^1$H NMR (400 MHz, Methanol-$d_4$) δ 8.26 (d, J=8.5 Hz, 1H), 7.19-6.97 (m, 4H), 6.55 (d, J=8.5 Hz, 1H), 5.08 (s, 1H), 4.66 (s, 1H), 4.61 (s, 2H), 4.55 (s, 1H), 4.29-4.18 (m, 1H), 3.99 (d, J=13.9 Hz, 1H), 3.90-3.83 (m, 2H), 3.75 (s, 2H), 3.43-3.37 (m, 1H), 2.99-2.83 (m, 6H), 2.80 (s, 1H), 2.73 (s, 1H), 2.63 (d, J=6.2 Hz, 2H), 2.55-2.43 (m, 2H), 2.14-2.03 (m, 2H), 1.90-1.77 (m, 2H).

Example 165: Synthesis of 4-[(2R)-3-(3,4-dihydro-1H-isoquinolin-2-yl)-2-hydroxypropyl]-8-[[1-[(3-methyloxetan-3-yl)methyl]-4-piperidyl]oxy]-2,3-dihydro-1,4-benzoxazepin-5-one

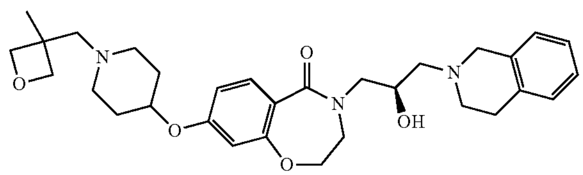 [SMILES: CC1(CN2CCC(Oc3ccc4c(c3)OCCN(C[C@H](O)CN3CCc5ccccc5C3)C4=O)CC2)COC1]

4-[(2R)-3-(3,4-dihydro-1H-isoquinolin-2-yl)-2-hydroxy-propyl]-8-(4-piperidyloxy)-2,3-dihydro-1,4-benzoxazepin-5-one (200 mg, 0.443 mmol) obtained in Example 78-1, cesium carbonate (288 mg, 0.886 mmol) and 3-(bromomethyl)-3-methyl-oxetan (110 mg, 0.665 mmol) were dissolved in dimethylformamide, heated to 60° C. and stirred. After completion of the reaction, the reaction solution was extracted with saturated aqueous sodium chloride solution and ethyl acetate, and purified by flash chromatography to obtain the title compound (6 mg).

$^1$H NMR (400 MHz, Methanol-$d_4$) δ 7.66 (d, J=8.7 Hz, 1H), 7.12 (d, J=3.1 Hz, 3H), 7.06 (d, J=6.6 Hz, 1H), 6.75 (d, J=8.7 Hz, 1H), 6.57 (d, J=3.2 Hz, 1H), 4.56-4.46 (m, 4H), 4.45 (s, 2H), 4.33 (d, J=5.7 Hz, 2H), 4.23 (s, 1H), 4.01-3.92 (m, 1H), 3.80-3.69 (m, 4H), 3.42 (dd, J=14.0, 7.6 Hz, 1H), 2.97-2.85 (m, 4H), 2.66 (d, J=6.7 Hz, 2H), 2.61 (s, 3H), 2.31 (t, J=10.3 Hz, 2H), 2.06-1.98 (m, 2H), 1.79 (t, J=10.2 Hz, 2H), 1.43 (s, 3H).

Example 166: Synthesis of 4-[[4-[(2R)-3-(3,4-dihydro-1H-isoquinolin-2-yl)-2-hydroxypropyl]-5-oxo-2,3-dihydro-1,4-benzoazepin-8-yl]oxy]piperidine-1-carbonitrile

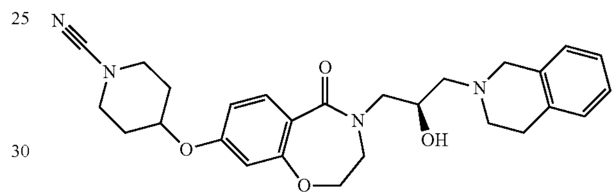

4-[(2R)-3-(3,4-dihydro-1H-isoquinolin-2-yl)-2-hydroxy-propyl]-8-(4-piperidyloxy)-2,3-dihydro-1,4-benzoxazepin-5-one (200 mg, 0.443 mmol) obtained in Example 78-1, cyanogen bromide (94 mg, 0.886 mmol) and cesium carbonate (433 mg, 1.329 mmol) were dissolved in dimethylformamide, and the reaction was carried out by the use of a microwave at 70° C. for 3 hours. After completion of the reaction, the reaction solution was extracted with saturated aqueous sodium chloride solution and ethyl acetate, and purified by flash chromatography to obtain the title compound (14 mg).

$^1$H NMR (400 MHz, Methanol-$d_4$) δ 7.68 (dd, J=8.7, 2.1 Hz, 1H), 7.14-7.09 (m, 3H), 7.05 (d, J=6.7 Hz, 1H), 6.79 (dd, J=8.8, 2.3 Hz, 1H), 6.63 (d, J=2.4 Hz, 1H), 4.65 (dq, J=7.1, 3.6 Hz, 1H), 4.51-4.43 (m, 2H), 4.23 (d, J=7.3 Hz, 1H), 3.97 (dt, J=14.1, 2.9 Hz, 1H), 3.82-3.69 (m, 4H), 3.55-3.37 (m, 3H), 3.26 (t, J=9.9 Hz, 2H), 2.93 (d, J=5.6 Hz, 2H), 2.91-2.84 (m, 2H), 2.65 (d, J=6.3 Hz, 2H), 2.09 (t, J=10.7 Hz, 2H), 1.94-1.81 (m, 2H).

Example 167: Synthesis of 8-[(4-acetylpiperazin-1-yl)methyl]-4-[(2R)-3-(3,4-dihydro-1H-isoquinolin-2-yl)-2-hydroxy-propyl]-2,2-dimethyl-3H-1,4-benzoxazepin-5-one

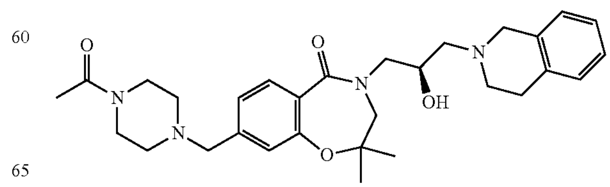

Example 167-1: Synthesis of 4-[(2R)-3-(3,4-dihydro-1H-isoquinolin-2-yl)-2-hydroxy-propyl]-2,2-dimethyl-8-(piperazin-1-ylmethyl)-3H-1,4-benzoxazepin-5-one; dihydrochloride 8-Bromo-4-[(2R)-3-(3,4-dihydro-1H-isoquinolin-2-yl)-2-hydroxy-propyl]-2,2-dimethyl-3H-1,4-benzoxazepin-5-one as a starting material was used in the same manner as in Examples 54-1 and 54-2 to obtain the title compound.

Example 167-2: Synthesis of 8-[(4-acetylpiperazin-1-yl)methyl]-4-[(2R)-3-(3,4-dihydro-1H-isoquinolin-2-yl)-2-hydroxy-propyl]-2,2-dimethyl-3H-1,4-benzoxazepin-5-one The material obtained in Example 167-1 as a starting material was used in the same manner as in Example 78-2 to obtain the title compound.

$^1$H NMR (400 MHz, Methanol-$d_4$) δ 7.61 (d, J=7.8 Hz, 1H), 7.23 (d, J=8.0 Hz, 1H), 7.17-7.02 (m, 4H), 7.00 (s, 1H), 4.29 (s, 1H), 4.06 (d, J=13.6 Hz, 1H), 3.77 (s, 2H), 3.59 (t, J=10.1 Hz, 6H), 3.48 (s, 2H), 3.43 (dd, J=14.0, 8.0 Hz, 2H), 2.93 (s, 4H), 2.74-2.56 (m, 2H), 2.55-2.41 (m, 4H), 2.10 (s, 3H), 1.43 (s, 3H), 1.33 (s, 3H).

Example 168: Synthesis of 3-[[4-[(2R)-3-(3,4-dihydro-1H-isoquinolin-2-yl)-2-hydroxy-propyl]-2,2-dimethyl-5-oxo-3H-1,4-benzoxazepin-8-yl]oxy]azetidin-1-carbaldehyde

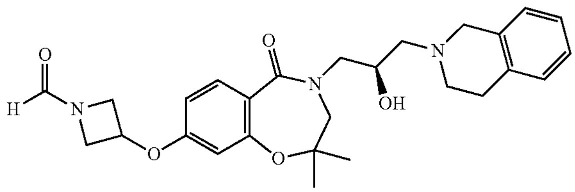 [SMILES: CC1(C)CN(C[C@H](O)CN2CCc3ccccc3C2)C(=O)c2ccc(OC3CN(C=O)C3)cc2O1]

Example 168-1: Synthesis of 8-(azetidin-3-yloxy)-4-[(2R)-3-(3,4-dihydro-1H-isoquinolin-2-yl)-2-hydroxy-propyl]-2,2-dimethyl-3H-1,4-benzoxazepin-5-one dihydrochloride 4-[(2R)-3-(3,4-dihydro-1H-isoquinolin-2-yl)-2-hydroxy-propyl]-8-hydroxy-2,2-dimethyl-3H-1,4-benzoxazepin-5-one as a starting material was used in the same manner as in Example 83-1 to obtain the title compound.

Example 168-2: Synthesis of 3-[[4-[(2R)-3-(3,4-dihydro-1H-isoquinolin-2-yl)-2-hydroxy-propyl]-2,2-dimethyl-5-oxo-3H-1,4-benzoxazepin-8-yl]oxy]azetidine-1-carbaldehyde The material (105 mg, 0.2 mmol) obtained in Example 168-1 was dissolved in 2 mL of acetonitrile, and formic acid (38 μL, 1.0 mmol), triethylamine (0.17 mL, 1.2 mL) and HATU (114 mg, 0.3 mmol) were added thereto and stirred at room temperature.

After confirming that the reaction was complete, saturated aqueous ammonium chloride solution was added and extracted with ethyl acetate 3 times. The combined organic layers were dried over anhydrous magnesium sulfate, concentrated under reduced pressure and purified by flash chromatography to obtain the title compound.

$^1$H NMR (400 MHz, Methanol-$d_4$) δ 8.03 (s, 1H), 7.62 (d, J=8.4 Hz, 1H), 7.21-7.03 (m, 4H), 6.72 (d, J=8.7 Hz, 1H), 6.45 (s, 1H), 5.19 (s, 1H), 4.68 (t, J=8.4 Hz, 1H), 4.52-4.42 (m, 1H), 4.35-4.18 (m, 2H), 4.02 (t, J=13.6 Hz, 2H), 3.79 (s, 2H), 3.51 (s, 2H), 3.43-3.37 (m, 1H), 2.93 (d, J=11.6 Hz, 4H), 2.73-2.59 (m, 2H), 1.44 (s, 3H), 1.35 (s, 3H).

Example 169: Synthesis of 4-[[4-[(2R)-3-(3,4-dihydro-1H-isoquinolin-2-yl)-2-hydroxy-propyl]-2,2-dimethyl-5-oxo-3H-1,4-benzoxazepin-8-yl]methyl]piperazine-1-carbaldehyde

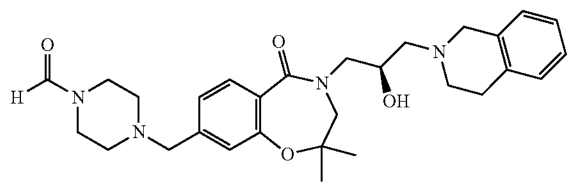 [SMILES: CC1(C)CN(C[C@H](O)CN2CCc3ccccc3C2)C(=O)c2ccc(CN3CCN(C=O)CC3)cc2O1]

The material obtained in Example 167-1 as a starting material was used in the same manner as in Example 168-2 to obtain the title compound.

$^1$H NMR (400 MHz, Methanol-$d_4$) δ 8.03 (s, 1H), 7.61 (d, J=7.9 Hz, 1H), 7.23 (d, J=8.0 Hz, 1H), 7.19-7.03 (m, 4H), 7.01 (s, 1H), 4.30 (s, 1H), 4.06 (d, J=13.8 Hz, 1H), 3.79 (s, 2H), 3.61 (s, 2H), 3.56 (s, 2H), 3.52-3.38 (m, 5H), 2.93 (d, J=11.0 Hz, 4H), 2.75-2.60 (m, 2H), 2.49 (d, J=17.2 Hz, 4H), 1.44 (s, 3H), 1.34 (s, 3H).

Example 170: Synthesis of 4-[(2R)-3-(3,4-dihydro-1H-isoquinolin-2-yl)-2-hydroxy-propyl]-2,2-dimethyl-8-(2-oxa-6-azaspiro[3.3]heptan-6-ylmethyl)-3H-1,4-benzoxazepin-5-one

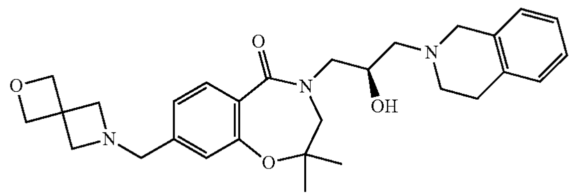 [SMILES: CC1(C)CN(C[C@H](O)CN2CCc3ccccc3C2)C(=O)c2ccc(CN3CC4(COC4)C3)cc2O1]

8-Bromo-4-[(2R)-3-(3,4-dihydro-1H-isoquinolin-2-yl)-2-hydroxy-propyl]-2,2-dimethyl-3H-1,4-benzoxazepin-5-one as a starting material was used in the same manner as in Example 28 to obtain the title compound.

$^1$H NMR (400 MHz, Methanol-$d_4$) δ 7.60 (d, J=7.8 Hz, 1H), 7.19-7.01 (m, 5H), 6.92 (s, 1H), 4.76 (s, 4H), 4.29 (s, 1H), 4.06 (d, J=13.8 Hz, 1H), 3.76 (s, 2H), 3.62 (s, 2H), 3.47 (s, 6H), 3.43-3.38 (m, 1H), 2.98-2.83 (m, 4H), 2.64 (s, 2H), 1.43 (s, 3H), 1.33 (s, 3H).

Example 171: Synthesis of 4-[(2R)-3-(3,4-dihydro-1H-isoquinolin-2-yl)-2-hydroxy-propyl]-8-[(8-ethyl-8-azabicyclo[3.2.1]octan-3-yl)oxy]-2,3-dihydro-1,4-benzoxazepin-5-one

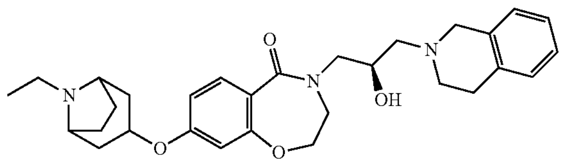 [SMILES: CCN1C2CCC1CC(Oc1ccc3c(c1)OCCN(C[C@H](O)CN1CCc4ccccc4C1)C3=O)C2]

Example 171-1: Synthesis of 8-[(8-azabicyclo[3.2.1]octan-3-yl)oxy]-4-[(2R)-3-(3,4-dihydro-1H-isoquinolin-2-yl)-2-hydroxy-propyl]-2,3-dihydro-1,4-benzoxazepin-5-one dihydrochloride The intermediate was synthesized by changing 4-chloro-tetrahydropyran to tert-butyl 3-methylsulfonyloxy-8-azabicyclo[3.2.1]octan-8-carboxylate in Example 64. The obtained intermediate as a starting material was used in the same manner as in Example 78-1 to obtain the title compound.

Example 171-2: Synthesis of 4-[(2R)-3-(3,4-dihydro-1H-isoquinolin-2-yl)-2-hydroxy-propyl]-8-[(8-ethyl-8-azabicyclo[3.2.1]octan-3-yl)oxy]-2,3-dihydro-1,4-benzoxazepin-5-one The material obtained in Example 171-1 as a starting material was used in the same manner as in Example 88 to obtain the title compound.

$^1$H NMR (400 MHz, Methanol-$d_4$) δ 7.60 (d, J=8.7 Hz, 1H), 7.09-6.92 (m, 4H), 6.61 (d, J=8.8 Hz, 1H), 6.42 (s, 1H), 4.56 (d, J=5.1 Hz, 1H), 4.38 (d, J=5.3 Hz, 2H), 4.13 (d, J=7.5 Hz, 1H), 4.00-3.87 (m, 1H), 3.65 (d, J=6.7 Hz, 4H), 3.42-3.27 (m, 3H), 2.96-2.71 (m, 4H), 2.53 (dd, J=14.6, 6.8 Hz, 4H), 2.09 (dd, J=29.8, 11.7 Hz, 4H), 2.01-1.78 (m, 4H), 1.09 (t, J=7.3 Hz, 3H).

Example 172: Synthesis of 4-[(2R)-3-(3,4-dihydro-1H-isoquinolin-2-yl)-2-hydroxy-propyl]-8-[(2-ethyl-2-azaspiro[3.3]heptan-6-yl)oxy]-2,3-dihydro-1,4-benzoxazepin-5-one

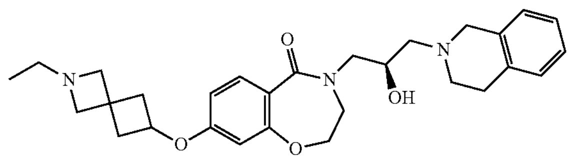 [SMILES: CCN1CC2(CC(Oc3ccc4c(c3)OCCN(C[C@H](O)CN3CCc5ccccc5C3)C4=O)C2)C1]

Example 172-1: Synthesis of 8-(2-azaspiro[3.3]heptan-6-yloxy)-4-[(2R)-3-(3,4-dihydro-1H-isoquinolin-2-yl)-2-hydroxy-propyl]-2,3-dihydro-1,4-benzoxazepin-5-one dihydrochloride The intermediate was synthesized by changing 4-chloro-tetrahydropyran to tert-butyl 6-methylsulfonyloxy-2-azaspiro[3.3]heptan-2-carboxylate in Example 64. The obtained intermediate as a starting material was used in the same manner as in Example 78-1 to obtain the title compound.

Example 172-2: Synthesis of 4-[(2R)-3-(3,4-dihydro-1H-isoquinolin-2-yl)-2-hydroxy-propyl]-8-[(2-ethyl-2-azaspiro[3.3]heptan-6-yl)oxy]-2,3-dihydro-1,4-benzoxazepin-5-one The material obtained in Example 172-1 as a starting material was used in the same manner as in Example 88 to obtain the title compound.

$^1$H NMR (400 MHz, Methanol-$d_4$) δ 7.65 (dd, J=8.7, 2.1 Hz, 1H), 7.18-6.99 (m, 4H), 6.65 (d, J=8.5 Hz, 1H), 6.44 (d, J=3.0 Hz, 1H), 4.66 (t, J=6.8 Hz, 1H), 4.45 (d, J=5.1 Hz, 2H), 4.33-4.18 (m, 1H), 3.97 (dt, J=14.1, 2.9 Hz, 1H), 3.82-3.70 (m, 4H), 3.45-3.28 (m, 7H), 2.92 (d, J=5.8 Hz, 2H), 2.87 (d, J=6.0 Hz, 2H), 2.73 (ddd, J=11.3, 7.0, 3.6 Hz, 2H), 2.63 (d, J=6.3 Hz, 2H), 2.58-2.48 (m, 2H), 2.26 (ddd, J=13.1, 6.2, 2.4 Hz, 2H), 0.99 (td, J=7.3, 2.0 Hz, 3H).

Example 173: Synthesis of 8-[(8-acetyl-8-azabicyclo[3.2.1]octan-3-yl)oxy]-4-[(2R)-3-(3,4-dihydro-1H-isoquinolin-2-yl)-2-hydroxy-propyl]-2,3-dihydro-1,4-benzoxazepin-5-one

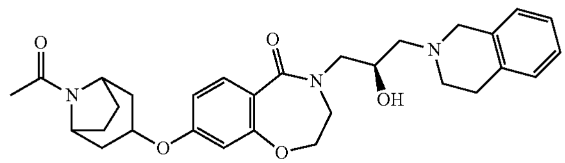 [SMILES: CC(=O)N1C2CCC1CC(Oc1ccc3c(c1)OCCN(C[C@H](O)CN1CCc4ccccc4C1)C3=O)C2]

8-(8-Azabicyclo[3.2.1]octan-3-yloxy)-4-[(2R)-3-(3,4-dihydro-1H-isoquinolin-2-yl)-2-hydroxy-propyl]-2,3-dihydro-1,4-benzoxazepin-5-one dihydrochloride obtained in Example 171-1 as a starting material was used in the same manner as in Example 78-2 to obtain the title compound.

$^1$H NMR (400 MHz, Methanol-$d_4$) δ 7.70 (dd, J=8.8, 2.0 Hz, 1H), 7.19-6.99 (m, 4H), 6.71 (dd, J=8.8, 2.6 Hz, 1H), 6.53 (d, J=2.5 Hz, 1H), 4.92 (s, 2H), 4.73 (d, J=4.9 Hz, 1H), 4.65-4.55 (m, 1H), 4.46 (d, J=5.1 Hz, 2H), 4.32-4.17 (m, 2H), 3.97 (dd, J=13.9, 3.4 Hz, 1H), 3.80-3.67 (m, 4H), 3.41 (dd, J=14.1, 7.6 Hz, 1H), 3.01-2.81 (m, 4H), 2.64 (d, J=6.2 Hz, 2H), 2.32-1.91 (m, 9H).

Example 174: Synthesis of 8-[(2-acetyl-2-azaspiro[3.3]heptan-6-yl)oxy]-4-[(2R)-3-(3,4-dihydro-1H-isoquinolin-2-yl)-2-hydroxy-propyl]-2,3-dihydro-1,4-benzoxazepin-5-one

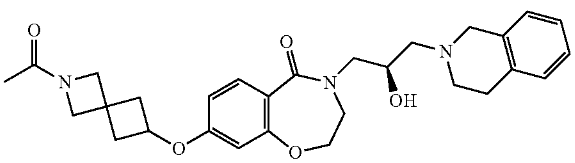 [SMILES: CC(=O)N1CC2(CC(Oc3ccc4c(c3)OCCN(C[C@H](O)CN3CCc5ccccc5C3)C4=O)C2)C1]

8-(2-Azaspiro[3.3]heptan-6-yloxy)-4-[(2R)-3-(3,4-dihydro-1H-isoquinolin-2-yl)-2-hydroxy-propyl]-2,3-dihydro-1,4-benzoxazepin-5-one dihydrochloride obtained in Example 172-1 as a starting material was used in the same manner as in Example 78-2 to obtain the title compound.

$^1$H NMR (400 MHz, Methanol-$d_4$) δ 7.54 (dd, J=8.9, 2.3 Hz, 1H), 7.12-6.87 (m, 4H), 6.53 (dd, J=7.2, 4.3 Hz, 1H), 6.35 (d, J=2.7 Hz, 1H), 4.57 (q, J=6.6 Hz, 1H), 4.33 (d, J=5.1 Hz, 2H), 4.23-4.04 (m, 3H), 3.93 (s, 1H), 3.84 (d, J=11.1 Hz, 2H), 3.75-3.51 (m, 4H), 3.36-3.26 (m, 1H), 2.89-2.72 (m, 4H), 2.67 (ddt, J=13.7, 6.7, 3.1 Hz, 2H), 2.61-2.46 (m, 2H), 2.22 (ddd, J=10.2, 6.6, 3.2 Hz, 2H), 1.74 (dd, J=6.7, 2.3 Hz, 3H).

Example 175: Synthesis of 4-[(2R)-3-(3,4-dihydro-1H-isoquinolin-2-yl)-2-hydroxy-propyl]-8-(pyrrolidin-1-carbonyl)-2,3-dihydro-1,4-benzoxazepin-5-one

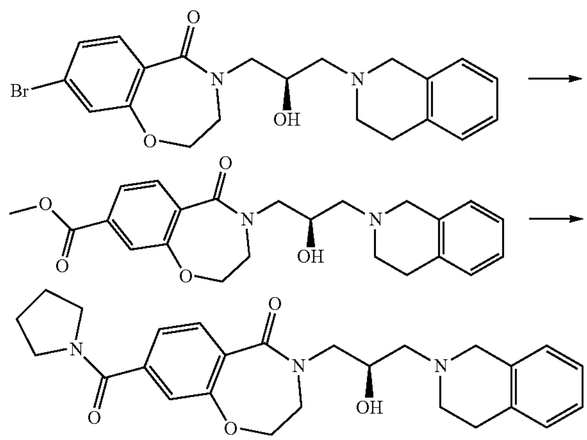

Example 175-1: Synthesis of methyl 4-[(2R)-3-(3,4-dihydro-1H-isoquinolin-2-yl)-2-hydroxy-propyl]-5-oxo-2,3-dihydro-1,4-benzoxazepine-8-carboxylate 8-Bromo-4-[(2R)-3-(3,4-dihydro-1H-isoquinolin-2-yl)-2-hydroxy-propyl]-2,3-dihydro-1,4-benzoxazepin-5-one (1.0 equiv), molybdenum hexacarbonyl (1.0 equiv), trans-bis(acetato)bis[o-(di-o-tolylphosphino)benzyl]dipalladium (II) (0.1 equiv), tri-tert-butylphosphonium tetrafluoroborate (0.2 equiv) and 1,8-diazabicyclo[5.4.0]undec-7-ene (1.5 equiv) were dissolved in methanol:acetonitrile (=1:1) and stirred at 150° C. for 3 hours. The reaction solution was cooled to room temperature, diluted with ethyl acetate and filtered through celite. The filtrate was concentrated under reduced pressure, distilled water was added, and the mixture was extracted with ethyl acetate 3 times. The combined organic layers were dried over anhydrous magnesium sulfate, concentrated and purified by flash chromatography to obtain the title compound.

Example 175-2: Synthesis of 4-[(2R)-3-(3,4-dihydro-1H-isoquinolin-2-yl)-2-hydroxy-propyl]-8-(pyrrolidin-1-carbonyl)-2,3-dihydro-1,4-benzoxazepin-5-one Methyl 4-[(2R)-3-(3,4-dihydro-1H-isoquinolin-2-yl)-2-hydroxy-propyl]-5-oxo-2,3-dihydro-1,4-benzoxazepin-8-carboxylate (1.0 equiv) obtained in Example 175-1, pyrrolidine (5.0 equiv) and 1,8-diazabicyclo[5.4.0]undec-7-ene (1 mL) were mixed and heated to 120° C. overnight. The reaction mixture was extracted with ethyl acetate, dried over magnesium sulfate and purified by flash chromatography to obtain the title compound.

$^1$H NMR (400 MHz, Methanol-$d_4$) δ 7.66 (dd, J=8.1, 2.2 Hz, 1H), 7.19 (d, J=8.0 Hz, 1H), 7.06 (s, 1H), 7.04-6.85 (m, 4H), 4.39 (t, J=5.2 Hz, 2H), 4.12 (dt, J=11.3, 4.9 Hz, 1H), 3.88 (dt, J=13.9, 3.1 Hz, 1H), 3.63 (d, J=11.4 Hz, 4H), 3.48 (t, J=7.1 Hz, 2H), 3.34 (q, J=7.3 Hz, 3H), 2.90-2.65 (m, 4H), 2.54 (d, J=5.9 Hz, 2H), 1.84 (dp, J=33.2, 6.7 Hz, 4H).

Example 176: Synthesis of 4-[(2R)-3-(3,4-dihydro-1H-isoquinolin-2-yl)-2-hydroxy-propyl]-8-(piperidine-1-carbonyl)-2,3-dihydro-1,4-benzoxazepin-5-one

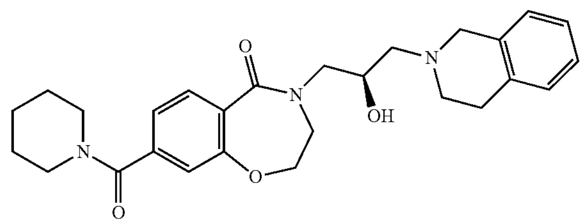 [SMILES: O=C(c1ccc2c(c1)OCCN(C[C@H](O)CN1CCc3ccccc3C1)C2=O)N1CCCCC1]

The title compound was synthesized in the same manner as in Example 175, except that piperidine was used instead of pyrrolidine in Example 175-2.

$^1$H NMR (400 MHz, Methanol-$d_4$) δ 7.67 (d, J=8.0 Hz, 1H), 7.07 (d, J=8.1 Hz, 1H), 6.97 (d, J=20.8 Hz, 5H), 4.41 (d, J=5.3 Hz, 2H), 4.13 (s, 1H), 3.88 (d, J=13.9 Hz, 1H), 3.74-3.53 (m, 6H), 3.35 (dd, J=14.0, 7.8 Hz, 1H), 2.79 (dd, J=18.3, 5.6 Hz, 4H), 2.54 (d, J=6.3 Hz, 2H), 1.75-1.49 (m, 5H).

Example 177: Synthesis of 8-(3,3-difluoropyrrolidin-1-carbonyl)-4-[(2R)-3-(3,4-dihydro-1H-isoquinolin-2-yl)-2-hydroxy-propyl]-2,3-dihydro-1,4-benzoxazepin-5-one

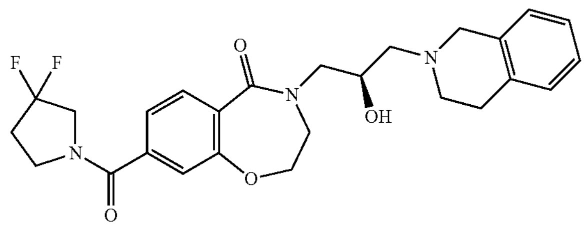 [SMILES: O=C(c1ccc2c(c1)OCCN(C[C@H](O)CN1CCc3ccccc3C1)C2=O)N1CCC(F)(F)C1]

The title compound was synthesized in the same manner as in Example 175, except that 3,3-difluoropyrrolidine was used instead of pyrrolidine in Example 175-2.

$^1$H NMR (400 MHz, Methanol-$d_4$) δ 7.80 (d, J=7.8 Hz, 1H), 7.22 (d, J=8.1 Hz, 1H), 7.12 (q, J=11.5, 8.0 Hz, 5H), 4.54 (d, J=5.4 Hz, 2H), 4.27 (s, 1H), 4.05-3.95 (m, 1H), 3.89-3.72 (m, 5H), 3.64-3.39 (m, 4H), 2.96 (s, 4H), 2.72 (d, J=6.7 Hz, 2H), 2.56 (s, 2H), 2.44 (s, 2H), 2.35 (d, J=2.1 Hz, 3H).

Example 178: Synthesis of 4-[(2R)-3-(3,4-dihydro-1H-isoquinolin-2-yl)-2-hydroxy-propyl]-8-(4-methylpiperazine-1-car bonyl)-2,3-dihydro-1,4-benzoxazepin-5-one

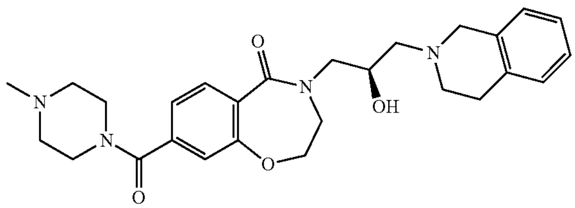 [SMILES: CN1CCN(C(=O)c2ccc3c(c2)OCCN(C[C@H](O)CN2CCc4ccccc4C2)C3=O)CC1]

The title compound was synthesized in the same manner as in Example 175, except that 1-methylpiperazine was used instead of pyrrolidine in Example 175-2.

$^1$H NMR (400 MHz, Methanol-$d_4$) δ 7.68 (dd, J=8.0, 2.2 Hz, 1H), 7.22 (t, J=6.7 Hz, 1H), 7.10 (s, 1H), 7.08-6.88 (m, 4H), 4.40 (d, J=5.5 Hz, 2H), 4.13 (s, 1H), 3.95-3.70 (m, 4H), 3.63 (d, J=7.8 Hz, 5H), 3.35 (dd, J=14.1, 7.8 Hz, 1H), 2.81 (d, J=5.7 Hz, 2H), 2.76 (t, J=5.7 Hz, 2H), 2.54 (d, J=6.1 Hz, 2H), 2.45-2.25 (m, 2H).

Example 179: Synthesis of 4-[(2R)-3-(3,4-dihydro-1H-isoquinolin-2-yl)-2-hydroxy-propyl]-2,2-dimethyl-8-(pyrrolidin-1-ylmethyl)-3H-1,4-benzoxazepin-5-one

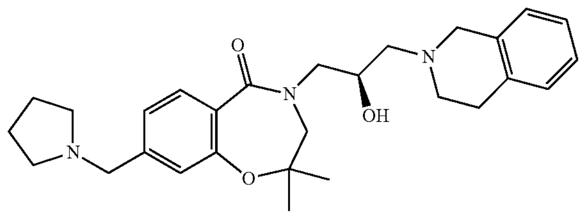 [SMILES: CC1(C)CN(C[C@H](O)CN2CCc3ccccc3C2)C(=O)c2ccc(CN3CCCC3)cc2O1]

8-Bromo-4-[(2R)-3-(3,4-dihydro-1H-isoquinolin-2-yl)-2-hydroxy-propyl]-2,2-dimethyl-3H-1,4-benzoxazepin-5-one as a starting material was used in the same manner as in Example 24 to obtain the title compound.

$^1$H NMR (400 MHz, Methanol-$d_4$) δ 7.62 (d, J=7.9 Hz, 1H), 7.23 (d, J=8.0 Hz, 1H), 7.17-7.03 (m, 4H), 7.01 (s, 1H), 4.29 (s, 1H), 4.06 (d, J=13.5 Hz, 1H), 3.76 (s, 2H), 3.72 (s, 2H), 3.49 (s, 2H), 3.43 (dd, J=13.7, 8.2 Hz, 1H), 2.98-2.83 (m, 4H), 2.64 (d, J=7.2 Hz, 6H), 1.86 (s, 4H), 1.44 (s, 3H), 1.34 (s, 3H).

Example 180: Synthesis of 8-[(1-acetyl-4-piperidyl)oxy]-4-[(2R)-3-(3,4-dihydro-1H-isoquinolin-2-yl)-2-hydroxy-propyl]-2,2-dimethyl-3H-1,4-benzoxazepin-5-one

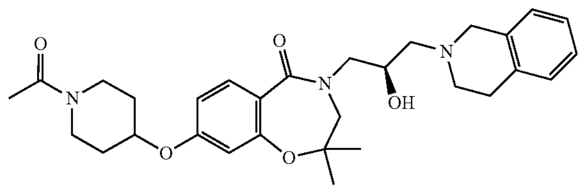 [SMILES: CC(=O)N1CCC(Oc2ccc3c(c2)OC(C)(C)CN(C[C@H](O)CN2CCc4ccccc4C2)C3=O)CC1]

4-[(2R)-3-(3,4-dihydro-1H-isoquinolin-2-yl)-2-hydroxy-propyl]-2,2-dimethyl-8-(4-piperidyloxy)-3H-1,4-benzoxazepin-5-one dihydrochloride obtained in Example 110-5 as a starting material was used in the same manner as in Example 78-2 to obtain the title compound.

$^1$H NMR (400 MHz, Methanol-$d_4$) δ 7.59 (dd, J=8.7, 2.5 Hz, 1H), 7.15-7.09 (m, 3H), 7.06 (d, J=6.4 Hz, 1H), 6.84 (d, J=8.8 Hz, 1H), 6.57 (s, 1H), 4.72 (dd, J=8.6, 4.9 Hz, 1H), 4.29 (s, 1H), 4.04 (d, J=13.8 Hz, 1H), 3.90-3.72 (m, 4H), 3.53 (d, J=17.0 Hz, 4H), 3.40 (dd, J=13.9, 8.3 Hz, 1H), 2.91 (dd, J=19.8, 5.2 Hz, 4H), 2.67-2.60 (m, 2H), 2.14 (d, J=2.4 Hz, 3H), 2.11-1.93 (m, 2H), 1.79 (d, J=31.6 Hz, 2H), 1.43 (s, 3H), 1.34 (d, J=2.4 Hz, 3H).

Example 181: Synthesis of 4-[[4-[(2R)-3-(3,4-dihydro-1H-isoquinolin-2-yl)-2-hydroxy-propyl]-2,2-dimethyl-5-oxo-3H-1,4-benzoxazepin-8-yl]oxy]piperidine-1-carbaldehyde

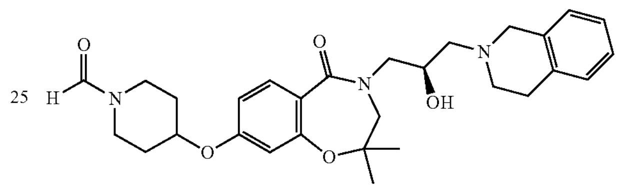

The material obtained in Example 110-5 as a starting material was used in the same manner as in Example 78 to obtain the title compound, except that formic acid was used instead of acetic anhydride in Example 78-2.

$^1$H NMR (400 MHz, Methanol-$d_4$) δ 8.06 (s, 1H), 7.63-7.56 (m, 1H), 7.12 (s, 3H), 7.07 (s, 1H), 6.85 (d, J=9.1 Hz, 1H), 6.58 (s, 1H), 4.77 (s, 1H), 4.28 (s, 1H), 4.04 (d, J=13.9 Hz, 1H), 3.73 (d, J=32.7 Hz, 5H), 3.57-3.37 (m, 6H), 2.89 (s, 2H), 2.64 (d, J=7.3 Hz, 2H), 2.03 (s, 2H), 1.77 (s, 2H), 1.43 (s, 3H), 1.33 (d, J=13.9 Hz, 3H).

Example 182: Synthesis of 4-[(2R)-3-(3,4-dihydro-1H-isoquinolin-2-yl)-2-hydroxy-propyl]-2,2-dimethyl-8-[[4-(oxetan-3-yl)piperazin-1-yl]methyl]-3H-1,4-benzoxazepin-5-one

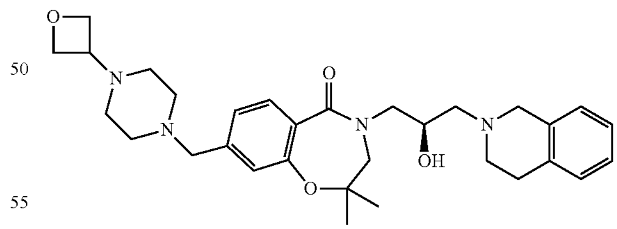

The material obtained in Example 167-1 as a starting material was used in the same manner as in Example 92 to obtain the title compound.

$^1$H NMR (400 MHz, Methanol-$d_4$) δ 7.60 (d, J=7.9 Hz, 1H), 7.21 (d, J=8.0 Hz, 1H), 7.17-7.01 (m, 4H), 6.99 (s, 1H), 4.70 (t, J=6.8 Hz, 2H), 4.66-4.53 (m, 2H), 4.29 (s, 1H), 4.06 (d, J=13.9 Hz, 1H), 3.77 (s, 2H), 3.59 (s, 2H), 3.53 (t, J=7.0 Hz, 1H), 3.48 (s, 2H), 3.42 (dd, J=13.5, 8.3 Hz, 1H), 3.01-2.81 (m, 4H), 2.71-2.27 (m, 10H), 1.43 (s, 3H), 1.33 (s, 3H).

Example 183: Synthesis of 4-[(2R)-3-(3,4-dihydro-1H-isoquinolin-2-yl)-2-hydroxy-propyl]-2,2-dimethyl-8-(2-oxa-7-azaspiro[3.4]octan-7-ylmethyl)-3H-1,4-benzoxazepin-5-one

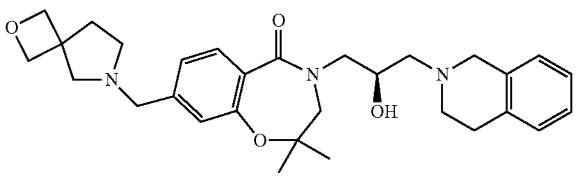 [SMILES: CC1(C)CN(C[C@H](O)CN2CCc3ccccc3C2)C(=O)c2ccc(CN3CCC4(COC4)C3)cc2O1]

8-Bromo-4-[(2R)-3-(3,4-dihydro-1H-isoquinolin-2-yl)-2-hydroxy-propyl]-2,2-dimethyl-3H-1,4-benzoxazepin-5-one as a starting material was used in the same manner as in Example 29 to obtain the title compound, except that 2-oxa-7-azaspiro[3.4]octane was used instead of 3-methoxyazetidine hydrochloride.

$^1$H NMR (400 MHz, Methanol-$d_4$) δ 7.49 (d, J=7.8 Hz, 1H), 7.08 (d, J=7.9 Hz, 1H), 7.04-6.90 (m, 4H), 6.86 (s, 1H), 4.51 (p, J=5.7, 5.2 Hz, 4H), 4.17 (s, 1H), 3.94 (d, J=13.6 Hz, 1H), 3.64 (s, 2H), 3.53 (s, 2H), 3.36 (s, 2H), 3.31 (dd, J=13.9, 8.2 Hz, 2H), 2.85-2.68 (m, 6H), 2.60-2.43 (m, 4H), 2.06 (t, J=7.3 Hz, 2H), 1.32 (s, 3H), 1.22 (s, 3H).

Example 184: Synthesis of 4-[(2R)-3-(3,4-dihydro-1H-isoquinolin-2-yl)-2-hydroxy-propyl]-8-(4-fluoropiperidine-1-carbonyl)-2,3-dihydro-1,4-benzoxazepin-5-one

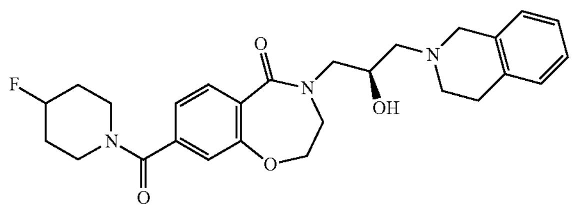 [SMILES: O=C(c1ccc2c(c1)OCCN(C[C@H](O)CN1CCc3ccccc3C1)C2=O)N1CCC(F)CC1]

The title compound was synthesized in the same manner as in Example 175, except that 4-fluoropiperidine was used instead of pyrrolidine in Example 175-2.

$^1$H NMR (400 MHz, Methanol-$d_4$) δ 7.80 (dd, J=7.9, 2.2 Hz, 1H), 7.22 (d, J=8.0 Hz, 1H), 7.17-6.97 (m, 5H), 5.00-4.76 (m, 1H), 4.52 (d, J=5.2 Hz, 2H), 4.24 (d, J=7.1 Hz, 1H), 4.07-3.83 (m, 2H), 3.76 (d, J=6.6 Hz, 5H), 3.63-3.36 (m, 4H), 2.94 (d, J=5.6 Hz, 2H), 2.89 (d, J=5.4 Hz, 2H), 2.67 (d, J=6.0 Hz, 2H), 2.13-1.70 (m, 3H).

Example 185: Synthesis of 4-[(2R)-3-(3,4-dihydro-1H-isoquinolin-2-yl)-2-hydroxy-propyl]-8-[3-(trifluoromethyl)piperidine-1-carbonyl]-2,3-dihydro-1,4-benzoxazepin-5-one

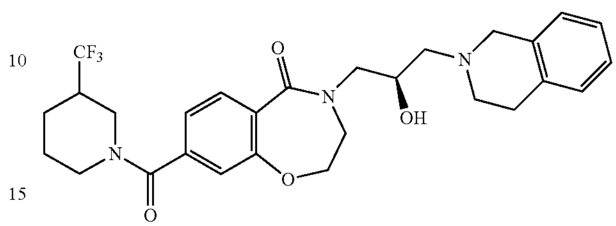

The title compound was synthesized in the same manner as in Example 175, except that 3-trifluoromethylpiperidine was used instead of pyrrolidine in Example 175-2.

$^1$H NMR (400 MHz, Methanol-$d_4$) δ 7.68 (d, J=7.9 Hz, 1H), 7.10 (d, J=8.1 Hz, 1H), 7.05-6.81 (m, 5H), 4.66-4.23 (m, 3H), 4.13 (q, J=6.1, 5.4 Hz, 1H), 3.88 (dt, J=14.2, 2.9 Hz, 1H), 3.64 (d, J=6.5 Hz, 5H), 3.34 (dd, J=14.1, 7.8 Hz, 1H), 2.97 (dt, J=45.9, 12.8 Hz, 2H), 2.81 (d, J=5.6 Hz, 2H), 2.77 (d, J=5.4 Hz, 2H), 2.54 (d, J=6.3 Hz, 2H), 2.45-2.29 (m, 1H), 1.99 (d, J=12.2 Hz, 1H), 1.70-1.37 (m, 3H).

Example 186: Synthesis of 4-[(2R)-3-(3,4-dihydro-1H-isoquinolin-2-yl)-2-hydroxy-propyl]-8-[4-(trifluoromethyl)piperidine-1-carbonyl]-2,3-dihydro-1,4-benzoxazepin-5-one

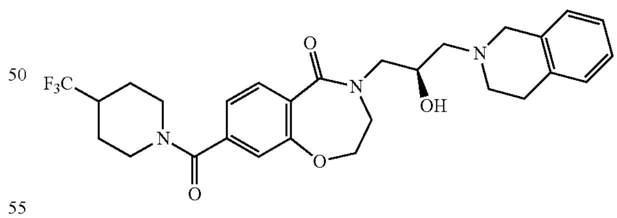

The title compound was synthesized in the same manner as in Example 175, except that 4-trifluoromethylpiperidine was used instead of pyrrolidine in Example 175-2.

$^1$H NMR (400 MHz, Methanol-$d_4$) δ 7.75-7.61 (m, 1H), 7.09 (d, J=8.0 Hz, 1H), 7.05-6.83 (m, 5H), 4.62 (d, J=13.2 Hz, 1H), 4.41 (d, J=5.6 Hz, 2H), 4.13 (d, J=6.7 Hz, 1H), 3.88 (dt, J=14.0, 3.1 Hz, 1H), 3.63 (s, 5H), 3.34 (dd, J=14.0, 7.7 Hz, 1H), 3.05 (t, J=13.9 Hz, 1H), 2.88-2.67 (m, 5H), 2.53 (d, J=6.3 Hz, 2H), 2.47-2.30 (m, 1H), 2.01-1.83 (m, 1H), 1.75 (d, J=12.8 Hz, 1H), 1.43 (q, J=13.5, 12.9 Hz, 2H).

Example 187: Synthesis of 4-[(2R)-3-(3,4-dihydro-1H-isoquinolin-2-yl)-2-hydroxy-propyl]-8-(2,6-dimethylmorpholin-4-carbonyl)-2,3-dihydro-1,4-benzoxazepin-5-one

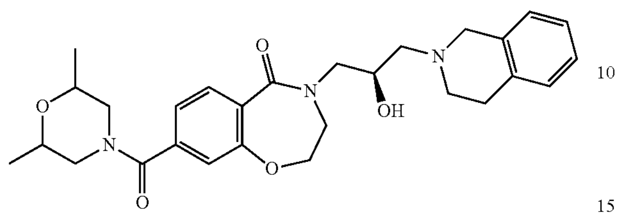

2,6-Dimethylmorpholine (33 μL, 1.1 equiv) was dissolved in 1,4-dioxane (1 mL), and 2 M trimethylaluminum toluene solution (134 μL, 1.1 equiv) was added thereto under the condition of nitrogen at 0° C. The reaction mixture was stirred at room temperature for 1 hour, and methyl 4-[(2R)-3-(3,4-dihydro-1H-isoquinolin-2-yl)-2-hydroxy-propyl]-5-oxo-2,3-dihydro-1,4-benzoxazepine-8-carboxylate (100 mg) dissolved in 1,4-dioxane was added thereto. The reaction solution was stirred at 110° C. for 3 hours, and the reaction was terminated with a saturated aqueous potassium sodium tartrate solution, followed by extraction with ethyl acetate. The combined organic layers were dried over anhydrous magnesium sulfate, concentrated and purified by flash chromatography to obtain the title compound.

$^1$H NMR (400 MHz, Methanol-$d_4$) δ 7.81 (d, J=7.8 Hz, 1H), 7.21 (d, J=8.1 Hz, 1H), 7.18-7.00 (m, 5H), 4.63-4.44 (m, 3H), 4.33-4.18 (m, 1H), 4.00 (dt, J=13.9, 2.8 Hz, 1H), 3.75 (d, J=7.6 Hz, 4H), 3.71-3.55 (m, 2H), 3.55-3.39 (m, 2H), 2.99-2.80 (m, 5H), 2.62 (dd, J=23.2, 9.1 Hz, 3H), 1.24 (d, J=6.5 Hz, 3H), 1.09 (dd, J=17.3, 6.2 Hz, 3H).

Example 188: Synthesis of 8-(2-azabicyclo[2.2.1]heptane-2-carbonyl)-4-[(2R)-3-(3,4-dihydro-1H-isoquinolin-2-yl)-2-hydroxy-propyl]-2,3-dihydro-1,4-benzoxazepin-5-one

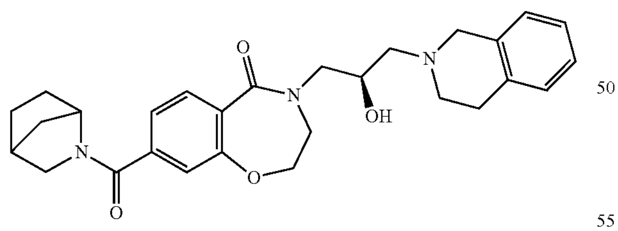

The title compound was synthesized in the same manner as in Example 187, except that 2-azabicyclo[2.2.1]heptane was used instead of 2,6-dimethylmorpholine.

$^1$H NMR (400 MHz, Methanol-$d_4$) δ 7.86-7.73 (m, 1H), 7.29 (d, J=8.1 Hz, 1H), 7.24-6.99 (m, 5H), 4.52 (q, J=6.0 Hz, 2H), 4.24 (dd, J=10.3, 5.4 Hz, 1H), 4.12 (s, 1H), 4.00 (dt, J=14.1, 3.2 Hz, 1H), 3.75 (d, J=8.9 Hz, 4H), 3.60-3.38 (m, 2H), 3.12 (dd, J=63.7, 10.4 Hz, 1H), 2.99-2.84 (m, 4H), 2.76-2.56 (m, 3H), 1.89-1.66 (m, 4H), 1.59 (d, J=9.9 Hz, 1H), 1.52 (q, J=10.4, 7.9 Hz, 1H).

Example 189: Synthesis of 4-[(2R)-3-(3,4-dihydro-1H-isoquinolin-2-yl)-2-hydroxy-propyl]-8-(3-oxa-8-azabicyclo[3.2.1]octan-8-carbonyl)-2,3-dihydro-1,4-benzoxazepin-5-one

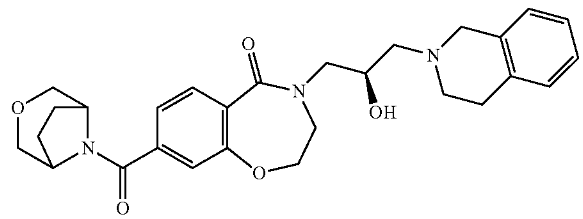 [SMILES: O=C1c2ccc(C(=O)N3C4CCC3COC4)cc2OCCN1C[C@H](O)CN1CCc2ccccc2C1]

The title compound was synthesized in the same manner as in Example 187, except that 3-oxa-8-azabicyclo [3.2.1] octane was used instead of 2,6-dimethylmorpholine.

$^1$H NMR (400 MHz, Methanol-$d_4$) δ 7.81 (d, J=7.8 Hz, 1H), 7.30 (d, J=8.0 Hz, 1H), 7.18 (s, 1H), 7.15-7.02 (m, 4H), 4.64 (s, 1H), 4.53 (d, J=5.3 Hz, 2H), 4.29-4.19 (m, 1H), 4.04-3.93 (m, 2H), 3.81 (d, J=11.5 Hz, 1H), 3.77-3.66 (m, 6H), 3.59 (d, J=11.1 Hz, 1H), 3.46 (dd, J=14.0, 7.8 Hz, 1H), 2.92 (d, J=5.7 Hz, 2H), 2.87 (d, J=5.8 Hz, 2H), 2.65 (d, J=6.2 Hz, 2H), 2.05 (dd, J=28.2, 10.9 Hz, 4H).

Example 190: Synthesis of 4-[(2R)-3-(3,4-dihydro-1H-isoquinolin-2-yl)-2-hydroxy-propyl]-8-(2-methylmorpholin-4-carbonyl)-2,3-dihydro-1,4-benzoxazepin-5-one

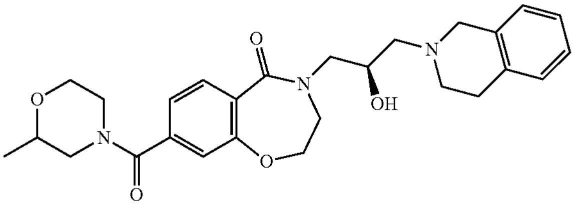 [SMILES: CC1CN(C(=O)c2ccc3c(c2)OCCN(C[C@H](O)CN2CCc4ccccc4C2)C3=O)CCO1]

The title compound was synthesized in the same manner as in Example 187, except that 2-methylmorpholine was used instead of 2,6-dimethylmorpholine.

$^1$H NMR (400 MHz, Methanol-$d_4$) δ 7.81 (d, J=7.9 Hz, 1H), 7.21 (d, J=8.0 Hz, 1H), 7.17-6.92 (m, 5H), 4.62-4.35 (m, 3H), 4.24 (dq, J=11.4, 6.7, 6.1 Hz, 1H), 4.08-3.68 (m, 6H), 3.65-3.18 (m, 5H), 2.92 (d, J=5.6 Hz, 2H), 2.87 (d, J=5.7 Hz, 2H), 2.66 (t, J=7.1 Hz, 2H), 1.23 (h, J=6.1, 5.0 Hz, 2H), 1.06 (d, J=6.2 Hz, 1H).

Example 191: Synthesis of 4-[(2R)-3-(3,4-dihydro-1H-isoquinolin-2-yl)-2-hydroxy-propyl]-8-(3-methylmorpholin-4-carbonyl)-2,3-dihydro-1,4-benzoxazepin-5-one

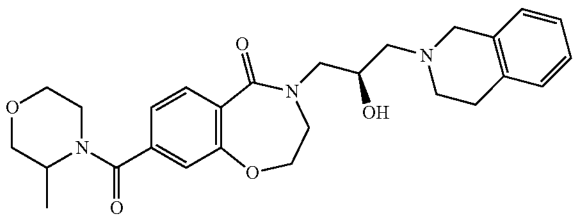 [SMILES: CC1COCCN1C(=O)c1ccc2c(c1)OCCN(C[C@H](O)CN1CCc3ccccc3C1)C2=O]

The title compound was synthesized in the same manner as in Example 187, except that 3-methylmorpholine was used instead of 2,6-dimethylmorpholine.

$^1$H NMR (400 MHz, Methanol-$d_4$) δ 7.81 (d, J=8.0 Hz, 1H), 7.28-6.97 (m, 6H), 4.51 (d, J=5.2 Hz, 2H), 4.24 (q, J=7.3, 6.0 Hz, 1H), 3.99 (dd, J=13.8, 3.3 Hz, 1H), 3.95-3.62 (m, 7H), 3.59-3.39 (m, 3H), 3.06-2.72 (m, 4H), 2.67 (d, J=6.1 Hz, 2H), 1.37 (d, J=7.0 Hz, 3H).

Example 192: Synthesis of 4-[(2R)-3-(3,4-dihydro-1H-isoquinolin-2-yl)-2-hydroxy-propyl]-2,2-dimethyl-8-(morpholino methyl)-3H-pyrido[3,2-f][1,4]oxazepin-5-one

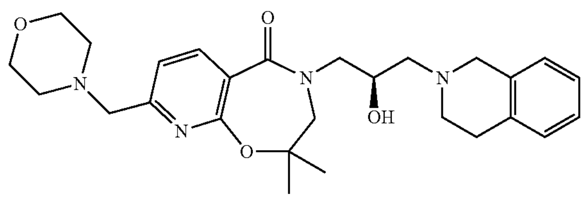 [SMILES: CC1(C)CN(C[C@H](O)CN2CCc3ccccc3C2)C(=O)c2ccc(CN3CCOCC3)nc2O1]

8-Chloro-4-[(2R)-3-(3,4-dihydro-1H-isoquinolin-2-yl)-2-hydroxy-propyl]-2,2-dimethyl-3H-pyrido[3,2-f][1,4]oxazepin-5-one as a starting material was used in the same manner as in Example 22 to obtain the title compound.

$^1$H NMR (400 MHz, Methanol-$d_4$) δ 8.14 (d, J=7.9 Hz, 1H), 7.43 (d, J=7.0 Hz, 1H), 7.19-7.01 (m, 4H), 4.35-4.21 (m, 1H), 4.05 (d, J=13.8 Hz, 1H), 3.77 (s, 2H), 3.73 (s, 4H), 3.62 (s, 4H), 3.45 (dd, J=14.0, 8.6 Hz, 1H), 2.92 (s, 2H), 2.89 (s, 2H), 2.66 (q, J=5.7, 4.1 Hz, 2H), 1.50 (s, 3H), 1.43 (s, 3H).

Example 193: Synthesis of 8-(3,3a,4,5,6,6a-hexahydro-1H-cyclopenta[c]pyrrol-2-carbonyl)-4-[(2R)-3-(3,4-dihydro-1H-isoquinolin-2-yl)-2-hydroxy-propyl]-2,3-dihydro-1,4-benzoxazepin-5-one

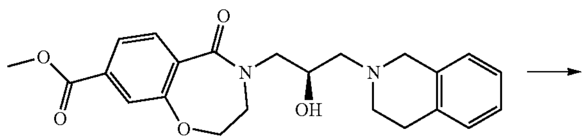

-continued

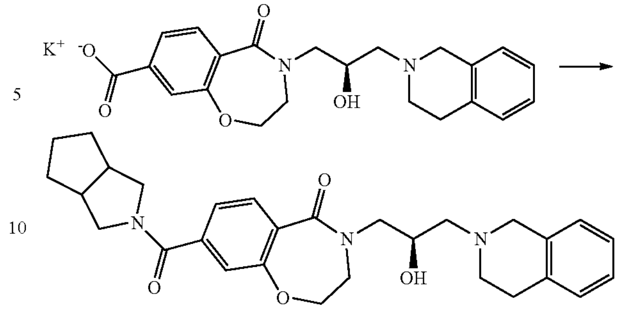

Example 193-1: Synthesis of potassium;4-[(2R)-3-(3,4-dihydro-1H-isoquinolin-2-yl)-2-hydroxy-propyl]-5-oxo-2,3-dihydro-1,4-benzoxazepin-8-carboxylate Methyl 4-[(2R)-3-(3,4-dihydro-1H-isoquinolin-2-yl)-2-hydroxy-propyl]-5-oxo-2,3-dihydro-1,4-benzoxazepin-8-carboxylate and potassium trimethylsilanoate were dissolved in tetrahydrofuran and stirred at room temperature overnight. The reaction solution was concentrated under reduced pressure and used in the next reaction without additional purification.

Example 193-2: Synthesis of 8-(3,3a,4,5,6,6a-hexahydro-1H-cyclopenta[c]pyrrol-2-carbonyl)-4-[(2R)-3-(3,4-dihydro-1H-isoquinolin-2-yl)-2-hydroxy-propyl]-2,3-dihydro-1,4-benzoxazepin-5-one The starting material (100 mg, 1.0 equiv) obtained in Example 193-1, octahydrocyclopenta[c]pyrrole (1.5 equiv), HATU (131 mg, 1.5 equiv) and diisopropylethylamine (120 μL, 3 equiv) were dissolved in methylene chloride and stirred at room temperature for 2 hours. The reaction solution was extracted with methylene chloride, dried over magnesium sulfate and purified by flash chromatography to obtain the title compound.

$^1$H NMR (400 MHz, Methanol-$d_4$) δ 7.66 (dd, J=8.0, 2.1 Hz, 1H), 7.16 (d, J=8.0 Hz, 1H), 7.08-6.89 (m, 5H), 4.41 (q, J=5.7 Hz, 2H), 4.13 (dd, J=9.8, 5.2 Hz, 1H), 3.88 (dt, J=14.2, 3.1 Hz, 1H), 3.75-3.60 (m, 5H), 3.55 (dd, J=11.4, 7.9 Hz, 1H), 3.43-3.34 (m, 2H), 3.21 (d, J=2.8 Hz, 2H), 3.18-3.07 (m, 1H), 2.89-2.73 (m, 4H), 2.73-2.46 (m, 4H), 1.73 (ddt, J=39.4, 20.0, 7.0 Hz, 3H), 1.49 (ddt, J=33.3, 12.5, 6.8 Hz, 2H), 1.28 (dt, J=11.8, 5.8 Hz, 1H).

Example 194: Synthesis of 4-[(2R)-3-(3,4-dihydro-1H-isoquinolin-2-yl)-2-hydroxy-propyl]-8-(3-fluoropiperidine-1-carbonyl)-2,3-dihydro-1,4-benzoxazepin-5-one

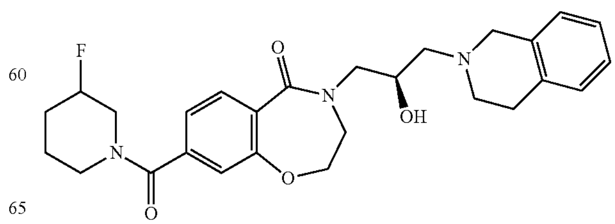

The title compound was synthesized in the same manner as in Example 193, except that 3-fluoropiperidine was used instead of octahydrocyclopenta[c]pyrrole in Example 193-2.

$^1$H NMR (400 MHz, Methanol-$d_4$) δ 7.67 (d, J=7.8 Hz, 1H), 7.08 (d, J=8.0 Hz, 1H), 7.06-6.89 (m, 5H), 4.57 (d, J=48.2 Hz, 1H), 4.41 (t, J=5.1 Hz, 2H), 4.33-4.08 (m, 2H), 3.89 (dd, J=13.8, 3.2 Hz, 1H), 3.64 (d, J=7.0 Hz, 5H), 3.52-3.23 (m, 3H), 3.17-2.95 (m, 1H), 2.90-2.71 (m, 4H), 2.54 (d, J=6.2 Hz, 2H), 1.89-1.65 (m, 2H), 1.50 (d, J=50.2 Hz, 1H).

Example 195: Synthesis of 8-(2,2-difluoromorpholin-4-carbonyl)-4-[(2R)-3-(3,4-dihydro-1H-isoquinolin-2-yl)-2-hydroxy-propyl]-2,3-dihydro-1,4-benzoxazepin-5-one

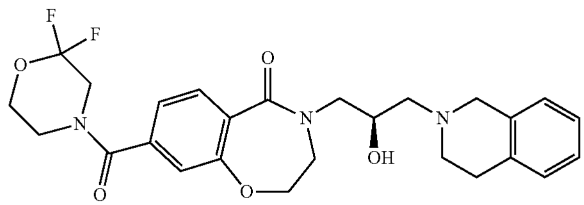 [SMILES: O=C(c1ccc2c(c1)OCCN(C[C@H](O)CN1CCc3ccccc3C1)C2=O)N1CCOC(F)(F)C1]

The title compound was synthesized in the same manner as in Example 193, except that 2,2-difluoromorpholine was used instead of octahydrocyclopenta[c]pyrrole in Example 193-2.

$^1$H NMR (400 MHz, Methanol-$d_4$) δ 7.70 (d, J=7.6 Hz, 1H), 7.13 (d, J=8.0 Hz, 1H), 7.08-6.89 (m, 5H), 4.41 (d, J=5.3 Hz, 2H), 4.14 (d, J=6.5 Hz, 1H), 4.08-3.77 (m, 5H), 3.71-3.42 (m, 6H), 3.36 (dd, J=14.1, 7.7 Hz, 1H), 3.23 (d, J=16.0 Hz, 2H), 2.87-2.74 (m, 4H), 2.56 (d, J=6.1 Hz, 2H).

Example 196: Synthesis of 8-(4,4-difluoropiperidine-1-carbonyl)-4-[(2R)-3-(3,4-dihydro-1H-isoquinolin-2-yl)-2-hydroxy-propyl]-2,3-dihydro-1,4-benzoxazepin-5-one

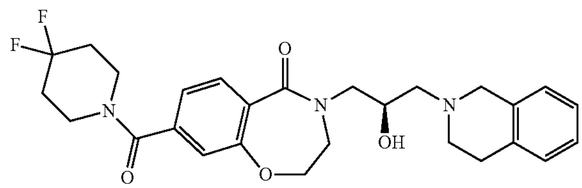 [SMILES: O=C(c1ccc2c(c1)OCCN(C[C@H](O)CN1CCc3ccccc3C1)C2=O)N1CCC(F)(F)CC1]

The title compound was synthesized in the same manner as in Example 193, except that 4,4-difluoropiperidine was used instead of octahydrocyclopenta[c]pyrrole in Example 193-2.

$^1$H NMR (400 MHz, Methanol-$d_4$) δ 7.68 (dd, J=8.0, 2.2 Hz, 1H), 7.13 (d, J=8.0 Hz, 1H), 7.06-6.91 (m, 5H), 4.46-4.34 (m, 2H), 4.14 (dd, J=7.2, 3.9 Hz, 1H), 3.85 (dt, J=14.0, 3.2 Hz, 1H), 3.75 (s, 1H), 3.70 (s, 2H), 3.62 (s, 2H), 3.42 (m, 3H), 2.93-2.78 (m, 4H), 2.59 (d, J=5.9 Hz, 2H), 2.12-1.78 (m, 4H).

Example 197: Synthesis of 4-[(2R)-3-(3,4-dihydro-1H-isoquinolin-2-yl)-2-hydroxy-propyl]-2,2-dimethyl-8-(1-piperidylmethyl)-3H-pyrido[3,2-f][1,4]oxazepin-5-one

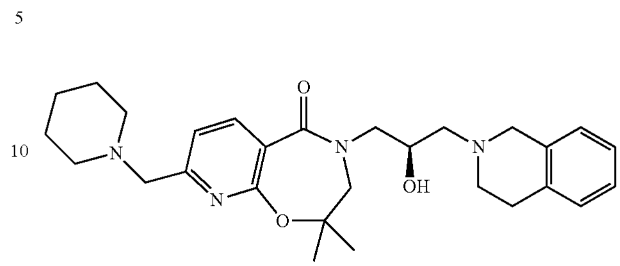

8-Chloro-4-[(2R)-3-(3,4-dihydro-1H-isoquinolin-2-yl)-2-hydroxy-propyl]-2,2-dimethyl-3H-pyrido[3,2-f][1,4]oxazepin-5-one as a starting material was used in the same manner as in Example 23 to obtain the title compound.

$^1$H NMR (400 MHz, Methanol-$d_4$) δ 8.13 (d, J=7.7 Hz, 1H), 7.42 (d, J=7.8 Hz, 1H), 7.19-7.01 (m, 4H), 4.29 (s, 1H), 4.06 (d, J=13.7 Hz, 1H), 3.75 (s, 2H), 3.69-3.54 (m, 4H), 3.45 (dd, J=13.7, 8.3 Hz, 1H), 3.00-2.80 (m, 4H), 2.72-2.57 (m, 2H), 2.50 (s, 4H), 1.70-1.58 (m, 4H), 1.50 (s, 5H), 1.44 (s, 3H).

Example 198: Synthesis of 4-[(2R)-3-(3,4-dihydro-1H-isoquinolin-2-yl)-2-hydroxypropyl]-8-[4-[methyl(oxetan-3-yl)amino]cyclohexoxy]-2,3-dihydro-1,4-benzoxazepin-5-one

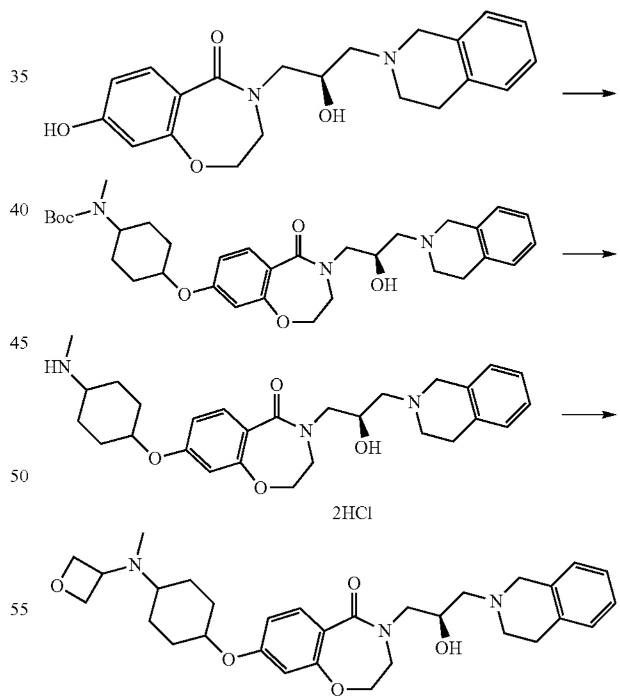

Example 198-1: Synthesis of tert-butyl N-[4-[[4-[(2R)-3-(3,4-dihydro-1H-isoquinolin-2-yl)-2-hydroxypropyl]-5-oxo-2,3-dihydro-1,4-benzoxazepin-8-yl]oxy]cyclohexyl]-N-methyl-carbamate The title compound was synthesized in the same manner as in Example 64, except that [4-[tert-butoxycarbonyl (methyl)amino]cyclohexyl] methanesulfonate, cesium carbonate and acetonitrile were used instead of 4-chlorotetrahydropyran, potassium carbonate and dimethylformamide, respectively.

Example 198-2: Synthesis of 4-[(2R)-3-(3,4-dihydro-1H-isoquinolin-2-yl)-2-hydroxypropyl]-8-[4-(methylamino)cyclohexoxy]-2,3-dihydro-1,4-benzoxazepin-5-one dihydrochloride Tert-butyl N-[4-[[4-[(2R)-3-(3,4-dihydro-1H-isoquinolin-2-yl)-2-hydroxypropyl]-5-oxo-2,3-dihydro-1,4-benzoxazepin-8-yl]oxy]cyclohexyl]-N-methyl-carbamate obtained in Example 198-1 was dissolved in methanol, and 4 M hydrochloric acid solution dissolved in 1,4-dioxane was slowly added thereto. The reaction solution was stirred at room temperature, diluted with diethyl ether and filtered to obtain the solid title compound.

Example 198-3: Synthesis of 4-[(2R)-3-(3,4-dihydro-1H-isoquinolin-2-yl)-2-hydroxypropyl]-8-[4-[methyl(oxetan-3-yl)amino]cyclohexoxy]-2,3-dihydro-1,4-benzoxazepin-5-one 4-[(2R)-3-(3,4-dihydro-1H-isoquinolin-2-yl)-2-hydroxypropyl]-8-[4-(methylamino)cycloexoxy]-2,3-dihydro-1,4-benzoxazepin-5-one dihydrochloride obtained in Example 198-2 as a starting material was used in the same manner as in Example 87 to obtain the title compound, except that oxetan-3-one was used instead of paraformaldehyde.

$^1$H NMR (400 MHz, Methanol-$d_4$) δ 7.67 (d, J=8.7 Hz, 1H), 7.12 (d, J=3.8 Hz, 3H), 7.06 (d, J=6.5 Hz, 1H), 6.76 (d, J=8.8 Hz, 1H), 6.58 (s, 1H), 4.67 (d, J=7.1 Hz, 4H), 4.61 (s, 1H), 4.46 (d, J=5.5 Hz, 2H), 4.23 (d, J=7.3 Hz, 1H), 4.06 (q, J=7.3 Hz, 1H), 3.97 (dd, J=14.0, 3.6 Hz, 1H), 3.78 (s, 2H), 3.73 (d, J=5.4 Hz, 2H), 3.43 (dd, J=14.0, 7.6 Hz, 1H), 2.97-2.86 (m, 4H), 2.67 (d, J=6.2 Hz, 2H), 2.47 (t, J=11.2 Hz, 1H), 2.24 (s, 3H), 2.12 (d, J=12.0 Hz, 2H), 1.64 (tt, J=23.8, 11.0 Hz, 6H).

Example 199: Synthesis of 4-[(2R)-3-(3,4-dihydro-1H-isoquinolin-2-yl)-2-hydroxypropyl]-8-[4-[2-fluoroethyl(methyl)amino]cyclohexoxy]-2,3-dihydro-1,4-benzoxazepin-5-one

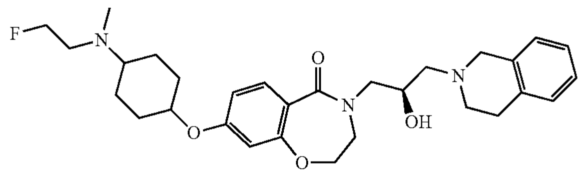 [SMILES: CN(CCF)C1CCC(Oc2ccc3c(c2)OCCN(C[C@H](O)CN2CCc4ccccc4C2)C3=O)CC1]

4-[(2R)-3-(3,4-dihydro-1H-isoquinolin-2-yl)-2-hydroxypropyl]-8-[4-(methylamino)cyclohexoxy]-2,3-dihydro-1,4-benzoxazepin-5-one dihydrochloride (200 mg, 0.362 mmol) obtained in Example 198-2, potassium carbonate (150 mg, 1.086 mmol) and 2-fluoroethyl 4-methylbenzenesulfonate (93 μl, 0.543 mmol) were dissolved in acetonitrile and stirred at 100° C. for one day. To the reaction mixture, saturated aqueous ammonium chloride aqueous solution was added and extracted with ethyl acetate 3 times. The oily liquid obtained by drying the combined organic layers over anhydrous sodium sulfate and concentrating under reduced pressure was purified by flash chromatography to obtain the title compound (45 mg).

$^1$H NMR (400 MHz, Methanol-$d_4$) δ 7.67 (dd, J=8.9, 2.5 Hz, 1H), 7.10 (d, J=3.5 Hz, 3H), 7.04 (d, J=6.6 Hz, 1H), 6.76 (d, J=8.6 Hz, 1H), 6.58 (s, 1H), 4.61 (q, J=4.0 Hz, 2H), 4.47 (dq, J=12.2, 4.3, 3.9 Hz, 3H), 4.22 (dq, J=10.0, 5.8, 5.0 Hz, 1H), 3.97 (dd, J=13.9, 3.1 Hz, 1H), 3.72 (d, J=9.9 Hz, 4H), 3.45-3.35 (m, 1H), 2.86 (td, J=23.1, 4.6 Hz, 6H), 2.69-2.50 (m, 3H), 2.37 (d, J=2.5 Hz, 3H), 2.12 (d, J=12.8 Hz, 2H), 1.75-1.56 (m, 6H).

Example 200: Synthesis of (2S)-4-[(2R)-3-(3,4-dihydro-1H-isoquinolin-2-yl)-2-hydroxy-propyl]-8-[(1-ethanethiol-4-piperidyl)oxy]-2-methyl-2,3-dihydro-1,4-benzoxazepin-5-one

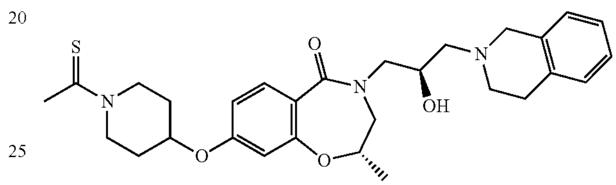

Example 200-1: Synthesis of 4-[(2R)-3-(3,4-dihydro-1H-isoquinolin-2-yl)-2-hydroxy-propyl]-8-(4-piperidyloxy)-2,3-dihydro-1,4-benzoxazepin-5-one dihydrochloride The material, which is obtained by changing [2-(tert-butoxycarbonylamino)-1-methyl-ethyl] methanesulfonate to [(1R)-2-(tert-butoxycarbonylamino)-1-methyl-ethyl] methanesulfonate in Example 140, as a starting material was used in the same manner as in Example 78-1 to obtain the title compound.

Example 200-2: Synthesis of 8-[(1-acetyl-4-piperidyl)oxy]-4-[(2R)-3-(3,4-dihydro-1H-isoquinolin-2-yl)-2-hydroxy-propyl]-2-methyl-2,3-dihydro-1,4-benzoxazepin-5-one The material obtained in Example 200-1 as a starting material was used in the same manner as in Example 78-2 to obtain the title compound Example 200-3: Synthesis of (2S)-4-[(2R)-3-(3,4-dihydro-1H-isoquinolin-2-yl)-2-hydroxy-propyl]-8-[(1-ethanethiol-4-piperidyl)oxy]-2-methyl-2,3-dihydro-1,4-benzoxazepin-5-one The material obtained in Example 200-2 as a starting material was dissolved in tetrahydrofuran, and Lawesson's reagent was added thereto. The reaction mixture was stirred at 50° C. until the reaction was completed, the reaction solution was cooled to room temperature, distilled water was added, and the mixture was extracted with ethyl acetate. The combined organic layers were dried over anhydrous magnesium sulfate, concentrated and purified by flash chromatography to obtain the title compound.

$^1$H NMR (400 MHz, Methanol-$d_4$) δ8.19-8.09 (m, 1H), 7.65-7.55 (m, 1H), 7.29 (d, J=9.3 Hz, 2H), 6.89 (dd, J=32.8, 8.6 Hz, 3H), 5.46 (s, 1H), 4.80 (s, 1H), 4.65 (s, 1H), 4.44 (s, 2H), 4.18-4.07 (m, 2H), 3.99 (s, 1H), 3.83 (d, J=2.4 Hz, 5H), 3.60-3.45 (m, 1H), 2.67 (s, 2H), 2.14-2.00 (m, 3H), 1.95-1.80 (m, 2H), 1.35-1.20 (m, 3H), 1.03 (d, J=6.3 Hz, 2H).

Example 201: Synthesis of (2S)-4-[(2R)-3-(3,4-dihydro-1H-isoquinolin-2-yl)-2-hydroxy-propyl]-8-[1-(2-fluoroethyl)azetidin-3-yl]oxy-2-methyl-2,3-dihydro-1,4-benzoxazepin-5-one

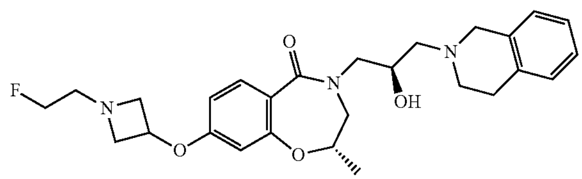 [SMILES: C[C@H]1CN(C[C@H](O)CN2CCc3ccccc3C2)C(=O)c2ccc(OC3CN(CCF)C3)cc2O1]

Example 201-1: Synthesis of 8-(azetidin-3-yloxy)-4-[(2R)-3-(3,4-dihydro-1H-isoquinolin-2-yl)-2-hydroxy-propyl]-2-methyl-2,3-dihydro-1,4-benzoxazepin-5-one dihydrochloride The intermediate in which Boc is substituted was synthesized by using the material obtained in the same manner as in Examples 140-1 to 140-5 except that [(1R)-2-(tert-butoxycarbonylamino)-1-methyl-ethyl] methanesulfonate was used instead of [2-(tert-butoxycarbonylamino)-1-methyl-ethyl] methanesulfonate as a starting material and the method in the same manner as in Example 64 except that tert-butyl 3-hydroxyazetidine-1-carboxylate is used instead of 4-chlorotetrahydropyran. The obtained intermediate was dissolved in methanol, and 4 N hydrochloric acid solution dissolved in 1,4-dioxane was added thereto. The reaction solution was stirred at room temperature until the reaction was terminated, diluted with ethyldiethyl ether and filtered to obtain the title compound as a white solid in the form of dihydrochloride.

Example 201-2: Synthesis of (2S)-4-[(2R)-3-(3,4-dihydro-1H-isoquinolin-2-yl)-2-hydroxy-propyl]-8-[1-(2-fluoroethyl)azetidin-3-yl]oxy-2-methyl-2,3-dihydro-1,4-benzoxazepin-5-one The material obtained in Example 201-1 as a starting material, 2-fluoroethyl para-toluenesulfonate and potassium carbonate were dissolved in acetonitrile, and the reaction solution was stirred at 60° C. for one day. The reaction mixture was cooled to room temperature, diluted with distilled water, and extracted with ethyl acetate 3 times. The combined organic layers were washed twice with a saturated aqueous sodium chloride solution, dried over anhydrous magnesium sulfate, filtered and concentrated under reduced pressure. The obtained concentrate was purified by flash chromatography to obtain the solid title compound.

$^1$H NMR (400 MHz, Methanol-$d_4$) δ 7.62 (dd, J=8.7, 2.5 Hz, 1H), 7.12 (d, J=3.7 Hz, 3H), 7.06 (d, J=6.6 Hz, 1H), 6.68 (d, J=8.5 Hz, 1H), 6.43 (d, J=3.2 Hz, 1H), 4.82 (ddd, J=10.1, 6.6, 3.4 Hz, 1H), 4.55 (q, J=3.9 Hz, 1H), 4.43 (q, J=3.9 Hz, 1H), 4.25 (td, J=6.8, 3.6 Hz, 1H), 3.90 (t, J=7.4 Hz, 2H), 3.80 (d, J=14.0 Hz, 3H), 3.62 (dt, J=15.2, 3.4 Hz, 2H), 3.46 (ddd, J=15.0, 9.8, 5.3 Hz, 1H), 2.90 (tdd, J=20.0, 9.1, 4.9 Hz, 7H), 2.68 (dd, J=6.4, 2.4 Hz, 2H), 1.38-1.25 (m, 4H).

Example 202: Synthesis of (2S)-4-[(2R)-3-(3,4-dihydro-1H-isoquinolin-2-yl)-2-hydroxy-propyl]-8-[1-(2-fluoroethyl)-4-piperidyl]oxy-2-methyl-2,3-dihydro-1,4-benzoxazepin-5-one

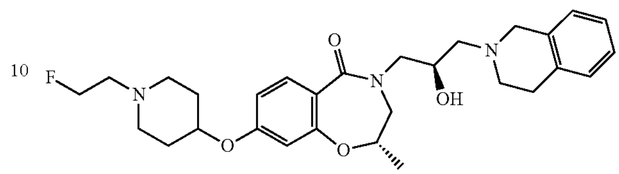

The material obtained by changing [2-(tert-butoxycarbonylamino)-1-methyl-ethyl]methanesulfonate to [(1R)-2-(tert-butoxycarbonylamino)-1-methyl-ethyl] methanesulfonate in Example 140 as a starting material was used in the same manner as in Example 163 to obtain the title compound.

$^1$H NMR (400 MHz, Methanol-$d_4$) δ 7.61 (dd, J=8.6, 2.1 Hz, 1H), 7.12 (d, J=3.2 Hz, 3H), 7.06 (d, J=6.5 Hz, 1H), 6.79 (d, J=8.7 Hz, 1H), 6.55 (s, 1H), 4.67 (s, 1H), 4.58-4.49 (m, 2H), 4.24 (s, 1H), 3.78 (d, J=8.0 Hz, 2H), 3.67-3.58 (m, 2H), 3.47 (dd, J=15.6, 9.3 Hz, 1H), 2.93 (d, J=5.4 Hz, 2H), 2.91-2.81 (m, 4H), 2.80 (s, 1H), 2.73 (t, J=5.2 Hz, 1H), 2.66 (d, J=6.4 Hz, 2H), 2.52 (t, J=10.2 Hz, 2H), 2.05 (d, J=10.5 Hz, 2H), 1.85 (s, 2H), 1.31-1.26 (m, 3H).

Example 203: Synthesis of 4-[(2R)-3-(3,4-dihydro-1H-isoquinolin-2-yl)-2-hydroxy-propyl]-2,2-dimethyl-8-(3-oxa-8-azabicyclo[3.2.1]octan-8-carbonyl)-3H-1,4-benzoxazepin-5-one

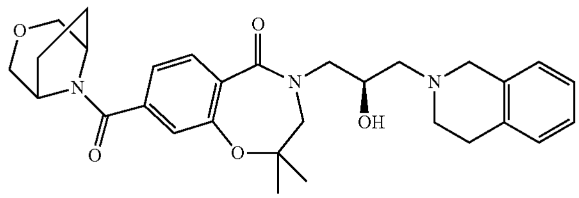 [SMILES: CC1(C)CN(C[C@H](O)CN2CCc3ccccc3C2)C(=O)c2ccc(C(=O)N3C4CCC3COC4)cc2O1]

Potassium; 4-[(2R)-3-(3,4-dihydro-1H-isoquinolin-2-yl)-2-hydroxy-propyl]-2,2-dimethyl-5-oxo-3H-1,4-benzoxazepine-8-carboxylate as a starting material was used in the same manner as in Example 193 to obtain the title compound, except that 3-oxa-8-azabicyclo [3.2.1]octane was used instead of octahydrocyclopenta[c]pyrrole in Example 193-2.

$^1$H NMR (400 MHz, Methanol-$d_4$) δ 7.62 (d, J=7.9 Hz, 1H), 7.28-7.15 (m, 1H), 7.06-6.88 (m, 5H), 4.53 (s, 1H), 4.26-4.08 (m, 1H), 3.98-3.92 (m, 1H), 3.84 (s, 1H), 3.70 (d, J=11.0 Hz, 1H), 3.61 (d, J=26.9 Hz, 4H), 3.48 (d, J=11.0 Hz, 1H), 3.39 (s, 2H), 3.32 (dd, J=13.7, 8.3 Hz, 1H), 2.84-2.72 (m, 4H), 2.58-2.48 (m, 2H), 1.33 (s, 3H), 1.23 (s, 3H).

Example 204: Synthesis of 4-[(2R)-3-(3,4-dihydro-1H-isoquinolin-2-yl)-2-hydroxy-propyl]-2,2-dimethyl-8-(2-oxa-5-azabicyclo[2.2.1]heptan-5-carbonyl)-3H-1,4-benzoxazepin-5-one

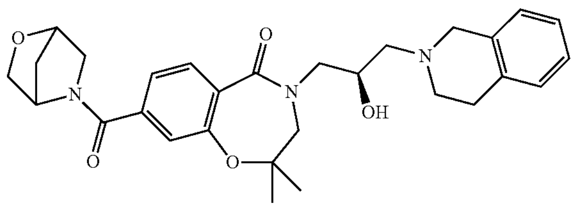 [SMILES: CC1(C)CN(C[C@H](O)CN2CCc3ccccc3C2)C(=O)c2ccc(C(=O)N3CC4CC3CO4)cc2O1]

Potassium; 4-[(2R)-3-(3,4-dihydro-1H-isoquinolin-2-yl)-2-hydroxy-propyl]-2,2-dimethyl-5-oxo-3H-1,4-benzoxazepine-8-carboxylate as a starting material was used in the same manner as in Example 193 to obtain the title compound, except that 2-oxa-5-azabicyclo[2.2.1]heptane was used instead of octahydrocyclopenta[c]pyrrole in Example 193-2.

$^1$H NMR (400 MHz, Methanol-$d_4$) δ 7.67-7.55 (m, 1H), 7.30-7.16 (m, 1H), 7.07-6.86 (m, 5H), 4.24-4.10 (m, 1H), 4.02-3.89 (m, 1H), 3.85 (dd, J=7.7, 3.4 Hz, 1H), 3.71 (ddd, J=31.5, 7.7, 1.6 Hz, 1H), 3.64 (s, 2H), 3.53-3.42 (m, 1H), 3.42-3.35 (m, 3H), 3.32 (td, J=6.5, 4.9, 2.5 Hz, 1H), 2.84-2.69 (m, 4H), 2.58-2.45 (m, 2H), 1.95-1.72 (m, 2H), 1.40-1.27 (m, 3H), 1.27-1.17 (m, 3H).

Example 205: Synthesis of 4-[(2R)-3-(3,4-dihydro-1H-isoquinolin-2-yl)-2-hydroxy-propyl]-8-(3,5-dimethylmorpholin-4-carbonyl)-2,2-dimethyl-3H-1,4-benzoxazepin-5-one

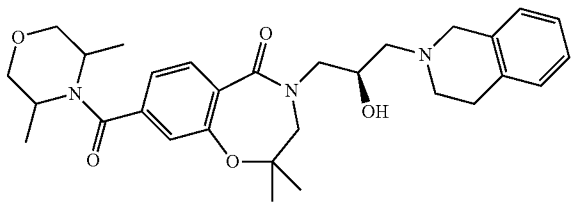 [SMILES: CC1COCC(C)N1C(=O)c1ccc2c(c1)OC(C)(C)CN(C[C@H](O)CN1CCc3ccccc3C1)C2=O]

Potassium; 4-[(2R)-3-(3,4-dihydro-1H-isoquinolin-2-yl)-2-hydroxy-propyl]-2,2-dimethyl-5-oxo-3H-1,4-benzoxazepine-8-carboxylate as a starting material was used in the same manner as in Example 193 to obtain the title compound, except that 3,5-dimethylmorpholine was used instead of octahydrocyclopenta[c]pyrrole in Example 193-2.

$^1$H NMR (400 MHz, Methanol-$d_4$) δ 7.58 (d, J=7.8 Hz, 1H), 7.13 (dd, J=7.8, 1.6 Hz, 1H), 7.05-6.91 (m, 4H), 6.89 (d, J=1.6 Hz, 1H), 4.16 (q, J=7.9, 6.8 Hz, 1H), 3.94 (dd, J=13.7, 3.7 Hz, 1H), 3.69-3.51 (m, 4H), 3.45-3.25 (m, 7H), 2.80 (d, J=5.7 Hz, 2H), 2.77-2.71 (m, 2H), 2.52 (dd, J=6.3, 3.8 Hz, 2H), 1.40 (s, 6H), 1.32 (s, 3H), 1.22 (s, 3H).

Example 206: Synthesis of 4-[(2R)-3-(3,4-dihydro-1H-isoquinolin-2-yl)-2-hydroxy-propyl]-8-[(3-fluoro-1-methyl-4-piperidyl)oxy]-2,3-dihydro-1,4-benzoxazepin-5-one

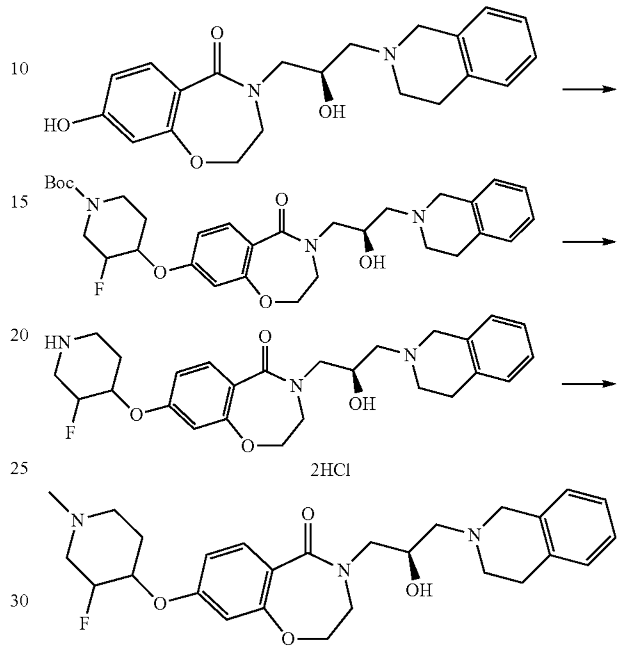

Example 206-1: Synthesis of tert-butyl 4-[[4-[(2R)-3-(3,4-dihydro-1H-isoquinolin-2-yl)-2-hydroxypropyl]-5-oxo-2,3-dihydro-1,4-benzoxazepin-8-yl]oxy]-3-fluoro-piperidine-1-carboxylate The title compound was synthesized in the same manner as in Example 64, except that tert-butyl 3-fluoro-4-methylsulfonyloxy-piperidine-1-carboxylate, cesium carbonate and acetonitrile were used instead of 4-chlorotetrahydropyran, potassium carbonate and dimethylformamide, respectively.

Example 206-2: Synthesis of 4-[(2R)-3-(3,4-dihydro-1H-isoquinolin-2-yl)-2-hydroxypropyl]-8-[(3-fluoro-4-piperidyl)oxy]-2,3-dihydro-1,4-benzoxazepin-5-one dihydrochloride Tert-butyl 4-[[4-[(2R)-3-(3,4-dihydro-1H-isoquinolin-2-yl)-2-hydroxypropyl]-5-oxo-2,3-dihydro-1,4-benzoxazepin-8-yl]oxy]-3-fluoro-piperidine-1-carboxylate obtained in Example 206-1 was dissolved in methanol, and 4 M hydrochloric acid solution dissolved in 1,4-dioxane was slowly added thereto. The reaction solution was stirred at room temperature, diluted with diethyl ether and filtered to obtain the solid title compound.

Example 206-3: Synthesis of 4-[(2R)-3-(3,4-dihydro-1H-isoquinolin-2-yl)-2-hydroxypropyl]-8-[(3-fluoro-1-methyl-4-piperidyl)oxy]-2,3-dihydro-1,4-benzoxazepin-5-one 4-[(2R)-3-(3,4-dihydro-1H-isoquinolin-2-yl)-2-hydroxypropyl]-8-[(3-fluoro-4-piperidyl)oxy]-2,3-dihydro-1,4-benzoxazepin-5-one dihydrochloride obtained in Example 206-2 as a starting material was used in the same manner as in Example 87 to obtain the title compound.

$^1$H NMR (400 MHz, Methanol-$d_4$) δ 7.68 (d, J=8.8 Hz, 1H), 7.18-7.06 (m, 3H), 7.06-7.01 (m, 1H), 6.82 (dd, J=8.8, 2.5 Hz, 1H), 6.65 (d, J=2.5 Hz, 1H), 4.79-4.43 (m, 4H), 4.29-4.18 (m, 1H), 3.98 (dd, J=13.9, 3.6 Hz, 1H), 3.78-3.64 (m, 4H), 3.42 (dd, J=13.9, 7.7 Hz, 1H), 3.07-2.83 (m, 5H), 2.74-2.58 (m, 3H), 2.51 (q, J=8.2, 7.7 Hz, 1H), 2.36 (s, 4H), 2.24-2.15 (m, 1H), 1.77 (dtd, J=13.1, 9.0, 3.7 Hz, 1H).

Example 207: Synthesis of 4-[(2R)-3-(3,4-dihydro-1H-isoquinolin-2-yl)-2-hydroxy-propyl]-8-[[3-fluoro-1-(2-fluoroethyl)-4-piperidyl]oxy]-2,3-dihydro-1,4-benzoxazepin-5-one

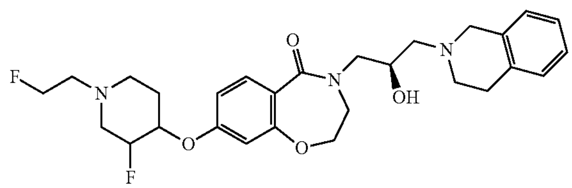 [SMILES: O=C1c2ccc(OC3CCN(CCF)CC3F)cc2OCCN1C[C@H](O)CN1CCc2ccccc2C1]

4-[(2R)-3-(3,4-dihydro-1H-isoquinolin-2-yl)-2-hydroxy-propyl]-8-[(3-fluoro-4-piperidyl)oxy]-2,3-dihydro-1,4-benzoxazepin-5-one dihydrochloride obtained in Example 206-2 as a starting material was used in the same manner as in Example 163 to obtain the title compound.

$^1$H NMR (400 MHz, Methanol-$d_4$) δ 7.67 (d, J=8.8 Hz, 1H), 7.17-7.02 (m, 4H), 6.82 (dd, J=8.8, 2.5 Hz, 1H), 6.65 (d, J=2.5 Hz, 1H), 4.65 (dq, J=5.6, 4.6 Hz, 2H), 4.56-4.45 (m, 4H), 4.27-4.17 (m, 1H), 3.98 (dd, J=13.9, 3.6 Hz, 1H), 3.81-3.69 (m, 4H), 3.43 (dd, J=13.9, 7.7 Hz, 1H), 2.94 (d, J=5.4 Hz, 2H), 2.90-2.83 (m, 4H), 2.79 (dt, J=9.4, 5.0 Hz, 2H), 2.76-2.71 (m, 1H), 2.68-2.62 (m, 2H), 2.53 (dd, J=11.2, 7.5 Hz, 1H), 2.47-2.38 (m, 1H), 2.21 (dd, J=9.7, 4.6 Hz, 1H), 1.76 (dd, J=11.9, 7.8 Hz, 1H).

Example 208: Synthesis of 4-[(2R)-3-(3,4-dihydro-1H-isoquinolin-2-yl)-2-hydroxy-propyl]-8-[[3-fluoro-1-(2-hydroxyeth yl)-4-piperidyl]oxy]-2,3-dihydro-1,4-benzoxazepin-5-one

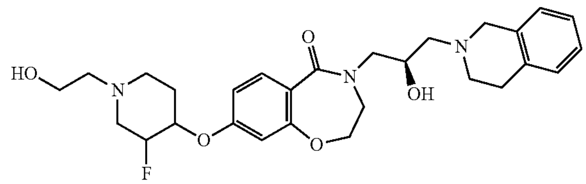 [SMILES: O=C1c2ccc(OC3CCN(CCO)CC3F)cc2OCCN1C[C@H](O)CN1CCc2ccccc2C1]

4-[(2R)-3-(3,4-dihydro-1H-isoquinolin-2-yl)-2-hydroxy-propyl]-8-[(3-fluoro-4-piperidyl)oxy]-2,3-dihydro-1,4-benzoxazepin-5-one dihydrochloride obtained in Example 206-2 as a starting material was used in the same manner as in Example 162 to obtain the title compound.

$^1$H NMR (400 MHz, Methanol-$d_4$) δ 7.67 (d, J=8.8 Hz, 1H), 7.17-7.00 (m, 4H), 6.81 (dd, J=8.8, 2.5 Hz, 1H), 6.65 (d, J=2.5 Hz, 1H), 4.67 (dtd, J=49.2, 8.2, 4.6 Hz, 1H), 4.48 (t, J=5.0 Hz, 3H), 4.23 (s, 1H), 3.98 (dd, J=13.9, 3.6 Hz, 1H), 3.82-3.62 (m, 6H), 3.43 (dd, J=13.9, 7.6 Hz, 1H), 3.26-3.14 (m, 1H), 2.98-2.80 (m, 5H), 2.71-2.56 (m, 4H), 2.47 (q, J=8.9, 8.3 Hz, 1H), 2.37 (t, J=10.4 Hz, 1H), 2.26-2.14 (m, 1H), 1.80-1.65 (m, 1H).

Example 209: Synthesis of 4-[(2R)-3-(3,4-dihydro-1H-isoquinolin-2-yl)-2-hydroxy-propyl]-8-(3,4-dihydro-1H-pyrrolo[1,2-a]pyrazine-2-carbonyl)-2,2-dimethyl-3H-1,4-benzoxazepin-5-one

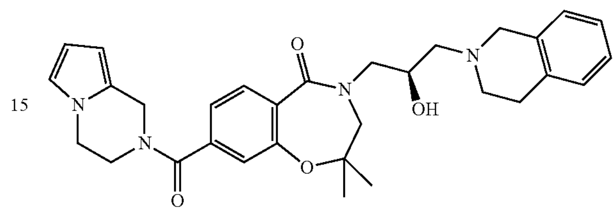

Potassium;4-[(2R)-3-(3,4-dihydro-1H-isoquinolin-2-yl)-2-hydroxy-propyl]-2,2-dimethyl-5-oxo-3H-1,4-benzoxazepin-8-carboxylate as a starting material was used in the same manner as in Example 193 to obtain the title compound, except that 1,2,3,4-tetrahydropyrrol[1,2-a]pyrazine was used instead of octahydrocyclopenta[c]pyrrole in Example 193-2.

$^1$H NMR (400 MHz, Methanol-$d_4$) δ 7.75 (d, J=7.9 Hz, 1H), 7.31 (d, J=7.9 Hz, 1H), 7.21-6.96 (m, 5H), 6.65 (s, 1H), 6.08 (d, J=16.4 Hz, 1H), 5.85 (d, J=81.0 Hz, 1H), 4.87 (s, 1H), 4.62 (s, 1H), 4.32 (tt, J=8.5, 4.3 Hz, 1H), 4.20-3.96 (m, 4H), 3.79 (d, J=20.8 Hz, 3H), 3.56-3.40 (m, 3H), 2.95 (q, J=5.0, 4.2 Hz, 4H), 2.70 (t, J=5.6 Hz, 2H), 1.45 (s, 3H), 1.36 (s, 3H).

Example 210: Synthesis of 8-(3,4,6,7,8,8a-hexahydro-1H-pyrrolo[1,2-a]pyrazine-2-carbonyl)-4-[(2R)-3-(3,4-dihydro-1H-isoquinolin-2-yl)-2-hydroxy-propyl]-2,2-dimethyl-3H-1,4-benzoxazepin-5-one

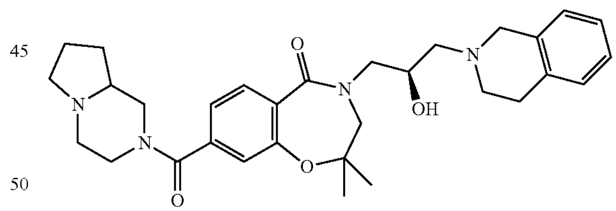

Potassium;4-[(2R)-3-(3,4-dihydro-1H-isoquinolin-2-yl)-2-hydroxy-propyl]-2,2-dimethyl-5-oxo-3H-1,4-benzoxazepin-8-carboxylate as a starting material was used in the same manner as in Example 193 to obtain the title compound, except that 1,2,3,4,6,7,8,8a-octahydropyrrol[1,2-a]pyrazine was used instead of octahydrocyclopenta[c]pyrrole in Example 193-2.

$^1$H NMR (400 MHz, Methanol-$d_4$ δ 7.73 (d, J=7.8 Hz, 1H), 7.26 (dd, J=7.8, 1.6 Hz, 1H), 7.18-6.96 (m, 5H), 4.70 (dd, J=50.1, 13.0 Hz, 1H), 4.30 (dd, J=7.5, 3.6 Hz, 1H), 4.07 (d, J=14.6 Hz, 1H), 3.79 (s, 3H), 3.52 (s, 2H), 3.44 (dd, J=13.8, 8.4 Hz, 1H), 3.33 (p, J=1.7 Hz, 4H), 3.23-3.05 (m, 2H), 2.98 (d, J=12.7 Hz, 1H), 2.75-2.63 (m, 2H), 2.25 (q, J=12.1, 11.3 Hz, 2H), 2.13-1.98 (m, 2H), 1.88 (dd, J=48.6, 16.4 Hz, 4H), 1.62-1.51 (m, 1H), 1.45 (s, 3H), 1.35 (s, 3H).

Example 211: Synthesis of 4-[(2R)-3-(3,4-dihydro-1H-isoquinolin-2-yl)-2-hydroxy-propyl]-8-(5-fluoro-pyrimidin-2-yl)oxy-2,3-dihydro-1,4-benzoxazepin-5-one

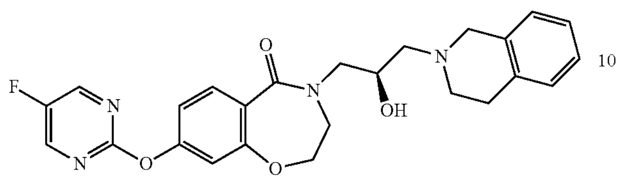

4-[(2R)-3-(3,4-dihydro-1H-isoquinolin-2-yl)-2-hydroxy-propyl]-8-hydroxy-2,3-dihydro-1,4-benzoxazepin-5-one (1.0 equiv), 2-chloro-5-fluoropyrimidine (1.5 equiv) and cesium carbonate (2 equiv) were dissolved in acetonitrile and heated to reflux overnight. The reaction solution was extracted with ethyl acetate. The separated organic layer was dried over magnesium sulfate, concentrated and purified by flash chromatography to obtain the title compound.

$^1$H NMR (400 MHz, Methanol-$d_4$) δ 8.46 (s, 2H), 7.67 (d, J=8.6 Hz, 1H), 7.08-6.92 (m, 4H), 6.89 (dd, J=8.6, 2.4 Hz, 1H), 6.77 (d, J=2.3 Hz, 1H), 4.39 (t, J=5.0 Hz, 2H), 4.14 (tt, J=7.6, 3.6 Hz, 1H), 3.87 (dd, J=13.9, 3.6 Hz, 1H), 3.70 (d, J=2.3 Hz, 2H), 3.65 (t, J=5.1 Hz, 2H), 3.35 (dd, J=13.9, 7.6 Hz, 1H), 2.87-2.75 (m, J=4.4, 3.8 Hz, 4H), 2.62-2.54 (m, 2H).

Example 212: Synthesis of 4-[(2R)-3-(3,4-dihydro-1H-isoquinolin-2-yl)-2-hydroxy-propyl]-8-[[1-(2-hydroxypropyl)-4-piperidyl]oxy]-2,3-dihydro-1,4-benzoxazepin-5-one

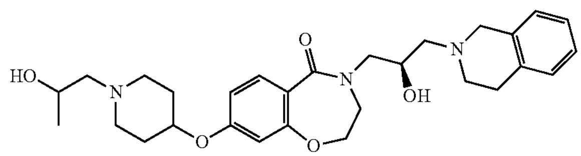 [SMILES: CC(O)CN1CCC(Oc2ccc3c(c2)OCCN(C[C@H](O)CN2CCc4ccccc4C2)C3=O)CC1]

4-[(2R)-3-(3,4-dihydro-1H-isoquinolin-2-yl)-2-hydroxy-propyl]-8-(4-piperidyloxy)-2,3-dihydro-1,4-benzoxazepin-5-one dihydrochloride obtained in Example 78-1 was dissolved in a mixture solution of water and acetonitrile, and 2-methoxirane and sodium hydroxide were added thereto and stirred at room temperature for 1 hour. To the reaction mixture, water was added and extracted with ethyl acetate 3 times. The oily liquid obtained by drying the combined organic layers over anhydrous sodium sulfate and concentrating under reduced pressure was purified by flash chromatography to obtain the title compound as a white solid.

$^1$H NMR (400 MHz, Methanol-$d_4$) δ 7.67 (d, J=8.8 Hz, 1H), 7.17-6.97 (m, 4H), 6.76 (dd, J=8.8, 2.5 Hz, 1H), 6.59 (d, J=2.5 Hz, 1H), 4.49 (dt, J=18.2, 4.4 Hz, 3H), 4.23 (t, J=5.4 Hz, 1H), 4.04-3.91 (m, 2H), 3.83-3.67 (m, 4H), 3.43 (dd, J=13.9, 7.6 Hz, 1H), 3.00-2.83 (m, 6H), 2.69-2.41 (m, 6H), 2.05 (d, J=14.9 Hz, 2H), 1.93-1.78 (m, 2H), 1.18 (d, J=6.2 Hz, 3H).

Example 213: Synthesis of 4-[(2R)-3-(3,4-dihydro-1H-isoquinolin-2-yl)-2-hydroxy-propyl]-8-[(1-methyl-3-piperidyl)oxy]-2,3-dihydro-1,4-benzoxazepin-5-one

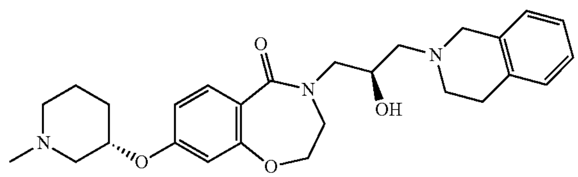 [SMILES: CN1CCC[C@H](Oc2ccc3c(c2)OCCN(C[C@H](O)CN2CCc4ccccc4C2)C3=O)C1]

Example 213-1: Synthesis of 4-[(2R)-3-(3,4-dihydro-1H-isoquinolin-2-yl)-2-hydroxy-propyl]-8-[(3-piperidyl)oxy]-2,3-dihydro-1,4-benzoxazepin-5-one dihydrochloride The title compound was synthesized in the same manner as in Examples 64 and 78-1, except that tert-butyl (S)-3-methylsulfonyloxypiperidine-1-carboxylate was used instead of 4-chlorotetrahydropyran in Example 64.

Example 213-2: Synthesis of 4-[(2R)-3-(3,4-dihydro-1H-isoquinolin-2-yl)-2-hydroxy-propyl]-8-[(1-methyl-3-piperidyl)oxy]-2,3-dihydro-1,4-benzoxazepin-5-one 4-[(2R)-3-(3,4-dihydro-1H-isoquinolin-2-yl)-2-hydroxy-propyl]-8-[(3-piperidyl)oxy]-2,3-dihydro-1,4-benzoxazepin-5-one dihydrochloride obtained in Example 213-1 as a starting material was used in the same manner as in Example 87 to obtain the title compound.

$^1$H NMR (400 MHz, Methanol-$d_4$) δ 7.60 (d, J=8.8 Hz, 1H), 7.12-6.92 (m, 4H), 6.70 (dd, J=8.8, 2.5 Hz, 1H), 6.53 (d, J=2.5 Hz, 1H), 4.40 (t, J=5.0 Hz, 3H), 4.15 (q, J=7.1, 5.2 Hz, 1H), 3.90 (dd, J=13.9, 3.6 Hz, 1H), 3.76-3.53 (m, 4H), 3.36 (dd, J=13.9, 7.6 Hz, 1H), 2.92-2.72 (m, 5H), 2.63-2.45 (m, 3H), 2.28 (s, 4H), 2.04-1.76 (m, 3H), 1.58 (d, J=20.6 Hz, 2H).

Example 214: Synthesis of 4-[(2R)-3-(3,4-dihydro-1H-isoquinolin-2-yl)-2-hydroxy-propyl]-8-propanoyl-2,3-dihydro-1,4-benzoxazepin-5-one

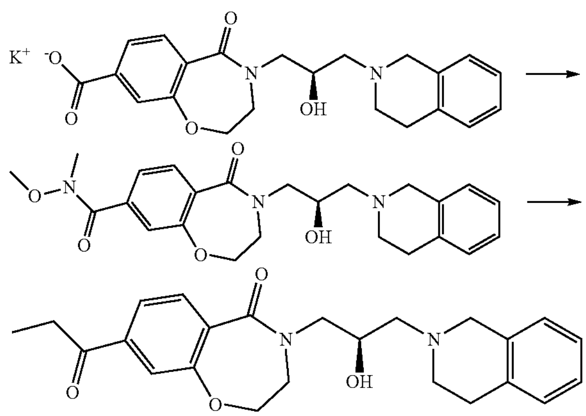

Example 214-1: Synthesis of 4-[(2R)-3-(3,4-dihydro-1H-isoquinolin-2-yl)-2-hydroxy-propyl]-N-methoxy-N-methyl-5-oxo-2,3-dihydro-1,4-benzoxazepine-8-carboxamide The title compound was synthesized in the same manner as in Example 193-2, except that N,O-dimethylhydroxyamine hydrochloride was used instead of octahydrocyclopenta[c]pyrrole.

Example 214-2: Synthesis of 4-[(2R)-3-(3,4-dihydro-1H-isoquinolin-2-yl)-2-hydroxy-propyl]-8-propanoyl-2,3-dihydro-1,4-benzoxazepin-5-one 4-[(2R)-3-(3,4-dihydro-1H-isoquinolin-2-yl)-2-hydroxy-propyl]-N-methoxy-N-methyl-5-oxo-2,3-dihydro-1,4-benzoxazepin-8-carboxamate (700 mg, 1 equiv) was dissolved in tetrahydrofuran, and 1 M ethylmagnesium bromide (2 mL, tetrahydrofuran solution) was added thereto at 0° C. The reaction solution was stirred at room temperature for 5 hours, extracted with ethyl acetate, dried over magnesium sulfate and purified by flash chromatography to obtain the title compound.

$^1$H NMR (400 MHz, Methanol-$d_4$) δ 7.74-7.59 (m, 2H), 7.50 (d, J=1.6 Hz, 1H), 7.05-6.86 (m, 4H), 4.40 (t, J=5.1 Hz, 2H), 4.12 (tdd, J=7.5, 5.4, 3.6 Hz, 1H), 3.88 (dd, J=13.8, 3.6 Hz, 1H), 3.70-3.61 (m, 2H), 3.60 (dt, J=5.0, 2.5 Hz, 2H), 3.40-3.30 (m, 1H), 2.94 (q, J=7.2 Hz, 2H), 2.89-2.69 (m, 4H), 2.58-2.52 (m, 2H), 1.07 (t, J=7.2 Hz, 3H).

Example 215: Synthesis of 4-[(2R)-3-(3,4-dihydro-1H-isoquinolin-2-yl)-2-hydroxy-propyl]-8-[[8-2-fluoroethyl]-8-azabicyclo[3.2.1]octan-3-yl)oxy]-2,3-dihydro-1,4-benzoxazepin-5-one

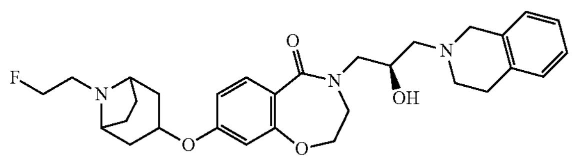 [SMILES: O=C1c2ccc(OC3CC4CCC(C3)N4CCF)cc2OCCN1C[C@H](O)CN1CCc2ccccc2C1]

Example 215-1: Synthesis of 4-[(2R)-3-(3,4-dihydro-1H-isoquinolin-2-yl)-2-hydroxy-propyl]-8-[-8-azabicyclo[3.2.1]octan-3-yl)oxy]-2,3-dihydro-1,4-benzoxazepin-5-one dihydrochloride The intermediate was synthesized by changing 4-chlorotetrahydropyran to tert-butyl 3-methylsulfonyloxy-8-azabicyclo[3.2.1]octane-8-carboxylate in Example 64. The obtained intermediate was dissolved in methanol, and 4 N hydrochloric acid solution dissolved in 1,4-dioxane was added thereto. The mixture was stirred at room temperature until the reaction was completed, diluted with ethyl diethyl ether and filtered to obtain the title compound as a white solid in the form of divalent dihydrochloride.

Example 215-2: Synthesis of 4-[(2R)-3-(3,4-dihydro-1H-isoquinolin-2-yl)-2-hydroxy-propyl]-8-[[8-2-fluoroethyl]-8-azabicyclo[3.2.1]octan-3-yl)oxy]-2,3-dihydro-1,4-benzoxazepin-5-one 4-[(2R)-3-(3,4-dihydro-1H-isoquinolin-2-yl)-2-hydroxy-propyl]-8-[–8-azabicyclo[3.2.1]octan-3-yl)oxy]-2,3-dihydro-1,4-benzoxazepin-5-one dihydrochloride obtained in Example 215-1 as a starting material was used in the same manner as in Example 163 to obtain the title compound.

$^1$H NMR (400 MHz, Methanol-$d_4$) δ 7.68 (d, J=8.8 Hz, 1H), 7.18-6.99 (m, 4H), 6.69 (dd, J=8.8, 2.5 Hz, 1H), 6.50 (d, J=2.4 Hz, 1H), 4.65 (dt, J=9.8, 5.0 Hz, 2H), 4.54 (t, J=5.0 Hz, 1H), 4.47 (t, J=5.0 Hz, 2H), 4.24 (d, J=5.7 Hz, 1H), 3.98 (dd, J=13.9, 3.7 Hz, 1H), 3.74 (dd, J=11.1, 6.0 Hz, 4H), 3.43 (dd, J=13.9, 7.6 Hz, 1H), 3.36 (s, 2H), 2.88 (ddd, J=26.4, 14.4, 5.1 Hz, 5H), 2.76 (t, J=5.0 Hz, 1H), 2.69-2.60 (m, 2H), 2.23 (d, J=15.2 Hz, 2H), 2.16-1.98 (m, 4H), 1.98-1.90 (m, 2H).

Example 216: Synthesis of 8-(cyclopropanecarbonyl)-4-[(2R)-3-(3,4-dihydro-1H-isoquinolin-2-yl)-2-hydroxy-propyl]-2,3-dihydro-1,4-benzoxazepin-5-one

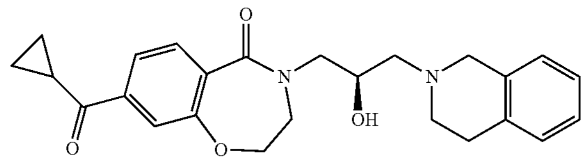 [SMILES: O=C(c1ccc2c(c1)OCCN(C[C@H](O)CN1CCc3ccccc3C1)C2=O)C1CC1]

The title compound was synthesized in the same manner as in Example 241, except that cyclopropylmagnesium bromide was used instead of ethylmagnesium bromide in Example 214-2.

$^1$H NMR (400 MHz, Methanol-$d_4$) δ 7.70 (d, J=1.1 Hz, 2H), 7.54 (d, J=1.1 Hz, 1H), 7.07-6.80 (m, 4H), 4.39 (t, J=5.1 Hz, 2H), 4.17-4.06 (m, 1H), 3.87 (dd, J=13.8, 3.6 Hz, 1H), 3.69-3.51 (m, 4H), 3.33 (dd, J=13.8, 7.7 Hz, 1H), 2.80 (t, J=6.2 Hz, 2H), 2.73 (dd, J=8.8, 3.7 Hz, 2H), 2.71-2.66 (m, 1H), 2.59-2.45 (m, 2H), 1.07-0.92 (m, 4H).

Example 217: Synthesis of 8-(cyclopentanecarbonyl)-4-[(2R)-3-(3,4-dihydro-1H-isoquinolin-2-yl)-2-hydroxy-propyl]-2,3-dihydro-1,4-benzoxazepin-5-one

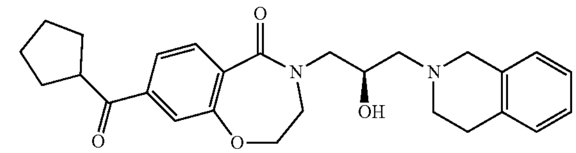 [SMILES: O=C(c1ccc2c(c1)OCCN(C[C@H](O)CN1CCc3ccccc3C1)C2=O)C1CCCC1]

The title compound was synthesized in the same manner as in Example 241, except that cyclopentylmagnesium bromide was used instead of ethylmagnesium bromide in Example 214-2.

$^1$H NMR (400 MHz, Methanol-$d_4$) δ 7.75-7.60 (m, 2H), 7.51 (d, J=1.5 Hz, 1H), 7.04-6.88 (m, 4H), 4.41 (t, J=5.1 Hz, 2H), 4.13 (tdd, J=7.5, 5.3, 3.5 Hz, 1H), 3.88 (dd, J=13.9, 3.6 Hz, 1H), 3.75-3.58 (m, 5H), 3.36 (dd, J=13.9, 7.7 Hz, 1H), 2.87-2.70 (m, 4H), 2.61-2.49 (m, 2H), 1.86 (dtdd, J=10.2, 7.6, 6.0, 2.9 Hz, 2H), 1.74 (dq, J=13.3, 7.2 Hz, 2H), 1.66-1.51 (m, 4H).

Example 218: Synthesis of 4-[(2R)-3-(3,4-dihydro-1H-isoquinolin-2-yl)-2-hydroxypropyl]-8-[(1-methyl-3-piperidyl)oxy]-2,3-dihydro-1,4-benzoxazepin-5-one

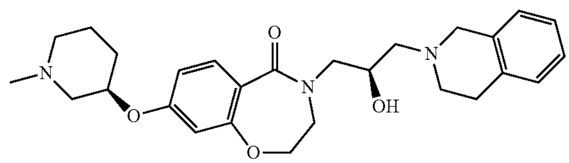 [SMILES: CN1CCC[C@@H](Oc2ccc3c(c2)OCCN(C[C@H](O)CN2CCc4ccccc4C2)C3=O)C1]

The title compound was synthesized in the same manner as in Example 64, except that [rac-(3R)-1-methyl-3-piperidyl] methanesulfonate was used instead of 4-chlorotetrahydropyran.

$^1$H NMR (400 MHz, Methanol-$d_4$) δ 7.67 (d, J=8.8 Hz, 1H), 7.18-7.00 (m, 4H), 6.77 (dd, J=8.8, 2.5 Hz, 1H), 6.60 (d, J=2.4 Hz, 1H), 4.49 (dt, J=14.9, 4.4 Hz, 3H), 4.27-4.18 (m, 1H), 3.98 (dd, J=13.9, 3.6 Hz, 1H), 3.81-3.68 (m, 4H), 3.42 (dd, J=13.9, 7.7 Hz, 1H), 2.94 (t, J=6.2 Hz, 2H), 2.90-2.79 (m, 3H), 2.68-2.54 (m, 3H), 2.33 (s, 4H), 2.08-1.80 (m, 3H), 1.73-1.53 (m, 2H).

Example 219: Synthesis of (2R)-4-[(2R)-3-(3,4-dihydro-1H-isoquinolin-2-yl)-2-hydroxy-propyl]-8-[[1-(2-hydroxyethyl)-4-piperidyl]oxy]-2-methyl-2,3-dihydro-1,4-benzoxazepin-5-one

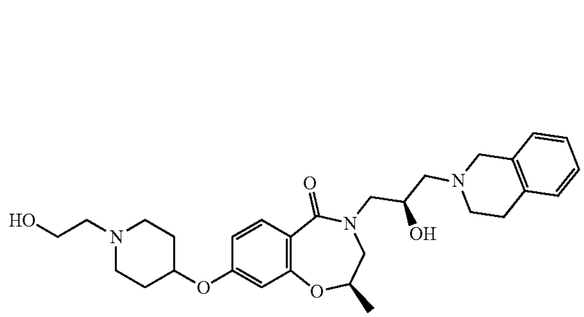 [SMILES: C[C@@H]1CN(C[C@H](O)CN2CCc3ccccc3C2)C(=O)c2ccc(OC3CCN(CCO)CC3)cc2O1]

The material, which is obtained by changing [2-(tert-butoxycarbonylamino)-1-methyl-ethyl] methanesulfonate to [(1 S)-2-(tert-butoxycarbonylamino)-1-methyl-ethyl] methanesulfonate in Example 140, as a starting material was used in the same manner as in Example 162 to obtain the title compound.

$^1$H NMR (400 MHz, Methanol-$d_4$) δ 7.62 (d, J=8.7 Hz, 1H), 7.18-7.02 (m, 4H), 6.80 (dd, J=8.7, 2.5 Hz, 1H), 6.58 (d, J=2.4 Hz, 1H), 4.79 (dt, J=7.2, 3.6 Hz, 1H), 4.56 (s, 1H), 4.30-4.20 (m, 1H), 4.15 (dd, J=13.7, 3.7 Hz, 1H), 3.84-3.70 (m, 3H), 3.64 (dd, J=15.5, 3.4 Hz, 1H), 3.50 (dd, J=15.5, 7.7 Hz, 1H), 3.26-3.18 (m, 2H), 2.93 (dd, J=15.1, 4.1 Hz, 5H), 2.79-2.58 (m, 5H), 2.08 (d, J=9.8 Hz, 2H), 1.89 (s, 2H), 1.32 (s, 3H).

Example 220: Synthesis of (2R)-4-[(2R)-3-(3,4-dihydro-1H-isoquinolin-2-yl)-2-hydroxy-propyl]-8-[[1-(2-hydroxy-2-methyl-propyl)-4-piperidyl]oxy]-2-methyl-2,3-dihydro-1,4-benzoxazepin-5-one

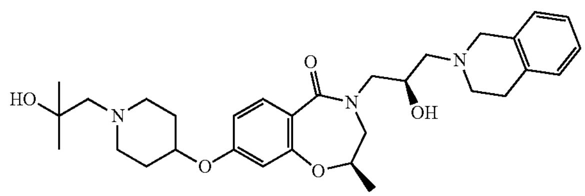 [SMILES: C[C@@H]1CN(C[C@H](O)CN2CCc3ccccc3C2)C(=O)c2ccc(OC3CCN(CC(C)(C)O)CC3)cc2O1]

The material obtained by changing [2-(tert-butoxycarbonylamino)-1-methyl-ethyl]methanesulfonate to [(1S)-2-(tert-butoxycarbonylamino)-1-methyl-ethyl] methanesulfonate in Example 140 as a starting material was used in the same manner as in Example 212 to obtain the title compound, except that 2,2-dimethyloxirane was used instead of 2-methoxirane.

$^1$H NMR (400 MHz, Methanol-$d_4$) δ 7.61 (d, J=8.7 Hz, 1H), 7.17-7.02 (m, 4H), 6.77 (dd, J=8.8, 2.5 Hz, 1H), 6.54 (d, J=2.4 Hz, 1H), 4.84-4.74 (m, 1H), 4.44 (dt, J=8.0, 4.1 Hz, 1H), 4.29-4.19 (m, 1H), 4.15 (dd, J=13.7, 3.6 Hz, 1H), 3.78 (d, J=11.8 Hz, 2H), 3.63 (dd, J=15.6, 3.4 Hz, 1H), 3.49 (dd, J=15.6, 7.6 Hz, 1H), 3.23 (dd, J=13.8, 8.2 Hz, 1H), 2.91 (dt, J=19.8, 5.5 Hz, 6H), 2.68-2.50 (m, 4H), 2.38 (s, 2H), 2.08-1.97 (m, 2H), 1.85-1.75 (m, 2H), 1.32 (dd, J=7.0, 3.1 Hz, 2H), 1.21 (s, 6H).

Example 221: Synthesis of 4-[(2R)-3-(3,4-dihydro-1H-isoquinolin-2-yl)-2-hydroxy-propyl]-8-(1-morpholinoethyl)-2,3-dihydro-1,4-benzoxazepin-5-one

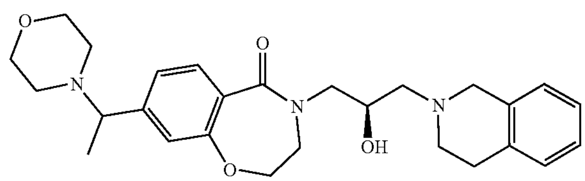 [SMILES: CC(c1ccc2c(c1)OCCN(C[C@H](O)CN1CCc3ccccc3C1)C2=O)N1CCOCC1]

Example 221-1: Synthesis of 8-acetyl-4-[(2R)-3-(3,4-dihydro-1H-isoquinolin-2-yl)-2-hydroxy-propyl]-2,3-dihydro-1,4-benzoxazepin-5-one The title compound was synthesized in the same manner as in Example 214-2, except that methylmagnesium bromide was used instead of ethylmagnesium bromide.

Example 221-2: Synthesis of 4-[(2R)-3-(3,4-dihydro-1H-isoquinolin-2-yl)-2-hydroxy-propyl]-8-(1-morpholinoethyl)-2,3-dihydro-1,4-benzoxazepin-5-one 8-Acetyl-4-[(2R)-3-(3,4-dihydro-1H-isoquinolin-2-yl)-2-hydroxy-propyl]-2,3-dihydro-1,4-benzoxazepin-5-one (100 mg, 1 equiv), morpholine (66 μL, 3 equiv), sodium cyanoborohydride (48 mg, 3 equiv) and acetic acid (1 drop) were dissolved in 1 mL of methanol and stirred at 80° C. for 6 hours. The reaction mixture was extracted with ethyl acetate, dried over magnesium sulfate and purified by flash chromatography to obtain the title compound.

$^1$H NMR (400 MHz, Methanol-$d_4$) δ 7.55 (d, J=8.0 Hz, 1H), 7.05 (dd, J=8.0, 1.5 Hz, 1H), 7.03-6.95 (m, 3H), 6.92 (d, J=7.2 Hz, 2H), 4.35 (t, J=5.1 Hz, 2H), 4.11 (dt, J=9.6, 3.5 Hz, 1H), 3.86 (dd, J=13.9, 3.6 Hz, 1H), 3.63 (s, 2H), 3.57 (dt, J=9.6, 4.8 Hz, 6H), 3.31 (dd, J=13.8, 7.6 Hz, 1H), 3.23 (s, 1H), 2.81 (t, J=6.1 Hz, 2H), 2.74 (t, J=5.7 Hz, 2H), 2.60-2.48 (m, 2H), 2.48-2.33 (m, 2H), 2.25 (dt, J=10.9, 4.7 Hz, 2H), 1.24 (d, J=6.6 Hz, 3H).

Example 222: Synthesis of 4-[(2R)-3-(3,4-dihydro-1H-isoquinolin-2-yl)-2-hydroxy-propyl]-8-[1-(2-oxa-6-azaspiro[3.3]heptan-6-yl)ethyl]-2,3-dihydro-1,4-benzoxazepin-5-one

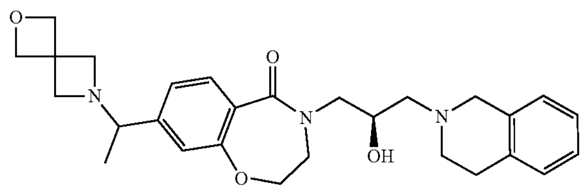 [SMILES: CC(c1ccc2c(c1)OCCN(C[C@H](O)CN1CCc3ccccc3C1)C2=O)N1CC2(COC2)C1]

The title compound was synthesized in the same manner as in Example 221, except that 2-oxa-6-azaspiro[3.3]heptane was used instead of morpholine in Example 221-2.

$^1$H NMR (400 MHz, Methanol-$d_4$) δ 7.56 (d, J=8.0 Hz, 1H), 7.05-6.91 (m, 5H), 6.88 (d, J=1.6 Hz, 1H), 4.61 (s, 4H), 4.35 (t, J=5.1 Hz, 2H), 4.18-4.04 (m, 1H), 3.85 (dd, J=13.9, 3.6 Hz, 1H), 3.65 (d, J=2.0 Hz, 2H), 3.62-3.50 (m, 2H), 3.35-3.16 (m, 6H), 2.89-2.69 (m, 4H), 2.62-2.47 (m, 2H), 1.10 (d, J=6.5 Hz, 3H).

Example 223: Synthesis of 4-[(2R)-3-(3,4-dihydro-1H-isoquinolin-2-yl)-2-hydroxy-propyl]-8-(3-hydroxypro-1-pynyl)-2,3-dihydro-1,4-benzoxazepin-5-one

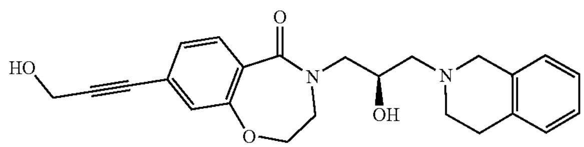 [SMILES: O=C1c2ccc(C#CCO)cc2OCCN1C[C@H](O)CN1CCc2ccccc2C1]

8-Bromo-4-[(2R)-3-(3,4-dihydro-1H-isoquinolin-2-yl)-2-hydroxy-propyl]-2,3-dihydro-1,4-benzoxazepin-5-one (100 mg, 1.0 equiv), prop-2-yn-1-ol (3 equiv), bis(triphenylphosphine)palladium (II) dichloride (8 mg, 0.05 equiv), copper (1) iodide (5 mg, 0.1 equiv) and triethylamine (97 μL, 3 equiv) were dissolved in N,N-dimethylformamide (1 mL) and stirred at 100° C. for 4 hours. The reaction solution was cooled to room temperature, filtered through celite and extracted with saturated aqueous ammonium chloride solution and ethyl acetate. The combined organic layers were washed with saturated aqueous sodium chloride solution and dried over magnesium sulfate. The obtained solution was concentrated under reduced pressure and purified by flash chromatography to obtain the title compound.

$^1$H NMR (400 MHz, Methanol-$d_4$) δ 7.67 (d, J=8.1 Hz, 1H), 7.23 (dd, J=8.1, 1.6 Hz, 1H), 7.19-6.99 (m, 5H), 4.48 (t, J=5.1 Hz, 2H), 4.42 (s, 2H), 4.31-4.18 (m, 1H), 3.98 (dd, J=13.9, 3.6 Hz, 1H), 3.82-3.76 (m, 2H), 3.76-3.68 (m, 2H), 3.45 (dd, J=13.9, 7.6 Hz, 1H), 3.01-2.82 (m, 4H), 2.73-2.62 (m, 2H).

Example 224: Synthesis of (2R)-4-[(2R)-3-(3,4-dihydro-1H-isoquinolin-2-yl)-2-hydroxy-propyl]-8-[[1-(2-methoxyethyl)-4-piperidyl]oxy]-2-methyl-2,3-dihydro-1,4-benzoxazepin-5-one

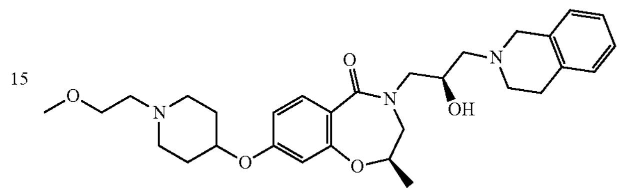

The material, which is obtained by changing [2-(tert-butoxycarbonylamino)-1-methyl-ethyl] methanesulfonate to [(1 S)-2-(tert-butoxycarbonylamino)-1-methyl-ethyl] methanesulfonate in Example 140, as a starting material was used in the same manner as in Example 163 to obtain the title compound, except that 1-bromo-2-methoxyethane was used instead of 2-fluoroethyl para-toluenesulfonate.

$^1$H NMR (400 MHz, Methanol-$d_4$) δ 7.62 (d, J=8.7 Hz, 1H), 7.17-7.02 (m, 4H), 6.78 (dd, J=8.7, 2.5 Hz, 1H), 6.55 (d, J=2.4 Hz, 1H), 4.79 (td, J=7.0, 3.3 Hz, 1H), 4.50 (t, J=3.7 Hz, 1H), 4.23 (dt, J=8.6, 4.0 Hz, 1H), 4.15 (dd, J=13.8, 3.7 Hz, 1H), 3.77 (s, 2H), 3.68-3.45 (m, 4H), 3.37 (s, 2H), 3.23 (dd, J=13.8, 8.2 Hz, 1H), 2.94 (d, J=5.3 Hz, 2H), 2.88 (t, J=5.5 Hz, 4H), 2.66 (dt, J=13.4, 6.6 Hz, 4H), 2.50 (d, J=10.2 Hz, 2H), 2.10-2.00 (m, 2H), 1.88-1.80 (m, 2H), 1.35-1.30 (m, 3H).

Example 225: Synthesis of 4-[(2R)-3-(3,4-dihydro-1H-isoquinolin-2-yl)-2-hydroxy-propyl]-8-(4-pyridyl)-2,3-dihydro-1,4-benzoxazepin-5-one

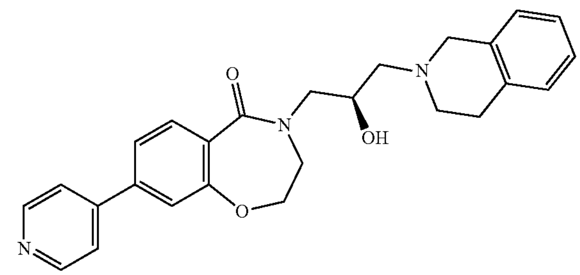 [SMILES: O=C1c2ccc(-c3ccncc3)cc2OCCN1C[C@H](O)CN1CCc2ccccc2C1]

The title compound was synthesized in the same manner as in Example 12, except that 4-pyridylboronic acid was used instead of isobutylboronic acid.

$^1$H NMR (400 MHz, Methanol-$d_4$) δ 8.70-8.56 (m, 2H), 7.87 (d, J=8.1 Hz, 1H), 7.81-7.69 (m, 2H), 7.60 (dd, J=8.2, 1.8 Hz, 1H), 7.48 (d, J=1.8 Hz, 1H), 7.17-7.04 (m, 4H), 4.56 (t, J=5.0 Hz, 2H), 4.27 (d, J=5.4 Hz, 1H), 4.03 (dd, J=13.9, 3.6 Hz, 1H), 3.79 (d, J=7.0 Hz, 4H), 3.48 (dd, J=13.9, 7.7 Hz, 1H), 2.95 (d, J=5.2 Hz, 2H), 2.89 (dd, J=8.9, 3.5 Hz, 2H), 2.68 (dd, J=6.2, 2.1 Hz, 2H).

Example 226: Synthesis of 4-[(2R)-3-(3,4-dihydro-1H-isoquinolin-2-yl)-2-hydroxy-propyl]-8-[2-(4-pyridyl)ethynyl]-2,3-dihydro-1,4-benzoxazepin-5-one

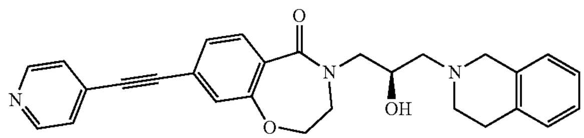 [SMILES: O=C1c2ccc(C#Cc3ccncc3)cc2OCCN1C[C@H](O)CN1CCc2ccccc2C1]

The title compound was synthesized in the same manner as in Example 223, except that 4-ethynylpyridine was used instead of prop-2-yn-1-ol.

$^1$H NMR (400 MHz, Methanol-$d_4$) δ 8.55-8.33 (m, 2H), 7.63 (d, J=8.0 Hz, 1H), 7.50-7.40 (m, 2H), 7.26 (dd, J=8.1, 1.6 Hz, 1H), 7.14 (d, J=1.6 Hz, 1H), 7.09-6.83 (m, 4H), 4.39 (t, J=5.1 Hz, 2H), 4.13 (dddd, J=9.0, 7.4, 4.6, 2.6 Hz, 1H), 3.87 (dd, J=13.9, 3.6 Hz, 1H), 3.70-3.52 (m, 4H), 3.35 (dd, J=13.8, 7.7 Hz, 1H), 2.88-2.69 (m, 4H), 2.65-2.48 (m, 2H).

Example 227: Synthesis of 4-[(2R)-3-(3,4-dihydro-1H-isoquinolin-2-yl)-2-hydroxy-propyl]-8-[2-(3-pyridyl)ethynyl]-2,3-dihydro-1,4-benzoxazepin-5-one

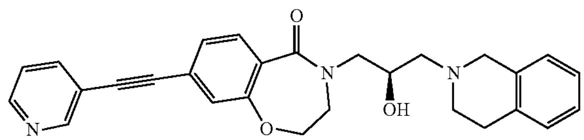 [SMILES: O=C1c2ccc(C#Cc3cccnc3)cc2OCCN1C[C@H](O)CN1CCc2ccccc2C1]

The title compound was synthesized in the same manner as in Example 223, except that 3-ethynylpyridine was used instead of prop-2-yn-1-ol.

$^1$H NMR (400 MHz, Methanol-$d_4$) δ 8.67-8.56 (m, 1H), 8.43 (dd, J=5.0, 1.6 Hz, 1H), 7.88 (dt, J=8.0, 1.9 Hz, 1H), 7.61 (d, J=8.0 Hz, 1H), 7.36 (ddd, J=8.0, 5.0, 0.9 Hz, 1H), 7.25 (dd, J=8.1, 1.6 Hz, 1H), 7.13 (d, J=1.5 Hz, 1H), 7.06-6.96 (m, 3H), 6.95-6.89 (m, 1H), 4.39 (t, J=5.1 Hz, 2H), 4.11 (ddd, J=7.4, 5.7, 3.4 Hz, 1H), 3.88 (dd, J=13.9, 3.5 Hz, 1H), 3.70-3.52 (m, 4H), 3.32 (dd, J=13.8, 7.8 Hz, 1H), 2.82 (t, J=6.2 Hz, 2H), 2.75 (t, J=5.5 Hz, 2H), 2.57-2.40 (m, 2H).

Example 228: Synthesis of 4-[(2R)-3-(3,4-dihydro-1H-isoquinolin-2-yl)-2-hydroxy-propyl]-8-(3-hydroxybu-1-tynyl)-2,3-dihydro-1,4-benzoxazepin-5-one

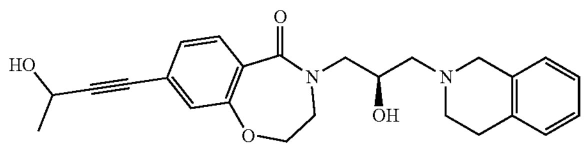 [SMILES: CC(O)C#Cc1ccc2c(c1)OCCN(C[C@H](O)CN1CCc3ccccc3C1)C2=O]

The title compound was synthesized in the same manner as in Example 223, except that but-3-yn-2-ol was used instead of prop-2-yn-1-ol.

$^1$H NMR (400 MHz, Methanol-$d_4$) δ 7.66 (d, J=8.0 Hz, 1H), 7.21 (dd, J=8.1, 1.6 Hz, 1H), 7.16-6.94 (m, 5H), 4.70 (q, J=6.6 Hz, 1H), 4.47 (t, J=5.1 Hz, 2H), 4.22 (dq, J=10.1, 5.6, 4.5 Hz, 1H), 3.98 (dd, J=13.9, 3.5 Hz, 1H), 3.75 (s, 2H), 3.73-3.64 (m, 2H), 3.43 (dd, J=13.9, 7.7 Hz, 1H), 2.92 (d, J=5.6 Hz, 2H), 2.86 (t, J=5.6 Hz, 2H), 2.64 (d, J=6.5 Hz, 2H), 1.50 (d, J=6.6 Hz, 3H).

Example 229: Synthesis of 4-[(2R)-3-(3,4-dihydro-1H-isoquinolin-2-yl)-2-hydroxy-propyl]-8-[3-(methylamino)pro-1-pynyl]-2,3-dihydro-1,4-benzoxazepin-5-one

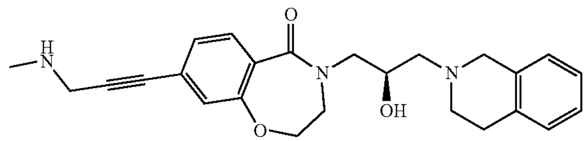 [SMILES: CNCC#Cc1ccc2c(c1)OCCN(C[C@H](O)CN1CCc3ccccc3C1)C2=O]

The title compound was synthesized in the same manner as in Example 223, except that N-methylprop-2-yn-1-amine was used instead of prop-2-yn-1-ol.

$^1$H NMR (400 MHz, Methanol-$d_4$) δ 7.55 (d, J=8.1 Hz, 1H), 7.11 (dd, J=8.1, 1.6 Hz, 1H), 7.06-6.89 (m, 5H), 4.36 (t, J=5.1 Hz, 2H), 4.18-4.05 (m, 1H), 3.86 (dd, J=13.9, 3.6 Hz, 1H), 3.68-3.63 (m, 2H), 3.59 (dt, J=5.0, 2.9 Hz, 2H), 3.52 (s, 2H), 3.33 (dd, J=13.9, 7.7 Hz, 1H), 2.81 (d, J=5.3 Hz, 2H), 2.75 (dd, J=8.9, 3.6 Hz, 2H), 2.57-2.50 (m, 2H), 2.39 (s, 3H).

Example 230: Synthesis of 4-[(2R)-3-(3,4-dihydro-1H-isoquinolin-2-yl)-2-hydroxy-propyl]-8-(3-pyridyl)-2,3-dihydro-1,4-benzoxazepin-5-one

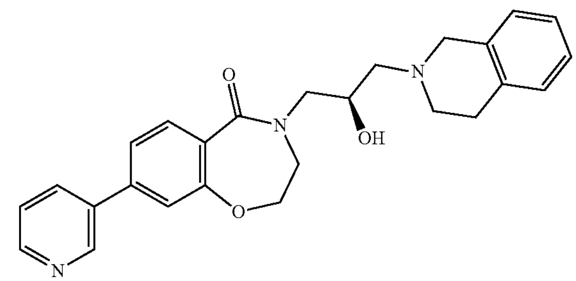 [SMILES: O=C1c2ccc(-c3cccnc3)cc2OCCN1C[C@H](O)CN1CCc2ccccc2C1]

The title compound was synthesized in the same manner as in Example 12, except that 3-pyridylboronic acid was used instead of isobutylboronic acid.

$^1$H NMR (400 MHz, Methanol-$d_4$) δ 8.94-8.83 (m, 1H), 8.64-8.53 (m, 1H), 8.21-8.09 (m, 1H), 7.85 (d, J=8.1 Hz, 1H), 7.64-7.46 (m, 2H), 7.40 (d, J=1.8 Hz, 1H), 7.18-6.92 (m, 4H), 4.56 (t, J=5.1 Hz, 2H), 4.31-4.23 (m, 1H), 4.03 (dd, J=13.8, 3.6 Hz, 1H), 3.84-3.75 (m, 4H), 3.49 (dd, J=13.9, 7.7 Hz, 1H), 3.00-2.87 (m, 4H), 2.70 (dd, J=6.3, 2.4 Hz, 2H).

Example 231: Synthesis of 4-[(2R)-3-(3,4-dihydro-1H-isoquinolin-2-yl)-2-hydroxy-propyl]-8-(1,3-dimethylpyrazol-4-yl)-2,3-dihydro-1,4-benzoxazepin-5-one

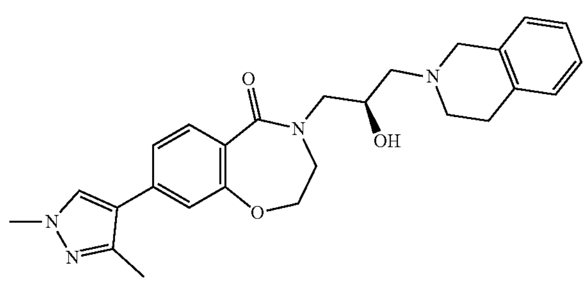 [SMILES: Cc1nn(C)cc1-c1ccc2c(c1)OCCN(C[C@H](O)CN1CCc3ccccc3C1)C2=O]

The title compound was synthesized in the same manner as in Example 12, except that 1,3-dimethylpyrazoleboronic acid was used instead of isobutylboronic acid.

$^1$H NMR (400 MHz, Methanol-$d_4$) δ 7.84 (s, 1H), 7.73 (d, J=8.1 Hz, 1H), 7.28 (dd, J=8.1, 1.8 Hz, 1H), 7.18-7.03 (m, 5H), 4.51 (t, J=5.1 Hz, 2H), 4.30-4.22 (m, 1H), 4.00 (dd, J=13.8, 3.6 Hz, 1H), 3.88 (s, 3H), 3.83-3.72 (m, 4H), 3.47 (dd, J=13.9, 7.6 Hz, 1H), 2.93 (ddd, J=11.9, 9.3, 4.3 Hz, 4H), 2.74-2.62 (m, 2H), 2.40 (s, 3H).

Example 232: Synthesis of 4-[(2R)-3-(3,4-dihydro-1H-isoquinolin-2-yl)-2-hydroxy-propyl]-8-(1-methylpyrazol-4-yl)-2,3-dihydro-1,4-benzoxazepin-5-one

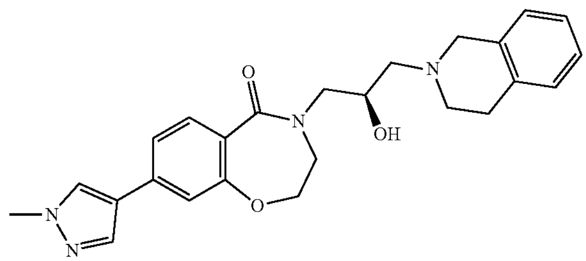 [SMILES: Cn1cc(-c2ccc3c(c2)OCCN(C[C@H](O)CN2CCc4ccccc4C2)C3=O)cn1]

The title compound was synthesized in the same manner as in Example 12, except that 1-methylpyrazoleboronic acid was used instead of isobutylboronic acid.

$^1$H NMR (400 MHz, Methanol-$d_4$) δ 8.06 (s, 1H), 7.93-7.81 (m, 1H), 7.74-7.66 (m, 1H), 7.39 (dd, J=8.1, 1.7 Hz, 1H), 7.25 (d, J=1.7 Hz, 1H), 7.16-7.02 (m, 4H), 4.50 (t, J=5.1 Hz, 2H), 4.31-4.21 (m, 1H), 4.03-3.89 (m, 4H), 3.81 (s, 2H), 3.78-3.71 (m, 2H), 3.47 (dd, J=13.9, 7.6 Hz, 1H), 2.94 (dd, J=9.5, 4.6 Hz, 4H), 2.72-2.66 (m, 2H).

Example 233: Synthesis of 4-[(2R)-3-(3,4-dihydro-1H-isoquinolin-2-yl)-2-hydroxy-propyl]-8-(1,5-dimethylpyrazol-4-yl)-2,3-dihydro-1,4-benzoxazepin-5-one

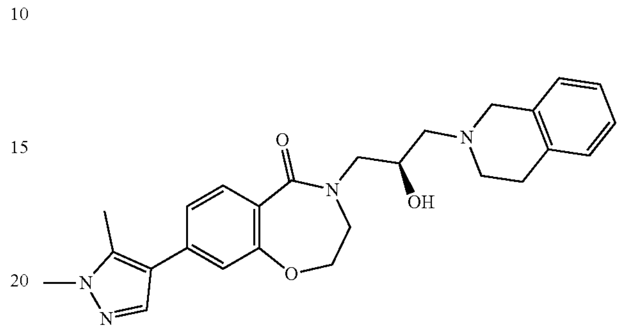

The title compound was synthesized in the same manner as in Example 12, except that 1,5-dimethylpyrazoleboronic acid was used instead of isobutylboronic acid.

$^1$H NMR (400 MHz, Methanol-$d_4$) δ 7.83-7.53 (m, 3H), 7.25 (dd, J=8.1, 1.7 Hz, 1H), 7.11 (ddd, J=14.4, 6.0, 2.5 Hz, 4H), 4.52 (t, J=5.1 Hz, 2H), 4.27 (d, J=9.2 Hz, 1H), 4.01 (dd, J=13.9, 3.7 Hz, 1H), 3.86 (s, 3H), 3.82-3.71 (m, 4H), 3.48 (dd, J=13.9, 7.6 Hz, 1H), 2.93 (dt, J=8.6, 4.9 Hz, 4H), 2.73-2.64 (m, 2H), 2.46 (s, 3H).

Example 234: Synthesis of 4-[(2R)-3-(3,4-dihydro-1H-isoquinolin-2-yl)-2-hydroxy-propyl]-8-[[1-(2-hydroxyethyl)-4-piperidyl]oxy]-2,2-dimethyl-3H-pyrido[3,2-f][1,4]oxazepin-5-one

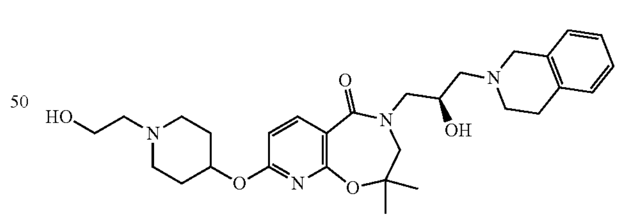

4-[(2R)-3-(3,4-dihydro-1H-isoquinolin-2-yl)-2-hydroxy-propyl]-2,2-dimethyl-8-(4-piperidyloxy)-3H-pyrido[3,2-f][1,4]oxazepin-5-one dihydrochloride as a starting material was used in the same manner as in Example 162 to obtain the title compound.

$^1$H NMR (400 MHz, Methanol-$d_4$) δ 8.04 (d, J=8.4 Hz, 1H), 7.16-7.00 (m, 4H), 6.61 (d, J=8.4 Hz, 1H), 5.14-5.00 (m, 1H), 4.27 (s, 1H), 4.04 (dd, J=13.8, 3.6 Hz, 1H), 3.78-3.57 (m, 6H), 3.40 (dd, J=13.7, 8.2 Hz, 1H), 2.97-2.79 (m, 6H), 2.66-2.53 (m, 4H), 2.48 (s, 2H), 2.12-2.02 (m, 2H), 1.89-1.76 (m, 2H), 1.48 (s, 3H), 1.43 (s, 3H).

Example 235: Synthesis of 4-[(2R)-3-(3,4-dihydro-1H-isoquinolin-2-yl)-2-hydroxy-propyl]-2,2-dimethyl-8-[[(3R)-1-meth yl-3-piperidyl]oxy]-3H-pyrido[3,2-f][1,4]oxazepin-5-one

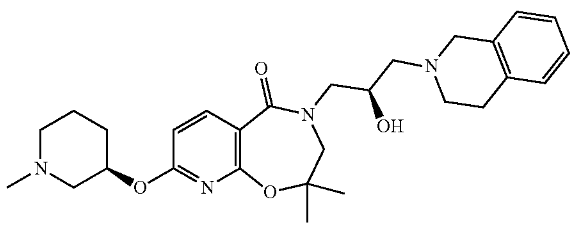 [SMILES: CN1CCC[C@@H](Oc2ccc3c(n2)OC(C)(C)CN(C[C@H](O)CN2CCc4ccccc4C2)C3=O)C1]

The title compound was synthesized in the same manner as in Examples 144-1 and 114-3 to 144-6, except that 1-[(4-methoxyphenyl)methylamino]-2-methyl-propan-2-ol was used instead of 1-[(4-methoxyphenyl)methylamino]propan-2-ol in Example 144-1, and tert-butyl 3-hydroxypiperidine-1-carboxylate was used instead of tert-butyl 4-hydroxypiperidine-1-carboxylate in Example 144-3.

$^1$H NMR (400 MHz, Methanol-$d_4$) δ 8.04 (d, J=8.4 Hz, 1H), 7.17-7.02 (m, 4H), 6.63 (d, J=8.4 Hz, 1H), 5.18 (s, 1H), 4.27 (s, 1H), 4.04 (dd, J=13.8, 3.6 Hz, 1H), 3.76 (s, 2H), 3.71-3.56 (m, 2H), 3.39 (dd, J=13.8, 8.3 Hz, 1H), 2.99-2.81 (m, 5H), 2.64 (dd, J=6.3, 2.8 Hz, 2H), 2.60 (d, J=6.8 Hz, 1H), 2.52-2.35 (m, 2H), 2.33 (s, 3H), 2.02-1.84 (m, 2H), 1.75-1.58 (m, 2H), 1.47 (s, 3H), 1.42 (s, 3H).

Example 236: Synthesis of 4-[(2R)-3-(3,4-dihydro-1H-isoquinolin-2-yl)-2-hydroxy-propyl]-8-[[(1-(2-fluoroethyl)-3-piperidyl)oxy]-2,3-dihydro-1,4-benzoxazepin-5-one

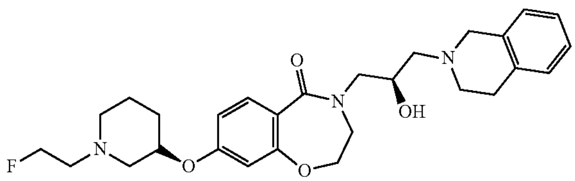

Example 236-1: Synthesis of 4-[(2R)-3-(3,4-dihydro-1H-isoquinolin-2-yl)-2-hydroxy-propyl]-8-(3-piperidyloxy)-2,3-dihydro-1,4-benzoxazepin-5-one; dihydrochloride The title compound was synthesized in the same manner as in Examples 77 and 78-1, except that tert-butyl (R)-3-methylsulfonyloxypiperidine-1-carboxylate was used instead of tert-butyl 4-methylsulfonyloxypiperidine-1-carboxylate in Example 77.

Example 236-2: Synthesis of 4-[(2R)-3-(3,4-dihydro-1H-isoquinolin-2-yl)-2-hydroxy-propyl]-8-[[(1-(2-fluoroethyl)-3-piperidyl)oxy]-2,3-dihydro-1,4-benzoxazepin-5-one 4-[(2R)-3-(3,4-dihydro-1H-isoquinolin-2-yl)-2-hydroxy-propyl]-8-(3-piperidyloxy)-2,3-dihydro-1,4-benzoxazepin-5-one; dihydrochloride obtained in Example 236-1 as a starting material was used in the same manner as in Example 163 to obtain the title compound.

$^1$H NMR (400 MHz, Methanol-$d_4$) δ 7.67 (d, J=8.8 Hz, 1H), 7.19-6.98 (m, 4H), 6.77 (dd, J=8.8, 2.5 Hz, 1H), 6.60 (d, J=2.5 Hz, 1H), 4.66 (td, J=5.0, 2.2 Hz, 1H), 4.57-4.41 (m, 4H), 4.23 (tdd, J=7.5, 5.4, 3.7 Hz, 1H), 3.97 (dd, J=13.9, 3.7 Hz, 1H), 3.80-3.68 (m, 4H), 3.43 (dd, J=13.9, 7.6 Hz, 1H), 3.06 (d, J=11.4 Hz, 1H), 2.98-2.85 (m, 4H), 2.85-2.71 (m, 3H), 2.70-2.61 (m, 2H), 2.36 (ddd, J=21.3, 11.4, 5.6 Hz, 2H), 2.04 (d, J=8.9 Hz, 1H), 1.86 (dt, J=8.4, 4.3 Hz, 1H), 1.76-1.62 (m, 1H), 1.59-1.48 (m, 1H).

Example 237: Synthesis of 4-[(2R)-3-(3,4-dihydro-1H-isoquinolin-2-yl)-2-hydroxy-propyl]-8-[[1-(2-hydroxy)-3-piperidyl)oxy]-2,3-dihydro-1,4-benzoxazepin-5-one

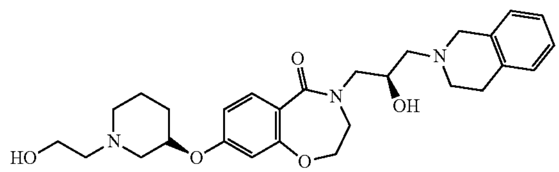

4-[(2R)-3-(3,4-dihydro-1H-isoquinolin-2-yl)-2-hydroxy-propyl]-8-(3-piperidyloxy)-2,3-dihydro-1,4-benzoxazepin-5-one; dihydrochloride obtained in Example 236-1 as a starting material was used in the same manner as in Example 162 to obtain the title compound.

$^1$H NMR (400 MHz, Methanol-$d_4$) δ 7.67 (d, J=8.8 Hz, 1H), 7.19-6.99 (m, 4H), 6.78 (dd, J=8.8, 2.5 Hz, 1H), 6.62 (d, J=2.4 Hz, 1H), 4.50 (dt, J=22.5, 4.6 Hz, 3H), 4.24 (tt, J=7.8, 4.1 Hz, 1H), 3.97 (dd, J=13.9, 3.7 Hz, 1H), 3.81 (s, 2H), 3.72 (q, J=5.9 Hz, 4H), 3.44 (dd, J=13.9, 7.5 Hz, 1H), 3.14-3.04 (m, 1H), 2.94 (dt, J=9.5, 4.8 Hz, 4H), 2.82 (dd, J=10.8, 5.0 Hz, 1H), 2.67 (dt, J=17.1, 5.2 Hz, 3H), 2.49-2.32 (m, 2H), 2.05 (d, J=10.2 Hz, 2H), 1.87 (s, 1H), 1.70 (dt, J=9.5, 4.1 Hz, 1H), 1.64-1.51 (m, 1H).

Example 238: Synthesis of 4-[(2R)-3-(3,4-dihydro-1H-isoquinolin-2-yl)-2-hydroxy-propyl]-8-[[1-(2-hydroxy-2-methyl-propyl)-4-piperidyl]oxy]-2,3-dihydro-1,4-benzoxazepin-5-one

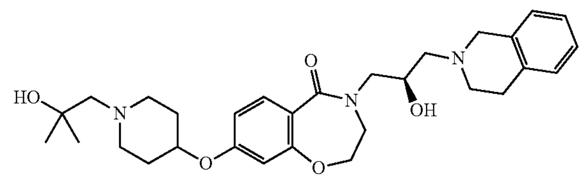 [SMILES: CC(C)(O)CN1CCC(Oc2ccc3c(c2)OCCN(C[C@H](O)CN2CCc4ccccc4C2)C3=O)CC1]

4-[(2R)-3-(3,4-dihydro-1H-isoquinolin-2-yl)-2-hydroxy-propyl]-8-(4-piperidyloxy)-2,3-dihydro-1,4-benzoxazepin-5-one dihydrochloride obtained in Example 78-1 as a starting material was used in the same manner as in Example 220 to obtain the title compound.

$^1$H NMR (400 MHz, Methanol-$d_4$) δ 7.66 (d, J=8.7 Hz, 1H), 7.17-6.99 (m, 4H), 6.76 (dd, J=8.8, 2.4 Hz, 1H), 6.58 (d, J=2.4 Hz, 1H), 4.46 (q, J=11.0, 8.0 Hz, 3H), 4.24 (s, 1H), 3.97 (dd, J=13.9, 3.7 Hz, 1H), 3.83-3.68 (m, 4H), 3.44 (dd, J=13.9, 7.6 Hz, 1H), 2.93 (dd, J=13.7, 4.6 Hz, 6H), 2.75-2.53 (m, 4H), 2.42 (d, J=7.6 Hz, 2H), 2.03 (s, 2H), 1.83 (d, J=9.5 Hz, 2H), 1.22 (s, 6H).

Example 239: Synthesis of 4-[(2R)-3-(3,4-dihydro-1H-isoquinolin-2-yl)-2-hydroxy-propyl]-8-(6-fluoro-2-pyridyl)-2,3-dihydro-1,4-benzoxazepin-5-one

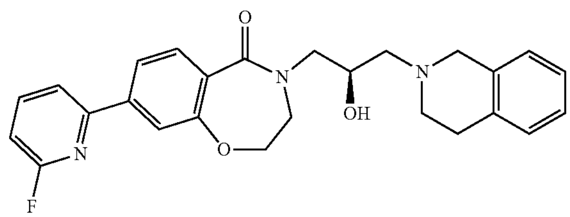 [SMILES: O=C1c2ccc(-c3cccc(F)n3)cc2OCCN1C[C@H](O)CN1CCc2ccccc2C1]

The title compound was synthesized in the same manner as in Example 12, except that 6-fluoro-2-pyridylboronic acid was used instead of isobutylboronic acid.

$^1$H NMR (400 MHz, Methanol-$d_4$) δ 8.03 (q, J=8.1 Hz, 1H), 7.92-7.78 (m, 3H), 7.75 (d, J=1.7 Hz, 1H), 7.17-7.01 (m, 5H), 4.55 (t, J=5.1 Hz, 2H), 4.33-4.21 (m, 1H), 4.02 (dd, J=13.8, 3.6 Hz, 1H), 3.85-3.70 (m, 4H), 3.49 (dd, J=13.8, 7.7 Hz, 1H), 3.01-2.86 (m, 4H), 2.75-2.64 (m, 2H).

Example 240: Synthesis of (2R)-4-[(2R)-3-(3,4-dihydro-1H-isoquinolin-2-yl)-2-hydroxy-propyl]-8-[[1-(2-ethoxyethyl)-4-piperidyl]oxy]-2-methyl-2,3-dihydro-1,4-benzoxazepin-5-one

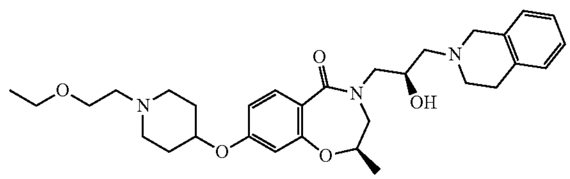 [SMILES: CCOCCN1CCC(Oc2ccc3c(c2)O[C@H](C)CN(C[C@H](O)CN2CCc4ccccc4C2)C3=O)CC1]

The material, which is obtained by changing [2-(tert-butoxycarbonylamino)-1-methyl-ethyl] methanesulfonate to [(1 S)-2-(tert-butoxycarbonylamino)-1-methyl-ethyl] methanesulfonate in Example 140, as a starting material was used in the same manner as in Example 163 to obtain the title compound, except that 1-bromo-2-ethoxyethane was used instead of 2-fluoroethyl para-toluenesulfonate.

$^1$H NMR (400 MHz, Methanol-$d_4$) δ 7.63 (d, J=8.7 Hz, 1H), 7.16-6.99 (m, 4H), 6.79 (dd, J=8.7, 2.5 Hz, 1H), 6.57 (d, J=2.4 Hz, 1H), 4.79 (td, J=6.9, 3.3 Hz, 1H), 4.53 (dp, J=7.7, 3.7 Hz, 1H), 4.29-4.19 (m, 1H), 4.14 (dd, J=13.9, 3.7 Hz, 1H), 3.79 (s, 2H), 3.68-3.58 (m, 3H), 3.58-3.43 (m, 3H), 3.24 (dd, J=13.8, 8.1 Hz, 1H), 2.93 (qd, J=9.2, 8.7, 4.5 Hz, 6H), 2.76 (t, J=5.6 Hz, 2H), 2.64 (dt, J=16.5, 7.0 Hz, 4H), 2.07 (ddd, J=16.6, 10.3, 6.3 Hz, 2H), 1.93-1.81 (m, 2H), 1.32 (d, J=6.4 Hz, 3H), 1.22 (t, J=7.0 Hz, 3H).

Example 241: Synthesis of (2R)-4-[(2R)-3-(3,4-dihydro-1H-isoquinolin-2-yl)-2-hydroxy-propyl]-8-[[8-2-hydroxy]-8-azabicyclo[3.2.1]octan-3-yl]oxy]-2-methyl-2,3-dihydro-1,4-benzoxazepin-5-one

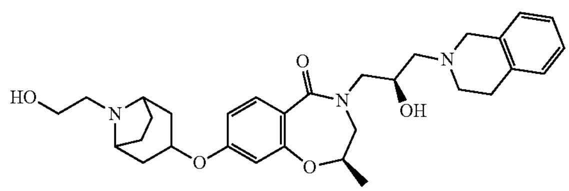 [SMILES: C[C@@H]1CN(C[C@H](O)CN2CCc3ccccc3C2)C(=O)c2ccc(OC3CC4CCC(C3)N4CCO)cc2O1]

Example 241-1: Synthesis of (2R)-4-[(2R)-3-(3,4-dihydro-1H-isoquinolin-2-yl)-2-hydroxy-propyl]-8-[−8-azabicyclo[3.2.1]octan-3-yl]oxy]-2-methyl-2,3-dihydro-1,4-benzoxazepin-5-one dihydrochloride The intermediate in which Boc is substituted was synthesized by using the material obtained in the same manner as in Example 140 except that [(1 S)-2-(tert-butoxycarbonylamino)-1-methyl-ethyl] methanesulfonate was used instead of [2-(tert-butoxycarbonylamino)-1-methyl-ethyl] methanesulfonate as a starting material and the method in the same manner as in Example 64 except that tert-butyl 3-methylsulfonyloxy-8-azabicyclo[3.2.1]octane-8-carboxylate is used instead of 4-chlorotetrahydropyran. The obtained intermediate was dissolved in methanol, and 4 N hydrochloric acid solution dissolved in 1,4-dioxane was added thereto. The reaction solution was stirred at room temperature until the reaction was terminated, diluted with ethyldiethyl ether and filtered to obtain the title compound as a white solid in the form of dihydrochloride.

Example 241-2: Synthesis of (2R)-4-[(2R)-3-(3,4-dihydro-1H-isoquinolin-2-yl)-2-hydroxy-propyl]-8-[[8-2-hydroxy]-8-azabicyclo[3.2.1]octan-3-yl]oxy]-2-methyl-2,3-dihydro-1,4-benzoxazepin-5-one (2R)-4-[(2R)-3-(3,4-dihydro-1H-isoquinolin-2-yl)-2-hydroxy-propyl]-8-[−8-azabicyclo[3.2.1]octan-3-yl)oxy]-2-methyl-2,3-dihydro-1,4-benzoxazepin-5-one dihydrochloride obtained in Example 241-1 as a starting material was used in the same manner as in Example 162 to obtain the title compound.

$^1$H NMR (400 MHz, Methanol-$d_4$) δ 7.62 (d, J=8.8 Hz, 1H), 7.19-6.99 (m, 4H), 6.79 (dd, J=8.7, 2.5 Hz, 1H), 6.55 (d, J=2.4 Hz, 1H), 4.81-4.74 (m, 2H), 4.24 (d, J=5.4 Hz, 1H), 4.15 (dd, J=13.8, 3.6 Hz, 1H), 3.79-3.58 (m, 7H), 3.55-3.45 (m, 1H), 3.23 (d, J=5.5 Hz, 1H), 3.00-2.77 (m, 6H), 2.66 (h, J=5.2 Hz, 2H), 2.15 (s, 4H), 1.97-1.80 (m, 4H), 1.33 (d, J=6.4 Hz, 3H).

Example 242: Synthesis of (2R)-4-[(2R)-3-(3,4-dihydro-1H-isoquinolin-2-yl)-2-hydroxy-propyl]-8-[[8-2-fluoroethyl]-8-azabicyclo[3.2.1]octan-3-yl]oxy]-2-methyl-2,3-dihydro-1,4-benzoxazepin-5-one

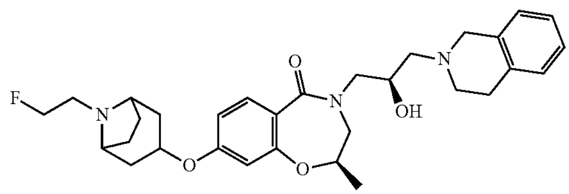 [SMILES: C[C@@H]1CN(C[C@H](O)CN2CCc3ccccc3C2)C(=O)c2ccc(OC3CC4CCC(C3)N4CCF)cc2O1]

(2R)-4-[(2R)-3-(3,4-dihydro-1H-isoquinolin-2-yl)-2-hydroxy-propyl]-8-[-8-azabicyclo[3.2.1]octan-3-yl]oxy]-2-methyl-2,3-dihydro-1,4-benzoxazepin-5-one dihydrochloride obtained in Example 241-1 as a starting material was used in the same manner as in Example 163 to obtain the title compound.

$^1$H NMR (400 MHz, Methanol-$d_4$) δ 7.61 (d, J=8.7 Hz, 1H), 7.17-7.00 (m, 4H), 6.77 (dd, J=8.7, 2.5 Hz, 1H), 6.52 (d, J=2.4 Hz, 1H), 4.78 (td, J=6.9, 3.3 Hz, 1H), 4.73-4.62 (m, 1H), 4.54 (t, J=5.0 Hz, 1H), 4.16 (ddd, J=23.5, 11.6, 8.0 Hz, 2H), 3.77 (d, J=9.9 Hz, 3H), 3.63 (dd, J=15.6, 3.4 Hz, 1H), 3.53-3.41 (m, 2H), 3.23 (dd, J=13.8, 8.2 Hz, 1H), 2.96-2.91 (m, 4H), 2.88 (td, J=6.4, 5.7, 2.7 Hz, 3H), 2.81 (t, J=5.0 Hz, 1H), 2.70 (dd, J=12.9, 4.1 Hz, 1H), 2.62 (dt, J=13.0, 6.5 Hz, 2H), 2.12-2.00 (m, 3H), 1.89-1.77 (m, 3H), 1.33 (d, J=6.4 Hz, 3H).

Example 243: Synthesis of 4-[(2R)-3-(3,4-dihydro-1H-isoquinolin-2-yl)-2-hydroxy-propyl]-8-[[1-(2-methoxyethyl)-4-pyridyl]oxy]-2-methyl-2,3-dihydro-1,4-benzoxazepin-5-one

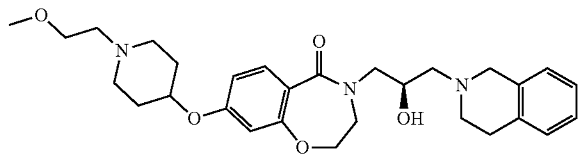 [SMILES: COCCN1CCC(Oc2ccc3c(c2)OCCN(C[C@H](O)CN2CCc4ccccc4C2)C3=O)CC1]

4-[(2R)-3-(3,4-dihydro-1H-isoquinolin-2-yl)-2-hydroxy-propyl]-8-(4-piperidyloxy)-2,3-dihydro-1,4-benzoxazepin-5-one dihydrochloride obtained in Example 78-1 as a starting material was used in the same manner as in Example 224 to obtain the title compound.

$^1$H NMR (400 MHz, Methanol-$d_4$) δ 7.67 (d, J=8.8 Hz, 1H), 7.20-7.01 (m, 4H), 6.77 (dd, J=8.8, 2.5 Hz, 1H), 6.59 (d, J=2.4 Hz, 1H), 4.50 (dt, J=25.8, 4.4 Hz, 3H), 4.30-4.19 (m, 1H), 3.97 (dd, J=13.9, 3.7 Hz, 1H), 3.84-3.67 (m, 4H), 3.60 (t, J=5.5 Hz, 2H), 3.45 (dd, J=13.9, 7.6 Hz, 1H), 3.38 (s, 3H), 2.93 (dt, J=11.0, 5.7 Hz, 6H), 2.76 (t, J=5.5 Hz, 2H), 2.72-2.54 (m, 4H), 2.06 (dd, J=18.1, 11.0 Hz, 2H), 1.93-1.82 (m, 2H).

Example 244: Synthesis of 4-[(2R)-3-(3,4-dihydro-1H-isoquinolin-2-yl)-2-hydroxy-propyl]-8-(6-methoxy-2-pyridyl)-2,3-dihydro-1,4-benzoxazepin-5-one

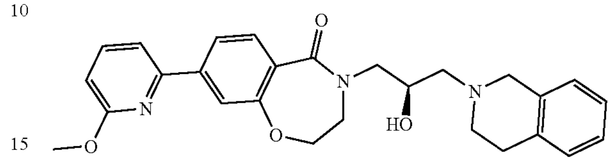

The title compound was synthesized in the same manner as in Example 12, except that 6-methoxy-2-pyridylboronic acid was used instead of isobutylboronic acid.

$^1$H NMR (400 MHz, Methanol-$d_4$) δ 7.90 (dd, J=8.3, 1.7 Hz, 1H), 7.84-7.69 (m, 3H), 7.52 (d, J=7.4 Hz, 1H), 7.18-7.01 (m, 4H), 6.78 (d, J=8.2 Hz, 1H), 4.54 (t, J=5.1 Hz, 2H), 4.33-4.21 (m, 1H), 4.03 (s, 4H), 3.82-3.71 (m, 4H), 3.49 (dd, J=13.9, 7.7 Hz, 1H), 3.00-2.82 (m, 4H), 2.74-2.62 (m, 2H).

Example 245: Synthesis of (2R)-4-[(2R)-3-(3,4-dihydro-1H-isoquinolin-2-yl)-2-hydroxy-propyl]-8-[[1-(2-hydroxypropyl)-4-piperidyl]oxy]-2-methyl-2,3-dihydro-1,4-benzoxazepin-5-one

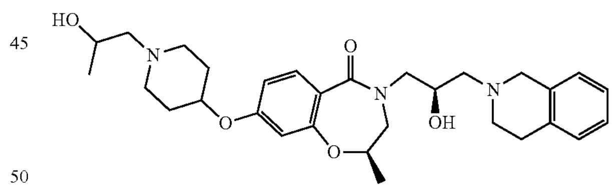

The material, which is obtained by changing [2-(tert-butoxycarbonylamino)-1-methyl-ethyl] methanesulfonate to [(1 S)-2-(tert-butoxycarbonylamino)-1-methyl-ethyl] methanesulfonate in Example 140, as a starting material was used in the same manner as in Example 212 to obtain the title compound.

$^1$H NMR (400 MHz, Methanol-$d_4$) δ 7.63 (d, J=8.7 Hz, 1H), 7.17-7.00 (m, 4H), 6.79 (dd, J=8.7, 2.4 Hz, 1H), 6.57 (d, J=2.4 Hz, 1H), 4.82-4.77 (m, 1H), 4.56 (s, 1H), 4.24 (tt, J=8.3, 4.6 Hz, 1H), 4.13 (ddd, J=13.9, 7.8, 5.4 Hz, 1H), 4.00 (p, J=6.3 Hz, 1H), 3.79 (s, 2H), 3.64 (dd, J=15.6, 3.4 Hz, 1H), 3.50 (dd, J=15.6, 7.6 Hz, 1H), 3.27-3.21 (m, 1H), 3.10-2.87 (m, 6H), 2.80-2.62 (m, 4H), 2.57 (d, J=6.4 Hz, 2H), 2.17-2.04 (m, 2H), 1.94 (s, 2H), 1.33 (d, J=6.4 Hz, 3H), 1.19 (d, J=6.2 Hz, 3H).

Example 246: Synthesis of 4-[(2R)-3-(3,4-dihydro-1H-isoquinolin-2-yl)-2-hydroxy-propyl]-2,2-dimethyl-8-(1-morpholinoethyl)-3H-pyrido[3,2-f][1,4]oxazepin-5-one

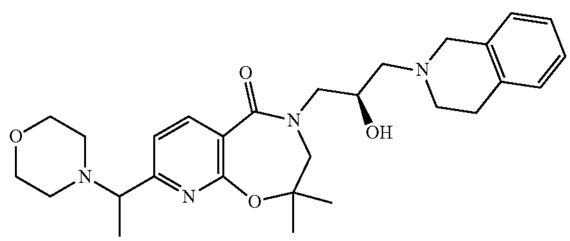 [SMILES: CC(c1ccc2c(n1)OC(C)(C)CN(C[C@H](O)CN1CCc3ccccc3C1)C2=O)N1CCOCC1]

Example 246-1: Synthesis of 8-acetyl-4-[(2R)-3-(3,4-dihydro-1H-isoquinolin-2-yl)-2-hydroxy-propyl]-2,2-dimethyl-3H-pyrido[3,2-f][1,4]oxazepin-5-one 8-Chloro-4-[(2R)-3-(3,4-dihydro-1H-isoquinolin-2-yl)-2-hydroxy-propyl]-2,2-dimethyl-3H-pyrido[3,2-f][1,4]oxazepin-5-one (200 mg, 0.48 mmol), tributyl (1-ethoxyvinyl)tin (0.21 mL, 0.62 mmol) and tetrakis(triphenylphosphine)palladium (28 mg, 0.024 mmol) were dissolved in 4 mL of toluene 4 mL, and the reaction was carried out by the use of a microwave at 120° C. for 2 hours. To the reaction solution concentrated hydrochloric acid aqueous solution and 1,4-dioxane were added, followed by stirring at room temperature for 10 minutes. The reaction solution was diluted with ethyl acetate and basified with sodium hydroxide aqueous solution. The mixture was extracted with ethyl acetate, dried over magnesium sulfate and purified by flash chromatography to obtain the title compound.

Example 246-2: Synthesis of 4-[(2R)-3-(3,4-dihydro-1H-isoquinolin-2-yl)-2-hydroxy-propyl]-2,2-dimethyl-8-(1-morpholinoethyl)-3H-pyrido[3,2-f][1,4]oxazepin-5-one 8-Acetyl-4-[(2R)-3-(3,4-dihydro-1H-isoquinolin-2-yl)-2-hydroxy-propyl]-2,2-dimethyl-3H-pyrido[3,2-f][1,4]oxazepin-5-one obtained in Example 246-1 as a starting material was used in the same manner as in Example 221-2 to obtain the title compound.

$^1$H NMR (400 MHz, Methanol-$d_4$) δ 8.13 (d, J=7.8 Hz, 1H), 7.39 (dd, J=7.8, 1.2 Hz, 1H), 7.17-7.00 (m, 4H), 4.29 (s, 1H), 4.05 (ddd, J=13.7, 7.3, 3.8 Hz, 1H), 3.77 (s, 2H), 3.70 (t, J=4.7 Hz, 4H), 3.62 (d, J=2.4 Hz, 2H), 3.55-3.39 (m, 2H), 2.99-2.80 (m, 4H), 2.72-2.61 (m, 2H), 2.64-2.52 (m, 2H), 2.41 (dt, J=11.0, 4.6 Hz, 2H), 1.50 (d, J=2.3 Hz, 3H), 1.44 (d, J=2.2 Hz, 3H), 1.39 (d, J=6.8 Hz, 3H).

Example 247: Synthesis of 4-[(2R)-3-(3,4-dihydro-1H-isoquinolin-2-yl)-2-hydroxy-propyl]-2,2-dimethyl-8-[1-(2-oxa-6-azaspiro[3.3]heptan-6-yl)ethyl]-3H-pyrido[3,2-f][1,4]oxazepin-5-one

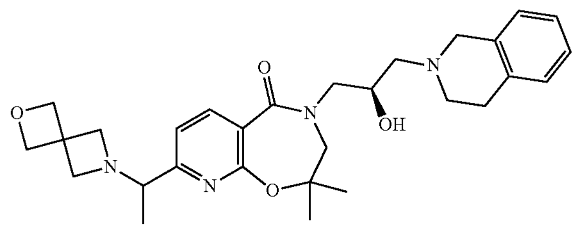 [SMILES: CC(c1ccc2c(n1)OC(C)(C)CN(C[C@H](O)CN1CCc3ccccc3C1)C2=O)N1CC2(COC2)C1]

8-Acetyl-4-[(2R)-3-(3,4-dihydro-1H-isoquinolin-2-yl)-2-hydroxy-propyl]-2,2-dimethyl-3H-pyrido[3,2-f][1,4]oxazepin-5-one obtained in Example 246-1 as a starting material was used in the same manner as in Example 222 to obtain the title compound.

$^1$H NMR (400 MHz, Methanol-$d_4$) δ 8.13 (d, J=7.8 Hz, 1H), 7.28 (d, J=7.8 Hz, 1H), 7.15-7.03 (m, 4H), 4.75 (s, 4H), 4.28 (s, 1H), 4.05 (ddd, J=12.9, 8.5, 3.8 Hz, 1H), 3.76 (s, 2H), 3.61 (d, J=2.1 Hz, 2H), 3.49-3.37 (m, 6H), 2.97-2.82 (m, 4H), 2.65 (dd, J=6.3, 3.8 Hz, 2H), 1.50 (d, J=2.8 Hz, 3H), 1.44 (d, J=2.8 Hz, 3H), 1.25 (d, J=6.6 Hz, 3H).

Example 248: Synthesis of 4-[(2R)-3-(3,4-dihydro-1H-isoquinolin-2-yl)-2-hydroxy-propyl]-8-[[1-(2-hydroxypropyl)-4-piperidyl]oxy]-2,2-dimethyl-3H-pyrido[3,2-f][1,4]oxazepin-5-one

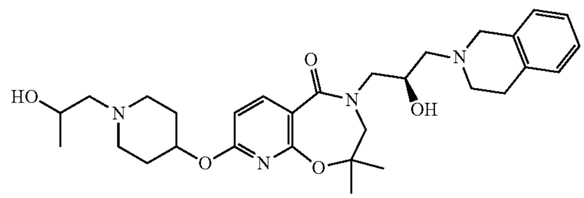 [SMILES: CC(O)CN1CCC(Oc2ccc3c(n2)OC(C)(C)CN(C[C@H](O)CN2CCc4ccccc4C2)C3=O)CC1]

4-[(2R)-3-(3,4-dihydro-1H-isoquinolin-2-yl)-2-hydroxy-propyl]-2,2-dimethyl-8-(4-piperidyloxy)-3H-pyrido[3,2-f][1,4]oxazepin-5-one dihydrochloride as a starting material was used in the same manner as in Example 212 to obtain the title compound.

$^1$H NMR (400 MHz, Methanol-$d_4$) δ 8.04 (d, J=8.4 Hz, 1H), 7.15-7.02 (m, 4H), 6.60 (d, J=8.4 Hz, 1H), 5.07 (s, 1H), 4.26 (s, 1H), 4.03 (dd, J=13.6, 3.6 Hz, 1H), 3.96 (q, J=6.0 Hz, 1H), 3.75 (s, 2H), 3.71-3.57 (m, 2H), 3.41 (dd, J=13.8, 8.2 Hz, 1H), 2.90 (dd, J=19.1, 5.4 Hz, 6H), 2.63 (dd, J=6.2, 3.0 Hz, 2H), 2.53 (s, 1H), 2.41 (d, J=8.6 Hz, 3H), 2.06 (s, 2H), 1.85 (s, 2H), 1.48 (s, 3H), 1.43 (s, 3H), 1.17 (d, J=6.2 Hz, 3H).

Example 249: Synthesis of 4-[(2R)-3-(3,4-dihydro-1H-isoquinolin-2-yl)-2-hydroxypropyl]-8-(3,4-dihydro-1H-pyrrolo[1,2-a]pyrazin-2-ylmethyl)-2,3-dihydro-1,4-benzoxazepin-5-one

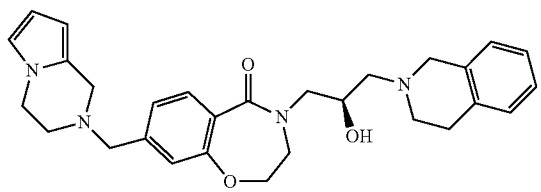 [SMILES: O=C1c2ccc(CN3CCn4cccc4C3)cc2OCCN1C[C@H](O)CN1CCc2ccccc2C1]

The title compound was synthesized in the same manner as in Example 29, except that 1,2,3,4-tetrahydropyrrolo[1,2-a]pyrazine was used instead of 3-methoxyazetidine hydrochloride.

$^1$H NMR (400 MHz, Methanol-$d_4$) δ 7.70 (d, J=8.0 Hz, 1H), 7.22 (dd, J=8.0, 1.6 Hz, 1H), 7.17-6.99 (m, 5H), 6.59-6.50 (m, 1H), 6.11-5.97 (m, 1H), 5.74 (dd, J=3.5, 1.6 Hz, 1H), 4.48 (t, J=5.1 Hz, 2H), 4.24 (tdd, J=7.3, 5.2, 3.5 Hz, 1H), 3.99 (ddd, J=9.5, 4.3, 2.6 Hz, 3H), 3.77 (d, J=2.3 Hz, 2H), 3.72 (d, J=7.3 Hz, 4H), 3.62 (s, 2H), 3.46 (dd, J=13.9, 7.6 Hz, 1H), 2.96-2.91 (m, 2H), 2.91-2.83 (m, 4H), 2.67 (dd, J=6.2, 2.2 Hz, 2H).

Example 250: Synthesis of (2R)-4-[(2R)-3-(3,4-dihydro-1H-isoquinolin-2-yl)-2-hydroxypropyl]-2-methyl-8-(2-oxa-6-aza spiro[3.3]heptan-6-ylmethyl)-2,3-dihydro-1,4-benzoxazepin-5-one

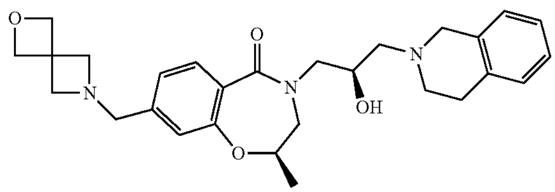 [SMILES: C[C@@H]1CN(C[C@H](O)CN2CCc3ccccc3C2)C(=O)c2ccc(CN3CC4(COC4)C3)cc2O1]

The title compound was synthesized in the same manner as in Example 28, except that (2R)-8-bromo-4-[(2R)-3-(3,4-dihydro-1H-isoquinolin-2-yl)-2-hydroxypropyl]-2-methyl-2,3-dihydro-1,4-benzoxazepin-5-one was used as a starting material.

$^1$H NMR (400 MHz, Methanol-$d_4$) δ 7.63 (d, J=7.9 Hz, 1H), 7.17-7.01 (m, 5H), 6.95 (d, J=1.6 Hz, 1H), 4.84-4.78 (m, 1H), 4.75 (s, 3H), 4.23 (td, J=7.9, 4.2 Hz, 1H), 4.15 (dd, J=13.8, 3.7 Hz, 1H), 3.77 (s, 2H), 3.66-3.56 (m, 3H), 3.46 (s, 5H), 3.26 (dd, J=13.8, 8.1 Hz, 1H), 2.97-2.83 (m, 4H), 2.64 (h, J=7.6 Hz, 2H), 1.31 (d, J=6.3 Hz, 4H).

Example 251: Synthesis of 4-[(2R)-3-(3,4-dihydro-1H-isoquinolin-2-yl)-2-hydroxypropyl]-8-(2-oxa-7-azaspiro[3.5]nonan-7-ylmethyl)-2,3-dihydro-1,4-benzoxazepin-5-one

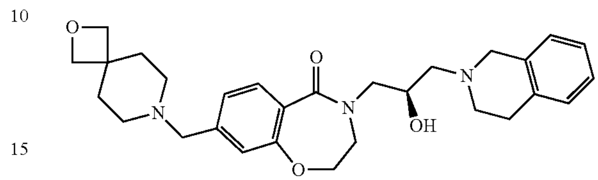

The title compound was synthesized in the same manner as in Example 29, except that 2-oxa-7-azaspiro[3.5]nonane oxalate was used instead of 3-methoxyazetidine hydrochloride.

$^1$H NMR (400 MHz, Methanol-$d_4$) δ 7.67 (d, J=8.0 Hz, 1H), 7.19-6.97 (m, 6H), 4.47 (t, J=5.1 Hz, 2H), 4.42 (s, 4H), 4.28-4.19 (m, 1H), 3.99 (dd, J=13.9, 3.6 Hz, 1H), 3.78-3.67 (m, 4H), 3.51-3.40 (m, 3H), 2.93 (dd, J=9.0, 4.0 Hz, 2H), 2.86 (dd, J=8.9, 3.7 Hz, 2H), 2.67-2.60 (m, 2H), 2.37 (s, 4H), 1.89 (t, J=5.5 Hz, 4H).

Example 252: Synthesis of (2R)-4-[(2R)-3-(3,4-dihydro-1H-isoquinolin-2-yl)-2-hydroxypropyl]-2-methyl-8-(2-oxa-7-aza spiro[3.5]nonan-7-ylmethyl)-2,3-dihydro-1,4-benzoxazepin-5-one

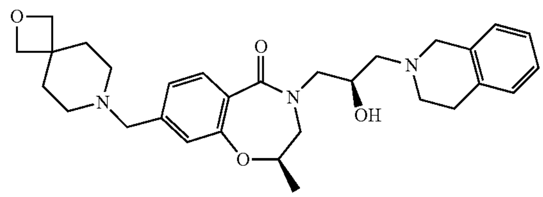 [SMILES: C[C@@H]1CN(C[C@H](O)CN2CCc3ccccc3C2)C(=O)c2ccc(CN3CCC4(CC3)COC4)cc2O1]

The title compound was synthesized in the same manner as in Example 251, except that (2R)-8-bromo-4-[(2R)-3-(3,4-dihydro-1H-isoquinolin-2-yl)-2-hydroxypropyl]-2-methyl-2,3-dihydro-1,4-benzoxazepin-5-one was used as a starting material.

$^1$H NMR (400 MHz, Methanol-$d_4$) δ 7.63 (d, J=7.9 Hz, 1H), 7.20-6.95 (m, 6H), 4.83-4.77 (m, 1H), 4.42 (s, 4H), 4.27-4.20 (m, 1H), 4.16 (dd, J=13.8, 3.7 Hz, 1H), 3.75 (d, J=5.4 Hz, 2H), 3.62 (dd, J=15.6, 3.6 Hz, 1H), 3.52-3.41 (m, 3H), 3.26 (dd, J=13.7, 8.1 Hz, 1H), 2.96-2.82 (m, 4H), 2.63 (h, J=7.5 Hz, 2H), 2.38 (s, 4H), 1.90 (t, J=5.6 Hz, 4H), 1.31 (d, J=6.4 Hz, 3H).

Example 253: Synthesis of 4-[(2R)-4-[(2R)-3-(3,4-dihydro-1H-isoquinolin-2-yl)-2-hydroxy-propyl]-8-[[(3R,4R)-3-fluoro-1-(2-hydroxyethyl)-4-piperidyl]oxy]-2-methyl-2,3-dihydro-1,4-benzoxazepin-5-one dihydrochloride

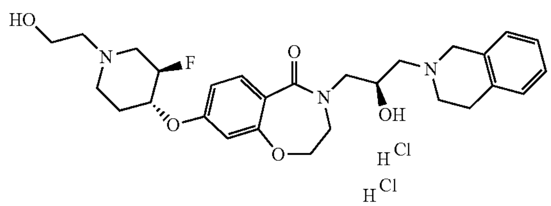

Example 253-1: Synthesis of 4-[(2R)-4-[(2R)-3-(3,4-dihydro-1H-isoquinolin-2-yl)]-8-[[(3R,4R)-3-fluoro-1-4-piperidyl]oxy]-2-methyl-2,3-dihydro-1,4-benzoxazepin-5-one dihydrochloride The intermediate in which Boc is substituted was synthesized in the same manner as in Example 140 except that (S)-tert-butyl 3-fluoro-4-methylsulfonyloxy-piperidine-1-carboxylate was used instead of 4-chlorotetrahydropyran. The obtained intermediate was dissolved in methanol, and 4 N hydrochloric acid solution dissolved in 1,4-dioxane was added thereto. The reaction solution was stirred at room temperature until the reaction was terminated, diluted with ethyldiethyl ether and filtered to obtain the title compound as a white solid in the form of dihydrochloride.

Example 253-2: Synthesis of 4-[(2R)-4-[(2R)-3-(3,4-dihydro-1H-isoquinolin-2-yl)-2-hydroxy-propyl]-8-[[(3R,4R)-3-fluoro-1-(2-hydroxyethyl)-4-piperidyl]oxy]-2-methyl-2,3-dihydro-1,4-benzoxazepin-5-one dihydrochloride The material obtained in Example 253-1 as a starting material was used in the same manner as in Example 162, and then the title compound was obtained by forming hydrochloride salt.

$^1$H NMR (400 MHz, Methanol-$d_4$) δ 7.76 (d, J=8.7 Hz, 1H), 7.40-7.19 (m, 4H), 6.94 (d, J=8.7 Hz, 1H), 6.80 (s, 1H), 5.13 (d, J=43.3 Hz, 1H), 4.97 (s, 1H), 4.67 (dd, J=15.4, 8.5 Hz, 1H), 4.57 (ddd, J=10.7, 7.0, 3.6 Hz, 1H), 4.53-4.42 (m, 3H), 4.05-3.83 (m, 5H), 3.77 (ddd, J=9.9, 8.1, 5.1 Hz, 5H), 3.65-3.57 (m, 2H), 3.54-3.36 (m, 6H), 3.29-3.07 (m, 2H), 2.53-2.18 (m, 2H).

Example 254: Synthesis of 4-[(2R)-3-(3,4-dihydro-1H-isoquinolin-2-yl)-2-hydroxy-propyl]-8-[[(3R,4R)-3-fluoro-1-(2-hydroxypropyl)-4-piperidyl]oxy]-2-methyl-2,3-dihydro-1,4-benzoxazepin-5-one divalent hydrochloride

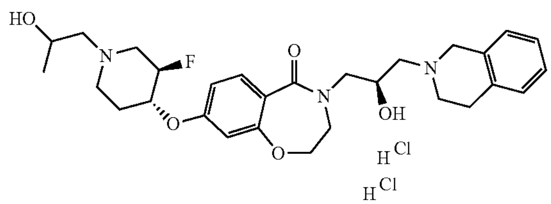

The material obtained in Example 253-1 as a starting material was used in the same manner as in Example 212, and then the title compound was obtained by forming hydrochloride salt.

$^1$H NMR (400 MHz, Methanol-$d_4$) δ 7.76 (d, J=8.6 Hz, 1H), 7.32 (q, J=7.5, 6.7 Hz, 3H), 7.23 (t, J=7.0 Hz, 1H), 6.93 (d, J=8.8 Hz, 1H), 6.79 (s, 1H), 5.23-5.01 (m, 1H), 4.96 (s, 1H), 4.67 (dd, J=15.4, 8.3 Hz, 1H), 4.56 (ddd, J=10.8, 7.0, 3.5 Hz, 1H), 4.52-4.41 (m, 3H), 4.26 (s, 1H), 3.98-3.70 (m, 7H), 3.63-3.35 (m, 7H), 3.29-3.06 (m, 4H), 2.60-2.18 (m, 2H), 1.29-1.25 (m, 3H).

Example 255: Synthesis of (2R)-4-[(2R)-3-[(2R)-3-(3,4-dihydro-1H-isoquinolin-2-yl)-2-hydroxy-propyl]-8-[[(3R,4R)-3-fluoro-1-(2-hydroxyethyl)-4-piperidyl]oxy]-2-methyl-2,3-dihydro-1,4-benzoxazepin-5-one dihydrochloride

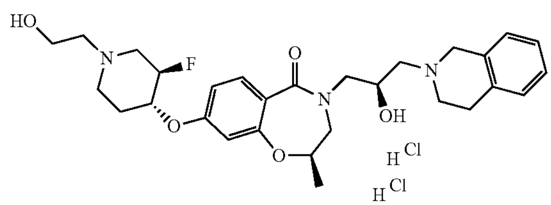

Example 255-1: Synthesis of (2R)-4-[(2R)-4-[(2R)-3-(3,4-dihydro-1H-isoquinolin-2-yl)]-8-[[(3R,4R)-3-fluoro-1-piperidyl]oxy]-2-methyl-2,3-dihydro-1,4-benzoxazepin-5-one dihydrochloride The intermediate in which Boc is substituted was synthesized by using the material obtained in the same manner as in Examples 140-1 to 140-5 except that [(1 S)-2-(tert-butoxycarbonylamino)-1-methyl-ethyl] methanesulfonate was used instead of [2-(tert-butoxycarbonylamino)-1-methyl-ethyl] methanesulfonate as a starting material and the method in the same manner as in Example 64 except that (S)-tert-butyl 3-fluoro-4-methylsulfonyloxy-piperidine-1-carboxylate is used instead of 4-chlorotetrahydropyran. The obtained intermediate was dissolved in methanol, and 4 N hydrochloric acid solution dissolved in 1,4-dioxane was added thereto. The reaction solution was stirred at room temperature until the reaction was terminated, diluted with ethyldiethyl ether and filtered to obtain the title compound as a white solid in the form of dihydrochloride.

Example 255-2: Synthesis of (2R)-4-[(2R)-4-[(2R)-3-(3,4-dihydro-1H-isoquinolin-2-yl)-2-hydroxy-propyl]-8-[[(3R,4R)-3-fluoro-1-(2-hydroxyethyl)-4-piperidyl]oxy]-2-methyl-2,3-dihydro-1,4-benzoxazepin-5-one dihydrochloride (2R)-4-[(2R)-4-[(2R)-3-(3,4-dihydro-1H-isoquinolin-2-yl)]-8-[[(3R,4R)-3-fluoro-1-piperidyl]oxy]-2-methyl-2,3-dihydro-1,4-benzoxazepin-5-one dihydrochloride obtained in Example 255-1 as a starting material was used in the same manner as in Example 162, and then the title compound was obtained by forming hydrochloride salt.

$^1$H NMR (400 MHz, Methanol-$d_4$) δ 7.70 (dd, J=8.8, 3.7 Hz, 1H), 7.39-7.20 (m, 4H), 6.96 (d, J=8.9 Hz, 1H), 6.77 (s, 1H), 5.13 (d, J=43.3 Hz, 1H), 4.97 (s, 1H), 4.79 (s, 1H), 4.68 (dd, J=15.3, 7.4 Hz, 1H), 4.55-4.42 (m, 2H), 3.96 (dt, J=14.4, 4.3 Hz, 5H), 3.71 (d, J=14.7 Hz, 3H), 3.64-3.35 (m, 1 OH), 3.30-3.13 (m, 2H), 2.57-2.20 (m, 2H), 1.36 (d, J=6.3 Hz, 3H).

Example 256: Synthesis of 8-[[3,3-difluoro-1-(2-hydroxyethyl)-4-piperidyl]oxy]-4-[(2R)-3-(3,4-dihydro-1H-isoquinolin-2-yl)-2-hydroxy-propyl]-2,2-dimethyl-3H-pyrido[3,2-f][1,4]oxazepin-5-one

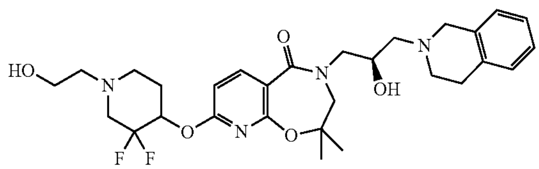 [SMILES: CC1(C)CN(C[C@H](O)CN2CCc3ccccc3C2)C(=O)c2ccc(OC3CCN(CCO)CC3(F)F)nc2O1]

Example 256-1: Synthesis of 8-[(3,3-difluoro-4-piperidyl)oxy]-2,2-dimethyl-3,4-dihydropyrido[3,2-f][1,4]oxazepin-5-one The material, which is obtained by changing 1-[(4-methoxyphenyl)methylamino]propan-2-ol to 1-[(4-methoxyphenyl)methylamino]-2-methyl-propan-2-ol in Example 144, as a starting material was used in the same manner as in Examples 144-1 to 144-4 to obtain the title compound, except that tert-butyl 3,3-difluoro-4-hydroxypiperidine-1-carboxylate was used instead of tert-butyl 4-hydroxypiperidine-1-carboxylate in Example 144-3.

Example 256-2: Synthesis of 8-[[3,3-difluoro-1-(2-hydroxyethyl)-4-piperidyl]oxy]-2,2-dimethyl-3,4-dihydropyrido[3,2-f][1,4]oxazepin-5-one 8-[(3,3-Difluoro-4-piperidyl)oxy]-2,2-dimethyl-3,4-dihydropyrido[3,2-f][1,4]oxazepin-5-one obtained in Example 256-1 as a starting material was used in the same manner as in Example 163 to obtain the title compound, except that 2-iodoethanol was used instead of 2-fluoroethyl para-toluenesulfonate.

Example 256-3: Synthesis of 8-[[3,3-difluoro-1-(2-hydroxyethyl)-4-piperidyl]oxy]-4-[(2R)-3-(3,4-dihydro-1H-isoquinolin-2-yl)-2-hydroxy-propyl]-2,2-dimethyl-3H-pyrido[3,2-f][1,4]oxazepin-5-one 8-[[3,3-Difluoro-1-(2-hydroxyethyl)-4-piperidyl]oxy]-2,2-dimethyl-3,4-dihydropyrido[3,2-f][1,4]oxazepin-5-one obtained in Example 256-2 as a starting material was used in the same manner as in Example 5 to obtain the title compound.

$^1$H NMR (400 MHz, Methanol-$d_4$) δ 8.10 (d, J=8.4 Hz, 1H), 7.18-7.02 (m, 4H), 6.70 (d, J=8.4 Hz, 1H), 5.49-5.36 (m, 1H), 4.27 (s, 1H), 4.11-3.97 (m, 1H), 3.77 (s, 2H), 3.71 (t, J=5.8 Hz, 2H), 3.69-3.58 (m, 2H), 3.44 (dd, J=14.4, 8.9 Hz, 1H), 3.08 (s, 1H), 2.91 (dd, J=16.5, 5.2 Hz, 4H), 2.81 (s, 2H), 2.73-2.54 (m, 5H), 2.23-2.09 (m, 1H, 1.94 (s, 1H), 1.48 (d, J=1.5 Hz, 3H), 1.44 (d, J=1.7 Hz, 3H).

Example 257: Synthesis of 4-[(2R)-3-(3,4-dihydro-1H-isoquinolin-2-yl)-2-hydroxypropyl]-8-[1-(1-piperidyl)ethyl]-2,3-dihydro-1,4-benzoxazepin-5-one

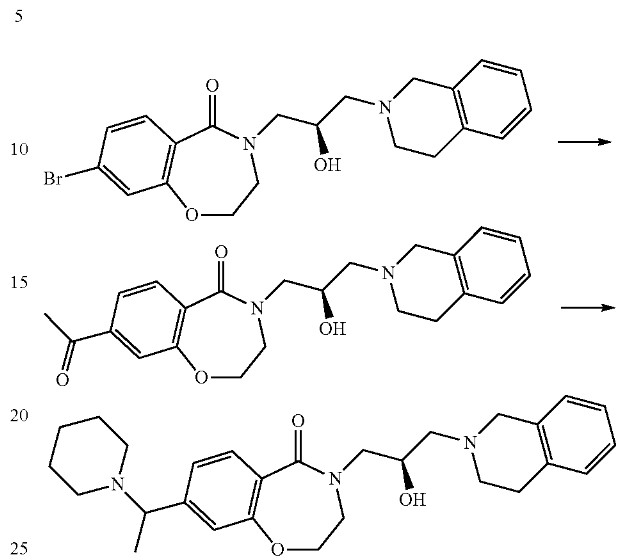

Example 257-1: Synthesis of 8-acetyl-4-[(2R)-3-(3,4-dihydro-1H-isoquinolin-2-yl)-2-hydroxypropyl]-2,3-dihydro-1,4-benz oxazepin-5-one 8-Bromo-4-[(2R)-3-(3,4-dihydro-1H-isoquinolin-2-yl)-2-hydroxy-propyl]-2,3-dihydro-1,4-benzoxazepin-5-one (200 mg, 0.464 mmol) obtained in Example 10-1, tributyl(1-ethoxyvinyl)tin (204 µl, 0.603 mmol), tetrakis(triphenylphosphine)palladium(0) (27 mg, 0.023 mmol) were added to 4 mL of toluene and heated to reflux for one day, while stirring. After completion of the reaction, 35% hydrochloric acid aqueous solution was added and stirred for 1 hour, followed by basification with sodium hydroxide aqueous solution until the pH reached 14, followed by extraction with ethyl acetate. The organic layer was dried over anhydrous magnesium sulfate, filtered, concentrated under reduced pressure and purified by flash chromatography to obtain the title compound (80 mg).

Example 257-2: Synthesis of 4-[(2R)-3-(3,4-dihydro-1H-isoquinolin-2-yl)-2-hydroxypropyl]-8-[1-(1-piperidyl)ethyl]-2,3-dihydro-1,4-benzoxazepin-5-one 8-Acetyl-4-[(2R)-3-(3,4-dihydro-1H-isoquinolin-2-yl)-2-hydroxypropyl]-2,3-dihydro-1,4-benzoxazepin-5-one (100 mg, 0.254 mmol) obtained in Example 257-1, piperidine (50 µl, 0.508 mmol) and titanium(IV) isopropoxide (223 µl, 0.762 mmol) were dissolved in tetrahydrofuran and heated to reflux for 4 hours. Then, sodium cyanoborohydride (64 mg, 1.016 mmol) was added thereto and heated to 45° C. and stirred for one day. After completion of the reaction, the reaction solution was extracted with saturated aqueous sodium chloride solution and ethyl acetate and purified by flash chromatography to obtain the title compound (6 mg).

$^1$H NMR (400 MHz, Methanol-$d_4$) δ 7.69 (d, J=8.0 Hz, 1H), 7.21-7.00 (m, 6H), 4.49 (t, J=5.1 Hz, 2H), 4.23 (q, J=7.3, 5.7 Hz, 1H), 3.99 (dd, J=13.9, 3.7 Hz, 1H), 3.81-3.68 (m, 4H), 3.55 (q, J=6.8 Hz, 1H), 3.47 (dd, J=13.9, 7.6 Hz, 1H), 2.99-2.85 (m, 4H), 2.71-2.62 (m, 2H), 2.56 (s, 2H), 2.51-2.41 (m, 2H), 2.04 (d, J=9.5 Hz, 1H), 1.62 (q, J=5.9, 5.3 Hz, 4H), 1.43 (d, J=6.8 Hz, 4H).

Example 258: Synthesis of 4-[(2R)-3-(3,4-dihydro-1H-isoquinolin-2-yl)-2-hydroxypropyl]-8-[1-(4-hydroxy-1-piperidyl)ethyl]-2,3-dihydro-1,4-benzoxazepin-5-one

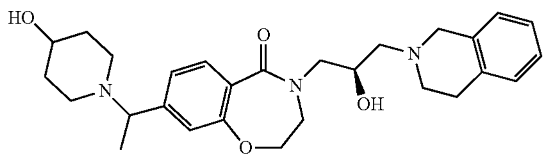 [SMILES: CC(c1ccc2c(c1)OCCN(C[C@H](O)CN1CCc3ccccc3C1)C2=O)N1CCC(O)CC1]

The title compound was synthesized in the same manner as in Example 257, except that 4-hydroxypiperidine was used instead of piperidine in Example 257-2.

$^{1}$H NMR (400 MHz, Methanol-$d_4$) δ 7.69 (d, J=8.0 Hz, 1H), 7.22-7.00 (m, 6H), 4.49 (t, J=5.1 Hz, 2H), 4.25 (dt, J=7.7, 3.7 Hz, 1H), 3.98 (dd, J=13.9, 3.7 Hz, 1H), 3.81 (s, 2H), 3.73 (t, J=5.1 Hz, 2H), 3.64-3.53 (m, 2H), 3.48 (dd, J=13.9, 7.5 Hz, 1H), 2.94 (dp, J=8.9, 4.6, 3.7 Hz, 5H), 2.83-2.73 (m, 1H), 2.73-2.61 (m, 2H), 2.24 (t, J=10.7 Hz, 2H), 1.93-1.79 (m, 2H), 1.70-1.50 (m, 2H), 1.43 (d, J=6.7 Hz, 3H).

Example 259: Synthesis of 4-[(2R)-3-(3,4-dihydro-1H-isoquinolin-2-yl)-2-hydroxypropyl]-8-[1-(4-methoxy-1-piperidyl)ethyl]-2,3-dihydro-1,4-benzoxazepin-5-one

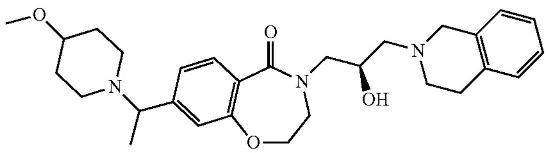 [SMILES: COC1CCN(C(C)c2ccc3c(c2)OCCN(C[C@H](O)CN2CCc4ccccc4C2)C3=O)CC1]

The title compound was synthesized in the same manner as in Example 257, except that 4-methoxypiperidine was used instead of piperidine in Example 257-2.

$^{1}$H NMR (400 MHz, Methanol-$d_4$) δ 7.69 (d, J=8.0 Hz, 1H), 7.20-7.00 (m, 6H), 4.49 (t, J=5.1 Hz, 2H), 4.30-4.19 (m, 1H), 3.98 (dd, J=13.9, 3.7 Hz, 1H), 3.79 (d, J=2.2 Hz, 2H), 3.73 (q, J=6.0, 5.1 Hz, 2H), 3.57-3.42 (m, 2H), 3.24 (tt, J=8.2, 3.9 Hz, 1H), 2.93 (dt, J=8.0, 4.2 Hz, 5H), 2.76-2.64 (m, 3H), 2.31-2.18 (m, 2H), 1.93 (d, J=11.5 Hz, 2H), 1.62-1.52 (m, 2H), 1.41 (d, J=6.8 Hz, 3H).

Example 260: Synthesis of 4-[(2R)-3-(3,4-dihydro-1H-isoquinolin-2-yl)-2-hydroxypropyl]-8-[1-(3-hydroxy-3-methyl-pyrrolidin-1-yl)ethyl]-2,3-dihydro-1,4-benzoxazepin-5-one

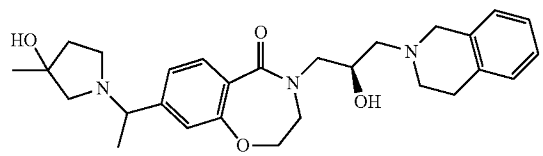 [SMILES: CC(c1ccc2c(c1)OCCN(C[C@H](O)CN1CCc3ccccc3C1)C2=O)N1CCC(C)(O)C1]

The title compound was synthesized in the same manner as in Example 257, except that 3-methylpyrrolidin-3-ol was used instead of piperidine in Example 257-2.

$^{1}$H NMR (400 MHz, Methanol-$d_4$) δ 7.69 (dd, J=8.0, 1.4 Hz, 1H), 7.21 (dd, J=8.1, 1.8 Hz, 1H), 7.16-6.96 (m, 5H), 4.49 (t, J=5.1 Hz, 2H), 4.25 (qd, J=7.6, 4.6 Hz, 1H), 3.98 (dd, J=13.9, 3.7 Hz, 1H), 3.80 (d, J=2.2 Hz, 2H), 3.73 (q, J=6.5, 5.1 Hz, 2H), 3.52-3.42 (m, 2H), 2.93 (dt, J=10.1, 5.1 Hz, 4H), 2.82-2.49 (m, 6H), 1.89 (td, J=7.4, 3.2 Hz, 2H), 1.42 (t, J=6.2 Hz, 3H), 1.35 (s, 3H).

Example 261: Synthesis of (2R)-4-[(2R)-3-(3,4-dihydro-1H-isoquinolin-2-yl)-2-hydroxy-propyl]-8-[[1-(2-hydroxyethyl)-4-piperidyl]oxy]-2-methyl-2,3-dihydro-1,4-benzoxazepin-5-one dihydrochloride

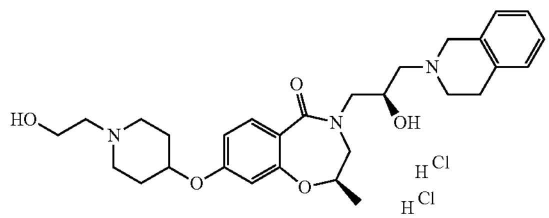

The title compound was obtained by forming hydrochloride salt with (2R)-4-[(2R)-3-(3,4-dihydro-1H-isoquinolin-2-yl)-2-hydroxy-propyl]-8-[[1-(2-hydroxyethyl)-4-piperidyl]oxy]-2-methyl-2,3-dihydro-1,4-benzoxazepin-5-one obtained in Example 219.

$^{1}$H NMR (400 MHz, Methanol-$d_4$) δ 7.67 (dt, J=9.1, 4.6 Hz, 1H), 7.40-7.18 (m, 4H), 6.95-6.80 (m, 1H), 6.68 (d, J=15.4 Hz, 1H), 4.81-4.62 (m, 4H), 4.47 (dd, J=15.3, 10.2 Hz, 2H), 4.12 (dd, J=10.9, 5.7 Hz, 1H), 4.04-3.80 (m, 5H), 3.78-3.36 (m, 9H), 3.31-3.01 (m, 4H), 2.40 (d, J=14.1 Hz, 1H), 2.23 (d, J=12.5 Hz, 2H), 2.07-1.94 (m, 1H), 1.36 (d, J=6.3 Hz, 3H).

Example 262: Synthesis of 4-[(2R)-3-(3,4-dihydro-1H-isoquinolin-2-yl)-2-hydroxy-propyl]-8-[[1-(2-methoxyethyl)-4-piperidyl]oxy]-2,2-dimethyl-3H-pyrido[3,2-f][1,4]oxazepin-5-one

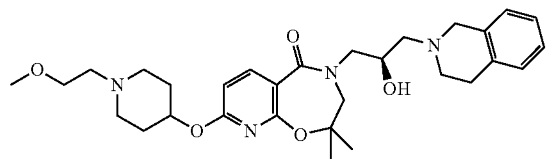 [SMILES: COCCN1CCC(Oc2ccc3c(n2)OC(C)(C)CN(C[C@H](O)CN2CCc4ccccc4C2)C3=O)CC1]

4-[(2R)-3-(3,4-dihydro-1H-isoquinolin-2-yl)-2-hydroxy-propyl]-2,2-dimethyl-8-(4-piperidyloxy)-3H-pyrido[3,2-f][1,4]oxazepin-5-one dihydrochloride as a starting material was used in the same manner as in Example 224 to obtain the title compound.

$^{1}$H NMR (400 MHz, Methanol-$d_4$) δ 8.04 (d, J=8.4 Hz, 1H), 7.16-7.01 (m, 4H), 6.60 (d, J=8.4 Hz, 1H), 5.07 (dt, J=8.3, 4.2 Hz, 1H), 4.32-4.20 (m, 1H), 4.03 (dd, J=13.8, 3.6 Hz, 1H), 3.75 (s, 2H), 3.71-3.60 (m, 2H), 3.57 (t, J=5.6 Hz, 2H), 3.41 (dd, J=13.8, 8.2 Hz, 3H), 3.36 (s, 4H), 2.93 (d, J=5.7 Hz, 2H), 2.91-2.78 (m, 4H), 2.64 (q, J=5.2, 4.4 Hz, 4H), 2.47 (t, J=9.9 Hz, 2H), 2.12-2.01 (m, 2H), 1.83 (q, J=16.6, 13.0 Hz, 2H), 1.48 (s, 3H), 1.43 (s, 3H).

Example 263: Synthesis of 4-[(2R)-3-(3,4-dihydro-1H-isoquinolin-2-yl)-2-hydroxy-propyl]-8-[(3S)-1-(oxetan-3-yl)pyrrolidin-3-yl]oxy-2,3-dihydro-1,4-benzoxazepin-5-one

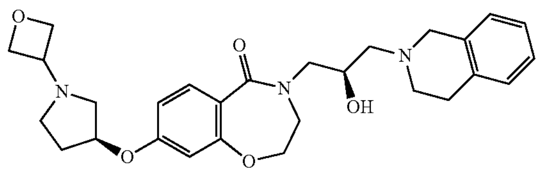 [SMILES: O=C1c2ccc(O[C@H]3CCN(C4COC4)C3)cc2OCCN1C[C@H](O)CN1CCc2ccccc2C1]

Example 263-1: Synthesis of 4-[(2R)-3-(3,4-dihydro-1H-isoquinolin-2-yl)-2-hydroxy-propyl]-8-[(3S)-pyrrolidin-3-yl]oxy-2,3-dihydro-1,4-benzoxazepin-5-one dihydrochloride The material, which is obtained by changing 4-chlorotetrahydropyran to (S)-1-(tert-butoxycarbonyl)-3-pyrrolidinol in Example 64, as a starting material was used in the same manner as in Example 78-1 to obtain the title compound.

Example 263-2: Synthesis of 4-[(2R)-3-(3,4-dihydro-1H-isoquinolin-2-yl)-2-hydroxy-propyl]-8-[(3S)-1-(oxetan-3-yl)pyrrolidin-3-yl]oxy-2,3-dihydro-1,4-benzoxazepin-5-one 4-[(2R)-3-(3,4-dihydro-1H-isoquinolin-2-yl)-2-hydroxy-propyl]-8-[(3S)-pyrrolidin-3-yl]oxy-2,3-dihydro-1,4-benzoxazepin-5-one dihydrochloride obtained in Example 263-1 as a starting material was used in the same manner as in Example 87 to obtain the title compound, except that oxetan-3-one was used instead of paraformaldehyde.

$^1$H NMR (400 MHz, Methanol-$d_4$) δ 7.68 (d, J=8.8 Hz, 1H), 7.19-7.00 (m, 4H), 6.73 (dd, J=8.8, 2.5 Hz, 1H), 6.54 (d, J=2.4 Hz, 1H), 5.02-4.94 (m, 1H), 4.75 (t, J=6.7 Hz, 2H), 4.64 (dt, J=11.8, 6.1 Hz, 2H), 4.48 (t, J=5.0 Hz, 2H), 4.23 (q, J=7.2, 5.8 Hz, 1H), 3.97 (dd, J=13.9, 3.7 Hz, 1H), 3.82-3.65 (m, 5H), 3.43 (dd, J=13.9, 7.6 Hz, 1H), 3.00-2.87 (m, 5H), 2.87-2.79 (m, 2H), 2.70-2.62 (m, 2H), 2.56 (td, J=8.5, 6.2 Hz, 1H), 2.38 (dq, J=14.0, 7.1 Hz, 1H), 2.06-1.95 (m, 1H).

Example 264: Synthesis of (2R)-4-[(2R)-3-(3,4-dihydro-1H-isoquinolin-2-yl)-2-hydroxy-propyl]-2-methyl-8-[(3S)-1-meth ylpyrrolidin-3-yl]oxy-2,3-dihydro-1,4-benzoxazepin-5-one

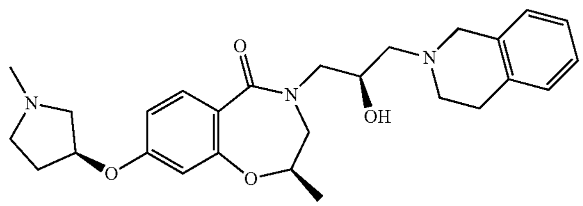 [SMILES: C[C@@H]1CN(C[C@H](O)CN2CCc3ccccc3C2)C(=O)c2ccc(O[C@H]3CCN(C)C3)cc2O1]

Example 264-1: Synthesis of (2R)-4-[(2R)-3-(3,4-dihydro-1H-isoquinolin-2-yl)-2-hydroxy-propyl]-8-hydroxy-2-methyl-2,3-dihydro-1,4-benzoxazepin-5-one The title compound was synthesized in the same manner as in Examples 140-1 to 140-5, except that [(1S)-2-(tert-butoxycarbonylamino)-1-methyl-ethyl] methanesulfonate was used instead of [2-(tert-butoxycarbonylamino)-1-methyl-ethyl] methanesulfonate in Example 140-1.

Example 264-2: Synthesis of (2R)-4-[(2R)-3-(3,4-dihydro-1H-isoquinolin-2-yl)-2-hydroxy-propyl]-2-methyl-8-[(3S)-pyrrolidin-3-yl]oxy-2,3-dihydro-1,4-benzoxazepin-5-one dihydrochloride The intermediate was synthesized by using (2R)-4-[(2R)-3-(3,4-dihydro-1H-isoquinolin-2-yl)-2-hydroxy-propyl]-8-hydroxy-2-methyl-2,3-dihydro-1,4-benzoxazepin-5-one obtained in Example 264-1 as a starting material in the same manner as in Example 64 except that (S)-1-(tert-butoxycarbonyl)-3-pyrrolidinol is used instead of 4-chlorotetrahydropyran. 4 M hydrochloric acid solution dissolved in 1,4-dioxane was slowly added thereto. The reaction solution was stirred at room temperature, diluted with diethyl ether and filtered to obtain the title compound as a white solid.

Example 264-3: Synthesis of (2R)-4-[(2R)-3-(3,4-dihydro-1H-isoquinolin-2-yl)-2-hydroxy-propyl]-2-methyl-8-[(3S)-1-meth ylpyrrolidin-3-yl]oxy-2,3-dihydro-1,4-benzoxazepin-5-one (2R)-4-[(2R)-3-(3,4-dihydro-1H-isoquinolin-2-yl)-2-hydroxy-propyl]-2-methyl-8-[(3S)-pyrrolidin-3-yl]oxy-2,3-dihydro-1,4-benzoxazepin-5-one dihydrochloride obtained in Example 264-2 as a starting material was used in the same manner as in Example 87 to obtain the title compound.

$^1$H NMR (400 MHz, Methanol-$d_4$) δ 7.56 (d, J=8.7 Hz, 1H), 7.11-6.92 (m, 4H), 6.67 (dd, J=8.7, 2.4 Hz, 1H), 6.45 (d, J=2.4 Hz, 1H), 4.93 (s, 1H), 4.72 (td, J=7.2, 3.4 Hz, 1H), 4.23-4.11 (m, 1H), 4.07 (dd, J=13.9, 3.7 Hz, 1H), 3.73 (s, 2H), 3.56 (dd, J=15.6, 3.4 Hz, 1H), 3.42 (dd, J=15.6, 7.6 Hz, 1H), 3.17 (dd, J=13.8, 8.1 Hz, 1H), 3.02-2.79 (m, 7H), 2.68-2.49 (m, 3H), 2.42 (s, 4H), 1.96 (dt, J=14.8, 6.6 Hz, 1H), 1.26 (d, J=6.4 Hz, 3H).

Example 265: Synthesis of 4-[(2R)-3-(3,4-dihydro-1H-isoquinolinon-2-yl)-2-hydroxy-propyl]-8-[(3R)-tetrahydrofuran-3-yl]oxy-2,3-dihydro-1,4-benzoxazepin-5-one

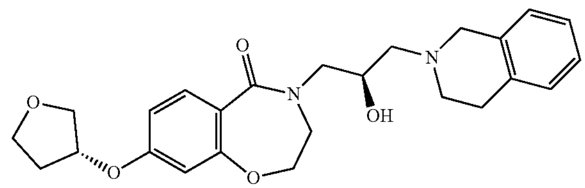 [SMILES: O=C1c2ccc(O[C@@H]3CCOC3)cc2OCCN1C[C@H](O)CN1CCc2ccccc2C1]

The title compound was synthesized in the same manner as in Example 64, except that [(3S)-tetrahydrofuran-3-yl] methanesulfonate was used instead of 4-chlorotetrahydropyran.

$^1$H NMR (400 MHz, Methanol-$d_4$) δ 7.68 (d, J=8.7 Hz, 1H), 7.21-6.98 (m, 4H), 6.74 (dd, J=8.8, 2.5 Hz, 1H), 6.56

(d, J=2.4 Hz, 1H), 5.07 (d, J=5.6 Hz, 1H), 4.48 (t, J=5.0 Hz, 2H), 4.24 (s, 1H), 4.04-3.85 (m, 5H), 3.85-3.67 (m, 4H), 3.44 (dd, J=13.8, 7.6 Hz, 1H), 3.03-2.84 (m, 4H), 2.75-2.60 (m, 2H), 2.33-2.23 (m, 1H), 2.16-2.05 (m, 1H).

Example 266: Synthesis of 4-[(2R)-3-(3,4-dihydro-1H-isoquinolinon-2-yl)-2-hydroxy-propyl]-8-[(3S)-tetrahydrofuran-3-yl]oxy-2,3-dihydro-1,4-benzoxazepin-5-one

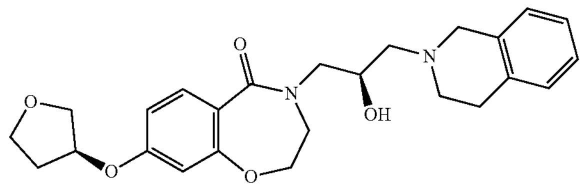 [SMILES: O=C1c2ccc(O[C@H]3CCOC3)cc2OCCN1C[C@H](O)CN1CCc2ccccc2C1]

The title compound was synthesized in the same manner as in Example 64, except that [(3R)-tetrahydrofuran-3-yl] methanesulfonate was used instead of 4-chlorotetrahydropyran.

$^1$H NMR (400 MHz, Methanol-d$_4$) δ 7.68 (d, J=8.8 Hz, 1H), 7.19-6.99 (m, 4H), 6.74 (dd, J=8.8, 2.5 Hz, 1H), 6.56 (d, J=2.4 Hz, 1H), 5.13-5.02 (m, 1H), 4.48 (t, J=5.0 Hz, 2H), 4.23 (q, J=7.5, 5.9 Hz, 1H), 4.02-3.84 (m, 5H), 3.82-3.69 (m, 4H), 3.44 (dd, J=13.9, 7.6 Hz, 1H), 3.00-2.82 (m, 4H), 2.67 (dd, J=6.2, 2.3 Hz, 2H), 2.36-2.21 (m, 1H), 2.12 (dt, J=12.7, 5.8 Hz, 1H).

Example 267: Synthesis of (2R)-4-[(2R)-3-(3,4-dihydro-1H-isoquinolin-2-yl)-2-hydroxy-propyl]-8-[[1-[(2S)-2-hydroxypropyl]-4-piperidyl]oxy]-2-methyl-2,3-dihydro-1,4-benzoxazepin-5-one

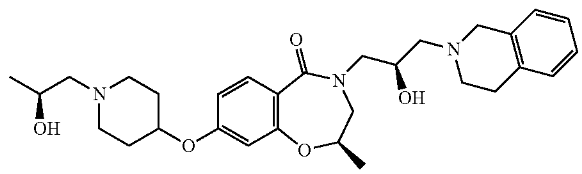 [SMILES: C[C@H](O)CN1CCC(Oc2ccc3c(c2)O[C@H](C)CN(C[C@H](O)CN2CCc4ccccc4C2)C3=O)CC1]

The material, which is obtained by changing [2-(tert-butoxycarbonylamino)-1-methyl-ethyl] methanesulfonate to [(1 S)-2-(tert-butoxycarbonylamino)-1-methyl-ethyl] methanesulfonate in Example 140, as a starting material was used in the same manner as in Example 212 to obtain the title compound, except that (S)-2-methoxirane was used instead of 2-methoxirane.

$^1$H NMR (400 MHz, Methanol-d$_4$) δ 7.62 (d, J=8.7 Hz, 1H), 7.16-6.97 (m, 4H), 6.78 (dd, J=8.7, 2.5 Hz, 1H), 6.56 (d, J=2.4 Hz, 1H), 4.79 (td, J=7.1, 3.3 Hz, 1H), 4.51 (s, 1H), 4.23 (q, J=8.0, 5.8 Hz, 1H), 4.15 (dd, J=13.7, 3.7 Hz, 1H), 3.97 (dt, J=12.5, 6.2 Hz, 1H), 3.77 (s, 2H), 3.64 (dd, J=15.6, 3.4 Hz, 1H), 3.49 (dd, J=15.6, 7.5 Hz, 1H), 3.23 (dd, J=13.7, 8.2 Hz, 1H), 2.99-2.79 (m, 6H), 2.70-2.40 (m, 6H), 2.06 (s, 2H), 1.86 (s, 2H), 1.33 (d, J=6.4 Hz, 3H), 1.18 (d, J=6.3 Hz, 3H).

Example 268: Synthesis of (2R)-4-[(2R)-3-(3,4-dihydro-1H-isoquinolin-2-yl)-2-hydroxy-propyl]-8-[[1-[(2R)-2-hydroxypropyl]-4-piperidyl]oxy]-2-methyl-2,3-dihydro-1,4-benzoxazepin-5-one

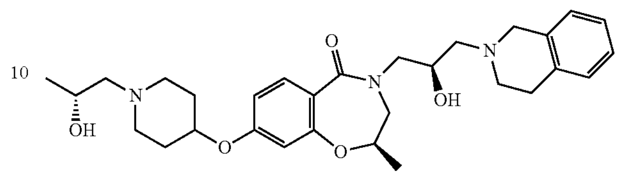

The material, which is obtained by changing [2-(tert-butoxycarbonylamino)-1-methyl-ethyl] methanesulfonate to [(1 S)-2-(tert-butoxycarbonylamino)-1-methyl-ethyl] methanesulfonate in Example 140, as a starting material was used in the same manner as in Example 212 to obtain the title compound, except that (R)-2-methoxirane was used instead of 2-methoxirane.

$^1$H NMR (400 MHz, Methanol-d$_4$) δ 7.62 (d, J=8.7 Hz, 1H), 7.16-6.99 (m, 4H), 6.78 (dd, J=8.8, 2.5 Hz, 1H), 6.56 (d, J=2.4 Hz, 1H), 4.79 (td, J=7.0, 3.3 Hz, 1H), 4.51 (s, 1H), 4.24 (dt, J=12.8, 6.1 Hz, 1H), 4.15 (dd, J=13.8, 3.6 Hz, 1H), 3.97 (h, J=6.2, 5.5 Hz, 1H), 3.77 (s, 2H), 3.63 (dd, J=15.6, 3.4 Hz, 1H), 3.49 (dd, J=15.6, 7.6 Hz, 1H), 3.23 (dd, J=13.8, 8.1 Hz, 1H), 2.99-2.80 (m, 6H), 2.69-2.40 (m, 6H), 2.05 (d, J=11.0 Hz, 2H), 1.93-1.80 (m, 2H), 1.33 (d, J=6.4 Hz, 3H), 1.18 (d, J=6.2 Hz, 3H).

Example 269: Synthesis of 8-[cyclopropyl(hydroxy) methyl]-4-[(2R)-3-(3,4-dihydro-1H-isoquinolin-2-yl)-2-hydroxy-propyl]-2,3-dihydro-1,4-benzoxazepin-5-one

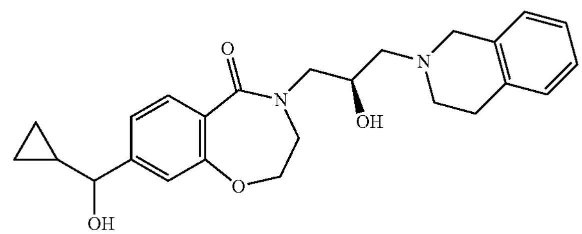 [SMILES: O=C1c2ccc(C(O)C3CC3)cc2OCCN1C[C@H](O)CN1CCc2ccccc2C1]

8-(Cyclopropanecarbonyl)-4-[(2R)-3-(3,4-dihydro-1H-isoquinolin-2-yl)-2-hydroxy-propyl]-2,3-dihydro-1,4-benzoxazepin-5-one (1 equiv) obtained in Example 216 was dissolved in methanol, and an excess of sodium borohydride was added thereto. The reaction solution was stirred at room temperature for 10 minutes and extracted with ethyl acetate. The extracted organic solution was concentrated under reduced pressure and purified by flash chromatography to obtain the title compound.

$^1$H NMR (400 MHz, Methanol-d$_4$) δ 7.47 (d, J=8.0 Hz, 1H), 7.05 (dd, J=8.1, 1.6 Hz, 1H), 6.97-6.82 (m, 5H), 4.28 (t, J=5.2 Hz, 2H), 4.10-4.00 (m, 1H), 3.84-3.73 (m, 2H), 3.60 (s, 2H), 3.58-3.44 (m, 3H), 3.26 (dd, J=13.9, 7.6 Hz, 1H), 2.74 (dd, J=10.0, 4.5 Hz, 4H), 2.56-2.42 (m, 2H), 0.93 (tdd, J=8.0, 5.4, 3.0 Hz, 1H), 0.48-0.37 (m, 1H), 0.37-0.26 (m, 2H), 0.25-0.15 (m, 1H)

Example 270: Synthesis of 8-[cyclopentyl(hydroxy)methyl]-4-[(2R)-3-(3,4-dihydro-1H-isoquinolin-2-yl)-2-hydroxy-propyl]-2,3-dihydro-1,4-benzoxazepin-5-one

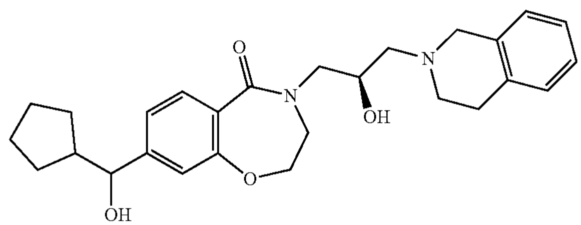 [SMILES: O=C1c2ccc(C(O)C3CCCC3)cc2OCCN1C[C@H](O)CN1CCc2ccccc2C1]

8-(Cyclopentanecarbonyl)-4-[(2R)-3-(3,4-dihydro-1H-isoquinolin-2-yl)-2-hydroxy-propyl]-2,3-dihydro-1,4-benzoxazepin-5-one obtained in Example 217 as a starting material was used in the same manner as in Example 269 to obtain the title compound.

$^1$H NMR (400 MHz, Methanol-$d_4$) δ 7.66 (d, J=8.0 Hz, 1H), 7.22-7.01 (m, 5H), 4.48 (t, J=5.1 Hz, 2H), 4.37 (d, J=8.2 Hz, 1H), 4.25 (s, 1H), 3.99 (dd, J=13.9, 3.7 Hz, 1H), 3.79 (s, 2H), 3.71 (t, J=5.3 Hz, 2H), 3.46 (dd, J=13.9, 7.7 Hz, 1H), 3.01-2.85 (m, 4H), 2.74-2.61 (m, 2H), 2.19 (q, J=8.2 Hz, 1H), 1.90-1.80 (m, 1H), 1.74-1.46 (m, 6H), 1.44-1.34 (m, 1H), 1.30-1.16 (m, 1H).

Example 271: Synthesis of 4-[(2R)-3-(3,4-dihydro-1H-isoquinolin-2-yl)-2-hydroxy-propyl]-8-[(3R)-1-(oxetan-3-yl)pyrrolidin-3-yl]oxy-2,3-dihydro-1,4-benzoxazepin-5-one

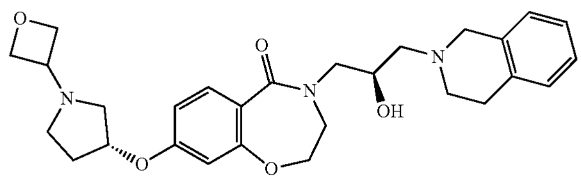 [SMILES: O=C1c2ccc(O[C@@H]3CCN(C4COC4)C3)cc2OCCN1C[C@H](O)CN1CCc2ccccc2C1]

Example 271-1: Synthesis of 4-[(2R)-3-(3,4-dihydro-1H-isoquinolin-2-yl)-2-hydroxy-propyl]-8-[(3R)-pyrrolidin-3-yl]oxy-2,3-dihydro-1,4-benzoxazepin-5-one dihydrochloride The material, which is obtained by changing 4-chlorotetrahydropyran to (R)-1-(tert-butoxycarbonyl)-3-pyrrolidinol in Example 64, as a starting material was used in the same manner as in Example 78-1 to obtain the title compound.

Example 271-2: Synthesis of 4-[(2R)-3-(3,4-dihydro-1H-isoquinolin-2-yl)-2-hydroxy-propyl]-8-[(3R)-1-(oxetan-3-yl)pyrrolidin-3-yl]oxy-2,3-dihydro-1,4-benzoxazepin-5-one 4-[(2R)-3-(3,4-dihydro-1H-isoquinolin-2-yl)-2-hydroxy-propyl]-8-[(3R)-pyrrolidin-3-yl]oxy-2,3-dihydro-1,4-benzoxazepin-5-one dihydrochloride obtained in Example 271-1 as a starting material was used in the same manner as in Example 87 to obtain the title compound except that oxetan-3-one was used instead of paraformaldehyde.

$^1$H NMR (400 MHz, Methanol-$d_4$) δ 7.68 (d, J=8.8 Hz, 1H), 7.16-7.02 (m, 4H), 6.73 (dd, J=8.8, 2.5 Hz, 1H), 6.54 (d, J=2.4 Hz, 1H), 4.98 (td, J=6.1, 5.3, 2.8 Hz, 1H), 4.75 (t, J=6.7 Hz, 2H), 4.64 (dt, J=11.8, 6.1 Hz, 2H), 4.48 (t, J=4.9 Hz, 2H), 4.23 (qd, J=7.2, 3.7 Hz, 1H), 3.98 (dd, J=13.9, 3.6 Hz, 1H), 3.80-3.71 (m, 5H), 3.42 (dd, J=13.9, 7.7 Hz, 1H), 2.98-2.80 (m, 7H), 2.69-2.62 (m, 2H), 2.56 (ddd, J=9.2, 7.8, 6.1 Hz, 1H), 2.38 (dq, J=14.0, 7.1 Hz, 1H), 2.01 (dt, J=13.7, 4.4 Hz, 1H).

Example 272: Synthesis of 4-[(2R)-3-(3,4-dihydro-1H-isoquinolin-2-yl)-2-hydroxy-propyl]-8-[(3R)-1-(2-methoxyethyl)pyrrolidin-3-yl]oxy-2,3-dihydro-1,4-benzoxazepin-5-one

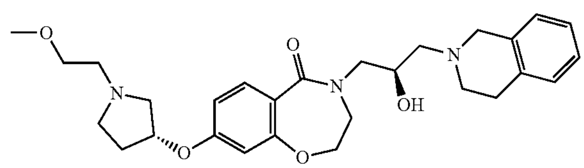 [SMILES: COCCN1CC[C@@H](Oc2ccc3c(c2)OCCN(C[C@H](O)CN2CCc4ccccc4C2)C3=O)C1]

4-[(2R)-3-(3,4-dihydro-1H-isoquinolin-2-yl)-2-hydroxy-propyl]-8-[(3R)-pyrrolidin-3-yl]oxy-2,3-dihydro-1,4-benzoxazepin-5-one dihydrochloride obtained in Example 271-1 as a starting material was used in the same manner as in Example 224 to obtain the title compound.

$^1$H NMR (400 MHz, Methanol-$d_4$) δ 7.68 (d, J=8.7 Hz, 1H), 7.18-7.00 (m, 4H), 6.71 (dd, J=8.8, 2.5 Hz, 1H), 6.53 (d, J=2.4 Hz, 1H), 4.95 (ddd, J=7.7, 5.7, 2.9 Hz, 1H), 4.48 (t, J=5.0 Hz, 2H), 4.23 (tdd, J=7.6, 6.3, 5.2, 3.7 Hz, 1H), 3.98 (dd, J=13.9, 3.6 Hz, 1H), 3.79-3.70 (m, 4H), 3.56 (t, J=5.6 Hz, 2H), 3.42 (dd, J=13.9, 7.7 Hz, 1H), 3.36 (s, 3H), 2.98-2.86 (m, 6H), 2.75 (tq, J=12.7, 6.4, 5.4 Hz, 2H), 2.66-2.60 (m, 2H), 2.37 (dtd, J=13.6, 7.6, 5.9 Hz, 1H), 1.96 (dtd, J=13.2, 6.8, 6.4, 2.2 Hz, 1H).

Example 273: Synthesis of (2R)-4-[(2R)-3-(3,4-dihydro-1H-isoquinolin-2-yl)-2-hydroxy-propyl]-2-methyl-8-[(3R)-1-meth ylpyrrolidin-3-yl]oxy-2,3-dihydro-1,4-benzoxazepin-5-one

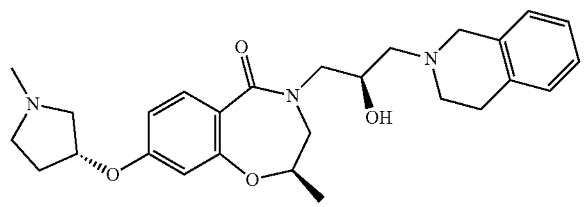 [SMILES: C[C@@H]1CN(C[C@H](O)CN2CCc3ccccc3C2)C(=O)c2ccc(O[C@@H]3CCN(C)C3)cc2O1]

Example 273-1: Synthesis of (2R)-4-[(2R)-3-(3,4-dihydro-1H-isoquinolin-2-yl)-2-hydroxy-propyl]-2-methyl-8-[(3R)-pyrrolidin-3-yl]oxy-2,3-dihydro-1,4-benzoxazepin-5-one dihydrochloride The intermediate was synthesized by using (2R)-4-[(2R)-3-(3,4-dihydro-1H-isoquinolin-2-yl)-2-hydroxy-propyl]-8-hydroxy-2-methyl-2,3-dihydro-1,4-benzoxazepin-5-one obtained in Example 264-1 as a starting material in the same manner as in Example 64 except that (R)-1-(tert-butoxycarbonyl)-3-pyrrolidinol was used instead of 4-chlorotetrahydropyran. 4 M hydrochloric acid solution dissolved in 1,4-dioxane was slowly added thereto. The reaction solution was stirred at room temperature, diluted with diethyl ether and filtered to obtain the title compound as a white solid.

Example 273-2: Synthesis of (2R)-4-[(2R)-3-(3,4-dihydro-1H-isoquinolin-2-yl)-2-hydroxy-propyl]-2-methyl-8-[(3R)-1-meth ylpyrrolidin-3-yl]oxy-2,3-dihydro-1,4-benzoxazepin-5-one (2R)-4-[(2R)-3-(3,4-dihydro-1H-isoquinolin-2-yl)-2-hydroxy-propyl]-2-methyl-8-[(3R)-pyrrolidin-3-yl]oxy-2,3-dihydro-1,4-benzoxazepin-5-one dihydrochloride obtained in Example 273-1 as a starting material was used in the same manner as in Example 87 to obtain the title compound.

$^1$H NMR (400 MHz, Methanol-$d_4$) δ 7.55 (d, J=8.7 Hz, 1H), 7.10-6.93 (m, 4H), 6.67 (dd, J=8.7, 2.5 Hz, 1H), 6.44 (d, J=2.5 Hz, 1H), 4.92 (d, J=6.9 Hz, 1H), 4.72 (td, J=7.0, 3.3 Hz, 1H), 4.16 (dt, J=8.2, 4.1 Hz, 1H), 4.06 (dd, J=13.8, 3.6 Hz, 1H), 3.72 (s, 2H), 3.56 (dd, J=15.6, 3.4 Hz, 1H), 3.42 (dd, J=15.6, 7.6 Hz, 1H), 3.17 (dd, J=13.8, 8.1 Hz, 1H), 2.88 (ddd, J=19.7, 9.7, 6.8 Hz, 7H), 2.65-2.46 (m, 3H), 2.41 (s, 4H), 2.00-1.91 (m, 1H), 1.25 (d, J=6.4 Hz, 3H).

Example 274: Synthesis of (2R)-4-[(2R)-3-(3,4-dihydro-1H-isoquinolin-2-yl)-2-hydroxy-propyl]-8-[(3R)-1-(2-methoxyeth yl)pyrrolidin-3-yl]oxy-2-methyl-2,3-dihydro-1,4-benzoxazepin-5-one

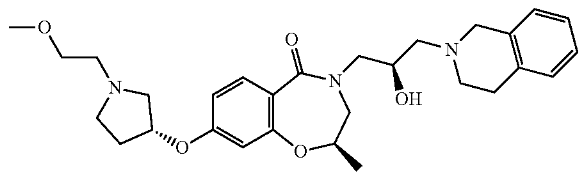 [SMILES: COCCN1CC[C@@H](Oc2ccc3c(c2)O[C@H](C)CN(C[C@H](O)CN2CCc4ccccc4C2)C3=O)C1]

(2R)-4-[(2R)-3-(3,4-dihydro-1H-isoquinolin-2-yl)-2-hydroxy-propyl]-2-methyl-8-[(3R)-pyrrolidin-3-yl]oxy-2,3-dihydro-1,4-benzoxazepin-5-one dihydrochloride obtained in Example 273-1 as a starting material was used in the same manner as in Example 224 to obtain the title compound.

$^1$H NMR (400 MHz, Methanol-$d_4$) δ 7.63 (d, J=8.7 Hz, 1H), 7.17-7.00 (m, 4H), 6.73 (dd, J=8.7, 2.5 Hz, 1H), 6.50 (d, J=2.4 Hz, 1H), 4.95 (ddt, J=7.7, 5.3, 2.5 Hz, 1H), 4.79 (td, J=7.1, 3.3 Hz, 1H), 4.28-4.20 (m, 1H), 4.15 (dd, J=13.8, 3.6 Hz, 1H), 3.77 (s, 2H), 3.63 (dd, J=15.6, 3.4 Hz, 1H), 3.56 (t, J=5.6 Hz, 2H), 3.49 (dd, J=15.6, 7.5 Hz, 1H), 3.36 (s, 3H), 3.23 (dd, J=13.8, 8.2 Hz, 1H), 2.94 (dddd, J=21.2, 15.4, 9.2, 3.8 Hz, 7H), 2.84-2.70 (m, 2H), 2.68-2.55 (m, 3H), 2.37 (dtd, J=13.6, 7.6, 5.9 Hz, 1H), 1.97 (dq, J=9.9, 7.4 Hz, 1H), 1.33 (d, J=6.4 Hz, 3H).

Example 275: Synthesis of 4-[(2R)-3-(3,4-dihydro-1H-isoquinolin-2-)–2-hydroxy-propyl]-8-[[1-(3,3,3-trifluoro-2-hydroxy-propyl)-4-piperidyl]oxy]-2,3-dihydro-1,4-benzoxazepin-5-one

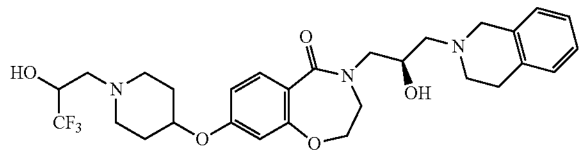 [SMILES: O=C1c2ccc(OC3CCN(CC(O)C(F)(F)F)CC3)cc2OCCN1C[C@H](O)CN1CCc2ccccc2C1]

4-[(2R)-3-(3,4-dihydro-1H-isoquinolin-2-yl)-2-hydroxy-propyl]-8-(4-piperidyloxy)-2,3-dihydro-1,4-benzoxazepin-5-one dihydrochloride obtained in Example 78-1 as a starting material was used in the same manner as in Example 212 to obtain the title compound, except that 2-(trifluoromethyl) oxirane was used instead of 2-methoxirane.

$^1$H NMR (400 MHz, Methanol-$d_4$) δ 7.67 (d, J=8.8 Hz, 1H), 7.17-7.02 (m, 4H), 6.76 (dd, J=8.8, 2.5 Hz, 1H), 6.58 (d, J=2.4 Hz, 1H), 4.48 (dt, J=9.9, 4.4 Hz, 3H), 4.27-4.14 (m, 2H), 3.97 (dd, J=13.9, 3.6 Hz, 1H), 3.78-3.70 (m, 4H), 3.43 (dd, J=13.9, 7.7 Hz, 1H), 2.93 (d, J=5.5 Hz, 2H), 2.91-2.81 (m, 4H), 2.70-2.59 (m, 4H), 2.52 (d, J=10.5 Hz, 2H), 2.03 (s, 2H), 1.84 (q, J=9.9, 8.8 Hz, 2H).

Example 276: Synthesis of (2R)-4-[(2R)-3-(3,4-dihydro-1H-isoquinolin-2-)–2-hydroxy-propyl]-2-methyl-8-[[1-(3,3,3-trifluoro-2-hydroxy-propyl)-4-piperidyl]oxy]-2,3-dihydro-1,4-benzoxazepin-5-one

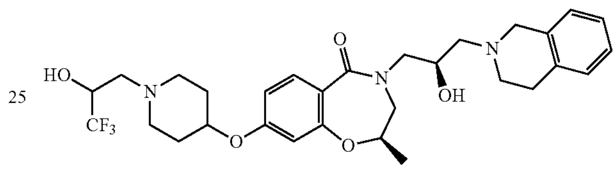

The material, which is obtained by changing [2-(tert-butoxycarbonylamino)-1-methyl-ethyl] methanesulfonate to [(1 S)-2-(tert-butoxycarbonylamino)-1-methyl-ethyl] methanesulfonate in Example 140, as a starting material was used in the same manner as in Example 212 to obtain the title compound, except that 2-(trifluoromethyl)oxirane was used instead of 2-methoxirane.

$^1$H NMR (400 MHz, Methanol-$d_4$) δ 7.62 (d, J=8.7 Hz, 1H), 7.20-6.98 (m, 4H), 6.78 (dd, J=8.8, 2.5 Hz, 1H), 6.55 (d, J=2.4 Hz, 1H), 4.78 (dd, J=6.8, 3.3 Hz, 1H), 4.53-4.44 (m, 1H), 4.28-4.09 (m, 3H), 3.78 (d, J=11.9 Hz, 2H), 3.63 (dd, J=15.7, 3.4 Hz, 1H), 3.49 (dd, J=15.5, 7.6 Hz, 1H), 3.24 (dd, J=13.7, 8.1 Hz, 1H), 3.00-2.80 (m, 6H), 2.64 (dt, J=7.7, 4.5 Hz, 4H), 2.52 (q, J=10.3 Hz, 2H), 2.03 (s, 2H), 1.85 (d, J=10.5 Hz, 2H), 1.33 (d, J=6.4 Hz, 3H).

Example 277: Synthesis of (2R)-4-[(2R)-3-(3,4-dihydro-1H-isoquinolin-2-yl)-2-hydroxypropyl]-2-methyl-8-[(3R)-1-(oxetan-3-yl)pyrrolidin-3-yl]oxy-2,3-dihydro-1,4-benzoxazepin-5-one

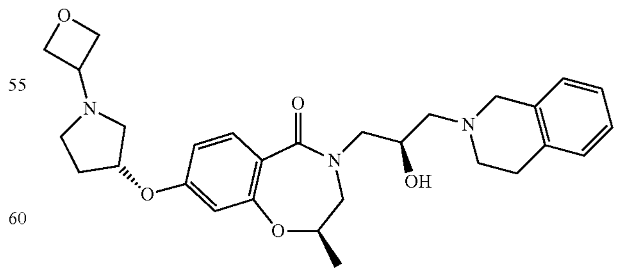

(2R)-4-[(2R)-3-(3,4-dihydro-1H-isoquinolin-2-yl)-2-hydroxy-propyl]-2-methyl-8-[(3R)-pyrrolidin-3-yl]oxy-2,3-dihydro-1,4-benzoxazepin-5-one dihydrochloride obtained in Example 273-1 as a starting material was used in the same manner as in Example 87 to obtain the title compound except that oxetan-3-one was used instead of paraformaldehyde.

$^1$H NMR (400 MHz, Methanol-$d_4$) δ 7.64 (d, J=8.7 Hz, 1H), 7.15-7.01 (m, 4H), 6.73 (dd, J=8.7, 2.5 Hz, 1H), 6.51 (d, J=2.4 Hz, 1H), 4.96 (ddt, J=8.2, 5.4, 2.5 Hz, 1H), 4.76 (dt, J=23.0, 6.8 Hz, 3H), 4.63 (dt, J=11.8, 6.1 Hz, 2H), 4.23 (td, J=7.9, 4.2 Hz, 1H), 4.14 (dd, J=13.8, 3.6 Hz, 1H), 3.79-3.69 (m, 3H), 3.62 (dd, J=15.6, 3.4 Hz, 1H), 3.48 (dd, J=15.6, 7.5 Hz, 1H), 3.21 (dd, J=13.8, 8.2 Hz, 1H), 2.98-2.76 (m, 7H), 2.66-2.59 (m, 2H), 2.54 (ddd, J=9.3, 7.8, 6.1 Hz, 1H), 2.36 (dq, J=14.0, 7.1 Hz, 1H), 2.07-1.94 (m, 1H), 1.32 (d, J=6.4 Hz, 3H).

Experimental Example

Method for Measuring Enzyme Activity

In vitro assay: PRMT5-MEP50 enzyme complex, cofactor S-adenosylmethionine (SAM) and histone H4 peptide were reacted in vitro, and methylation of arginine (H4R3)—which is the third amino acid of histone H4—was measured in order to measure the enzyme activity of PRMT5.

Reagents: PRMT5-MEP50 enzyme complex (Catalog No. 51045), blocking buffer (52100-B), histone methyltransferase reaction buffer 2 (4×HMT assay buffer 2, Catalog No. 52170), and primary antibody (primary antibody 4-3, Catalog No. 52150) were purchased from BPS Bioscience (USA). The histone H4 peptide (1-20 amino acids) was custom made by Komabiotech (Korea) and used. S-adenosylmethionine was purchased from NEB (New England Biolabs, USA, Catalog No. B9003S). Plates for coating histone H4 peptide, washing buffer and color development reagent were purchased from the following vendors: Plate (Immobilizer™-Amino Plate, NUNC, Denmark, Catalog No. 436023), carbonate-bicarbonate buffer (Sigma-Aldrich, USA, Catalog No. C3041), washing buffer (10×TBST, Biosesang, Korea, Catalog No. T2005), TMB ELISA substrate (Abcam, UK, Catalog No. ab210902), horseradish peroxidase (HRP)-conjugated antibody (Abcam, UK, Catalog No. ab6721).

Experimental procedure: The histone H4 peptide was diluted with carbonate-bicarbonate buffer and prepared to 100 μg/mL, and then dispensed onto the plate per 100 μL and reacted at 37° C. for 1 hour. PRMT5-MEP50 enzyme complex and S-adenosylmethionine were diluted with histone methyltransferase reaction buffer to prepare 5 μg/mL and 2 μM, respectively, and then 20 μL of PRMT5-MEP50 enzyme complex and 25 μL of S-adenosylmethionine were dispensed onto the plate prepared above. 5 μL of the compound diluted with 10% dimethyl sulfoxide solution was added thereto and reacted at room temperature for 2 hours (final volume=50 μL). The concentration of the compound was diluted 1:5 from 10 μM until the lowest concentration of 0.128 nM, and 8 points were used for the test. After preparing the primary antibody by diluting 1:2000 with blocking buffer, 100 μL was added to the plate and reacted at room temperature for 1 hour. After preparing horseradish peroxidase-conjugated antibody by diluting 1:10,000 with blocking buffer, 100 μL was added to the plate and reacted at room temperature for 1 hour. 100 μL of TMB substrate was added and reacted for 3 minutes at room temperature, and 100 μL of 1 N sulfuric acid was then added to terminate the reaction. Then, the absorbance at 450 nm was measured to calculate the $IC_{50}$ value of the compound. (+++: 1 to 100 nM, ++: greater than 100 to 1,000 nM, +: greater than 1,000 to 10,000 nM)

TABLE 2

| Compound | PRMT5 enzyme $IC_{50}$ (nM) |
|---|---|
| Example 1 | ++ |
| Example 2 | ++ |
| Example 4 | ++ |
| Example 5 | ++ |
| Example 6 | +++ |
| Example 7 | ++ |
| Example 8 | ++ |
| Example 9 | ++ |
| Example 10 | ++ |
| Example 11 | ++ |
| Example 12 | +++ |
| Example 13 | +++ |
| Example 14 | ++ |
| Example 15 | +++ |
| Example 16 | +++ |
| Example 17 | +++ |
| Example 18 | ++ |
| Example 19 | ++ |
| Example 20 | ++ |
| Example 21 | ++ |
| Example 22 | +++ |
| Example 23 | +++ |
| Example 24 | +++ |
| Example 25 | ++ |
| Example 26 | ++ |
| Example 27 | +++ |
| Example 28 | +++ |
| Example 29 | ++ |
| Example 30 | +++ |
| Example 31 | +++ |
| Example 32 | +++ |
| Example 33 | ++ |
| Example 34 | +++ |
| Example 35 | ++ |
| Example 36 | ++ |
| Example 37 | + |
| Example 38 | ++ |
| Example 39 | ++ |
| Example 40 | +++ |
| Example 41 | ++ |
| Example 42 | ++ |
| Example 43 | +++ |
| Example 44 | +++ |
| Example 45 | +++ |
| Example 46 | ++ |
| Example 47 | ++ |
| Example 48 | ++ |
| Example 49 | ++ |
| Example 50 | +++ |
| Example 51 | ++ |
| Example 52 | ++ |
| Example 53 | ++ |
| Example 54 | +++ |
| Example 55 | ++ |
| Example 56 | ++ |
| Example 57 | +++ |
| Example 58 | +++ |
| Example 59 | ++ |
| Example 60 | ++ |
| Example 61 | ++ |
| Example 62 | +++ |
| Example 63 | +++ |
| Example 64 | +++ |
| Example 65 | ++ |
| Example 66 | ++ |
| Example 67 | ++ |
| Example 68 | ++ |
| Example 69 | +++ |
| Example 70 | ++ |
| Example 71 | ++ |
| Example 72 | ++ |
| Example 73 | ++ |
| Example 74 | ++ |
| Example 75 | ++ |
| Example 76 | ++ |
| Example 77 | +++ |
| Example 78 | +++ |

TABLE 2-continued

| Compound | PRMT5 enzyme $IC_{50}$ (nM) |
|---|---|
| Example 79 | ++ |
| Example 80 | ++ |
| Example 81 | +++ |
| Example 82 | ++ |
| Example 83 | ++ |
| Example 84 | ++ |
| Example 85 | +++ |
| Example 86 | ++ |
| Example 87 | +++ |
| Example 88 | +++ |
| Example 89 | +++ |
| Example 90 | +++ |
| Example 91 | ++ |
| Example 92 | ++ |
| Example 93 | ++ |
| Example 94 | ++ |
| Example 95 | ++ |
| Example 96 | ++ |
| Example 97 | ++ |
| Example 98 | ++ |
| Example 99 | ++ |
| Example 101 | ++ |
| Example 102 | ++ |
| Example 103 | ++ |
| Example 104 | ++ |
| Example 105 | ++ |
| Example 106 | ++ |
| Example 107 | +++ |
| Example 108 | + |
| Example 109 | ++ |
| Example 110 | ++ |
| Example 111 | ++ |
| Example 112 | ++ |
| Example 113 | ++ |
| Example 114 | +++ |
| Example 115 | +++ |
| Example 116 | ++ |
| Example 117 | ++ |
| Example 118 | +++ |
| Example 119 | ++ |
| Example 120 | +++ |
| Example 121 | ++ |
| Example 122 | ++ |
| Example 123 | ++ |
| Example 124 | ++ |
| Example 125 | ++ |
| Example 126 | ++ |
| Example 127 | +++ |
| Example 128 | ++ |
| Example 129 | ++ |
| Example 130 | ++ |
| Example 131 | ++ |
| Example 132 | ++ |
| Example 133 | +++ |
| Example 134 | +++ |
| Example 135 | ++ |
| Example 136 | ++ |
| Example 137 | +++ |
| Example 138 | ++ |
| Example 139 | ++ |
| Example 140 | ++ |
| Example 141 | +++ |
| Example 142 | +++ |
| Example 143 | ++ |
| Example 144 | ++ |
| Example 145 | ++ |
| Example 146 | ++ |
| Example 147 | ++ |
| Example 148 | + |
| Example 149 | ++ |
| Example 150 | ++ |
| Example 151 | +++ |
| Example 152 | ++ |
| Example 153 | ++ |
| Example 154 | +++ |
| Example 155 | +++ |
| Example 156 | +++ |

TABLE 2-continued

| Compound | PRMT5 enzyme $IC_{50}$ (nM) |
|---|---|
| Example 157 | +++ |
| Example 158 | ++ |
| Example 159 | ++ |
| Example 160 | +++ |
| Example 161 | +++ |
| Example 162 | ++ |
| Example 163 | ++ |
| Example 164 | ++ |
| Example 165 | +++ |
| Example 166 | ++ |
| Example 167 | ++ |
| Example 168 | +++ |
| Example 169 | ++ |
| Example 170 | ++ |
| Example 171 | +++ |
| Example 172 | ++ |
| Example 173 | +++ |
| Example 174 | +++ |
| Example 175 | ++ |
| Example 176 | ++ |
| Example 177 | ++ |
| Example 178 | ++ |
| Example 179 | ++ |
| Example 180 | +++ |
| Example 181 | ++ |
| Example 182 | ++ |
| Example 183 | ++ |
| Example 184 | ++ |
| Example 185 | ++ |
| Example 186 | ++ |
| Example 187 | ++ |
| Example 188 | ++ |
| Example 189 | ++ |
| Example 190 | ++ |
| Example 191 | ++ |
| Example 192 | ++ |
| Example 193 | ++ |
| Example 194 | ++ |
| Example 195 | ++ |
| Example 196 | ++ |
| Example 197 | ++ |
| Example 198 | +++ |
| Example 199 | +++ |
| Example 201 | ++ |
| Example 202 | +++ |
| Example 203 | ++ |
| Example 204 | ++ |
| Example 205 | ++ |
| Example 206 | ++ |
| Example 207 | ++ |
| Example 208 | ++ |
| Example 209 | ++ |
| Example 210 | ++ |
| Example 211 | ++ |
| Example 212 | ++ |
| Example 213 | ++ |
| Example 214 | ++ |
| Example 215 | ++ |
| Example 216 | +++ |
| Example 217 | ++ |
| Example 218 | ++ |
| Example 219 | +++ |
| Example 220 | ++ |
| Example 221 | ++ |
| Example 222 | ++ |
| Example 223 | ++ |
| Example 224 | ++ |
| Example 225 | ++ |
| Example 226 | +++ |
| Example 227 | +++ |
| Example 228 | +++ |
| Example 229 | ++ |
| Example 230 | +++ |
| Example 231 | +++ |
| Example 232 | ++ |
| Example 233 | ++ |
| Example 234 | +++ |

TABLE 2-continued

| Compound | PRMT5 enzyme $IC_{50}$ (nM) |
|---|---|
| Example 238 | ++ |
| Example 240 | ++ |
| Example 241 | ++ |
| Example 242 | +++ |
| Example 243 | +++ |
| Example 245 | ++ |
| Example 246 | ++ |
| Example 247 | ++ |
| Example 248 | +++ |
| Example 249 | ++ |
| Example 250 | ++ |
| Example 251 | ++ |
| Example 252 | ++ |
| Example 253 | ++ |
| Example 254 | ++ |
| Example 255 | ++ |
| Example 256 | ++ |
| Example 261 | ++ |
| Example 262 | ++ |
| Example 264 | ++ |
| Example 267 | ++ |
| Example 268 | ++ |
| Example 272 | ++ |
| Example 273 | ++ |
| Example 274 | ++ |

Test for In Vivo Target Inhibitory Activity

After U87MG tumor cells were implanted subcutaneously in nude mice, a PRMT5 inhibitor was administered orally (25 or 50 mg/kg) 1-2 times daily for one week, and then the degree to which SDMA levels in the tumor decreased was measured.

Reagents: Bradford's solution (Catalog No. 500-0006) was purchased from Bio-rad (USA). SDMA antibody (Catalog No. 13222s) was purchased from Cell Signaling Technology (USA). SmD3 antibody (Catalog No. ap12451a) was purchased from Abgent (USA), and secondary antibody (Catalog No. ab6721) and TMB substrate (Catalog No. ab210902) were purchased from Abcam (UK).

Experimental procedure: The tumor tissues transplanted into the mice were excised, the cells were lysed, and then quantified with Bradford's solution. 5-10 μg of protein per sample was diluted with carbonate-bicarbonate buffer and dispensed into a 96-well plate and reacted at room temperature for 2 hours. After washing with phosphate buffered saline (PBST) containing 0.05% Tween-20 3 times, 200 μL of PBST containing 5% bovine serum albumin (BSA-PBST) was added and reacted at room temperature for 2 hours. After washing with PBST 3 times, the SDMA antibody and the SmD3 antibody were diluted in BSA-PBST, and 100 μL of each was dispensed onto the plate and reacted at 4° C. overnight. After washing with PBST 3 times the next day, 100 μL of the secondary antibody diluted in BSA-PBST was added and reacted at room temperature for 1 hour. After washing with PBST 3 times, 100 μL of TMB substrate was added and reacted at room temperature for 10-20 minutes, and 100 μL of 1N sulfuric acid solution was added to terminate the reaction. Then, the absorbance at 450 nm was measured to calculate the degree of SDMA inhibition by the compound. (+++: more than 70%, ++: more than 30% and 70% or less, +: 30% or less)

TABLE 3

| Compound | SDMA inhibition (%) |
|---|---|
| Example 11 | ++ |
| Example 22 | +++ |
| Example 87 | +++ |
| Example 88 | +++ |
| Example 92 | +++ |
| Example 112 | +++ |
| Example 155 | + |
| Example 156 | ++ |

What is claimed is:

1. A composition comprising a compound of Formula 1 or a pharmaceutically acceptable salt thereof and a pharmaceutically acceptable carrier:

[Formula 1]

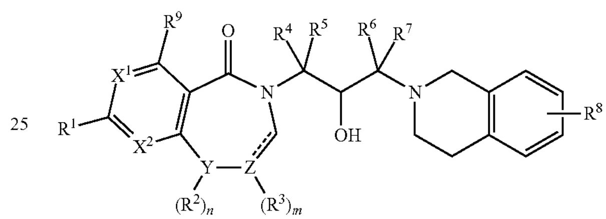

wherein $X^1$ and $X^2$ are each independently carbon or nitrogen;

Y is carbon, oxygen or nitrogen;

Z is carbon;

n is an integer of 0 or 1;

m is an integer of 0 to 2;

$\overset{\text{---}}{=}$ is a single bond or a double bond;

$R^1$ is -D-$R^{10}$; wherein D is a direct bond, —O—, —C(═O)—, —C≡C— or —$CR^{11}R^{12}$; $R^{10}$ is hydrogen, halo, hydroxy, cyano, alkyl, hydroxyalkyl, haloalkyl, haloalkylsulfonate, dialkylamino, alkylaminoalkyl, dialkylaminoalkyl, dialkylaminocarbonylalkyl, saturated or unsaturated carbocyclyl, saturated or unsaturated heterocyclyl, saturated or unsaturated carbocyclyl-alkyl, or saturated or unsaturated heterocyclyl-alkyl; $R^{11}$ and $R^{12}$ are each independently hydrogen, hydroxy or alkyl; the carbocycle or heterocycle is optionally substituted with one or more substituents selected from hydroxy, halo, oxo, formyl (—CHO), nitrile, alkyl, alkoxy, hydroxyalkyl, hydroxyhaloalkyl, alkoxyalkyl, haloalkyl, nitrilealkyl, alkylcarbonyl, alkylthiocarbonyl, alkoxycarbonyl, haloalkylcarbonyl, carbocyclyl, carbocyclylcarbonyl, (alkyl)(haloalkyl)amino, (alkyl)(heterocyclyl)amino, heterocyclyl and heterocyclyl-alkyl;

$R^2$ is hydrogen or alkyl;

$R^3$ is hydrogen or alkyl;

$R^4$, $R^5$, $R^6$ and $R^7$ are each independently hydrogen or alkyl;

$R^8$ is hydrogen, halo, alkyl, alkoxy or amino; and $R^9$ is hydrogen, halo or alkyl;

wherein the disease associated with PRMT5 inhibition is selected from the group consisting of cancer, blood disease, autoimmune disease, inflammatory disease and neurodegenerative disease; and wherein the composition comprises 0.5 to 100 mg/kg per day of the compound.

2. The composition according to claim 1, wherein the composition is an oral composition, an injection composition, an aerosol composition, a parenteral composition, or a topical composition.

3. The composition according to claim 1, wherein the composition is a tablet, a pill, a hard capsule, a soft capsule, a solution, a suspension, an emulsifier, a syrup, a granule or an elixir.

4. The composition according to claim 1, wherein the carrier is one or more selected from the group consisting of a preservative, a stabilizer, a hydrating, an emulsifying accelerator, a salt for osmotic pressure regulation, and a buffer.

5. The composition according to claim 1, wherein $X^1$ and $X^2$ are each independently CH or N;

Y is $CH_2$, O or NH, when n is 0; Y is CH or N, when n is 1;

Z is $CH_2$ or CH, when m is 0; Z is CH or C, when m is 1; Z is C, when m is 2; and $\overline{\overline{---}}$ is a single bond or a double bond.

6. The composition according to claim 1, wherein $R^1$ is -D-$R^{10}$; wherein D is a direct bond, —O—, —C(═O)—, —C≡C— or —$CR^{11}R^{12}$; $R^{10}$ is hydrogen, halo, hydroxy, cyano, $C_1$-$C_7$ alkyl, hydroxy-$C_1$-$C_7$ alkyl, halo-$C_1$-$C_7$ alkyl, halo-$C_1$-$C_7$ alkylsulfonate, di($C_1$-$C_7$ alkyl)amino, $C_1$-$C_7$ alkylamino-$C_1$-$C_7$ alkyl, di($C_1$-$C_7$ alkyl)amino-$C_1$-$C_7$ alkyl, di($C_1$-$C_7$ alkyl)aminocarbonyl-$C_1$-$C_7$ alkyl, saturated or unsaturated $C_3$-$C_{10}$ carbocyclyl, saturated or unsaturated, 4- to 10-membered heterocyclyl, saturated or unsaturated $C_3$-$C_{10}$ carbocyclyl-$C_1$-$C_7$ alkyl, or saturated or unsaturated, 4- to 10-membered heterocyclyl-alkyl; and $R^{11}$ and $R^{12}$ are each independently hydrogen, hydroxy or $C_1$-$C_7$ alkyl.

7. The composition according to claim 1, wherein the carbocycle or heterocycle is optionally substituted with 1 to 5 substituents selected from hydroxy, halo, oxo, formyl, nitrile, $C_1$-$C_7$ alkyl, $C_1$-$C_7$ alkoxy, hydroxy-$C_1$-$C_7$ alkyl, hydroxyhalo-$C_1$-$C_7$ alkyl, $C_1$-$C_7$ alkoxy-$C_1$-$C_7$ alkyl, halo-$C_1$-$C_7$ alkyl, nitrile-$C_1$-$C_7$ alkyl, $C_1$-$C_7$ alkylcarbonyl, $C_1$-$C_7$ alkylthiocarbonyl, $C_1$-$C_7$ alkoxycarbonyl, halo-$C_1$-$C_7$ alkylcarbonyl, saturated or unsaturated $C_3$-$C_{10}$ carbocyclyl, saturated or unsaturated $C_3$-$C_{10}$ carbocyclylcarbonyl, ($C_1$-$C_7$ alkyl)(halo-$C_1$-$C_7$ alkyl)amino, ($C_1$-$C_7$ alkyl)(saturated or unsaturated, 4- to 10-membered heterocyclyl)amino, saturated or unsaturated, 4- to 10-membered heterocyclyl and saturated or unsaturated, 4- to 10-membered heterocyclyl-$C_1$-$C_7$ alkyl.

8. The composition according to claim 1, wherein the carbocycle or heterocycle is optionally substituted with 1 to 5 substituents selected from hydroxy, halo, formyl, $C_1$-$C_7$ alkyl, hydroxy-$C_1$-$C_7$ alkyl, $C_1$-$C_7$ alkoxy-$C_1$-$C_7$ alkyl, halo-$C_1$-$C_7$ alkyl, $C_1$-$C_7$ alkylcarbonyl, $C_1$-$C_7$ alkoxycarbonyl, halo-$C_1$-$C_7$ alkylcarbonyl, saturated or unsaturated $C_3$-$C_{10}$ carbocyclyl, saturated or unsaturated $C_3$-$C_{10}$ carbocyclylcarbonyl, ($C_1$-$C_7$ alkyl)(halo-$C_1$-$C_7$ alkyl)amino, ($C_1$-$C_7$ alkyl)(saturated or unsaturated, 4- to 10-membered heterocyclyl)amino and saturated or unsaturated, 4- to 10-membered heterocyclyl-$C_1$-$C_7$ alkyl.

9. The composition according to claim 1, wherein the heterocycle is optionally substituted with 1 or 2 substituents selected from hydroxy, halo, formyl, $C_1$-$C_7$ alkyl, hydroxy-$C_1$-$C_7$ alkyl, $C_1$-$C_7$ alkoxy-$C_1$-$C_7$ alkyl, halo-$C_1$-$C_7$ alkyl, $C_1$-$C_7$ alkylcarbonyl, $C_1$-$C_7$ alkoxycarbonyl, halo-$C_1$-$C_7$ alkylcarbonyl, saturated or unsaturated $C_3$-$C_{10}$ carbocyclyl, saturated or unsaturated $C_3$-$C_{10}$ carbocyclylcarbonyl and saturated or unsaturated, 4- to 10-membered heterocyclyl-$C_1$-$C_7$ alkyl.

10. The composition according to claim 1, wherein the carbocycle is optionally substituted with 1 or 2 substituents selected from halo-$C_1$-$C_7$ alkyl, ($C_1$-$C_7$ alkyl)(halo-$C_1$-$C_7$ alkyl)amino and ($C_1$-$C_7$ alkyl)(saturated or unsaturated, 4- to 10-membered heterocyclyl)amino.

11. The composition according to claim 1, wherein $R^1$ is -D-$R^{10}$; wherein D is a direct bond;

$R^{10}$ is hydrogen, halo, cyano, $C_1$-$C_7$ alkyl, halo-$C_1$-$C_7$ alkyl, di($C_1$-$C_7$ alkyl)amino-$C_1$-$C_7$ alkyl, saturated or unsaturated, 4- to 10-membered heterocyclyl, saturated or unsaturated $C_3$-$C_{10}$ carbocyclyl, or saturated or unsaturated, 4- to 10-membered heterocyclyl-alkyl; and the heterocycle is optionally substituted with 1 or 2 substituents selected from hydroxy, halo, formyl, $C_1$-$C_7$ alkyl, $C_1$-$C_7$ alkoxy, hydroxy-$C_1$-$C_7$ alkyl, halo-$C_1$-$C_7$ alkyl, nitrile-$C_1$-$C_7$ alkyl, $C_1$-$C_7$ alkylcarbonyl, $C_1$-$C_7$ alkoxy-$C_1$-$C_7$ alkyl, $C_1$-$C_7$ alkoxycarbonyl, halo-$C_1$-$C_7$ alkylcarbonyl, and saturated or unsaturated, 4- to 10-membered heterocyclyl.

12. The composition according to claim 1, wherein $R^2$ is hydrogen or $C_1$-$C_7$ alkyl;

$R^3$ is hydrogen or $C_1$-$C_7$ alkyl;

$R^4$, $R^5$, $R^6$ and $R^7$ are each independently hydrogen or $C_1$-$C_7$ alkyl;

$R^8$ is hydrogen, halo, $C_1$-$C_7$ alkyl, $C_1$-$C_7$ alkoxy or amino; and $R^9$ is hydrogen, halo or $C_1$-$C_7$ alkyl.

13. The composition according to claim 1, wherein $\overline{\overline{---}}$ is a single bond.

14. The composition according to claim 1, wherein the heterocycle is a saturated or unsaturated, 4- to 8-membered hydrocarbon having 1 or 2 heteroatoms selected from N and O.

15. The composition according to claim 1, wherein the heterocycle is selected from the group consisting of tetrahydropyridine, dihydropyridine, piperidine, dihydropyran, tetrahydropyran, pyrrolidine, 2-oxa-6-azaspiroheptane, azetidine, morpholine, 3,3a,4,5,6,6a-hexahydro-1H-cyclopenta[c]pyrrole, oxazepane, 2-oxa-5-azabicyclo[2.2.1]heptane, pyridyl, tetrahydrofuran, 8-azabicyclo[3.2.1]octane, piperazine, 2-azaspiro[3.3]heptane, 2-oxa-7-azaspiro[3.4]octane, 2-azabicyclo[2.2.1]heptane, 3-oxa-8-azabicyclo[3.2.1]octane, 3,4-dihydro-1H-pyrrolo[1,2-a]pyrazine, 3,4,6,7,8,8a-hexahydro-1H-pyrrolo[1,2]-a]pyrazine, pyrimidine, pyrazole, 2-oxa-7-azaspiro[3.5]nonane, and oxetane.

16. The composition according to claim 15, wherein the heterocycle is selected from the group consisting of tetrahydropyridine, dihydropyridine, piperidine, tetrahydropyran, pyrrolidine, 2-oxa-6-azaspiroheptane, azetidine, morpholine, 3,3a,4,5,6,6a-hexahydro-1H-cyclopenta[c]pyrrole, pyridyl, 8-azabicyclo[3.2.1]octane, piperazine, 2-azaspiro[3.3]heptane, pyrazole, and oxetane.

17. The composition according to claim 1, wherein the carbocycle is selected from the group consisting of cyclohexane, cyclohexene, cyclopropane, cyclobutane, and cyclopentane.

18. The composition according to claim 15, wherein

D is a direct bond, —O—, —C(═O)— or —C≡C—;

$R^{10}$ is halo, $C_1$-$C_7$ alkyl, hydroxy-$C_1$-$C_7$ alkyl, halo-$C_1$-$C_7$ alkyl, saturated or unsaturated $C_3$-$C_{10}$ carbocyclyl, saturated or unsaturated, 4- to 10-membered heterocyclyl, or saturated or unsaturated, 4- to 10-membered heterocyclyl-alkyl;

the carbocycle or heterocycle is optionally substituted with 1 to 5 substituents selected from hydroxy, halo, formyl, $C_1$-$C_7$ alkyl, hydroxy-$C_1$-$C_7$ alkyl, $C_1$-$C_7$ alkoxy-$C_1$-$C_7$ alkyl, halo-$C_1$-$C_7$ alkyl, $C_1$-$C_7$ alkylcarbonyl, $C_1$-$C_7$ alkoxycarbonyl, halo-$C_1$-$C_7$ alkylcarbonyl, saturated or unsaturated $C_3$-$C_{10}$ carbocyclyl, saturated or unsaturated $C_3$-$C_{10}$ carbocyclylcarbonyl, ($C_1$-$C_7$ alkyl)(halo-$C_1$-$C_7$ alkyl)amino, ($C_1$-$C_7$ alkyl)(saturated or unsaturated, 4- to 10-membered heterocyclyl)amino, and saturated or unsaturated, 4- to 10-membered heterocyclyl-$C_1$-$C_7$ alkyl;

the heterocycle is selected from the group consisting of tetrahydropyridine, dihydropyridine, piperidine, tetrahydropyran, pyrrolidine, 2-oxa-6-azaspiroheptane, azetidine, morpholine, 3,3a,4,5,6,6a-hexahydro-1H-cyclopenta[c]pyrrole, pyridyl, 8-azabicyclo[3.2.1]octane, piperazine, 2-azaspiro[3.3]heptane, pyrazole, and oxetane; and the carbocycle is selected from the group consisting of cyclohexane, cyclohexene, and cyclopropane.

19. The composition according to claim 1, wherein the compound is selected from the group consisting of:

4-[3-(3,4-dihydro-1H-isoquinolin-2-yl)-2-hydroxy-propyl]-8-methoxy-2,3-dihydro-1,4-benzoxazepin-5-one;

2-[3-(3,4-dihydro-1H-isoquinolin-2-yl)-2-hydroxy-propyl]-7-methoxy-4,5-dihydro-3H-2-benzazepin-1-one;

2-[3-(3,4-dihydro-1H-isoquinolin-2-yl)-2-hydroxy-propyl]-7-hydroxy-4,5-dihydro-3H-2-benzazepin-1-one;

2-[3-(3,4-dihydro-1H-isoquinolin-2-yl)-2-hydroxy-propyl]-7-(trifluoromethoxy)-4,5-dihydro-3H-2-benzazepin-1-one;

4-[(2R)-3-(3,4-dihydro-1H-isoquinolin-2-yl)-2-hydroxy-propyl]-8-(trifluoromethyl)-2,3-dihydro-1,4-benzoxazepin-5-one;

2-[(2R)-3-(3,4-dihydro-1H-isoquinolin-2-yl)-2-hydroxy-propyl]-7-(trifluoromethoxy)-4,5-dihydro-3H-2-benzazepin-1-one;

2-[(2R)-3-(3,4-dihydro-1H-isoquinolin-2-yl)-2-hydroxy-propyl]-7-ethoxy-4,5-dihydro-3H-2-benzazepin-1-one;

[2-[(2R)-3-(3,4-dihydro-1H-isoquinolin-2-yl)-2-hydroxy-propyl]-1-oxo-4,5-dihydro-3H-2-benzazepin-7yl] trifluoromethanesulfonate;

2-[(2R)-3-(3,4-dihydro-1H-isoquinolin-2-yl)-2-hydroxy-propyl]-1-oxo-4,5-dihydro-3H-2-benzazepin-7-carbonitrile;

4-[(2R)-3-(3,4-dihydro-1H-isoquinolin-2-yl)-2-hydroxy-propyl]-8-methyl-2,3-dihydro-1,4-benzoxazepin-5-one;

4-[(2R)-3-(3,4-dihydro-1H-isoquinolin-2-yl)-2-hydroxy-propyl]-8-propyl-2,3-dihydro-1,4-benzoxazepin-5-one;

4-[(2R)-3-(3,4-dihydro-1H-isoquinolin-2-yl)-2-hydroxy-propyl]-8-isobutyl-2,3-dihydro-1,4-benzoxazepin-5-one;

4-[(2R)-3-(3,4-dihydro-1H-isoquinolin-2-yl)-2-hydroxy-propyl]-8-(3,3,3-trifluoropropyl)-2,3-dihydro-1,4-benzoxazepin-5-one;

tert-butyl 4-[4-[(2R)-3-(3,4-dihydro-1H-isoquinolin-2-yl)-2-hydroxy-propyl]-5-oxo-2,3-dihydro-1,4-benzoxazepin-8-yl]-3,6-dihydro-2H-pyridine-1-carboxylate;

4-[(2R)-3-(3,4-dihydro-1H-isoquinolin-2-yl)-2-hydroxy-propyl]-8-(1,2,3,6-tetrahydropyridin-4-yl)-2,3-dihydro-1,4-benzoxazepin-5-one;

8-(1-acetyl-3,6-dihydro-2H-pyridin-4-yl)-4-[(2R)-3-(3,4-dihydro-1H-isoquinolin-2-yl)-2-hydroxy-propyl]-2,3-dihydro-1,4-benzoxazepin-5-one;

8-(1-acetyl-4-piperidyl)-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-(1-ethyl-3,6-dihydro-2H-pyridin-4-yl)-2,3-dihydro-1,4-benzoxazepin-5-one;

4-[(2R)-3-(3,4-dihydro-1H-isoquinolin-2-yl)-2-hydroxy-propyl]-8-(1-isopropyl-3,6-dihydro-2H-pyridin-4-yl)-2,3-dihydro-1,4-benzoxazepin-5-one;

4-[(2R)-3-(3,4-dihydro-1H-isoquinolin-2-yl)-2-hydroxy-propyl]-8-(3,6-dihydro-2H-pyran-4-yl)-2,3-dihydro-1,4-benzoxazepin-5-one;

4-[(2R)-3-(3,4-dihydro-1H-isoquinolin-2-yl)-2-hydroxy-propyl]-8-tetrahydropyran-4-yl-2,3-dihydro-1,4-benzoxazepin-5-one;

4-[(2R)-3-(3,4-dihydro-1H-isoquinolin-2-yl)-2-hydroxy-propyl]-8-(morpholinomethyl)-2,3-dihydro-1,4-benzoxazepin-5-one;

4-[(2R)-3-(3,4-dihydro-1H-isoquinolin-2-yl)-2-hydroxy-propyl]-8-(1-piperidylmethyl)-2,3-dihydro-1,4-benzoxazepin-5-one;

4-[(2R)-3-(3,4-dihydro-1H-isoquinolin-2-yl)-2-hydroxy-propyl]-8-(pyrrolidin-1-ylmethyl)-2,3-dihydro-1,4-benzoxazepin-5-one;

4-[(2R)-3-(3,4-dihydro-1H-isoquinolin-2-yl)-2-hydroxy-propyl]-8-[(dimethylamino)methyl]-2,3-dihydro-1,4-benzoxazepin-5-one;

8-(diethylaminomethyl)-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-[(4-methyl-1-piperidyl)methyl]-2,3-dihydro-1,4-benzoxazepin-5-one;

4-[(2R)-3-(3,4-dihydro-1H-isoquinolin-2-yl)-2-hydroxy-propyl]-8-(2-oxa-6-azaspiro[3.3]heptan-6-ylmethyl)-2,3-dihydro-1,4-benzoxazepin-5-one;

4-[(2R)-3-(3,4-dihydro-1H-isoquinolin-2-yl)-2-hydroxy-propyl]-8-[(3-methoxyazetidin-1-yl)methyl]-2,3-dihydro-1,4-benzoxazepin-5-one;

4-[(2R)-3-(3,4-dihydro-1H-isoquinolin-2-yl)-2-hydroxy-propyl]-8-[(2-methylmorpholin-4-yl)methyl]-2,3-dihydro-1,4-benzoxazepin-5-one;

8-[(4,4-difluoro-1-piperidyl)methyl]-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-[(4-fluoro-1-piperidyl)methyl]-2,3-dihydro-1,4-benzoxazepin-5-one;

4-[(2R)-3-(3,4-dihydro-1H-isoquinolin-2-yl)-2-hydroxy-propyl]-8-[(3,5-dimethyl-1-piperidyl)methyl]-2,3-dihydro-1,4-benzoxazepin-5-one;

8-(3,3a,4,5,6,6a-hexahydro-1H-cyclopenta[c]pyrrol-2-ylmethyl)-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-[(3-hydroxypyrrolidin-1-yl)methyl]-2,3-dihydro-1,4-benzoxazepin-5-one;

4-[(2R)-3-(3,4-dihydro-1H-isoquinolin-2-yl)-2-hydroxy-propyl]-8-[[(2R)-2-methylpyrrolidin-1-yl]methyl]-2,3-dihydro-1,4-benzoxazepin-5-one;

4-[(2R)-3-(3,4-dihydro-1H-isoquinolin-2-yl)-2-hydroxy-propyl]-8-[[3-(hydroxymethyl)-1-piperidyl]methyl]-2,3-dihydro-1,4-benzoxazepin-5-one;

4-[(2R)-3-(3,4-dihydro-1H-isoquinolin-2-yl)-2-hydroxy-propyl]-8-[(4-methoxy-1-piperidyl)methyl]-2,3-dihydro-1,4-benzoxazepin-5-one;

4-[(2R)-3-(3,4-dihydro-1H-isoquinolin-2-yl)-2-hydroxy-propyl]-8-(1,4-oxazepan-4-ylmethyl)-2,3-dihydro-1,4-benzoxazepin-5-one;

4-[(2R)-3-(3,4-dihydro-1H-isoquinolin-2-yl)-2-hydroxy-propyl]-8-[(3-hydroxy-3-methyl-pyrrolidin-1-yl)methyl]-2,3-dihydro-1,4-benzoxazepin-5-one;

4-[(2R)-3-(3,4-dihydro-1H-isoquinolin-2-yl)-2-hydroxy-propyl]-8-[[3-(hydroxymethyl)morpholin-4-yl]methyl]-2,3-dihydro-1,4-benzoxazepin-5-one;

8-[(3,3-difluoro-1-piperidyl)methyl]-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-[(3-fluoro-1-piperidyl)methyl]-2,3-dihydro-1,4-benzoxazepin-5-one;

4-[(2R)-3-(3,4-dihydro-1H-isoquinolin-2-yl)-2-hydroxy-propyl]-8-[(3-hydroxy-1-piperidyl)methyl]-2,3-dihydro-1,4-benzoxazepin-5-one;

4-[(2R)-3-(3,4-dihydro-1H-isoquinolin-2-yl)-2-hydroxy-propyl]-8-[(4-hydroxy-1-piperidyl)methyl]-2,3-dihydro-1,4-benzoxazepin-5-one;

4-[(2R)-3-(3,4-dihydro-1H-isoquinolin-2-yl)-2-hydroxy-propyl]-8-[[(2S)-2-(hydroxymethyl)pyrrolidin-1-yl]methyl]-2,3-dihydro-1,4-benzoxazepin-5-one;

4-[(2R)-3-(3,4-dihydro-1H-isoquinolin-2-yl)-2-hydroxy-propyl]-8-[[(2R)-2-(hydroxymethyl)pyrrolidin-1-yl]methyl]-2,3-dihydro-1,4-benzoxazepin-5-one;

4-[(2R)-3-(3,4-dihydro-1H-isoquinolin-2-yl)-2-hydroxy-propyl]-8-[(2-ethylpyrrolidin-1-yl)methyl]-2,3-dihydro-1,4-benzoxazepin-5-one;

4-[(2R)-3-(3,4-dihydro-1H-isoquinolin-2-yl)-2-hydroxy-propyl]-8-[[(2S)-2-(methoxymethyl)pyrrolidin-1-yl]methyl]-2,3-dihydro-1,4-benzoxazepin-5-one;

4-[(2R)-3-(3,4-dihydro-1H-isoquinolin-2-yl)-2-hydroxy-propyl]-8-[[(2R)-2-(methoxymethyl)pyrrolidin-1-yl]methyl]-2,3-dihydro-1,4-benzoxazepin-5-one;

4-[(2R)-3-(3,4-dihydro-1H-isoquinolin-2-yl)-2-hydroxy-propyl]-8-[(3-fluoropyrrolidin-1-yl)methyl]-2,3-dihydro-1,4-benzoxazepin-5-one;

8-[(3,3-difluoropyrrolidin-1-yl)methyl]-4-[(2R)-3-(3,4-dihydro-1H-isoquinolin-2-yl)-2-hydroxy-propyl]-2,3-dihydro-1,4-benzoxazepin-5-one;

8-[(4-acetylpiperazin-1-yl)methyl]-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-[(4-methylpiperazin-1-yl)methyl]-2,3-dihydro-1,4-benzoxazepin-5-one;

4-[(2R)-3-(3,4-dihydro-1H-isoquinolin-2-yl)-2-hydroxy-propyl]-8-(2-oxa-5-azabicyclo[2.2.1]heptan-5-ylmethyl)-2,3-dihydro-1,4-benzoxazepin-5-one;

4-[(2R)-3-(3,4-dihydro-1H-isoquinolin-2-yl)-2-hydroxy-propyl]-8-(3-pyridylmethoxy)-2,3-dihydro-1,4-benzoxazepin-5-one;

4-[(2R)-3-(3,4-dihydro-1H-isoquinolin-2-yl)-2-hydroxy-propyl]-8-(4-pyridylmethoxy)-2,3-dihydro-1,4-benzoxazepin-5-one;

4-[(2R)-3-(3,4-dihydro-1H-isoquinolin-2-yl)-2-hydroxy-propyl]-8-[(2-fluoro-4-pyridyl)methoxy]-2,3-dihydro-1,4-benzoxazepin-5-one;

8-[(2,6-dichloro-4-pyridyl)methoxy]-4-[(2R)-3-(3,4-dihydro-1H-isoquinolin-2-yl)-2-hydroxy-propyl]-2,3-dihydro-1,4-benzoxazepin-5-one;

8-[(2,3-difluoro-4-pyridyl)methoxy]-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-[(6-fluoro-3-pyridyl)methoxy]-2,3-dihydro-1,4-benzoxazepin-5-one;

4-[(2R)-3-(3,4-dihydro-1H-isoquinolin-2-yl)-2-hydroxy-propyl]-8-[(3-fluoro-4-pyridyl)methoxy]-2,3-dihydro-1,4-benzoxazepin-5-one;

4-[(2R)-3-(3,4-dihydro-1H-isoquinolin-2-yl)-2-hydroxy-propyl]-8-[(5-fluoro-2-pyridyl)methoxy]-2,3-dihydro-1,4-benzoxazepin-5-one;

4-[(2R)-3-(3,4-dihydro-1H-isoquinolin-2-yl)-2-hydroxy-propyl]-8-tetrahydropyran-4-yloxy-2,3-dihydro-1,4-benzoxazepin-5-one;

4-[(2R)-3-(3,4-dihydro-1H-isoquinolin-2-yl)-2-hydroxy-propyl]-8-(tetrahydropyran-2-ylmethoxy)-2,3-dihydro-1,4-benzoxazepin-5-one;

8-(cyclohexylmethoxy)-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-(tetrahydrofuran-2-ylmethoxy)-2,3-dihydro-1,4-benzoxazepin-5-one;

4-[(2R)-3-(3,4-dihydro-1H-isoquinolin-2-yl)-2-hydroxy-propyl]-8-[(1-methyl-3-piperidyl)oxy]-2,3-dihydro-1,4-benzoxazepin-5-one;

4-[(2R)-3-(3,4-dihydro-1H-isoquinolin-2-yl)-2-hydroxy-propyl]-8-[(1-ethyl-3-piperidyl)oxy]-2,3-dihydro-1,4-benzoxazepin-5-one;

8-[(1-acetyl-4-piperidyl)methoxy]-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-(2,2,2-trifluoroethoxy)-2,3-dihydro-1,4-benzoxazepin-5-one;

4-[(2R)-3-(3,4-dihydro-1H-isoquinolin-2-yl)-2-hydroxy-propyl]-8-[2-(dimethylamino)ethoxy]-2,3-dihydro-1,4-benzoxazepin-5-one;

4-[(2R)-3-(3,4-dihydro-1H-isoquinolin-2-yl)-2-hydroxy-propyl]-8-(2-morpholinoethoxy)-2,3-dihydro-1,4-benzoxazepin-5-one;

4-[(2R)-3-(3,4-dihydro-1H-isoquinolin-2-yl)-2-hydroxy-propyl]-8-[2-(2-oxopyrrolidin-1-yl)ethoxy]-2,3-dihydro-1,4-benzoxazepin-5-one;

4-[(2R)-3-(3,4-dihydro-1H-isoquinolin-2-yl)-2-hydroxy-propyl]-8-(2-pyridyloxy)-2,3-dihydro-1,4-benzoxazepin-5-one;

4-[(2R)-3-(3,4-dihydro-1H-isoquinolin-2-yl)-2-hydroxy-propyl]-8-[(6-oxo-3-piperidyl)oxy]-2,3-dihydro-1,4-benzoxazepin-5-one;

tert-butyl 4-[[4-[(2R)-3-(3,4-dihydro-1H-isoquinolin-2-yl)-2-hydroxy-propyl]-5-oxo-2,3-dihydro-1,4-benzoxazepin-8-yl]oxy]piperidine-1-carboxylate;

8-[(1-acetyl-4-piperidyl)oxy]-4-[(2R)-3-(3,4-dihydro-1H-isoquinolin-2-yl)-2-hydroxy-propyl]-2,3-dihydro-1,4-benzoxazepin-5-one;

8-[(1-acetyl-3-piperidyl)oxy]-4-[(2R)-3-(3,4-dihydro-1H-isoquinolin-2-yl)-2-hydroxy-propyl]-2,3-dihydro-1,4-benzoxazepin-5-one;

8-(1-acetylpyrrolidin-3-yl)oxy-4-[(2R)-3-(3,4-dihydro-1H-isoquinolin-2-yl)-2-hydroxy-propyl]-2,3-dihydro-1,4-benzoxazepin-5-one;

8-[(3R)-1-acetylpyrrolidin-3-yl]oxy-4-[(2R)-3-(3,4-dihydro-1H-isoquinolin-2-yl)-2-hydroxy-propyl]-2,3-dihydro-1,4-benzoxazepin-5-one;

8-[(3S)-1-acetylpyrrolidin-3-yl]oxy-4-[(2R)-3-(3,4-dihydro-1H-isoquinolin-2-yl)-2-hydroxy-propyl]-2,3-dihydro-1,4-benzoxazepin-5-one;

8-(1-acetylazetidin-3-yl)oxy-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-(1-propanoylazetidin-3-yl)oxy-2,3-dihydro-1,4-benzoxazepin-5-one;

8-[1-(cyclopropanecarbonyl)azetidin-3-yl]oxy-4-[(2R)-3-(3,4-dihydro-1H-isoquinolin-2-yl)-2-hydroxy-propyl]-2,3-dihydro-1,4-benzoxazepin-5-one;

methyl 3-[[4-[(2R)-3-(3,4-dihydro-1H-isoquinolin-2-yl)-2-hydroxy-propyl]-5-oxo-2,3-dihydro-1,4-benzoxazepin-8-yl]oxy]azetidin-1-carboxylate;

4-[(2R)-3-(3,4-dihydro-1H-isoquinolin-2-yl)-2-hydroxy-propyl]-8-[(1-methyl-4-piperidyl)oxy]-2,3-dihydro-1,4-benzoxazepin-5-one;

4-[(2R)-3-(3,4-dihydro-1H-isoquinolin-2-yl)-2-hydroxy-propyl]-8-[(1-ethyl-4-piperidyl)oxy]-2,3-dihydro-1,4-benzoxazepin-5-one;

4-[(2R)-3-(3,4-dihydro-1H-isoquinolin-2-yl)-2-hydroxy-propyl]-8-[(1-isopropyl-4-piperidyl)oxy]-2,3-dihydro-1,4-benzoxazepin-5-one;

8-[(1-cyclopropyl-4-piperidyl)oxy]-4-[(2R)-3-(3,4-dihydro-1H-isoquinolin-2-yl)-2-hydroxy-propyl]-2,3-dihydro-1,4-benzoxazepin-5-one;

8-[(1-cyclobutyl-4-piperidyl)oxy]-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-[[1-(oxetan-3-yl)-4-piperidyl]oxy]-2,3-dihydro-1,4-benzoxazepin-5-one;

4-[(2R)-3-(3,4-dihydro-1H-isoquinolin-2-yl)-2-hydroxy-propyl]-8-(1-methylazetidin-3-yl)oxy-2,3-dihydro-1,4-benzoxazepin-5-one;

4-[(2R)-3-(3,4-dihydro-1H-isoquinolin-2-yl)-2-hydroxy-propyl]-8-(1-ethylazetidin-3-yl)oxy-2,3-dihydro-1,4-benzoxazepin-5-one;

4-[(2R)-3-(3,4-dihydro-1H-isoquinolin-2-yl)-2-hydroxy-propyl]-8-(1-isopropylazetidin-3-yl)oxy-2,3-dihydro-1,4-benzoxazepin-5-one;

4-[(2R)-3-(3,4-dihydro-1H-isoquinolin-2-yl)-2-hydroxy-propyl]-8-[1-(oxetan-3-yl)azetidin-3-yl]oxy-2,3-dihydro-1,4-benzoxazepin-5-one;

4-[(2R)-3-(3,4-dihydro-1H-isoquinolin-2-yl)-2-hydroxy-propyl]-8-[(1-ethylazetidin-3-yl)methoxy]-2,3-dihydro-1,4-benzoxazepin-5-one;

4-[(2R)-3-(3,4-dihydro-1H-isoquinolin-2-yl)-2-hydroxy-propyl]-8-(1-methylpyrrolidin-3-yl)oxy-2,3-dihydro-1,4-benzoxazepin-5-one;

4-[(2R)-3-(3,4-dihydro-1H-isoquinolin-2-yl)-2-hydroxy-propyl]-8-[(3R)-1-ethylpyrrolidin-3-yl]oxy-2,3-dihydro-1,4-benzoxazepin-5-one;

4-[(2R)-3-(3,4-dihydro-1H-isoquinolin-2-yl)-2-hydroxy-propyl]-8-(2-pyridyloxy)-2,3-dihydro-1,4-benzoxazepin-5-one;

4-[(2R)-3-(3,4-dihydro-1H-isoquinolin-2-yl)-2-hydroxy-propyl]-8-[[(2S)-1-isopropylpyrrolidin-2-yl]methoxy]-2,3-dihydro-1,4-benzoxazepin-5-one;

4-[(2R)-3-(3,4-dihydro-1H-isoquinolin-2-yl)-2-hydroxy-propyl]-8-[(1-methyl-4-piperidyl)methoxy]-2,3-dihydro-1,4-benzoxazepin-5-one;

4-[(2R)-3-(3,4-dihydro-1H-isoquinolin-2-yl)-2-hydroxy-propyl]-8-[(1-ethyl-4-piperidyl)methoxy]-2,3-dihydro-1,4-benzoxazepin-5-one;

4-[(2R)-3-(3,4-dihydro-1H-isoquinolin-2-yl)-2-hydroxy-propyl]-8-[(4-methylmorpholin-2-yl)methoxy]-2,3-dihydro-1,4-benzoxazepin-5-one;

4-[(2R)-3-(3,4-dihydro-1H-isoquinolin-2-yl)-2-hydroxy-propyl]-8-[(4-ethylmorpholin-2-yl)methoxy]-2,3-dihydro-1,4-benzoxazepin-5-one;

4-[(2R)-3-(3,4-dihydro-1H-isoquinolin-2-yl)-2-hydroxy-propyl]-8-[(1-methylpyrrolidin-3-yl)methoxy]-2,3-dihydro-1,4-benzoxazepin-5-one;

4-[(2R)-3-(3,4-dihydro-1H-isoquinolin-2-yl)-2-hydroxy-propyl]-8-[(1-methyl-3-piperidyl)methoxy]-2,3-dihydro-1,4-benzoxazepin-5-one;

4-[(2R)-3-(3,4-dihydro-1H-isoquinolin-2-yl)-2-hydroxy-propyl]-6-fluoro-8-(morpholinomethyl)-2,3-dihydro-1,4-benzoxazepin-5-one;

4-[(2R)-3-(3,4-dihydro-1H-isoquinolin-2-yl)-2-hydroxy-propyl]-6-fluoro-8-[(1-methyl-4-piperidyl)oxy]-2,3-dihydro-1,4-benzoxazepin-5-one;

4-[(2R)-3-(3,4-dihydro-1H-isoquinolin-2-yl)-2-hydroxy-propyl]-8-[(1-ethyl-4-piperidyl)oxy]-2,2-dimethyl-3H-1,4-benzoxazepin-5-one;

4-[(2R)-3-(3,4-dihydro-1H-isoquinolin-2-yl)-2-hydroxy-propyl]-2,2-dimethyl-8-(morpholinomethyl)-3H-1,4-benzoxazepin-5-one;

4-[(2R)-3-(3,4-dihydro-1H-isoquinolin-2-yl)-2-hydroxy-propyl]-2,2-dimethyl-8-[(1-methyl-4-piperidyl)oxy]-3H-1,4-benzoxazepin-5-one;

4-[(2R)-3-(3,4-dihydro-1H-isoquinolin-2-yl)-2-hydroxy-propyl]-2,2-dimethyl-8-(4-pyridylmethoxy)-3H-1,4-benzoxazepin-5-one;

8-(1-acetylazetidin-3-yl)oxy-4-[(2R)-3-(3,4-dihydro-1H-isoquinolin-2-yl)-2-hydroxy-propyl]-2,2-dimethyl-3H-1,4-benzoxazepin-5-one;

4-[(2R)-3-(3,4-dihydro-1H-isoquinolin-2-yl)-2-hydroxy-propyl]-1-methyl-8-(morpholinomethyl)-2,3-dihydro-1,4-benzodiazepin-5-one;

4-[(2R)-3-(3,4-dihydro-1H-isoquinolin-2-yl)-2-hydroxy-propyl]-1-methyl-8-(3,3,3-trifluoropropyl)-2,3-dihydro-1,4-benzodiazepin-5-one;

8-(cyclohexylmethyl)-4-[(2R)-3-(3,4-dihydro-1H-isoquinolin-2-yl)-2-hydroxy-propyl]-1-methyl-2,3-dihydro-1,4-benzodiazepin-5-one;

8-(cyclohexen-1-yl)-4-[(2R)-3-(3,4-dihydro-1H-isoquinolin-2-yl)-2-hydroxy-propyl]-1-methyl-2,3-dihydro-1,4-benzodiazepin-5-one;

4-[(2R)-3-(3,4-dihydro-1H-isoquinolin-2-yl)-2-hydroxy-propyl]-1-methyl-8-[4-(trifluoromethyl)cyclohexen-1-yl]-2,3-dihydro-1,4-benzodiazepin-5-one;

tert-butyl 4-[4-[(2R)-3-(3,4-dihydro-1H-isoquinolin-2-yl)-2-hydroxy-propyl]-1-methyl-5-oxo-2,3-dihydro-1,4-benzodiazepin-8-yl]-3,6-dihydro-2H-pyridine-1-carboxylate;

8-[(1-acetyl-4-piperidyl)oxy]-4-[(2R)-3-(3,4-dihydro-1H-isoquinolin-2-yl)-2-hydroxy-propyl]-1-methyl-2,3-dihydro-1,4-benzodiazepin-5-one;

8-(1-acetylazetidin-3-yl)oxy-4-[(2R)-3-(3,4-dihydro-1H-isoquinolin-2-yl)-2-hydroxy-propyl]-1-methyl-2,3-dihydro-1,4-benzodiazepin-5-one;

8-[(3R)-1-acetylpyrrolidin-3-yl]oxy-4-[(2R)-3-(3,4-dihydro-1H-isoquinolin-2-yl)-2-hydroxy-propyl]-1-methyl-2,3-dihydro-1,4-benzodiazepin-5-one;

8-[(3S)-1-acetylpyrrolidin-3-yl]oxy-4-[(2R)-3-(3,4-dihydro-1H-isoquinolin-2-yl)-2-hydroxy-propyl]-1-methyl-2,3-dihydro-1,4-benzodiazepin-5-one;

4-[(2R)-3-(3,4-dihydro-1H-isoquinolin-2-yl)-2-hydroxy-propyl]-1-methyl-8-[(1-methyl-4-piperidyl)oxy]-2,3-dihydro-1,4-benzodiazepin-5-one;

4-[(2R)-3-(3,4-dihydro-1H-isoquinolin-2-yl)-2-hydroxy-propyl]-8-[(1-ethyl-4-piperidyl)oxy]-1-methyl-2,3-dihydro-1,4-benzodiazepin-5-one;

8-[(1-cyclobutyl-4-piperidyl)oxy]-4-[(2R)-3-(3,4-dihydro-1H-isoquinolin-2-yl)-2-hydroxy-propyl]-1-methyl-2,3-dihydro-1,4-benzodiazepin-5-one;

4-[(2R)-3-(3,4-dihydro-1H-isoquinolin-2-yl)-2-hydroxy-propyl]-1-methyl-8-[(1-tetrahydrofuran-3-yl-4-piperidyl)oxy]-2,3-dihydro-1,4-benzodiazepin-5-one;

4-[(2R)-3-(3,4-dihydro-1H-isoquinolin-2-yl)-2-hydroxy-propyl]-1-methyl-8-[[1-(oxetan-3-yl)-4-piperidyl]oxy]-2,3-dihydro-1,4-benzodiazepin-5-one;

4-[(2R)-3-(3,4-dihydro-1H-isoquinolin-2-yl)-2-hydroxy-propyl]-1-methyl-8-[(1-methyl-3-piperidyl)oxy]-2,3-dihydro-1,4-benzodiazepin-5-one;

4-[(2R)-3-(3,4-dihydro-1H-isoquinolin-2-yl)-2-hydroxy-propyl]-1-methyl-8-[(1-methylpyrrolidin-3-yl)methoxy]-2,3-dihydro-1,4-benzodiazepin-5-one;

4-[(2R)-3-(3,4-dihydro-1H-isoquinolin-2-yl)-2-hydroxy-propyl]-1-methyl-8-(1-methylpyrrolidin-3-yl)oxy-2,3-dihydro-1,4-benzodiazepin-5-one;

4-[(2R)-3-(3,4-dihydro-1H-isoquinolin-2-yl)-2-hydroxy-propyl]-1-methyl-8-[(1-methyl-3-piperidyl)methoxy]-2,3-dihydro-1,4-benzodiazepin-5-one;

4-[(2R)-3-(3,4-dihydro-1H-isoquinolin-2-yl)-2-hydroxy-propyl]-8-[(3-fluoro-4-pyridyl)methoxy]-1-methyl-2,3-dihydro-1,4-benzodiazepin-5-one;

4-[(2R)-3-(3,4-dihydro-1H-isoquinolin-2-yl)-2-hydroxy-propyl]-8-[(3-fluoro-4-piperidyl)oxy]-1-methyl-2,3-dihydro-1,4-benzodiazepin-5-one dihydrochloride;

4-[(2R)-3-(3,4-dihydro-1H-isoquinolin-2-yl)-2-hydroxy-propyl]-8-[(1-ethyl-3-fluoro-4-piperidyl)oxy]-1-methyl-2,3-dihydro-1,4-benzodiazepin-5-one;

4-[(2R)-3-(3,4-dihydro-1H-isoquinolin-2-yl)-2-hydroxy-propyl]-8-[(8-ethyl-8-azabicyclo[3.2.1]octan-3-yl)oxy]-1-methyl-2,3-dihydro-1,4-benzodiazepin-5-one;

4-[(2R)-3-(3,4-dihydro-1H-isoquinolin-2-yl)-2-hydroxy-propyl]-1-methyl-8-[(2-methyl-4-piperidyl)oxy]-2,3-dihydro-1,4-benzodiazepin-5-one dihydrochloride;

4-[(2R)-3-(3,4-dihydro-1H-isoquinolin-2-yl)-2-hydroxy-propyl]-8-[(5-fluoro-2-pyridyl)methoxy]-1-methyl-2,3-dihydro-1,4-benzodiazepin-5-one;

4-[(2R)-3-(3,4-dihydro-1H-isoquinolin-2-yl)-2-hydroxy-propyl]-2-methyl-8-(4-piperidyloxy)-2,3-dihydro-1,4-benzoxazepin-5-one dihydrochloride;

4-[(2R)-3-(3,4-dihydro-1H-isoquinolin-2-yl)-2-hydroxy-propyl]-2-methyl-8-[(1-methyl-4-piperidyl)oxy]-2,3-dihydro-1,4-benzoxazepin-5-one;

(2R)-8-(1-acetylazetidin-3-yl)oxy-4-[(2R)-3-(3,4-dihydro-1H-isoquinolin-2-yl)-2-hydroxypropyl]-2-methyl-2,3-dihydro-1,4-benzoxazepin-5-one;

(2R)-4-[(2R)-3-(3,4-dihydro-1H-isoquinolin-2-yl)-2-hydroxypropyl]-2-methyl-8-[(1-methyl-4-piperidyl)oxy]-2,3-dihydro-1,4-benzoxazepin-5-one;

4-[(2R)-3-(3,4-dihydro-1H-isoquinolin-2-yl)-2-hydroxy-propyl]-2-methyl-8-[(1-methyl-4-piperidyl)oxy]-2,3-dihydropyrido[3,2-f][1,4]oxazepin-5-one;

4-[(2R)-3-(3,4-dihydro-1H-isoquinolin-2-yl)-2-hydroxy-propyl]-2,2-dimethyl-8-[(1-methyl-4-piperidyl)oxy]-3H-pyrido[3,2-f][1,4]oxazepin-5-one;

(2S)-4-[(2R)-3-(3,4-dihydro-1H-isoquinolin-2-yl)-2-hydroxypropyl]-2-methyl-8-[(1-methyl-4-piperidyl)oxy]-2,3-dihydro-1,4-benzoxazepin-5-one;

4-[3-(3,4-dihydro-1H-isoquinolin-2-yl)-2-hydroxy-propyl]-2,3-dihydro-1,4-benzoxazepin-5-one;

2-[3-(3,4-dihydro-1H-isoquinolin-2-yl)-2-hydroxy-propyl]-4,5-dihydro-3H-2-benzazepin-1-one;

4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-fluoro-2,3-dihydro-1,4-benzoxazepin-5-one;

8-bromo-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-2,3-dihydropyrido[4,3-f][1,4]oxazepin-5-one;

8-chloro-4-[(2R)-3-(3,4-dihydro-1H-isoquinolin-2-yl)-2-hydroxy-propyl]-2,3-dihydropyrido[3,2-f][1,4]oxazepin-5-one;

7-chloro-2-[(2R)-3-(3,4-dihydro-1H-isoquinolin-2-yl)-2-hydroxy-propyl]-4,5-dihydro-3H-2-benzazepin-1-one;

7-bromo-2-[(2R)-3-(3,4-dihydro-1H-isoquinolin-2-yl)-2-hydroxy-propyl]-4,5-dihydro-3H-2-benzazepin-1-one;

8-bromo-4-[(2R)-3-(3,4-dihydro-1H-isoquinolin-2-yl)-2-hydroxy-propyl]-1-methyl-2,3-dihydro-1,4-benzodiazepin-5-one;

8-bromo-4-[(2R)-3-(3,4-dihydro-1H-isoquinolin-2-yl)-2-hydroxy-propyl]-1-ethyl-2,3-dihydro-1,4-benzodiazepin-5-one;

8-bromo-4-[(2R)-3-(3,4-dihydro-1H-isoquinolin-2-yl)-2-hydroxy-propyl]-1-ethyl-3H-1,4-benzodiazepin-2,5-dione;

2-[4-[[4-(2R)-3-(3,4,-dihydro-1H-isoquinolin-2-yl)-2-hydroxy-propyl]-5-oxo-2,3,-dihydro-1,4,-benzoxazepin-8-yl]-1-piperidyl]acetonitrile;

8-[[1-(2,2-difluoroacetyl)-4-piperidyl]oxy]-4-[(2R)-3-(3,4-dihydro-1H-isoquinolin-2-yl)-2-hydroxy-propyl]-2,3-dihydro-1,4-benzoxazepin-5-one;

8-[[1-(2,2-difluoroacetyl)azetidin-3-yl]oxy-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-[[1-(2-hydroxyethyl)-4-piperidyl]oxy]-2,3-dihydro-1,4-benzoxazepin-5-one;

4-[(2R)-3-(3,4-dihydro-1H-isoquinolin-2-yl)-2-hydroxy-propyl]-8-[[1-(2-fluoroethyl)-4-piperidyl]oxy]-2,3-dihydro-1,4-benzoxazepin-5-one;

4-[(2R)-3-(3,4-dihydro-1H-isoquinolin-2-yl)-2-hydroxy-propyl]-8-[[1-(2-fluoroethyl)-4-piperidyl]oxy]-2,3-dihydropyrido[3,2-f][1,4]oxazepin-5-one;

4-[(2R)-3-(3,4-dihydro-1H-isoquinolin-2-yl)-2-hydroxy-propyl]-8[[1-[(3-methyloxetan-3-yl)methyl]-4-piperidyl]oxy]-2,3-dihydro-1,4-benzoxazepin-5-one;

4-[[4-[(2R)-3-(3,4-dihydro-1H-isoquinolin-2-yl)-2-hydroxypropyl]-5-oxo-2,3-dihydro-1,4-benzoazepin-8-yl]oxy]piperidine-1-carbonitrile;

8-[(4-acetylpiperazin-1-yl)methyl]-4-[(2R)-3-(3,4-dihydro-1H-isoquinolin-2-yl)-2-hydroxy-propyl]-2,2-dimethyl-3H-1,4-benzoxazepin-5-one;

3-[[4-[(2R)-3-(3,4-dihydro-1H-isoquinolin-2-yl)-2-hydroxy-propyl]-2,2-dimethyl-5-oxo-3H-1,4-benzoxazepin-8-yl]oxy]azetidin-1-carbaldehyde;

4-[[4-[(2R)-3-(3,4-dihydro-1H-isoquinolin-2-yl)-2-hydroxy-propyl]-2,2-dimethyl-5-oxo-3H-1,4-benzoxazepin-8-yl]methyl]piperazine-1-carbaldehyde;

4-[(2R)-3-(3,4-dihydro-1H-isoquinolin-2-yl)-2-hydroxy-propyl]-2,2-dimethyl-8-(2-oxa-6-azaspiro[3.3]heptan-6-ylmethyl)-3H-1,4-benzoxazepin-5-one;

4-[(2R)-3-(3,4-dihydro-1H-isoquinolin-2-yl)-2-hydroxy-propyl]-8-[(8-ethyl-8-azabicyclo[3.2.1]octan-3-yl)oxy]-2,3-dihydro-1,4-benzoxazepin-5-one;

4-[(2R)-3-(3,4-dihydro-1H-isoquinolin-2-yl)-2-hydroxy-propyl]-8-[(2-ethyl-2-azaspiro[3.3]heptan-6-yl)oxy]-2,3-dihydro-1,4-benzoxazepin-5-one;

8-[(8-acetyl-8-azabicyclo[3.2.1]octan-3-yl)oxy]-4-[(2R)-3-(3,4-dihydro-1H-isoquinolin-2-yl)-2-hydroxy-propyl]-2,3-dihydro-1,4-benzoxazepin-5-one;

8-[(2-acetyl-2-azaspiro[3.3]heptan-6-yl)oxy]-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-(pyrrolidin-1-carbonyl)-2,3-dihydro-1,4-benzoxazepin-5-one;

4-[(2R)-3-(3,4-dihydro-1H-isoquinolin-2-yl)-2-hydroxy-propyl]-8-(piperidine-1-carbonyl)-2,3-dihydro-1,4-benzoxazepin-5-one;

8-(3,3-difluoropyrrolidin-1-carbonyl)-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-(4-methylpiperazine-1-carbonyl)-2,3-dihydro-1,4-benzoxazepin-5-one;

4-[(2R)-3-(3,4-dihydro-1H-isoquinolin-2-yl)-2-hydroxy-propyl]-2,2-dimethyl-8-(pyrrolidin-1-ylmethyl)-3H-1,4-benzoxazepin-5-one;

8-[(1-acetyl-4-piperidyl)oxy]-4-[(2R)-3-(3,4-dihydro-1H-isoquinolin-2-yl)-2-hydroxy-propyl]-2,2-dimethyl-3H-1,4-benzoxazepin-5-one;

4-[[4-[(2R)-3-(3,4-dihydro-1H-isoquinolin-2-yl)-2-hydroxy-propyl]-2,2-dimethyl-5-oxo-3H-1,4-benzoxazepin-8-yl]oxy]piperidine-1-carbaldehyde;

4-[(2R)-3-(3,4-dihydro-1H-isoquinolin-2-yl)-2-hydroxy-propyl]-2,2-dimethyl-8-[[4-(oxetan-3-yl)piperazin-1-yl]methyl]-3H-1,4-benzoxazepin-5-one;

4-[(2R)-3-(3,4-dihydro-1H-isoquinolin-2-yl)-2-hydroxy-propyl]-2,2-dimethyl-8-(2-oxa-7-azaspiro[3.4]octan-7-ylmethyl)-3H-1,4-benzoxazepin-5-one;

4-[(2R)-3-(3,4-dihydro-1H-isoquinolin-2-yl)-2-hydroxy-propyl]-8-(4-fluoropiperidine-1-carbonyl)-2,3-dihydro-1,4-benzoxazepin-5-one;

4-[(2R)-3-(3,4-dihydro-1H-isoquinolin-2-yl)-2-hydroxy-propyl]-8-[3-(trifluoromethyl)piperidine-1-carbonyl]-2,3-dihydro-1,4-benzoxazepin-5-one;

4-[(2R)-3-(3,4-dihydro-1H-isoquinolin-2-yl)-2-hydroxy-propyl]-8-[4-(trifluoromethyl)piperidine-1-carbonyl]-2,3-dihydro-1,4-benzoxazepin-5-one;

4-[(2R)-3-(3,4-dihydro-1H-isoquinolin-2-yl)-2-hydroxy-propyl]-8-(2,6-dimethylmorpholin-4-carbonyl)-2,3-dihydro-1,4-benzoxazepin-5-one;

8-(2-azabicyclo[2.2.1]heptane-2-carbonyl)-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-(3-oxa-8-azabicyclo[3.2.1]octan-8-carbonyl)-2,3-dihydro-1,4-benzoxazepin-5-one;

4-[(2R)-3-(3,4-dihydro-1H-isoquinolin-2-yl)-2-hydroxy-propyl]-8-(2-methylmorpholin-4-carbonyl)-2,3-dihydro-1,4-benzoxazepin-5-one;

4-[(2R)-3-(3,4-dihydro-1H-isoquinolin-2-yl)-2-hydroxy-propyl]-8-(3-methylmorpholin-4-carbonyl)-2,3-dihydro-1,4-benzoxazepin-5-one;

4-[(2R)-3-(3,4-dihydro-1H-isoquinolin-2-yl)-2-hydroxy-propyl]-2,2-dimethyl-8-(morpholinomethyl)-3H-pyrido[3,2-f][1,4]oxazepin-5-one;

8-(3,3a,4,5,6,6a-hexahydro-1H-cyclopenta[c]pyrrol-2-carbonyl)-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-(3-fluoropiperidine-1-carbonyl)-2,3-dihydro-1,4-benzoxazepin-5-one;

8-(2,2-difluoromorpholin-4-carbonyl)-4-[(2R)-3-(3,4-dihydro-1H-isoquinolin-2-yl)-2-hydroxy-propyl]-2,3-dihydro-1,4-benzoxazepin-5-one;

8-(4,4-difluoropiperidine-1-carbonyl)-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-2,2-dimethyl-8-(1-piperidylmethyl)-3H-pyrido[3,2-f][1,4]oxazepin-5-one;

4-[(2R)-3-(3,4-dihydro-1H-isoquinolin-2-yl)-2-hydroxy-propyl]-8-[4-[methyl(oxetan-3-yl)amino]cyclohexoxy]-2,3-dihydro-1,4-benzoxazepin-5-one;

4-[(2R)-3-(3,4-dihydro-1H-isoquinolin-2-yl)-2-hydroxy-propyl]-8-[4-[2-fluoroethyl(methyl)amino]cyclohexoxy]-2,3-dihydro-1,4-benzoxazepin-5-one;

(2S)-4-[(2R)-3-(3,4-dihydro-1H-isoquinolin-2-yl)-2-hydroxy-propyl]-8-[(1-ethanethiol-4-piperidyl)oxy]-2-methyl-2,3-dihydro-1,4-benzoxazepin-5-one;

(2S)-4-[(2R)-3-(3,4-dihydro-1H-isoquinolin-2-yl)-2-hydroxy-propyl]-8-[1-(2-fluoroethyl)azetidin-3-yl]oxy-2-methyl-2,3-dihydro-1,4-benzoxazepin-5-one;

(2S)-4-[(2R)-3-(3,4-dihydro-1H-isoquinolin-2-yl)-2-hydroxy-propyl]-8-[1-(2-fluoroethyl)-4-piperidyl]oxy-2-methyl-2,3-dihydro-1,4-benzoxazepin-5-one;

4-[(2R)-3-(3,4-dihydro-1H-isoquinolin-2-yl)-2-hydroxy-propyl]-2,2-dimethyl-8-(3-oxa-8-azabicyclo[3.2.1]octan-8-carbonyl)-3H-1,4-benzoxazepin-5-one;

4-[(2R)-3-(3,4-dihydro-1H-isoquinolin-2-yl)-2-hydroxy-propyl]-2,2-dimethyl-8-(2-oxa-5-azabicyclo[2.2.1]heptan-5-carbonyl)-3H-1,4-benzoxazepin-5-one;

4-[(2R)-3-(3,4-dihydro-1H-isoquinolin-2-yl)-2-hydroxy-propyl]-8-(3,5-dimethylmorpholin-4-carbonyl)-2,2-dimethyl-3H-1,4-benzoxazepin-5-one;

4-[(2R)-3-(3,4-dihydro-1H-isoquinolin-2-yl)-2-hydroxy-propyl]-8-[(3-fluoro-1-methyl-4-piperidyl)oxy]-2,3-dihydro-1,4-benzoxazepin-5-one;

4-[(2R)-3-(3,4-dihydro-1H-isoquinolin-2-yl)-2-hydroxy-propyl]-8-[[3-fluoro-1-(2-fluoroethyl)-4-piperidyl]oxy]-2,3-dihydro-1,4-benzoxazepin-5-one;

4-[(2R)-3-(3,4-dihydro-1H-isoquinolin-2-yl)-2-hydroxy-propyl]-8-[[3-fluoro-1-(2-hydroxyethyl)-4-piperidyl]oxy]-2,3-dihydro-1,4-benzoxazepin-5-one;

4-[(2R)-3-(3,4-dihydro-1H-isoquinolin-2-yl)-2-hydroxy-propyl]-8-(3,4-dihydro-1H-pyrrolo[1,2-a]pyrazine-2-carbonyl)-2,2-dimethyl-3H-1,4-benzoxazepin-5-one;

8-(3,4,6,7,8,8a-hexahydro-1H-pyrrolo[1,2-a]pyrazine-2-carbonyl)-4-[(2R)-3-(3,4-dihydro-1H-isoquinolin-2-yl)-2-hydroxy-propyl]-2,2-dimethyl-3H-1,4-benzoxazepin-5-one;

4-[(2R)-3-(3,4-dihydro-1H-isoquinolin-2-yl)-2-hydroxy-propyl]-8-(5-fluoropyrimidin-2-yl)oxy-2,3-dihydro-1,4-benzoxazepin-5-one;

4-[(2R)-3-(3,4-dihydro-1H-isoquinolin-2-yl)-2-hydroxy-propyl]-8-[[1-(2-hydroxypropyl)-4-piperidyl]oxy]-2,3-dihydro-1,4-benzoxazepin-5-one;

4-[(2R)-3-(3,4-dihydro-1H-isoquinolin-2-yl)-2-hydroxy-propyl]-8-[(1-methyl-3-piperidyl)oxy]-2,3-dihydro-1,4-benzoxazepin-5-one;

4-[(2R)-3-(3,4-dihydro-1H-isoquinolin-2-yl)-2-hydroxy-propyl]-8-propanoyl-2,3-dihydro-1,4-benzoxazepin-5-one;

4-[(2R)-3-(3,4-dihydro-1H-isoquinolin-2-yl)-2-hydroxy-propyl]-8-[[8-2-fluoroethyl]-8-azabicyclo[3.2.1]octan-3-yl)oxy]-2,3-dihydro-1,4-benzoxazepin-5-one;

8-(cyclopropanecarbonyl)-4-[(2R)-3-(3,4-dihydro-1H-isoquinolin-2-yl)-2-hydroxy-propyl]-2,3-dihydro-1,4-benzoxazepin-5-one;

8-(cyclopentanecarbonyl)-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-[(1-methyl-3-piperidyl)oxy]-2,3-dihydro-1,4-benzoxazepin-5-one;

(2R)-4-[(2R)-3-(3,4-dihydro-1H-isoquinolin-2-yl)-2-hydroxy-propyl]-8-[[1-(2-hydroxyethyl)-4-piperidyl]oxy]-2-methyl-2,3-dihydro-1,4-benzoxazepin-5-one;

(2R)-4-[(2R)-3-(3,4-dihydro-1H-isoquinolin-2-yl)-2-hydroxy-propyl]-8-[[1-(2-hydroxy-2-methyl-propyl)-4-piperidyl]oxy]-2-methyl-2,3-dihydro-1,4-benzoxazepin-5-one;

4-[(2R)-3-(3,4-dihydro-1H-isoquinolin-2-yl)-2-hydroxy-propyl]-8-(1-morpholinoethyl)-2,3-dihydro-1,4-benzoxazepin-5-one;

4-[(2R)-3-(3,4-dihydro-1H-isoquinolin-2-yl)-2-hydroxy-propyl]-8-[1-(2-oxa-6-azaspiro[3.3]heptan-6-yl)ethyl]-2,3-dihydro-1,4-benzoxazepin-5-one;

4-[(2R)-3-(3,4-dihydro-1H-isoquinolin-2-yl)-2-hydroxy-propyl]-8-(3-hydroxypro-1-pynyl)-2,3-dihydro-1,4-benzoxazepin-5-one;

(2R)-4-[(2R)-3-(3,4-dihydro-1H-isoquinolin-2-yl)-2-hydroxy-propyl]-8-[[1-(2-methoxyethyl)-4-piperidyl]oxy]-2-methyl-2,3-dihydro-1,4-benzoxazepin-5-one;

4-[(2R)-3-(3,4-dihydro-1H-isoquinolin-2-yl)-2-hydroxy-propyl]-8-(4-pyridyl)-2,3-dihydro-1,4-benzoxazepin-5-one;

4-[(2R)-3-(3,4-dihydro-1H-isoquinolin-2-yl)-2-hydroxy-propyl]-8-[2-(4-pyridyl)ethynyl]-2,3-dihydro-1,4-benzoxazepin-5-one;

4-[(2R)-3-(3,4-dihydro-1H-isoquinolin-2-yl)-2-hydroxy-propyl]-8-[2-(3-pyridyl)ethynyl]-2,3-dihydro-1,4-benzoxazepin-5-one;

4-[(2R)-3-(3,4-dihydro-1H-isoquinolin-2-yl)-2-hydroxy-propyl]-8-(3-hydroxybu-1-tynyl)-2,3-dihydro-1,4-benzoxazepin-5-one;

4-[(2R)-3-(3,4-dihydro-1H-isoquinolin-2-yl)-2-hydroxy-propyl]-8-[3-(methylamino)pro-1-pynyl]-2,3-dihydro-1,4-benzoxazepin-5-one;

4-[(2R)-3-(3,4-dihydro-1H-isoquinolin-2-yl)-2-hydroxy-propyl]-8-(3-pyridyl)-2,3-dihydro-1,4-benzoxazepin-5-one;

4-[(2R)-3-(3,4-dihydro-1H-isoquinolin-2-yl)-2-hydroxy-propyl]-8-(1,3-dimethylpyrazol-4-yl)-2,3-dihydro-1,4-benzoxazepin-5-one;

4-[(2R)-3-(3,4-dihydro-1H-isoquinolin-2-yl)-2-hydroxy-propyl]-8-(1-methylpyrazol-4-yl)-2,3-dihydro-1,4-benzoxazepin-5-one;

4-[(2R)-3-(3,4-dihydro-1H-isoquinolin-2-yl)-2-hydroxy-propyl]-8-(1,5-dimethylpyrazol-4-yl)-2,3-dihydro-1,4-benzoxazepin-5-one;

4-[(2R)-3-(3,4-dihydro-1H-isoquinolin-2-yl)-2-hydroxy-propyl]-8-[[1-(2-hydroxyethyl)-4-piperidyl]oxy]-2,2-dimethyl-3H-pyrido[3,2-f][1,4]oxazepin-5-one;

4-[(2R)-3-(3,4-dihydro-1H-isoquinolin-2-yl)-2-hydroxy-propyl]-2,2-dimethyl-8-[[(3R)-1-methyl-3-piperidyl]oxy]-3H-pyrido[3,2-f][1,4]oxazepin-5-one;

4-[(2R)-3-(3,4-dihydro-1H-isoquinolin-2-yl)-2-hydroxy-propyl]-8-[[(1-(2-fluoroethyl)-3-piperidyl)oxy]-2,3-dihydro-1,4-benzoxazepin-5-one;

4-[(2R)-3-(3,4-dihydro-1H-isoquinolin-2-yl)-2-hydroxy-propyl]-8-[[(1-(2-hydroxy)-3-piperidyl)oxy]-2,3-dihydro-1,4-benzoxazepin-5-one;

4-[(2R)-3-(3,4-dihydro-1H-isoquinolin-2-yl)-2-hydroxy-propyl]-8-[[1-(2-hydroxy-2-methyl-propyl)-4-piperidyl]oxy]-2,3-dihydro-1,4-benzoxazepin-5-one;

4-[(2R)-3-(3,4-dihydro-1H-isoquinolin-2-yl)-2-hydroxy-propyl]-8-(6-fluoro-2-pyridyl)-2,3-dihydro-1,4-benzoxazepin-5-one;

(2R)-4-[(2R)-3-(3,4-dihydro-1H-isoquinolin-2-yl)-2-hydroxy-propyl]-8-[[1-(2-ethoxyethyl)-4-piperidyl]oxy]-2-methyl-2,3-dihydro-1,4-benzoxazepin-5-one;

(2R)-4-[(2R)-3-(3,4-dihydro-1H-isoquinolin-2-yl)-2-hydroxy-propyl]-8-[[8-2-hydroxy]-8-azabicyclo[3.2.1]octan-3-yl]oxy]-2-methyl-2,3-dihydro-1,4-benzoxazepin-5-one;

(2R)-4-[(2R)-3-(3,4-dihydro-1H-isoquinolin-2-yl)-2-hydroxy-propyl]-8-[[8-2-fluoroethyl]-8-azabicyclo[3.2.1]octan-3-yl]oxy]-2-methyl-2,3-dihydro-1,4-benzoxazepin-5-one;

4-[(2R)-3-(3,4-dihydro-1H-isoquinolin-2-yl)-2-hydroxy-propyl]-8-[[1-(2-methoxyethyl)-4-pyridyl]oxy]-2-methyl-2,3-dihydro-1,4-benzoxazepin-5-one;

4-[(2R)-3-(3,4-dihydro-1H-isoquinolin-2-yl)-2-hydroxy-propyl]-8-(6-methoxy-2-pyridyl)-2,3-dihydro-1,4-benzoxazepin-5-one;

(2R)-4-[(2R)-3-(3,4-dihydro-1H-isoquinolin-2-yl)-2-hydroxy-propyl]-8-[[1-(2-hydroxypropyl)-4-piperidyl]oxy]-2-methyl-2,3-dihydro-1,4-benzoxazepin-5-one;

4-[(2R)-3-(3,4-dihydro-1H-isoquinolin-2-yl)-2-hydroxy-propyl]-2,2-dimethyl-8-(1-morpholinoethyl)-3H-pyrido[3,2-f][1,4]oxazepin-5-one;

4-[(2R)-3-(3,4-dihydro-1H-isoquinolin-2-yl)-2-hydroxy-propyl]-2,2-dimethyl-8-[1-(2-oxa-6-azaspiro[3.3]heptan-6-yl)ethyl]-3H-pyrido[3,2-f][1,4]oxazepin-5-one;

4-[(2R)-3-(3,4-dihydro-1H-isoquinolin-2-yl)-2-hydroxy-propyl]-8-[[1-(2-hydroxypropyl)-4-piperidyl]oxy]-2,2-dimethyl-3H-pyrido[3,2-f][1,4]oxazepin-5-one;

4-[(2R)-3-(3,4-dihydro-1H-isoquinolin-2-yl)-2-hydroxy-propyl]-8-(3,4-dihydro-1H-pyrrolo[1,2-a]pyrazin-2-ylmethyl)-2,3-dihydro-1,4-benzoxazepin-5-one;

(2R)-4-[(2R)-3-(3,4-dihydro-1H-isoquinolin-2-yl)-2-hydroxypropyl]-2-methyl-8-(2-oxa-6-azaspiro[3.3]heptan-6-ylmethyl)-2,3-dihydro-1,4-benzoxazepin-5-one;

4-[(2R)-3-(3,4-dihydro-1H-isoquinolin-2-yl)-2-hydroxy-propyl]-8-(2-oxa-7-azaspiro[3.5]nonan-7-ylmethyl)-2,3-dihydro-1,4-benzoxazepin-5-one;

(2R)-4-[(2R)-3-(3,4-dihydro-1H-isoquinolin-2-yl)-2-hydroxypropyl]-2-methyl-8-(2-oxa-7-azaspiro[3.5]nonan-7-ylmethyl)-2,3-dihydro-1,4-benzoxazepin-5-one;

4-[(2R)-4-[(2R)-3-(3,4-dihydro-1H-isoquinolin-2-yl)-2-hydroxy-propyl]-8-[(3R,4R)-3-fluoro-1-(2-hydroxyethyl)-4-piperidyl]oxy]-2-methyl-2,3-dihydro-1,4-benzoxazepin-5-one dihydrochloride;

4-[(2R)-3-(3,4-dihydro-1H-isoquinolin-2-yl)-2-hydroxy-propyl]-8-[[(3R,4R)-3-fluoro-1-(2-hydroxypropyl)-4-piperidyl]oxy]-2-methyl-2,3-dihydro-1,4-benzoxazepin-5-one dihydrochloride;

(2R)-4-[(2R)-3-[(2R)-3-(3,4-dihydro-1H-isoquinolin-2-yl)-2-hydroxy-propyl]-8-[(3R,4R)-3-fluoro-1-(2-hydroxyethyl)-4-piperidyl]oxy]-2-methyl-2,3-dihydro-1,4-benzoxazepin-5-one dihydrochloride;

8-[[3,3-difluoro-1-(2-hydroxyethyl)-4-piperidyl]oxy]-4-[(2R)-3-(3,4-dihydro-1H-isoquinolin-2-yl)-2-hydroxy-propyl]-2,2-dimethyl-3H-pyrido[3,2-f][1,4]oxazepin-5-one;

4-[(2R)-3-(3,4-dihydro-1H-isoquinolin-2-yl)-2-hydroxy-propyl]-8-[1-(1-piperidyl)ethyl]-2,3-dihydro-1,4-benzoxazepin-5-one;

4-[(2R)-3-(3,4-dihydro-1H-isoquinolin-2-yl)-2-hydroxy-propyl]-8-[1-(4-hydroxy-1-piperidyl)ethyl]-2,3-dihydro-1,4-benzoxazepin-5-one;

4-[(2R)-3-(3,4-dihydro-1H-isoquinolin-2-yl)-2-hydroxy-propyl]-8-[1-(4-methoxy-1-piperidyl)ethyl]-2,3-dihydro-1,4-benzoxazepin-5-one;

4-[(2R)-3-(3,4-dihydro-1H-isoquinolin-2-yl)-2-hydroxy-propyl]-8-[1-(3-hydroxy-3-methyl-pyrrolidin-1-yl)ethyl]-2,3-dihydro-1,4-benzoxazepin-5-one;

(2R)-4-[(2R)-3-(3,4-dihydro-1H-isoquinolin-2-yl)-2-hydroxy-propyl]-8-[[1-(2-hydroxyethyl)-4-piperidyl]oxy]-2-methyl-2,3-dihydro-1,4-benzoxazepin-5-one dihydrochloride;

4-[(2R)-3-(3,4-dihydro-1H-isoquinolin-2-yl)-2-hydroxy-propyl]-8-[[1-(2-methoxyethyl)-4-piperidyl]oxy]-2,2-dimethyl-3H-pyrido[3,2-f][1,4]oxazepin-5-one;

4-[(2R)-3-(3,4-dihydro-1H-isoquinolin-2-yl)-2-hydroxy-propyl]-8-[(3S)-1-(oxetan-3-yl)pyrrolidin-3-yl]oxy-2,3-dihydro-1,4-benzoxazepin-5-one;

(2R)-4-[(2R)-3-(3,4-dihydro-1H-isoquinolin-2-yl)-2-hydroxy-propyl]-2-methyl-8-[(3S)-1-methylpyrrolidin-3-yl]oxy-2,3-dihydro-1,4-benzoxazepin-5-one;

4-[(2R)-3-(3,4-dihydro-1H-isoquinolinon-2-yl)-2-hydroxy-propyl]-8-[(3R)-tetrahydrofuran-3-yl]oxy-2,3-dihydro-1,4-benzoxazepin-5-one;

4-[(2R)-3-(3,4-dihydro-1H-isoquinolinon-2-yl)-2-hydroxy-propyl]-8-[(3S)-tetrahydrofuran-3-yl]oxy-2,3-dihydro-1,4-benzoxazepin-5-one;

(2R)-4-[(2R)-3-(3,4-dihydro-1H-isoquinolin-2-yl)-2-hydroxy-propyl]-8-[[1-[(2S)-2-hydroxypropyl]-4-piperidyl]oxy]-2-methyl-2,3-dihydro-1,4-benzoxazepin-5-one;

(2R)-4-[(2R)-3-(3,4-dihydro-1H-isoquinolin-2-yl)-2-hydroxy-propyl]-8-[1-[[(2R)-2-hydroxypropyl]-4-piperidyl]oxy]-2-methyl-2,3-dihydro-1,4-benzoxazepin-5-one;

8-[cyclopropyl(hydroxy)methyl]-4-[(2R)-3-(3,4-dihydro-1H-isoquinolin-2-yl)-2-hydroxy-propyl]-2,3-dihydro-1,4-benzoxazepin-5-one;

8-[cyclopentyl(hydroxy)methyl]-4-[(2R)-3-(3,4-dihydro-1H-isoquinolin-2-yl)-2-hydroxy-propyl]-2,3-dihydro-1,4-benzoxazepin-5-one;

4-[(2R)-3-(3,4-dihydro-1H-isoquinolin-2-yl)-2-hydroxy-propyl]-8-[(3R)-1-(oxetan-3-yl)pyrrolidin-3-yl]oxy-2,3-dihydro-1,4-benzoxazepin-5-one;

4-[(2R)-3-(3,4-dihydro-1H-isoquinolin-2-yl)-2-hydroxy-propyl]-8-[(3R)-1-(2-methoxyethyl)pyrrolidin-3-yl]oxy-2,3-dihydro-1,4-benzoxazepin-5-one;

(2R)-4-[(2R)-3-(3,4-dihydro-1H-isoquinolin-2-yl)-2-hydroxy-propyl]-2-methyl-8-[(3R)-1-methylpyrrolidin-3-yl]oxy-2,3-dihydro-1,4-benzoxazepin-5-one;

(2R)-4-[(2R)-3-(3,4-dihydro-1H-isoquinolin-2-yl)-2-hydroxy-propyl]-8-[(3R)-1-(2-methoxyethyl)pyrrolidin-3-yl]oxy-2-methyl-2,3-dihydro-1,4-benzoxazepin-5-one;

4-[(2R)-3-(3,4-dihydro-1H-isoquinolin-2-)-2-hydroxy-propyl]-8-[[1-(3,3,3-trifluoro-2-hydroxy-propyl)-4-piperidyl]oxy]-2,3-dihydro-1,4-benzoxazepin-5-one;

(2R)-4-[(2R)-3-(3,4-dihydro-1H-isoquinolin-2-)-2-hydroxy-propyl]-2-methyl-8-[[1-(3,3,3-trifluoro-2-hydroxy-propyl)-4-piperidyl]oxy]-2,3-dihydro-1,4-benzoxazepin-5-one; and (2R)-4-[(2R)-3-(3,4-dihydro-1H-isoquinolin-2-yl)-2-hydroxypropyl]-2-methyl-8-[(3R)-1-(oxetan-3-yl)pyrrolidin-3-yl]oxy-2,3-dihydro-1,4-benzoxazepin-5-one.

* * * * *